United States Patent
Purschke et al.

(10) Patent No.: US 9,988,636 B2
(45) Date of Patent: *Jun. 5, 2018

(54) SDF-1 BINDING NUCLEIC ACIDS AND THE USE THEREOF

(71) Applicant: NOXXON Pharma AG, Berlin (DE)

(72) Inventors: Werner Purschke, Berlin (DE); Florian Jarosch, Berlin (DE); Dirk Eulberg, Berlin (DE); Sven Klussmann, Berlin (DE); Klaus Buchner, Berlin (DE); Christian Maasch, Berlin (DE); Nicole Dinse, Berlin (DE)

(73) Assignee: NOXXON Pharma AG, Berlin (DE)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/219,891

(22) Filed: Jul. 26, 2016

(65) Prior Publication Data

US 2016/0326531 A1 Nov. 10, 2016

Related U.S. Application Data

(60) Continuation of application No. 14/324,199, filed on Jul. 6, 2014, now abandoned, which is a division of application No. 12/672,449, filed as application No. PCT/EP2008/006473 on Aug. 6, 2008, now Pat. No. 8,772,257.

(30) Foreign Application Priority Data

| Aug. 6, 2007 | (EP) | 07015379 |
| Apr. 30, 2008 | (EP) | 08008312 |
| Jun. 18, 2008 | (EP) | 08011024 |

(51) Int. Cl.

| C12N 15/115 | (2010.01) |
| A61K 31/713 | (2006.01) |
| C07K 14/52 | (2006.01) |
| C07K 16/24 | (2006.01) |
| A61K 31/7105 | (2006.01) |
| A61K 47/60 | (2017.01) |

(52) U.S. Cl.
CPC .......... *C12N 15/115* (2013.01); *A61K 31/713* (2013.01); *A61K 31/7105* (2013.01); *A61K 47/60* (2017.08); *C07K 14/521* (2013.01); *C07K 16/24* (2013.01); *C12N 2310/16* (2013.01); *C12N 2310/351* (2013.01); *C12N 2320/30* (2013.01)

(58) Field of Classification Search
None
See application file for complete search history.

(56) References Cited

U.S. PATENT DOCUMENTS

| 5,567,588 | A | 10/1996 | Gold et al. |
| 5,582,981 | A | 12/1996 | Toole et al. |
| 5,840,867 | A | 11/1998 | Toole et al. |
| 6,011,020 | A | 1/2000 | Gold et al. |
| 6,949,243 | B1 | 9/2005 | Mueller et al. |
| 7,282,338 | B2 | 10/2007 | Wei |
| 7,396,653 | B2 | 7/2008 | Wei |
| 7,468,253 | B2 | 12/2008 | Wei et al. |
| 8,314,223 | B2 | 11/2012 | Purschke et al. |
| 8,772,257 | B2 | 7/2014 | Purschke et al. |
| 9,035,038 | B2 | 5/2015 | Purschke et al. |
| 2003/0017485 | A1 | 1/2003 | Wei |
| 2003/0186906 | A1 | 10/2003 | Schlingensiepen et al. |
| 2004/0209837 | A1 | 10/2004 | Kishimoto et al. |
| 2006/0234926 | A1 | 10/2006 | Stockley et al. |
| 2007/0203089 | A1 | 8/2007 | Rodrigues et al. |
| 2008/0063682 | A1 | 3/2008 | Cashman et al. |
| 2009/0274687 | A1 | 11/2009 | Young et al. |
| 2010/0074887 | A1 | 3/2010 | Mehrad et al. |
| 2010/0104508 | A1 | 4/2010 | Kuhne et al. |

OTHER PUBLICATIONS

Netelenbos et al., Leukemia 17:175-184, 2003.
Guleng et al., "Blockade . . . manner," Canc Res 65:5684-5871, 2005.
Hong et al., Canc Lett 236:39-45, 2006.
Wu et al., J Cell Biochem 103:245-255, 2007.
Flomenburg et al., Blood 106:1867-1874, 2005.
Kato et al., Breast Canc Res 5:144-150, 2003.
Tang et al., Asian Pac J Canc Prev 13:5281-5286, 2012.
Andrews et al., Stem Cells 17:210-218, 1999.
Li et al., "Retina-committed . . . retina," Ann Meet Assoc Res Vision 46:Supp 8:3247, 2005.
Luker & Luker, "Functions . . . cancer," Canc Lett 238:30, 2006.
Smith et al., Genbank XP002465983, 2004.
Burger & Kipps, "CXCR4 . . . microenvironment," Blood 107:1761, 2006.
Kucia et al., "CXCR4 . . . adhesion," J Mol Hist 35:233, 2004.
Chalasani et al., "A chemokine . . . pathfinding," J Neurosci 23:1360-1371, 2003.
Azab et al. "CXCR4 . . . therapy," Blood 113(18)4341-4351, 2009.
Burger et al., "Small . . . cells," Blood 106(5)1824-1830, 2005.
Rajagopalan et al., "Structural . . . selectivity," Biosci Rep 26(5)325-339, 2006.
Crump et al., "Solution . . . HIV-1," EMBO J 16(23)6996-7007, 1997.
Balabanian et al., "The . . . lymphocytes," JBC 280(42)35760-35766, 2005.
Sayyed et al. "Podocytes . . . diabetes," Diabet 52:2445-2454, 2009.
Hachet-Haas et al., JBC 280(34)23189-23199, 2008.
Otuska et al., J Thorac Oncol 3:1379-1383, 2008.
Vaday et al., Clin Canc Res 10:5630-5639, 2004.
Curran et al., Drugs 69(7)859-888, 2009.
Gelboin et al., Chem Res Tox 9:1023-1030, 1996.

*Primary Examiner* — Richard A Schnizer
(74) *Attorney, Agent, or Firm* — MDIP LLC

(57) ABSTRACT

The present invention is related to a nucleic acid molecule binding to SDF-1, whereby the nucleic acid molecule influences migration of cells.

14 Claims, 50 Drawing Sheets

Type A SDF-1 binding nucleic acids

| Name (SEQ.ID NO:) | nt. | Sequence: 5'-3' | Comp. |
|---|---|---|---|
| 192-A10-001 (5) | 38 | GCUGUGAAAGCAACAUGUCAA-UGAAAGGUAGCCGCAGC | |
| 192-G10 (6) | 38 | GCUGUGAAAGUAACAUGUCAA-UGAAAGGUAACCACAGC | < |
| 192-F10 (7) | 38 | GCUGUGAAAGUAACACGUCAA-UGAAAGGUAACCGCAGC | < |
| 192-B11 (8) | 38 | GCUGUGAAAGUAACACGUCAA-UGAAAGGUAACCACAGC | = |
| 192-C9 (9) | 38 | GCUGUAAAAGUAACAUGUCAA-UGAAAGGUAACUACAGC | < |
| 192-E10 (10) | 38 | GCUGUAAAAGUAACAAGUCAA-UGAAAGGUAACUACAGC | < |
| 192-C10 (11) | 38 | GCUGUGAAAGUAACAAGUCAA-UGAAAGGUAACCACAGC | = |
| 192-D11 (12) | 38 | GCAGUGAAAGUAACAUGUCAA-UGAAAGGUAACCACAGC | < |
| 192-G11 (13) | 38 | GCUGUGAAAGUAACAUGUCAA-UGAAAGGUAACCACUGC | < |
| 192-H11 (14) | 38 | GCUAUGAAAGUAACAUGUCAA-UGAAAGGUAACCAUAGC | < |
| 192-D10 (15) | 38 | GCUGCGAAAGCGACAUGUCAA-UGAAAGGUAGCCGCAGC | << |
| 192-E9 (16) | 38 | GCUGUGAAAGCAACAUGUCAA-UGAAAGGUAGCCACAGC | << |
| 192-H9 (17) | 38 | GCUGUGAAAGUAACAUGUCAA-UGAAAGGUAGCCGCAGC | << |
| 191-A6 (18) | 39 | AGCGUGAAAGUAACACGUAAAAUGAAAGGUAACCACGCU | < |
| | | | |
| Type A Formula-1 (19) | 26 | AAAGYRACAHGUMAAXUGAAAGGUARC | |
| Type A Formula-2 (20) | 26 | AAAGYRACAHGUMAA-UGAAAGGUARC | |
| Type A Formula-3 (21) | 27 | AAAGYRACAHGUMAAAUGAAAGGUARC | |
| Type A Formula-4 (22) | 26 | AAAGYAACAHGUCAA-UGAAAGGUARC | |
| Type A Formula-5-5' (23) | | RSHRYR | |
| Type A Formula-5-3' (24) | | YRYDSY | | terminal nucleotides that may hybridize to each other (bold)
nucleotides which may mainly comprise a SDF-binding motif nt.:= nucleotides    variable position^

Fig. 1

Comp.:= Clones were tested as aptamers in a competition binding assay vs. 192-A10-001
=:= equal binding affinity as 192-A10-001; <:= weaker binding affinity than 192-A1-001
<<:= much weaker binding affinity than 192-A10-001

Fig. 1 continued

Derivatives of Type A SDF Binding Nucleic Acid 192-A10-001

| Name (SEQ ID NO:) | nt. | Sequence: 5′-3′ | Comp. | PD: $K_D$ [nM] | Biacore: $K_D$ [nM] | TAX $IC_{50}$ [nM] |
|---|---|---|---|---|---|---|
| 192-A10-001 (5) | 38 | GCUGUGAAAGCAACAUGUCAAUGAAAGGUAGCCGCAGC | | 1.5 | 1.0 | 0.1 - 0.2 |
| | | | | | | |
| 192-A10-002 (25) | 36 | CUGUGAAAGCAACAUGUCAAUGAAAGGUAGCCGCAG | = | | | = |
| 192-A10-003 (26) | 34 | UGUGAAAGCAACAUGUCAAUGAAAGGUAGCCGCA | < | | | < |
| 192-A10-004 (27) | 32 | GUGAAAGCAACAUGUCAAUGAAAGGUAGCCGC | << | | | << |
| 192-A10-005 (28) | 30 | UGAAAGCAACAUGUCAAUGAAAGGUAGCCG | << | | | << |
| 192-A10-006 (29) | 28 | GAAAGCAACAUGUCAAUGAAAGGUAGCC | <<< | | | |
| 192-A10-007 (30) | 26 | AAAGCAACAUGUCAAUGAAAGGUAGC | i.a. | | | | terminal nucleotides at the 5′- and the 3′-end that may hybridize to each other (bold) nt.:= nucleotides nucleotides which may mainly comprise a SDF-binding motif i.a.:= inactive =:= equal binding affinity as 192-A10-001

</<</<<<:= weaker (<), much weaker (<<) or very much weaker (<<<) binding affinity than 192-A1-001

Comp.:= Clones were tested as aptamers in a competition binding assay vs. 193-A10-001

PD.:= Clones were tested as aptamers in a pull-down binding assay

TAX:= Clones were tested as Spiegelmers in a cell culture *in vitro* chemotaxis assay

Fig. 2A

Derivatives of Type A SDF Binding Nucleic Acid 192-A10-001

| Name (SEQ ID NO:) | nt. | Sequence: 5'-3'

Type B SDF-1 binding nucleic acids

| Name (SEQ. ID. NO:) | nt. | Sequence: 5'-3' | Comp. |
|---|---|---|---|
| 193-C2-001 (46) | 47 | AGCGUG GUGUGAUCUAGAUGAGUGGCUGAUCCUAGUCAGG UACGCU | + |
| 193-G2-001 (47) | 47 | AGCGUG GUGUGAUCUAGAUGAUUGGCUGAUCCUAGUCAGG UACGCU | + |
| 193-F2-001 (48) | 47 | AGCGUG GUGUGAUCUAGAUGAUGGCUGAUCCUAGUCAGG UGCGCU | + |
| 193-G1-002 (49) | 45 | GCGAG GUGUGAUCUAGAUGAGUGGCUGAUCCUAGUCAGG UGCGC | << |
| 193-D2-002 (50) | 45 | GCGUG GUGUGAUCUAGAUGAGUGGCUGAUCCUAGUCAGG UGCGC | < |
| 193-A1-002 (51) | 45 | GCAUG GUGUGAUCUAGAUGAUGGCUGAUCCUAGUCAGG UGCCC | <<< |
| 193-D3-002 (52) | 45 | GCGUG GUGUGAUCUAGAUGAUAUGGCUGAUCCUAGUCAGG GACGC | < |
| 193-B3-002 (53) | 45 | GCGUG GUGUGAUCUAGAUGAUGAGGCUGAUCCUAGUCAGG UACGC | << |
| 193-H3-002 (54) | 45 | GCGUG GUGUGAUCUAGAUGAUGAAAGCUGAUCCUAGUCAGG UACGC | < |
| 193-E3-002 (55) | 45 | GCGUG GUGUGAUCUAGAUGAUGGCUGUGAUCCUAGUCAGG UAUGC | << |
| 193-D1-002 (56) | 45 | GCGUG GUGUGAUCUAGAUGAUGGCUGAUCCUAGUUAGG UACGC | <<< |
| Type B Formula-1 (57) | 35 | GUGUGAUCUAGAUGAUGGCUGADWGGCUGWUCCUAGUYAGG | |
| Type B Formula-2 (58) | 35 | GUGUGAUCUAGAUGAUGAUDUGGCUGAUCCUAGUCAGG | |
| Type B Formula-3-5' (59) | | X₁GCRWG | |
| Type B Formula-3-3' (60) | | KRYSCX₄ | | terminal nucleotides that may hybridize to each other (bold)

nucleotides which may mainly comprise a SDF-binding motif variable position nt.:= nucleotides Comp.:= Clones C2, G2, and F2 were tested as aptamers in a competition binding assay vs. 192-A10-001; all other clones were tested as aptamers in a competition binding assay vs. 193-G2-012 that has the identical binding affinity to SDF-1 as 193-G2-001 (see Fig. 4B)

+:= better binding affinity than 192-A10-001

</</<</<<< weaker (<), much weaker (<<) or very much weaker (<<<) binding affinity than 193-G2-001/-012

$X_1$ = 'A' or absent      $X_4$ = 'U' or absent

Fig. 3

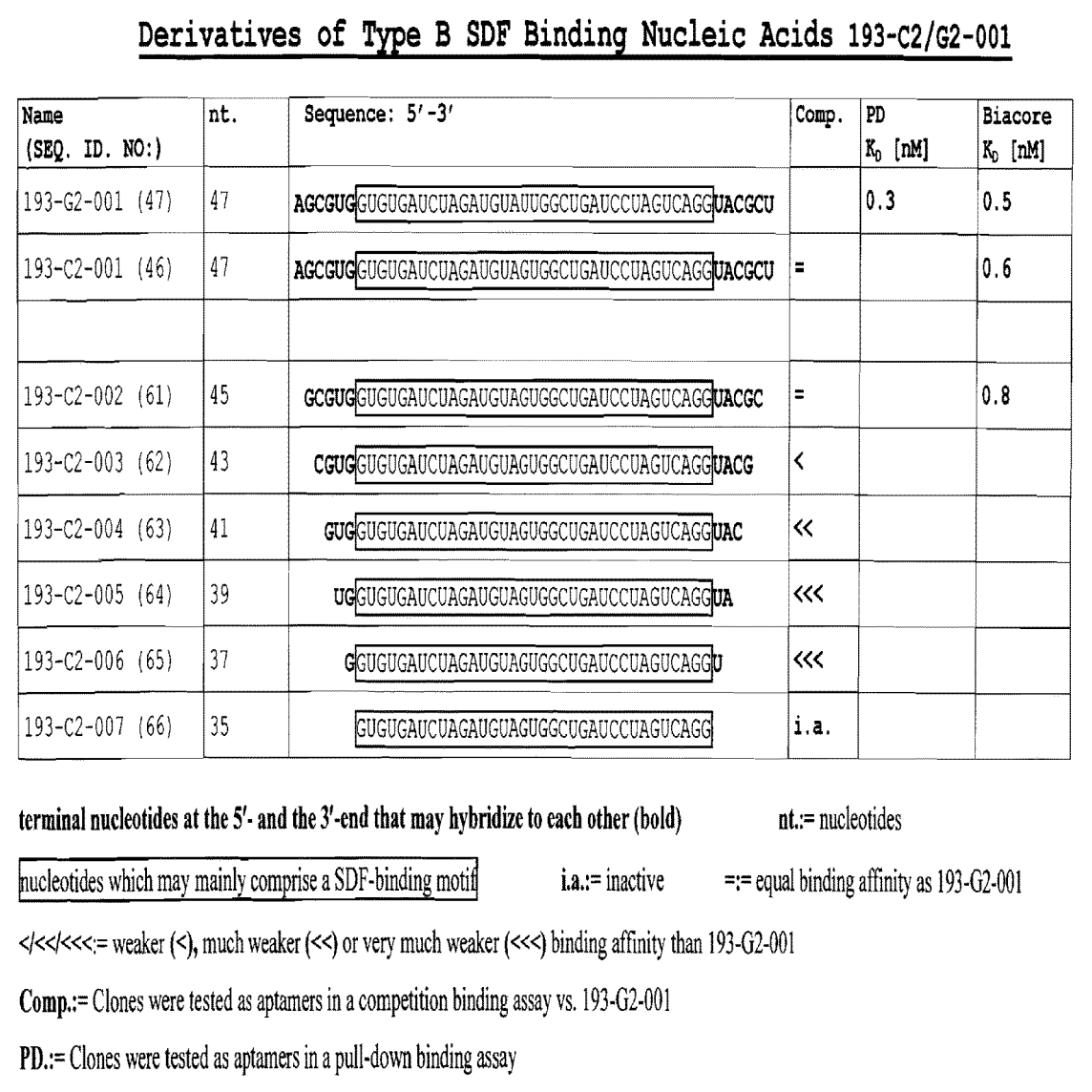

Derivatives of Type B SDF Binding Nucleic Acids 193-C2/G2-001

| Name (SEQ. ID. NO:) | nt. | Sequence: 5'-3' | Comp. | P

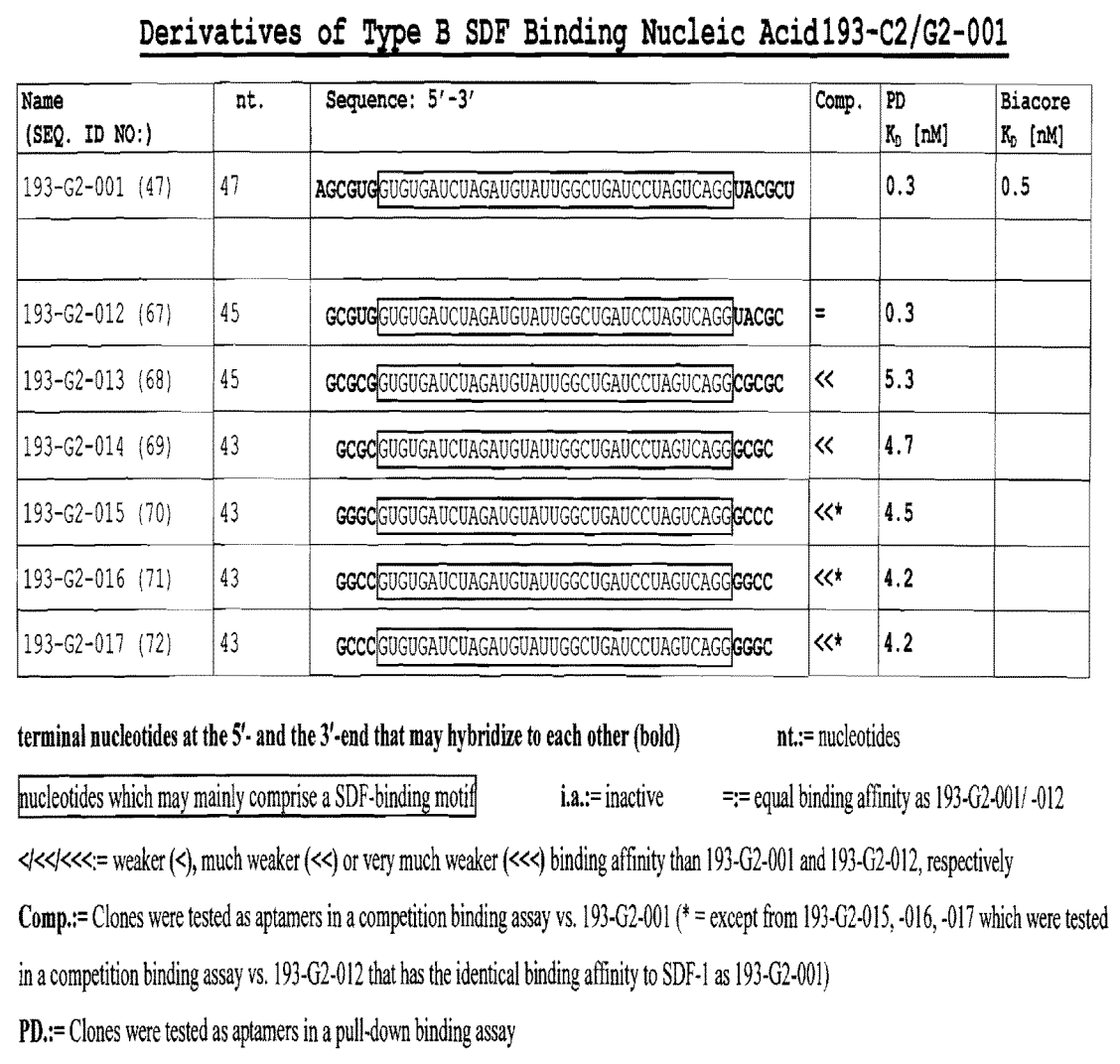

Derivatives of Type B SDF Binding Nucleic Acid 193-C2/G2-001

| Name (SEQ. ID NO:) | nt. | Sequence: 5'-

Type C SDF-1 binding nucleic acids

| Name (SEQ. ID. NO:) | nt. | Sequence: 5'-3' | Comp. |
|---|---|---|---|
| 197-B2 (79) | 39 | GUGCUGCGGG GGUUAGGGCUAGAAGUCGG CCUGCAGCAC | < |
| 191-D5-001 (80) | 39 | AGCGUGGCGA GGUUAGGGCUAGAAGUCGG UCGACACGCU | < |
| 197-H1 (81) | 39 | GUGUUGCGGA GGUUAGGGCUAGAAGUCGG UCAGCAGCAC | < |
| 190-D3 (242) | 48 | CGUGCGGCCUAAGA GGUUAGGGCUUAAAGUCGG UCUUUGGCCAACACG | << |
| 190-A3-001 (82) | 48 | CGUGCGCUUGAGAUAGG GGUUAGGGCUUAAAGUCGG CUGAUUCUCACG | < |
| 190-A3-001* (82) | 48 | CGUGCGCUUGAGAUAGG GGUUAGGGCUUAAAGUCGG CUGAUUCUCACG | < |
| 190-A2 (243) | 48 | CGUGAUUGGUGAGG GGUUAGGGCUUGAAGUCGG CCUUGUCCAGUCACG | << |
| 191-A5 (83) | 39 | AGCGUGAAGG GGUUAGGGCUCGAAGUCGG CUGACACGCU | << |
| 197-H3 (84) | 39 | GUGCUGCGGG GGUUAGGGCUCGAAGUCGG CCCGCAGCAC | < |
| 197-B1 (85) | 39 | GUGUUCCCGG GGUUAGGGCUUGAAGUCGG CCGGCAGCAC | << |
| 197-E3 (86) | 39 | GUGUUGCAGG GGUUAGGGCUUGAAGUCGG CCUGCAGCAC | < |
| 197-H2 (87) | 39 | GUGCUGCGGG GGUUAGGGCUCAAAGUCGG CCUGCAGCAC | << |
| 197-D1 (88) | 38 | GUGCUGCCGG GGUUAGGGCUAA-AGUCGG CCGACAGCAC | << |
| 197-D2 (89) | 39 | GUGCUGUGGG GGUCAGGGCUAGAAGUCGG CCUGCAGCAC | << |
| Type C Formula-1 (90) | 19 | GGUYAGGGCUHRXAGUCGG | |
| Type C Formula-2 (91) | 18 | GGUYAGGGCUHRAAGUCGG | |
| Type C Formula-3 (92) | 19 | GGUYAGGGCUHR-AGUCGG | |
| Type C Formula-4 (93) | 19 | GGUUAGGGCUHGAAGUCGG | | terminal nucleotides that may hybridize to each other (bold)   nucleotides which may mainly comprise a SDF-binding motif nt.:= nucleotides   variable position   Comp.:= Clones were tested as aptamers in a competition binding assay vs. 192-A10-001

=:= equal binding affinity as 192-A10;   <:= weaker binding affinity than 192-A10   <<:= much weaker binding affinity than 192-A10

*:= alternative hybridization

Fig. 5

Derivatives of Type C SDF Binding Nucleic Acid 190-A3-001

| Name (SEQ. ID. NO:) | nt. | Sequence: 5'-3' | Comp. |
|---|---|---|---|
| 190-A3-001 (82) | 48 | CGUGCGCUUGAGAUAGG[GGUUAGGGCUUAAAGUCGG]CUGAUUCUCACG | |
| 190-A3-001* (82) | 48 | CGUGCGCUUGAGAUAGG[GGUUAGGGCUUAAAGUCGG]CUGAUUCUCACG | |
| | | | |
| 190-A3-003 (94) | 38 | UGAGAUAGG[GGUUAGGGCUUAAAGUCGG]CUGAUUCUCA | = |
| 190-A3-004 (95) | 36 | GAGAUAGG[GGUUAGGGCUUAAAGUCGG]CUGAUUCUC | = |
| 190-A3-007 (96) | 29 | GG[GGUUAGGGCUUAAAGUCGG]CUGAUUCU | <<< | terminal nucleotides at the 5'- and the 3'-end that may hybridize to each other (bold) nt.:= nucleotides

[nucleotides which may mainly comprise a SDF-binding motif] i.a.:= inactive =:= equal binding affinity as 190-A3-001

</<</<<<:= weaker (<), much weaker (<<) or very much weaker (<<<) binding affinity than 190-A3-001

Comp.:= Clones were tested as aptamers in a competition binding assay vs. 190-A3-001

*:= alternative hybridization of the terminal nucleotides

Fig. 6

Derivatives of Type C SDF Binding Nucleic Acid 191-D5-001

| Name (SEQ ID NO:) | nt. | Sequence: 5'-3' | Comp. vs. 191-D5-001 | Comp. vs. 191-D5-007 | Biacore $K_D$ [nM] |
|---|---|---|---|---|---|
| 191-D5-001 (80) | 39 | AGCGUGGCGAGGUUAGGGCUAGAAGUCGGUCGACACGCU | | < | 0.73 |
| | | | | | |
| 191-D5-002 (97) | 37 | GCGUGGCGAGGUUAGGGCUAGAAGUCGGUCGACACGC | = | | |
| 191-D5-003 (98) | 35 | CGUGGCGAGGUUAGGGCUAGAAGUCGGUCGACACG | = | | |
| 191-D5-004 (99) | 33 | CG-GGCGAGGUUAGGGCUAGAAGUCGG**UCGAC-CG** | < | | |
| 191-D5-005 (100) | 33 | CG-GGCGAGGUUAGGGCUAGAAGUCGG**UCGCC-CG** | = | | |
| 191-D5-006 (101) | 31 | CG--GCGAGGUUAGGGCUAGAAGUCGG**UCGC—-CG** | = | | |
| 191-D5-007 (102) | 29 | CG—-G-GAGGUUAGGGCUAGAAGUCGG**UC-C--CG** | + | | 0.75 |
| 191-D5-010 (103) | 27 | G—-G-GAGGUUAGGGCUAGAAGUCGG**UC-C—-C** | | < | | terminal nucleotides at the 5'- and the 3'-end that may hybridize to each other (bold) nt.:= nucleotides nucleotides which may mainly comprise a SDF-binding motif (boxed) i.a.:= inactive =:= equal binding affinity as 191-D5-001/ -007

</<</<<<:= weaker (<), much weaker (<<) or very much weaker (<<<) binding affinity than 191-D5-001/ -007

Comp.:= Clones were tested as aptamers in a competition binding assay vs. 191-D5-001 or 191-D5-007 whereas both clones have the identical binding affinity to SDF-1 as 191-D5-001

Fig. 7A

Derivatives of Type C SDF Binding Nucleic Acid 191-D5-001

| Name (SEQ. ID. NO:) | nt. | Sequence: 5'-3' | Comp. vs. 191-D5-007 |
|---|---|---|---|
| 191-D5-007 (102) | 29 | CG---G-GA GGUUAGGGCUAGAAGUCGG UC-C--CG | |
| 191-D5-010 (103) | 27 | G---G-GA GGUUAGGGCUAGAAGUCGG UC-C--C | < |
| | | | |
| 191-D5-017 (104) | 27 | CCGC GGUUAGGGCUAGAAGUCGG GCGG | < |
| 191-D5-029 (105) | 27 | CCCG GGUUAGGGCUAGAAGUCGG CGGG | < |
| 191-D5-024 (106) | 27 | GGCG GGUUAGGGCUAGAAGUCGG CGCC | < |
| 191-D5-017-29a (107) | 29 | CCCGC GGUUAGGGCUAGAAGUCGG GCGGG | < |
| 191-D5-017-29b (108) | 29 | GCCGC GGUUAGGGCUAGAAGUCGG GCGGC | < |
| 191-D5-019-29a (109) | 29 | CCCCG GGUUAGGGCUAGAAGUCGG CGGGG | < |
| 191-D5-024-29a (110) | 29 | CGGCG GGUUAGGGCUAGAAGUCGG CGCCG | = |
| 191-D5-024-29b (111) | 29 | GGGCG GGUUAGGGCUAGAAGUCGG CGCCC | = | terminal nucleotides at the 5'- and the 3'-end that may hybridize to each other (bold)   nt.:= nucleotides nucleotides which may mainly comprise a SDF-binding motif   i.a.:= inactive   =:= equal binding affinity as 191-D5-007

</<</<<<:= weaker (<), much weaker (<<) or very much weaker (<<<) binding affinity than 191-D5-007

Comp.:= Clones were tested as aptamers in a competition binding assay vs. 191-D5-007

Fig. 7B

Derivatives of Type C SDF Binding Nucleic Acid 197-B2

| Name (SEQ. ID. NO:) | nt. | Sequence: 5'-3' | Comp.vs. 197-B2 | Comp. vs. 191-D5-007 | Biacore $K_D$ [nM] | TAX $IC_{50}$ [nM] |
|---|---|---|---|---|---|---|
| 197-B2 (79) | 39 | GUGCUGCGGGGGUUAGGGCUAGAAGUCGGCCUGCAGCAC | | = | 0.9 | 0.1-0.2 |
| 197-B2-001 (112) | 37 | UGCUGCGGGGGUUAGGGCUAGAAGUCGGCCUGCAGCA | = | | 1.1 | |
| 197-B2-002 (113) | 35 | GCUGCGGGGGUUAGGGCUAGAAGUCGGCCUGCAGC | = | | | |
| 197-B2-003 (114) | 33 | CUGCGGGGGUUAGGGCUAGAAGUCGGCCUGCAG | = | | | |
| 197-B2-004 (115) | 31 | UGCGGGGGUUAGGGCUAGAAGUCGGCCUGCA | = | | | |
| 197-B2-005 (116) | 29 | GCGGGGGUUAGGGCUAGAAGUCGGCCUGC | = | | | |
| 197-B2-006 (117) | 29 | GCCGGGGUUAGGGCUAGAAGUCGGCCGGC | = | = | | 0.1-0.2 |
| 197-B2-006-31a (118) | 31 | GGCCGGGGUUAGGGCUAGAAGUCGGCCGGCC | | = | | |
| 197-B2-006-31b (119)S | 31 | CGCCGGGGUUAGGGCUAGAAGUCGGCCGGCG | | = | | | terminal nucleotides at the 5'- and the 3'-end that may hybridize to each other (bold) nt.:= nucleotides nucleotides which may mainly comprise a SDF-binding motif (boxed) i.a.:= inactive =:= equal binding affinity as 197-B2 or 191-D5-007

</<</<<<:= weaker (<), much weaker (<<) or very much weaker (<<<) binding affinity than as 197-B2 or 191-D5-007

Comp.:= Clones were tested as aptamers in a competition binding assay vs. 197-B2 or 191-D5-007 whereas both clones have the identical binding affinity to SDF-1

TAX:= Clones were tested as Spiegelmers in a cell culture *in vitro* chemotaxis assay

Fig. 8

Further SDF-1 Binding Nucleic Acids

| Name (SEQ ID NO:) | nt. | Sequence: 5'-3' | PD K_D [nM] |
|---|---|---|---|
| 194-A2-001 (142) | 48 | CGUGGUCCGUUGUGUCAGGUCUAUUCGCCCCGGUGCAGGGCAUCCGCG | 12.0 |
| 196-B12-003 (143) | 49 | GCAGUGUGACGCGGACGUGAUAGGACAGAGCUGAUCCCGCUCAGGUGAG | 7.6 |
| 196-B12-004 (144) | 49 | CAACAGCAGUGUGACGCGGACGUGAUAGGACAGAGCUGAUCCCGCUCAG | 5.3 | terminal nucleotides at the 5'- and the 3'-end that may hybridize to each other (bold)      nt.:= nucleotides PD.:= Clones were tested as aptamers in a pull-down binding assay

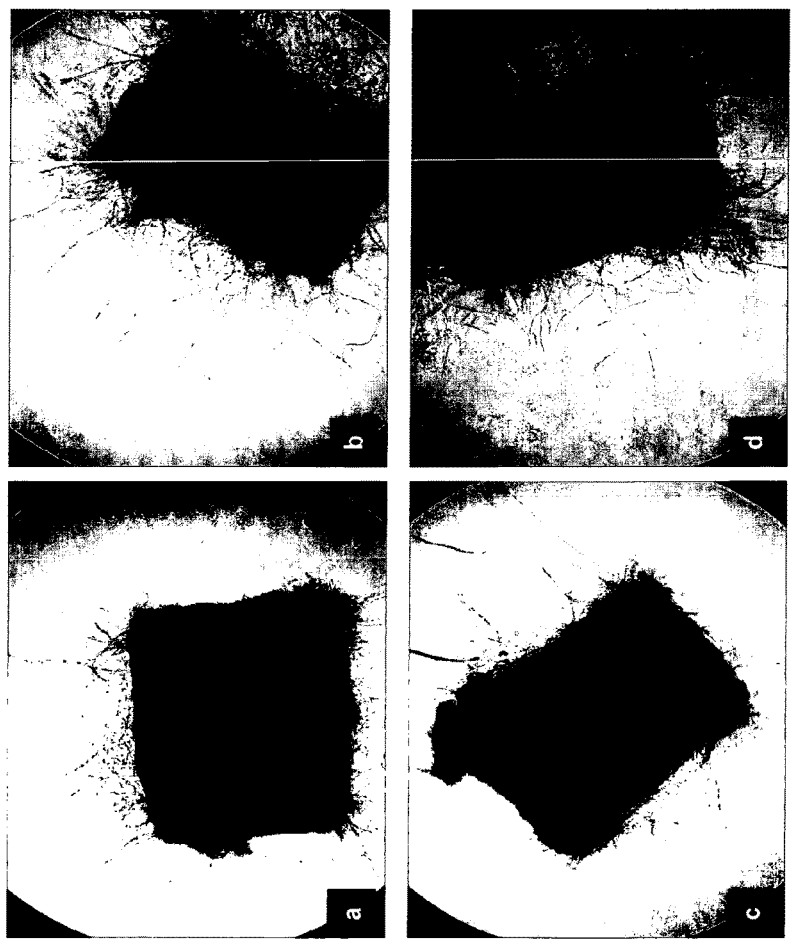
Fig. 31: SDF-1 induced sprouting in an aortic ring sprouting assay. Rings from rat aorta were embedded in collagen matrix and incubated for 6 days with SDF-1 with or without Spiegelmers. a: control; b: 10 nM SDF-1; c: 10 nM SDF-1 + 1 µM 193-G2-012-5'-PEG; d: 10 nM SDF-1 + 1 µM PEGylated Control Spiegelmer

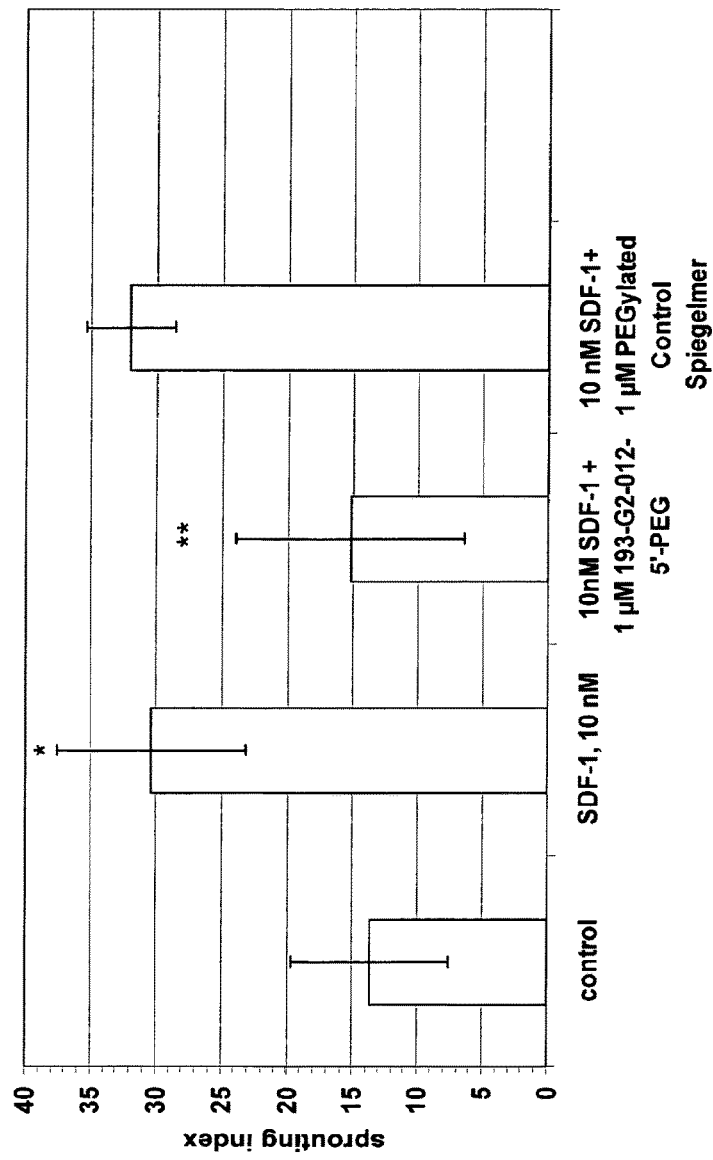

Fig. 32: SDF-1 induced sprouting and the blockage thereof by Spiegelmers in an aortic ring sprouting assay. Rings from rat aorta were embedded in collagen matrix and incubated for 6 days with SDF-1 with or without Spiegelmers. Sprouting indices are shown as mean +/- SD for 5 rings per condition. *: the value for SDF-1 is significantly different from control (Mann-Whitney-test; p= 0.009); **: the value for SDF-1 + 193-G2-012-5'-PEG is significantly different from that for SDF-1 (Mann-Whitney-test; p= 0.028).

The mean retinopathy scores is depicted as a star.

Statistics: Wilcoxon-Signed-Rank Test / p-values

|  | Fluorescein (n=24) | Isolectin (n=15) |
|---|---|---|
| Clusters (n) | 0.210 | 0.057 |
| Cluster-area absolute | 0.210 | 0.501 |
| Cluster-area relative | 0.501 | 0.365 |
| Tufts (n) | 0.008 | 0.0215 |
| Avascular zone absolute | 0.3531 | 0.2524 |
| Avascular zone relative | 0.398 | 0.359 |
| Retinopathy Score | 0.009 | |

Fig. 40

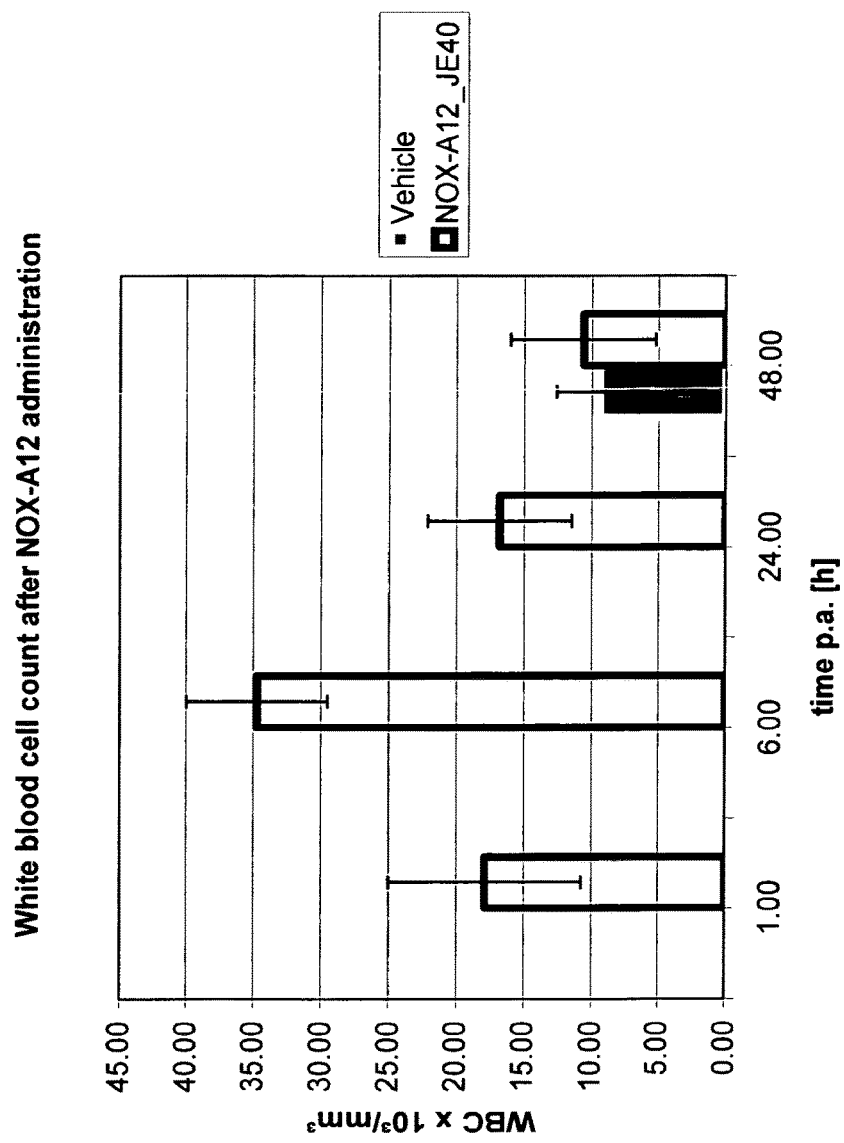

Indications for allogeneic HSCT in Europe 1990-2000

|  | No. of patients | | | |
|---|---|---|---|---|
|  | Total 1990-2000 | % | Total 2000 | % |
| Leukemias | 33 509 | 75.9 | 4653 | 72.7 |
| Acute myeloid leukemia | 10 990 | 24.9 | 1627 | 25.4 |
| Acute lymphocytic leukemia | 8 871 | 20.1 | 1135 | 17.7 |
| Chronic myeloid leukemia | 10 559 | 23.9 | 1315 | 20.5 |
| Myelodysplastic syndromes | 2 680 | 6.1 | 454 | 7.1 |
| Chronic lymphocytic leukemia | 409 | 0.9 | 122 | 1.9 |
| Lymphoproliferative disorders | 3 930 | 8.9 | 820 | 12.8 |
| Multiple myeloma | 1 470 | 3.3 | 295 | 4.6 |
| Hodgkin disease | 320 | 0.7 | 68 | 1.1 |
| Non-Hodgkin lymphoma | 2 140 | 4.8 | 457 | 7.1 |
| Solid tumors | 272 | 0.6 | 104 | 1.6 |
| Neuroblastoma | 30 | 0.1 | 1 | 0.0 |
| Glioma | 2 | 0.0 | 1 | 0.0 |
| Soft tissue sarcoma | 13 | 0.0 | 5 | 0.1 |
| Germinal tumors | 10 | 0.0 | 3 | 0.0 |
| Breast cancer | 57 | 0.1 | 16 | 0.2 |
| Ewing sarcoma | 28 | 0.1 | 4 | 0.1 |
| Lung cancer | 1 | 0.0 | 0 | 0.0 |
| Ovarian cancer | 11 | 0.0 | 7 | 0.1 |
| Other solid tumors | 120 | 0.3 | 67 | 1.0 |
| Nonmalignant disorders | 5 695 | 12.9 | 700 | 10.9 |
| Aplastic anemia + Fanconi | 2 483 | 5.6 | 287 | 4.5 |
| Thalassemia | 1 349 | 3.1 | 147 | 2.3 |
| Combined immune deficiencies | 724 | 1.6 | 103 | 1.6 |
| Inborn errors | 1 112 | 2.5 | 153 | 2.4 |
| Autoimmune diseases | 27 | 0.1 | 10 | 0.2 |
| Others | 759 | 1.7 | 127 | 2.0 |
| Total | 44 165 |  | 6404 |  |

Fig. 42

. Indications for autologous HSCT in Europe 1990-2000

|  | No. of patients | | | |
|---|---|---|---|---|
|  | Total 1990-2000 | % | Total 2000 | % |
| Leukemias | 15 052 | 17.0 | 1 764 | 13.9 |
| Acute myeloid leukemia | 8 129 | 9.2 | 1 047 | 8.2 |
| Acute lymphocytic leukemia | 3 765 | 4.2 | 302 | 2.4 |
| Chronic myeloid leukemia | 1 967 | 2.2 | 148 | 1.2 |
| Myelodysplastic syndromes | 297 | 0.3 | 50 | 0.4 |
| Chronic lymphocytic leukemia | 894 | 1.0 | 217 | 1.7 |
| Lymphoproliferative disorders | 48 917 | 55.1 | 8 498 | 66.7 |
| Multiple myeloma | 16 206 | 18.3 | 3 388 | 26.6 |
| Hodgkin disease | 9 078 | 10.2 | 1 226 | 9.6 |
| Non-Hodgkin lymphoma | 23 633 | 26.6 | 3 884 | 30.5 |
| Solid tumors | 24 016 | 27.0 | 2 286 | 18.0 |
| Neuroblastoma | 1 912 | 2.2 | 262 | 2.1 |
| Glioma | 544 | 0.6 | 73 | 0.6 |
| Soft tissue sarcoma | 1 013 | 1.1 | 144 | 1.1 |
| Germinal tumors | 2 658 | 3.0 | 304 | 2.4 |
| Breast cancer | 12 598 | 14.2 | 781 | 6.1 |
| Ewing sarcoma | 1 401 | 1.6 | 244 | 1.9 |
| Lung cancer | 318 | 0.4 | 62 | 0.5 |
| Ovarian cancer | 628 | 0.7 | 100 | 0.8 |
| Other solid tumors | 2 944 | 3.3 | 316 | 2.5 |
| Nonmalignant disorders | 321 | 0.4 | 100 | 0.8 |
| Aplastic anemia + Fanconi | 7 | 0.0 | 1 | 0.0 |
| Thalassemia | 0 | 0.0 | 0 | 0.0 |
| Combined immune deficiencies | 10 | 0.0 | 2 | 0.0 |
| Inborn errors | 4 | 0.0 | 0 | 0.0 |
| Autoimmune diseases | 300 | 0.3 | 97 | 0.8 |
| Others | 492 | 0.6 | 84 | 0.7 |
| Total | 88 798 |  | 12 732 |  |

Fig. 43

```
                        SEQUENCE LISTING

<160> NUMBER OF SEQ ID NOS: 251

<210> SEQ ID NO 1
<211> LENGTH: 68
<212> TYPE: PRT
<213> ORGANISM: Homo sapiens

<400> SEQUENCE: 1

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 2
<211> LENGTH: 72
<212> TYPE: PRT
<213> ORGANISM: Homo sapiens
```

-continued

```
<400> SEQUENCE: 2

Lys Pro Val Ser Leu Ser Tyr Arg Cys Pro Cys Arg Phe Phe Glu Ser
1               5                  10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys Arg Phe Lys Met
65                  70

<210> SEQ ID NO 3
<211> LENGTH: 68
<212> TYPE: PRT
<213> ORGANISM: Mus musculus

<400> SEQUENCE: 3

Lys Pro Val Ser Leu Ser Tyr Arg Cys Pro Cys Arg Phe Phe Glu Ser
1               5                  10                  15

His Ile Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 4
<211> LENGTH: 71
<212> TYPE: PRT
<213> ORGANISM: Homo sapiens
<220> FEATURE:
<221> NAME/KEY: misc_feature
<222> LOCATION: (1)..(71)
<223> OTHER INFORMATION: D-peptide
<220> FEATURE:
<221> NAME/KEY: misc_feature
<222> LOCATION: (71)..(71)
<223> OTHER INFORMATION: biotinylated

<400> SEQUENCE: 4

Lys Pro Val Ser Leu Ser Tyr Arg Cys Pro Cys Arg Phe Phe Glu Ser
1               5                  10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys Arg Phe Lys
65                  70

<210> SEQ ID NO 5
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: misc_feature
<222> LOCATION: (1)..(38)
<223> OTHER INFORMATION: L-RNA

<400> SEQUENCE: 5
gcugugaaag caacauguca augaaaggua gccgcagc                                  38

<210> SEQ ID NO 6
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(38)
<223> OTHER INFORMATION: L-RNA

<400> SEQUENCE: 6
gcugugaaag uaacauguca augaaaggua accacagc                                  38

<210> SEQ ID NO 7
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(38)
<223> OTHER INFORMATION: L-RNA

<400> SEQUENCE: 7
gcugugaaag uaacacguca augaaaggua accgcagc                                  38

<210> SEQ ID NO 8
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(38)
<223> OTHER INFORMATION: L-RNA

<400> SEQUENCE: 8
gcugugaaag uaacacguca augaaaggua accacagc                                  38

<210> SEQ ID NO 9
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(38)
<223> OTHER INFORMATION: L-RNA

<400> SEQUENCE: 9
gcuguaaaag uaacauguca augaaaggua acuacagc                                  38

<210> SEQ ID NO 10
```

```
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(38)
<223> OTHER INFORMATION: L-RNA

<400> SEQUENCE: 10
gcuguaaaag uaacaaguca augaaaggua acuacagc                              38

<210> SEQ ID NO 11
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(38)
<223> OTHER INFORMATION: L-RNA

<400> SEQUENCE: 11
gcugugaaag uaacaaguca augaaaggua accacagc                              38

<210> SEQ ID NO 12
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(38)
<223> OTHER INFORMATION: L-RNA

<400> SEQUENCE: 12
gcagugaaag uaacauguca augaaaggua accacagc                              38

<210> SEQ ID NO 13
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(38)
<223> OTHER INFORMATION: L-RNA

<400> SEQUENCE: 13
gcugugaaag uaacauguca augaaaggua accacugc                              38

<210> SEQ ID NO 14
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(38)
<223> OTHER INFORMATION: L-RNA
```

<400> SEQUENCE: 14
gcuaugaaag uaacauguca augaaaggua accauagc                                38

<210> SEQ ID NO 15
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(38)
<223> OTHER INFORMATION: L-RNA

<400> SEQUENCE: 15
gcugcgaaag cgacauguca augaaaggua gccgcagc                                38

<210> SEQ ID NO 16
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(38)
<223> OTHER INFORMATION: L-RNA

<400> SEQUENCE: 16
gcugugaaag caacauguca augaaaggua gccacagc                                38

<210> SEQ ID NO 17
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(38)
<223> OTHER INFORMATION: L-RNA

<400> SEQUENCE: 17
gcugugaaag uaacauguca augaaaggua gccgcagc                                38

<210> SEQ ID NO 18
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(39)
<223> OTHER INFORMATION: L-RNA

<400> SEQUENCE: 18
agcgugaaag uaacacguaa aaugaaaggu aaccacgcu                               39

<210> SEQ ID NO 19
<211> LENGTH: 27
<212> TYPE: RNA
<213> ORGANISM: Artificial Sequence
<220> FEATURE:
<223> OTHER INFORMATION: Description of Artificial Sequence: Synthetic

```
         oligonucleotide
<220> FEATURE:
<221> NAME/KEY: misc_feature
<222> LOCATION: (1)..(27)
<223> OTHER INFORMATION: L-RNA
<220> FEATURE:
<221> NAME/KEY: modified_base
<222> LOCATION: (16)..(16)
<223> OTHER INFORMATION: May or may not be present

<400> SEQUENCE: 19
aaagyracah gumaaaugaa agguarc                                          27

<210> SEQ ID NO 20
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(26)
<223> OTHER INFORMATION: L-RNA

<400> SEQUENCE: 20
aaagyracah gumaaugaaa gguarc                                           26

<210> SEQ ID NO 21
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(27)
<223> OTHER INFORMATION: L-RNA

<400> SEQUENCE: 21
aaagyracah gumaaaugaa agguarc                                          27

<210> SEQ ID NO 22
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(26)
<223> OTHER INFORMATION: L-RNA

<400> SEQUENCE: 22
aaagyaacah gucaaugaaa gguarc                                           26

<210> SEQ ID NO 23
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: L-RNA

<400> SEQUENCE: 23
```

-continued rshryr                                                                                          6

<210> SEQ ID NO 24
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: L-RNA

<400> SEQUENCE: 24 yrydsy                                                                                          6

<210> SEQ ID NO 25
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(36)
<223> OTHER INFORMATION: L-RNA

<400> SEQUENCE: 25
cugugaaagc aacaugucaa ugaaagguag ccgcag                                                         36

<210> SEQ ID NO 26
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(34)
<223> OTHER INFORMATION: L-RNA

<400> SEQUENCE: 26
ugugaaagca acaugucaau gaaagguagc cgca                                                           34

<210> SEQ ID NO 27
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(32)
<223> OTHER INFORMATION: L-RNA

<400> SEQUENCE: 27
gugaaagcaa caugucaaug aaagguagcc gc                                                             32

<210> SEQ ID NO 28
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: misc_feature
<222> LOCATION: (1)..(30)
<223> OTHER INFORMATION: L-RNA

<400> SEQUENCE: 28
ugaaagcaac augucaauga aagguagccg                                    30

<210> SEQ ID NO 29
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(28)
<223> OTHER INFORMATION: L-RNA

<400> SEQUENCE: 29
gaaagcaaca ugucaaugaa agguagcc                                      28

<210> SEQ ID NO 30
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(26)
<223> OTHER INFORMATION: L-RNA

<400> SEQUENCE: 30
aaagcaacau gucaaugaaa gguagc                                        26

<210> SEQ ID NO 31
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(36)
<223> OTHER INFORMATION: L-RNA

<400> SEQUENCE: 31
gcgugaaagc aacaugucaa ugaaagguag ccgcgc                             36

<210> SEQ ID NO 32
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(36)
<223> OTHER INFORMATION: L-RNA

<400> SEQUENCE: 32
gcgcgaaagc aacaugucaa ugaaaggguag ccgcgc                            36

<210> SEQ ID NO 33
```

```
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(34)
<223> OTHER INFORMATION: L-RNA

<400> SEQUENCE: 33
gcggaaagca acaugucaau gaaagguagc ccgc                              34

<210> SEQ ID NO 34
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(34)
<223> OTHER INFORMATION: L-RNA

<400> SEQUENCE: 34
cgugaaagca acaugucaau gaaagguagc cgcg                              34

<210> SEQ ID NO 35
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(34)
<223> OTHER INFORMATION: L-RNA

<400> SEQUENCE: 35
gcgcaaagca acaugucaau gaaagguagc gugc                              34

<210> SEQ ID NO 36
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(34)
<223> OTHER INFORMATION: L-RNA

<400> SEQUENCE: 36
gugcaaagca acaugucaau gaaagguagc gcgc                              34

<210> SEQ ID NO 37
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(34)
<223> OTHER INFORMATION: L-RNA
```

```
<400> SEQUENCE: 37
cgcgaaagca acaugucaau gaaagguagc cgug                            34

<210> SEQ ID NO 38
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(34)
<223> OTHER INFORMATION: L-RNA

<400> SEQUENCE: 38
gggcaaagca acaugucaau gaaagguagc gccc                            34

<210> SEQ ID NO 39
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(34)
<223> OTHER INFORMATION: L-RNA

<400> SEQUENCE: 39
ggccaaagca acaugucaau gaaagguagc ggcc                            34

<210> SEQ ID NO 40
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(34)
<223> OTHER INFORMATION: L-RNA

<400> SEQUENCE: 40
gcccaaagca acaugucaau gaaagguagc gggc                            34

<210> SEQ ID NO 41
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(34)
<223> OTHER INFORMATION: L-RNA

<400> SEQUENCE: 41
ccccaaagca acaugucaau gaaagguagc gggg                            34

<210> SEQ ID NO 42
<211> LENGTH: 5
<212> TYPE: RNA
<213> ORGANISM: Artificial Sequence
<220> FEATURE:
<223> OTHER INFORMATION: Description of Artificial Sequence: Synthetic
```

```
                    oligonucleotide
<220> FEATURE:
<221> NAME/KEY: misc_feature
<222> LOCATION: (1)..(5)
<223> OTHER INFORMATION: L-RNA
<220> FEATURE:
<221> NAME/KEY: modified_base
<222> LOCATION: (1)..(1)
<223> OTHER INFORMATION: May or may not be present

<400> SEQUENCE: 42 sbbbs                                                                    5

<210> SEQ ID NO 43
<211> LENGTH: 5
<212> TYPE: RNA
<213> ORGANISM: Artificial Sequence
<220> FEATURE:
<223> OTHER INFORMATION: Description of Artificial Sequence: Synthetic
                    oligonucleotide
<220> FEATURE:
<221> NAME/KEY: misc_feature
<222> LOCATION: (1)..(5)
<223> OTHER INFORMATION: L-RNA
<220> FEATURE:
<221> NAME/KEY: modified_base
<222> LOCATION: (5)..(5)
<223> OTHER INFORMATION: May or may not be present

<400> SEQUENCE: 43 sbbvs                                                                    5

<210> SEQ ID NO 44
<211> LENGTH: 6
<212> TYPE: RNA
<213> ORGANISM: Artificial Sequence
<220> FEATURE:
<223> OTHER INFORMATION: Description of Artificial Sequence: Synthetic
                    oligonucleotide
<220> FEATURE:
<221> NAME/KEY: misc_feature
<222> LOCATION: (1)..(6)
<223> OTHER INFORMATION: L-RNA
<220> FEATURE:
<221> NAME/KEY: modified_base
<222> LOCATION: (1)..(1)
<223> OTHER INFORMATION: May or may not be present
<220> FEATURE:
<221> NAME/KEY: modified_base
<222> LOCATION: (2)..(2)
<223> OTHER INFORMATION: May or may not be present
<220> FEATURE:
<221> NAME/KEY: modified_base
<222> LOCATION: (3)..(3)
<223> OTHER INFORMATION: a, g, c or u
<220> FEATURE:
<221> NAME/KEY: modified_base
<222> LOCATION: (4)..(4)
<223> OTHER INFORMATION: a, g, c or u

<400> SEQUENCE: 44 rsnnbv                                                                   6

<210> SEQ ID NO 45
<211> LENGTH: 6
<212> TYPE: RNA
<213> ORGANISM: Artificial Sequence
<220> FEATURE:
<223> OTHER INFORMATION: Description of Artificial Sequence: Synthetic
                    oligonucleotide
<220> FEATURE:
<221> NAME/KEY: misc_feature
<222> LOCATION: (1)..(6)
```

```
<223> OTHER INFORMATION: L-RNA
<220> FEATURE:
<221> NAME/KEY: modified_base
<222> LOCATION: (2)..(2)
<223> OTHER INFORMATION: a, g, c or u
<220> FEATURE:
<221> NAME/KEY: modified_base
<222> LOCATION: (4)..(4)
<223> OTHER INFORMATION: a, g, c or u
<220> FEATURE:
<221> NAME/KEY: modified_base
<222> LOCATION: (5)..(5)
<223> OTHER INFORMATION: May or may not be present
<220> FEATURE:
<221> NAME/KEY: modified_base
<222> LOCATION: (6)..(6)
<223> OTHER INFORMATION: May or may not be present

<400> SEQUENCE: 45 bnbnry                                                                    6

<210> SEQ ID NO 46
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(47)
<223> OTHER INFORMATION: L-RNA

<400> SEQUENCE: 46
agcguggugu gaucuagaug uaguggcuga uccuagucag guacgcu                      47

<210> SEQ ID NO 47
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(47)
<223> OTHER INFORMATION: L-RNA

<400> SEQUENCE: 47
agcguggugu gaucuagaug uauuggcuga uccuagucag guacgcu                      47

<210> SEQ ID NO 48
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(47)
<223> OTHER INFORMATION: L-RNA

<400> SEQUENCE: 48
agcguggugu gaucuagaug uaauggcuga uccuagucag gugcgcu                      47

<210> SEQ ID NO 49
<211> LENGTH: 45
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: misc_feature
<222> LOCATION: (1)..(45)
<223> OTHER INFORMATION: L-RNA

<400> SEQUENCE: 49
gcgaggugug aucuagaugu aguggcugau ccuagucagg ugcgc              45

<210> SEQ ID NO 50
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(45)
<223> OTHER INFORMATION: L-RNA

<400> SEQUENCE: 50
gcguggugug aucuagaugu aguggcugau ccuagucagg ugcgc              45

<210> SEQ ID NO 51
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(45)
<223> OTHER INFORMATION: L-RNA

<400> SEQUENCE: 51
gcauggugug aucuagaugu aguggcugau ccuagucagg ugccc              45

<210> SEQ ID NO 52
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(45)
<223> OTHER INFORMATION: L-RNA

<400> SEQUENCE: 52
gcguggugug aucuagaugu aauggcugau ccuagucagg gacgc              45

<210> SEQ ID NO 53
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(45)
<223> OTHER INFORMATION: L-RNA

<400> SEQUENCE: 53
gcguggugug aucuagaugu agaggcugau ccuagucagg uacgc              45
```

```
<210> SEQ ID NO 54
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(45)
<223> OTHER INFORMATION: L-RNA

<400> SEQUENCE: 54
gcguggugug aucuagaugu aaaggcugau ccuagucagg uacgc              45

<210> SEQ ID NO 55
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(45)
<223> OTHER INFORMATION: L-RNA

<400> SEQUENCE: 55
gcguggugug aucuagaugu aguggcuguu ccuagucagg uaugc              45

<210> SEQ ID NO 56
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(45)
<223> OTHER INFORMATION: L-RNA

<400> SEQUENCE: 56
gcguggugug aucuagaugu aguggcugau ccuaguuagg uacgc              45

<210> SEQ ID NO 57
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(35)
<223> OTHER INFORMATION: L-RNA

<400> SEQUENCE: 57
gugugaucua gauguadwgg cugwuccuag uyagg                         35

<210> SEQ ID NO 58
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(35)
```

<223> OTHER INFORMATION: L-RNA

<400> SEQUENCE: 58
gugugaucua gauguadugg cugauccuag ucagg                                    35

<210> SEQ ID NO 59
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: L-RNA
<220> FEATURE:
<221> NAME/KEY: modified_base
<222> LOCATION: (1)..(1)
<223> OTHER INFORMATION: May or may not be present

<400> SEQUENCE: 59 agcrwg                                                                     6

<210> SEQ ID NO 60
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: L-RNA
<220> FEATURE:
<221> NAME/KEY: modified_base
<222> LOCATION: (6)..(6)
<223> OTHER INFORMATION: May or may not be present

<400> SEQUENCE: 60 kryscu                                                                     6

<210> SEQ ID NO 61
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(45)
<223> OTHER INFORMATION: L-RNA

<400> SEQUENCE: 61
gcguggugug aucuagaugu aguggcugau ccuagucagg uacgc                         45

<210> SEQ ID NO 62
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(43)
<223> OTHER INFORMATION: L-RNA

<400> SEQUENCE: 62
cgugguguga ucuagaugua guggcugauc cuagucaggu acg         43

<210> SEQ ID NO 63
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(41)
<223> OTHER INFORMATION: L-RNA

<400> SEQUENCE: 63
guggugugau cuagauguag uggcugaucc uagucaggua c          41

<210> SEQ ID NO 64
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(39)
<223> OTHER INFORMATION: L-RNA

<400> SEQUENCE: 64
uggugugauc uagauguagu ggcugauccu agucaggua              39

<210> SEQ ID NO 65
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(37)
<223> OTHER INFORMATION: L-RNA

<400> SEQUENCE: 65
ggugugaucu agauguagug gcugauccua gucaggu                37

<210> SEQ ID NO 66
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(35)
<223> OTHER INFORMATION: L-RNA

<400> SEQUENCE: 66
gugugaucua gauguagugg cugauccuag ucagg                  35

<210> SEQ ID NO 67
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: misc_feature
<222> LOCATION: (1)..(45)
<223> OTHER INFORMATION: L-RNA

<400> SEQUENCE: 67
gcguggugug aucuagaugu auuggcugau ccuagucagg uacgc          45

<210> SEQ ID NO 68
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(45)
<223> OTHER INFORMATION: L-RNA

<400> SEQUENCE: 68
gcgcggugug aucuagaugu auuggcugau ccuagucagg cgcgc          45

<210> SEQ ID NO 69
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(43)
<223> OTHER INFORMATION: L-RNA

<400> SEQUENCE: 69
gcgcguguga ucuagaugua uuggcugauc cuagucaggg cgc            43

<210> SEQ ID NO 70
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(43)
<223> OTHER INFORMATION: L-RNA

<400> SEQUENCE: 70
gggcguguga ucuagaugua uuggcugauc cuagucaggg ccc            43

<210> SEQ ID NO 71
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(43)
<223> OTHER INFORMATION: L-RNA

<400> SEQUENCE: 71
ggccguguga ucuagaugua uuggcugauc cuagucaggg gcc            43

<210> SEQ ID NO 72
```

```
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(43)
<223> OTHER INFORMATION: L-RNA

<400> SEQUENCE: 72
gcccguguga ucuagaugua uuggcugauc cuagucaggg ggc                43

<210> SEQ ID NO 73
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(5)
<223> OTHER INFORMATION: L-RNA
<220> FEATURE:
<221> NAME/KEY: modified_base
<222> LOCATION: (1)..(1)
<223> OTHER INFORMATION: May or may not be present

<400> SEQUENCE: 73 gssbs                                                            5

<210> SEQ ID NO 74
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(5)
<223> OTHER INFORMATION: L-RNA
<220> FEATURE:
<221> NAME/KEY: modified_base
<222> LOCATION: (5)..(5)
<223> OTHER INFORMATION: May or may not be present

<400> SEQUENCE: 74 bvssc                                                            5

<210> SEQ ID NO 75
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: L-RNA
<220> FEATURE:
<221> NAME/KEY: modified_base
<222> LOCATION: (1)..(1)
<223> OTHER INFORMATION: May or may not be present

<400> SEQUENCE: 75 agcgug                                                           6
```

```
<210> SEQ ID NO 76
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: L-RNA
<220> FEATURE:
<221> NAME/KEY: modified_base
<222> LOCATION: (6)..(6)
<223> OTHER INFORMATION: May or may not be present

<400> SEQUENCE: 76 uacgcu                                                                    6

<210> SEQ ID NO 77
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: L-RNA
<220> FEATURE:
<221> NAME/KEY: modified_base
<222> LOCATION: (1)..(1)
<223> OTHER INFORMATION: May or may not be present
<220> FEATURE:
<221> NAME/KEY: modified_base
<222> LOCATION: (2)..(2)
<223> OTHER INFORMATION: May or may not be present
<220> FEATURE:
<221> NAME/KEY: modified_base
<222> LOCATION: (5)..(5)
<223> OTHER INFORMATION: a, g, c or u

<400> SEQUENCE: 77 agsvns                                                                    6

<210> SEQ ID NO 78
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: L-RNA
<220> FEATURE:
<221> NAME/KEY: modified_base
<222> LOCATION: (5)..(5)
<223> OTHER INFORMATION: May or may not be present
<220> FEATURE:
<221> NAME/KEY: modified_base
<222> LOCATION: (6)..(6)
<223> OTHER INFORMATION: May or may not be present

<400> SEQUENCE: 78 bvbscu                                                                    6

<210> SEQ ID NO 79
<211> LENGTH: 39
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(39)
<223> OTHER INFORMATION: L-RNA

<400> SEQUENCE: 79
gugcugcggg gguuagggcu agaagucggc cugcagcac                           39

<210> SEQ ID NO 80
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(39)
<223> OTHER INFORMATION: L-RNA

<400> SEQUENCE: 80
agcguggcga gguuagggcu agaagucggu cgacacgcu                           39

<210> SEQ ID NO 81
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(39)
<223> OTHER INFORMATION: L-RNA

<400> SEQUENCE: 81
guguugcgga gguuagggcu agaagucggu cagcagcac                           39

<210> SEQ ID NO 82
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(48)
<223> OTHER INFORMATION: L-RNA

<400> SEQUENCE: 82
cgugcgcuug agauaggggu uagggcuuaa agucggcuga uucucacg                 48

<210> SEQ ID NO 83
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(39)
<223> OTHER INFORMATION: L-RNA

<400> SEQUENCE: 83
agcgugaagg gguuagggcu cgaagucggc ugacacgcu                           39
```

```
<210> SEQ ID NO 84
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(39)
<223> OTHER INFORMATION: L-RNA

<400> SEQUENCE: 84
gugcugcggg gguuagggcu cgaagucggc ccgcagcac                              39

<210> SEQ ID NO 85
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(39)
<223> OTHER INFORMATION: L-RNA

<400> SEQUENCE: 85
guguucccgg gguuagggcu ugaagucggc cggcagcac                              39

<210> SEQ ID NO 86
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(39)
<223> OTHER INFORMATION: L-RNA

<400> SEQUENCE: 86
guguugcagg gguuagggcu ugaagucggc cugcagcac                              39

<210> SEQ ID NO 87
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(39)
<223> OTHER INFORMATION: L-RNA

<400> SEQUENCE: 87
gugcugcggg gguuagggcu caaagucggc cugcagcac                              39

<210> SEQ ID NO 88
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
```

```
<222> LOCATION: (1)..(38)
<223> OTHER INFORMATION: L-RNA

<400> SEQUENCE: 88
gugcugccgg gguuagggcu aaagucggcc gacagcac                              38

<210> SEQ ID NO 89
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(39)
<223> OTHER INFORMATION: L-RNA

<400> SEQUENCE: 89 gugcugugggg ggucagggcu agaagucggc cugcagcac                            39

<210> SEQ ID NO 90
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: L-RNA
<220> FEATURE:
<221> NAME/KEY: modified_base
<222> LOCATION: (13)..(13)
<223> OTHER INFORMATION: May or may not be present

<400> SEQUENCE: 90
gguyagggcu hraagucgg                                                   19

<210> SEQ ID NO 91
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: L-RNA

<400> SEQUENCE: 91
gguyagggcu hraagucgg                                                   19

<210> SEQ ID NO 92
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: L-RNA

<400> SEQUENCE: 92
gguyagggcu hragucgg                                                    18
```

<210> SEQ ID NO 93
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: L-RNA

<400> SEQUENCE: 93
gguuagggcu hgaagucgg                                                    19

<210> SEQ ID NO 94
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(38)
<223> OTHER INFORMATION: L-RNA

<400> SEQUENCE: 94
ugagauaggg guuagggcuu aaagucggcu gauucuca                               38

<210> SEQ ID NO 95
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(36)
<223> OTHER INFORMATION: L-RNA

<400> SEQUENCE: 95
gagauagggg uuagggcuua aagucggcug auucuc                                 36

<210> SEQ ID NO 96
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(29)
<223> OTHER INFORMATION: L-RNA

<400> SEQUENCE: 96
gggguuaggg cuuaaagucg gcugauucu                                         29

<210> SEQ ID NO 97
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(37)

<223> OTHER INFORMATION: L-RNA

<400> SEQUENCE: 97
gcguggcgag guuagggcua gaagucgguc gacacgc          37

<210> SEQ ID NO 98
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(35)
<223> OTHER INFORMATION: L-RNA

<400> SEQUENCE: 98
cguggcgagg uuagggcuag aagucggucg acacg          35

<210> SEQ ID NO 99
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(33)
<223> OTHER INFORMATION: L-RNA

<400> SEQUENCE: 99
cgggcgaggu uagggcuaga agucggucga ccg          33

<210> SEQ ID NO 100
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(32)
<223> OTHER INFORMATION: L-RNA

<400> SEQUENCE: 100
gggcgagguu agggcuagaa gucggucgcc cg          32

<210> SEQ ID NO 101
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(31)
<223> OTHER INFORMATION: L-RNA

<400> SEQUENCE: 101
cggcgagguu agggcuagaa gucggucgcc g          31

<210> SEQ ID NO 102
<211> LENGTH: 29
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(29)
<223> OTHER INFORMATION: L-RNA

<400> SEQUENCE: 102
cgggagguua gggcuagaag ucggucccg                                            29

<210> SEQ ID NO 103
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(27)
<223> OTHER INFORMATION: L-RNA

<400> SEQUENCE: 103
gggagguuag ggcuagaagu cgguccc                                              27

<210> SEQ ID NO 104
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(27)
<223> OTHER INFORMATION: L-RNA

<400> SEQUENCE: 104
ccgcgguuag ggcuagaagu cgggcgg                                              27

<210> SEQ ID NO 105
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(27)
<223> OTHER INFORMATION: L-RNA

<400> SEQUENCE: 105
cccggguuag ggcuagaagu cggcggg                                              27

<210> SEQ ID NO 106
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(27)
<223> OTHER INFORMATION: L-RNA

<400> SEQUENCE: 106
ggcggguuag ggcuagaagu cggcgcc                                              27
```

<210> SEQ ID NO 107
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(29)
<223> OTHER INFORMATION: L-RNA

<400> SEQUENCE: 107
cccgcgguua gggcuagaag ucgggcggg                                29

<210> SEQ ID NO 108
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(29)
<223> OTHER INFORMATION: L-RNA

<400> SEQUENCE: 108
gccgcgguua gggcuagaag ucgggcggc                                29

<210> SEQ ID NO 109
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(29)
<223> OTHER INFORMATION: L-RNA

<400> SEQUENCE: 109
ccccggguua gggcuagaag ucggcgggg                                29

<210> SEQ ID NO 110
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(29)
<223> OTHER INFORMATION: L-RNA

<400> SEQUENCE: 110
cggcggguua gggcuagaag ucggcgccg                                29

<210> SEQ ID NO 111
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature

<222> LOCATION: (1)..(29)
<223> OTHER INFORMATION: L-RNA

<400> SEQUENCE: 111
gggcgggyua gggcuagaag ucggcgccc                              29

<210> SEQ ID NO 112
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(37)
<223> OTHER INFORMATION: L-RNA

<400> SEQUENCE: 112
ugcugcgggg guuagggcua gaagucggcc ugcagca                     37

<210> SEQ ID NO 113
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(35)
<223> OTHER INFORMATION: L-RNA

<400> SEQUENCE: 113
gcugcggggg uuagggcuag aagucggccu gcagc                       35

<210> SEQ ID NO 114
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(33)
<223> OTHER INFORMATION: L-RNA

<400> SEQUENCE: 114 cugcggggu uagggcuaga agucggccug cag                          33

<210> SEQ ID NO 115
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(31)
<223> OTHER INFORMATION: L-RNA

<400> SEQUENCE: 115
ugcggggguu agggcuagaa gucggccugc a                           31

<210> SEQ ID NO 116
<211> LENGTH: 29
<212> TYPE: RNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(29)
<223> OTHER INFORMATION: L-RNA

<400> SEQUENCE: 116 gcgggguua gggcuagaag ucggccugc                                            29

<210> SEQ ID NO 117
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(29)
<223> OTHER INFORMATION: L-RNA

<400> SEQUENCE: 117
gccgggguua gggcuagaag ucggccggc                                           29

<210> SEQ ID NO 118
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(31)
<223> OTHER INFORMATION: L-RNA

<400> SEQUENCE: 118
ggccgggguu agggcuagaa gucggccggc c                                        31

<210> SEQ ID NO 119
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(31)
<223> OTHER INFORMATION: L-RNA

<400> SEQUENCE: 119
cgccgggguu agggcuagaa gucggccggc g                                        31

<210> SEQ ID NO 120
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: L-RNA
<220> FEATURE:
<221> NAME/KEY: modified_base
<222> LOCATION: (7)..(7)
```

<223> OTHER INFORMATION: a, g, c or u

<400> SEQUENCE: 120 rksbusnvgr                                                                                              10

<210> SEQ ID NO 121
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: L-RNA
<220> FEATURE:
<221> NAME/KEY: modified_base
<222> LOCATION: (3)..(3)
<223> OTHER INFORMATION: a, g, c or u

<400> SEQUENCE: 121 yynrcassmy                                                                                              10

<210> SEQ ID NO 122
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: L-RNA

<400> SEQUENCE: 122 rksbugsvgr                                                                                              10

<210> SEQ ID NO 123
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: L-RNA
<220> FEATURE:
<221> NAME/KEY: modified_base
<222> LOCATION: (3)..(3)
<223> OTHER INFORMATION: a, g, c or u

<400> SEQUENCE: 123 ycnrcassmy                                                                                              10

<210> SEQ ID NO 124
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(5)
<223> OTHER INFORMATION: L-RNA
<220> FEATURE:
<221> NAME/KEY: modified_base

```
<222> LOCATION: (1)..(1)
<223> OTHER INFORMATION: May or may not be present

<400> SEQUENCE: 124 ssssv                                                                      5

<210> SEQ ID NO 125
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(5)
<223> OTHER INFORMATION: L-RNA
<220> FEATURE:
<221> NAME/KEY: modified_base
<222> LOCATION: (5)..(5)
<223> OTHER INFORMATION: May or may not be present

<400> SEQUENCE: 125 bssss                                                                      5

<210> SEQ ID NO 126
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(5)
<223> OTHER INFORMATION: L-RNA

<400> SEQUENCE: 126 sggsv                                                                      5

<210> SEQ ID NO 127
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(5)
<223> OTHER INFORMATION: L-RNA

<400> SEQUENCE: 127 ysccs                                                                      5

<210> SEQ ID NO 128
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(5)
<223> OTHER INFORMATION: L-RNA

<400> SEQUENCE: 128 gcsgg                                                                      5
```

```
<210> SEQ ID NO 129
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(5)
<223> OTHER INFORMATION: L-RNA

<400> SEQUENCE: 129 cckgc                                                                       5

<210> SEQ ID NO 130
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(5)
<223> OTHER INFORMATION: L-RNA

<400> SEQUENCE: 130 ssssr                                                                       5

<210> SEQ ID NO 131
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(5)
<223> OTHER INFORMATION: L-RNA

<400> SEQUENCE: 131 ysbss                                                                       5

<210> SEQ ID NO 132
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(45)
<223> OTHER INFORMATION: L-RNA
<220> FEATURE:
<221> NAME/KEY: modified_base
<222> LOCATION: (1)..(1)
<223> OTHER INFORMATION: 40 kDa-PEG

<400> SEQUENCE: 132
gcguggugug aucuagaugu auuggcugau ccuagucagg uacgc                          45

<210> SEQ ID NO 133
<211> LENGTH: 36
<212> TYPE: RNA
<213> ORGANISM: Artificial Sequence
<220> FEATURE:
<223> OTHER INFORMATION: Description of Artificial Sequence: Synthetic
```

```
        oligonucleotide
<220> FEATURE:
<221> NAME/KEY: misc_feature
<222> LOCATION: (1)..(36)
<223> OTHER INFORMATION: L-RNA
<220> FEATURE:
<221> NAME/KEY: modified_base
<222> LOCATION: (1)..(1)
<223> OTHER INFORMATION: 40 kDa-PEG

<400> SEQUENCE: 133
gcgugaaagc aacaugucaa ugaaagguag ccgcgc                              36

<210> SEQ ID NO 134
<211> LENGTH: 29
<212> TYPE: RNA
<213> ORGANISM: Artificial Sequence
<220> FEATURE:
<223> OTHER INFORMATION: Description of Artificial Sequence: Synthetic
        oligonucleotide
<220> FEATURE:
<221> NAME/KEY: misc_feature
<222> LOCATION: (1)..(29)
<223> OTHER INFORMATION: L-RNA
<220> FEATURE:
<221> NAME/KEY: modified_base
<222> LOCATION: (1)..(1)
<223> OTHER INFORMATION: 40 kDa-PEG

<400> SEQUENCE: 134
cgggagguua gggcuagaag ucgguccog                                      29

<210> SEQ ID NO 135
<211> LENGTH: 29
<212> TYPE: RNA
<213> ORGANISM: Artificial Sequence
<220> FEATURE:
<223> OTHER INFORMATION: Description of Artificial Sequence: Synthetic
        oligonucleotide
<220> FEATURE:
<221> NAME/KEY: misc_feature
<222> LOCATION: (1)..(29)
<223> OTHER INFORMATION: L-RNA
<220> FEATURE:
<221> NAME/KEY: modified_base
<222> LOCATION: (1)..(1)
<223> OTHER INFORMATION: 40 kDa-PEG

<400> SEQUENCE: 135 gccggguua gggcuagaag ucggccggc                                       29

<210> SEQ ID NO 136
<211> LENGTH: 31
<212> TYPE: RNA
<213> ORGANISM: Artificial Sequence
<220> FEATURE:
<223> OTHER INFORMATION: Description of Artificial Sequence: Synthetic
        oligonucleotide
<220> FEATURE:
<221> NAME/KEY: misc_feature
<222> LOCATION: (1)..(31)
<223> OTHER INFORMATION: L-RNA
<220> FEATURE:
<221> NAME/KEY: modified_base
<222> LOCATION: (1)..(1)
<223> OTHER INFORMATION: 40 kDa-PEG

<400> SEQUENCE: 136
cgccgggguu agggcuagaa gucggccggc g                                   31

<210> SEQ ID NO 137
```

```
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(38)
<223> OTHER INFORMATION: L-RNA
<220> FEATURE:
<221> NAME/KEY: modified_base
<222> LOCATION: (1)..(1)
<223> OTHER INFORMATION: 40 kDa-PEG

<400> SEQUENCE: 137
gcugugaaag caacauguca augaaaggua gccgcagc                              38

<210> SEQ ID NO 138
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(40)
<223> OTHER INFORMATION: L-RNA

<400> SEQUENCE: 138
uaaggaaacu cggucugaug cgguagcgcu gugcagagcu                            40

<210> SEQ ID NO 139
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(38)
<223> OTHER INFORMATION: L-RNA
<220> FEATURE:
<221> NAME/KEY: modified_base
<222> LOCATION: (1)..(1)
<223> OTHER INFORMATION: 30 kDa-PEG

<400> SEQUENCE: 139
gcugugaaag caacauguca augaaaggua gccgcagc                              38

<210> SEQ ID NO 140
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(38)
<223> OTHER INFORMATION: L-RNA
<220> FEATURE:
<221> NAME/KEY: modified_base
<222> LOCATION: (1)..(1)
<223> OTHER INFORMATION: 100 kDa-HES

<400> SEQUENCE: 140
gcugugaaag caacauguca augaaaggua gccgcagc                              38
```

```
<210> SEQ ID NO 141
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(38)
<223> OTHER INFORMATION: L-RNA
<220> FEATURE:
<221> NAME/KEY: modified_base
<222> LOCATION: (1)..(1)
<223> OTHER INFORMATION: 130 kDa-HES

<400> SEQUENCE: 141
gcugugaaag caacauguca augaaaggua gccgcagc                                  38

<210> SEQ ID NO 142
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(48)
<223> OTHER INFORMATION: L-RNA

<400> SEQUENCE: 142
cgugguccgu ugugucaggu cuauucgccc cggugcaggg cauccgcg                       48

<210> SEQ ID NO 143
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(49)
<223> OTHER INFORMATION: L-RNA

<400> SEQUENCE: 143
gcagugugac gcggacguga uaggacagag cugaucccgc ucaggugag                      49

<210> SEQ ID NO 144
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(49)
<223> OTHER INFORMATION: L-RNA

<400> SEQUENCE: 144
caacagcagu gugacgcgga cgugauagga cagagcugau cccgcucag                      49

<210> SEQ ID NO 145
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 145
gcugugaaag caacauguca augaaaggua gccgcagc                                    38

<210> SEQ ID NO 146
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
gcugugaaag uaacauguca augaaaggua accacagc                                    38

<210> SEQ ID NO 147
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
gcugugaaag uaacacguca augaaaggua accgcagc                                    38

<210> SEQ ID NO 148
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
gcugugaaag uaacacguca augaaaggua accacagc                                    38

<210> SEQ ID NO 149
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
gcuguaaaag uaacauguca augaaaggua acuacagc                                    38

<210> SEQ ID NO 150
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
gcuguaaaag uaacaaguca augaaaggua acuacagc                                    38

<210> SEQ ID NO 151
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
gcugugaaag uaacaaguca augaaaggua accacagc                              38

<210> SEQ ID NO 152
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
gcagugaaag uaacauguca augaaaggua accacagc                              38

<210> SEQ ID NO 153
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
gcugugaaag uaacauguca augaaaggua accacugc                              38

<210> SEQ ID NO 154
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
gcuaugaaag uaacauguca augaaaggua accauagc                              38

<210> SEQ ID NO 155
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
gcugcgaaag cgacauguca augaaaggua gccgcagc                              38

<210> SEQ ID NO 156
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
gcugugaaag caacauguca augaaaggua gccacagc                              38

<210> SEQ ID NO 157
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157

```
gcugugaaag uaacauguca augaaaggua gccgcagc                              38
```

<210> SEQ ID NO 158
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158

```
agcgugaaag uaacacguaa aaugaaaggu aaccacgcu                             39
```

<210> SEQ ID NO 159
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159

```
cugugaaagc aacaugucaa ugaaagguag ccgcag                                36
```

<210> SEQ ID NO 160
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160

```
ugugaaagca acaugucaau gaaagguagc cgca                                  34
```

<210> SEQ ID NO 161
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161

```
gugaaagcaa caugucaaug aaagguagcc gc                                    32
```

<210> SEQ ID NO 162
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162

```
ugaaagcaac augucaauga aagguagccg                                       30
```

<210> SEQ ID NO 163
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
gaaagcaaca ugucaaugaa agguagcc                                            28

<210> SEQ ID NO 164
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
aaagcaacau gucaaugaaa gguagc                                              26

<210> SEQ ID NO 165
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
gcgugaaagc aacaugucaa ugaaagguag ccgcgc                                   36

<210> SEQ ID NO 166
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
gcgcgaaagc aacaugucaa ugaaagguag ccgcgc                                   36

<210> SEQ ID NO 167
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
gcggaaagca acaugucaau gaaagguagc ccgc                                     34

<210> SEQ ID NO 168
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
cgugaaagca acaugucaau gaaagguagc cgcg                                     34

<210> SEQ ID NO 169
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
gcgcaaagca acaugucaau gaaagguagc gugc                                     34

```
<210> SEQ ID NO 170
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
gugcaaagca acaugucaau gaaagguagc gcgc                                   34

<210> SEQ ID NO 171
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
cgcgaaagca acaugucaau gaaagguagc cgug                                   34

<210> SEQ ID NO 172
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
gggcaaagca acaugucaau gaaagguagc gccc                                   34

<210> SEQ ID NO 173
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
ggccaaagca acaugucaau gaaagguagc ggcc                                   34

<210> SEQ ID NO 174
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
gcccaaagca acaugucaau gaaagguagc gggc                                   34

<210> SEQ ID NO 175
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
ccccaaagca acaugucaau gaaagguagc gggg                                   34
```

<210> SEQ ID NO 176
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
agcguggugu gaucuagaug uaguggcuga uccagucag guacgcu                     47

<210> SEQ ID NO 177
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
agcguggugu gaucuagaug uauuggcuga uccagucag guacgcu                     47

<210> SEQ ID NO 178
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
agcguggugu gaucuagaug uaauggcuga uccagucag gugcgcu                     47

<210> SEQ ID NO 179
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
gcgaggugug aucuagaugu aguggcugau ccagucagg ugcgc                       45

<210> SEQ ID NO 180
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
gcguggugug aucuagaugu aguggcugau ccagucagg ugcgc                       45

<210> SEQ ID NO 181
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
gcauggugug aucuagaugu aguggcugau ccagucagg ugccc                       45

```
<210> SEQ ID NO 182
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
gcguggugug aucuagaugu aauggcugau ccuagucagg gacgc            45

<210> SEQ ID NO 183
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
gcguggugug aucuagaugu agaggcugau ccuagucagg uacgc            45

<210> SEQ ID NO 184
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
gcguggugug aucuagaugu aaaggcugau ccuagucagg uacgc            45

<210> SEQ ID NO 185
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
gcguggugug aucuagaugu aguggcuguu ccuagucagg uaugc            45

<210> SEQ ID NO 186
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
gcguggugug aucuagaugu aguggcugau ccuaguuagg uacgc            45

<210> SEQ ID NO 187
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
gcguggugug aucuagaugu aguggcugau ccuagucagg uacgc            45

<210> SEQ ID NO 188
```

```
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
cgugguguga ucuagaugua guggcugauc cuagucaggu acg                         43

<210> SEQ ID NO 189
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
guggugugau cuagauguag uggcugaucc uagucaggua c                           41

<210> SEQ ID NO 190
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
uggugugauc uagauguagu ggcugauccu agucaggua                              39

<210> SEQ ID NO 191
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
ggugugaucu agauguagug gcugauccua gucaggu                                37

<210> SEQ ID NO 192
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
gugugaucua gauguagugg cugauccuag ucagg                                  35

<210> SEQ ID NO 193
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
gcguggugug aucuagaugu auuggcugau ccuagucagg uacgc                       45

<210> SEQ ID NO 194
<211> LENGTH: 45
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
gcgcggugug aucuagaugu auuggcugau ccuagucagg cgcgc                    45

<210> SEQ ID NO 195
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
gcgcguguga ucuagaugua uuggcugauc cuagucaggg cgc                     43

<210> SEQ ID NO 196
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
gggcguguga ucuagaugua uuggcugauc cuagucaggg ccc                     43

<210> SEQ ID NO 197
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
ggccguguga ucuagaugua uuggcugauc cuagucaggg gcc                     43

<210> SEQ ID NO 198
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
gcccguguga ucuagaugua uuggcugauc cuagucaggg ggc                     43

<210> SEQ ID NO 199
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
gugcugcggg gguuagggcu agaagucggc cugcagcac                          39

<210> SEQ ID NO 200
<211> LENGTH: 39
<212> TYPE: RNA
```

-continued

```
<213> ORGANISM: Artificial Sequence
<220> FEATURE:
<223> OTHER INFORMATION: Description of Artificial Sequence: Synthetic
      oligonucleotide

<400> SEQUENCE: 200
agcguggcga gguuagggcu agaagucggu cgacacgcu                                39

<210> SEQ ID NO 201
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
guguugcgga gguuagggcu agaagucggu cagcagcac                                39

<210> SEQ ID NO 202
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
cgugcgcuug agauaggggu uagggcuuaa agucggcuga uucucacg                      48

<210> SEQ ID NO 203
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
agcgugaagg gguuagggcu cgaagucggc ugacacgcu                                39

<210> SEQ ID NO 204
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
gugcugcggg gguuagggcu cgaagucggc ccgcagcac                                39

<210> SEQ ID NO 205
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
guguucccgg gguuagggcu ugaagucggc cggcagcac                                39

<210> SEQ ID NO 206
<211> LENGTH: 39
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 206
guguugcagg gguuagggcu ugaagucggc cugcagcac                                 39

<210> SEQ ID NO 207
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
gugcugcggg gguuagggcu caaagucggc cugcagcac                                 39

<210> SEQ ID NO 208
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
gugcugccgg gguuagggcu aaagucggcc gacagcac                                  38

<210> SEQ ID NO 209
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
gugcuguggg ggucagggcu agaagucggc cugcagcac                                 39

<210> SEQ ID NO 210
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
ugagauaggg guuagggcuu aaagucggcu gauucuca                                  38

<210> SEQ ID NO 211
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
gagauagggg uuagggcuua aagucggcug auucuc                                    36

<210> SEQ ID NO 212
<211> LENGTH: 29
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 212 ggggguuaggg cuuaaagucg gcugauucu                                    29

<210> SEQ ID NO 213
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
gcguggcgag guuagggcua gaagucgguc gacacgc                            37

<210> SEQ ID NO 214
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
cguggcgagg uuagggcuag aagucggucg acacg                              35

<210> SEQ ID NO 215
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
cgggcgaggu uagggcuaga agucggucga ccg                                33

<210> SEQ ID NO 216
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
cgggcgaggu uagggcuaga agucggucgc ccg                                33

<210> SEQ ID NO 217
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
cggcgagguu agggcuagaa gucggucgcc g                                  31

<210> SEQ ID NO 218
<211> LENGTH: 29
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 218
cgggagguua gggcuagaag ucggucccg                                      29

<210> SEQ ID NO 219
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
gggagguuag ggcuagaagu cgguccc                                        27

<210> SEQ ID NO 220
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
ccgcgguuag ggcuagaagu cgggcgg                                        27

<210> SEQ ID NO 221
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
cccggguuag ggcuagaagu cggcggg                                        27

<210> SEQ ID NO 222
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
ggcggguuag ggcuagaagu cggcgcc                                        27

<210> SEQ ID NO 223
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
cccgcgguua gggcuagaag ucgggcggg                                      29

<210> SEQ ID NO 224
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 224
gccgcgguua gggcuagaag ucgggcggc                                            29

<210> SEQ ID NO 225
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
ccccggguua gggcuagaag ucggcgggg                                            29

<210> SEQ ID NO 226
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
cggcggguua gggcuagaag ucggcgccg                                            29

<210> SEQ ID NO 227
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
gggcggguua gggcuagaag ucggcgccc                                            29

<210> SEQ ID NO 228
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
ugcugcgggg guuagggcua gaagucggcc ugcagca                                   37

<210> SEQ ID NO 229
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
gcugcggggg uuagggcuag aagucggccu gcagc                                     35

<210> SEQ ID NO 230
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 230
cugcgggggu uagggcuaga agucggccug cag                                33

<210> SEQ ID NO 231
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231 ugcgggguu agggcuagaa gucggccugc a                                   31

<210> SEQ ID NO 232
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
gcggggguua gggcuagaag ucggccugc                                     29

<210> SEQ ID NO 233
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233 gccggguua gggcuagaag ucggccggc                                      29

<210> SEQ ID NO 234
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
ggccgggguu agggcuagaa gucggccggc c                                  31

<210> SEQ ID NO 235
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
cgccgggguu agggcuagaa gucggccggc g                                  31

<210> SEQ ID NO 236
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
```
cgugguccgu ugugucaggu cuauucgccc cggugcaggg cauccgcg         48

<210> SEQ ID NO 237
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
gcagugugac gcggacguga uaggacagag cugaucccgc ucaggugag         49

<210> SEQ ID NO 238
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
caacagcagu gugacgcgga cgugauagga cagagcugau cccgcucag         49

<210> SEQ ID NO 239
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(40)
<223> OTHER INFORMATION: L-RNA
<220> FEATURE:
<221> NAME/KEY: modified_base
<222> LOCATION: (1)..(1)
<223> OTHER INFORMATION: Pegylated

<400> SEQUENCE: 239
uaaggaaacu cggucugaug cgguagcgcu gugcagagcu                 40

<210> SEQ ID NO 240
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(45)
<223> OTHER INFORMATION: L-RNA
<220> FEATURE:
<221> NAME/KEY: modified_base
<222> LOCATION: (1)..(1)
<223> OTHER INFORMATION: 30-kDa-PEG

<400> SEQUENCE: 240
gcguggugug aucuagaugu auuggcugau ccuagucagg uacgc           45

<210> SEQ ID NO 241
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: misc_feature
<222> LOCATION: (1)..(45)
<223> OTHER INFORMATION: L-RNA
<220> FEATURE:
<221> NAME/KEY: modified_base
<222> LOCATION: (1)..(1)
<223> OTHER INFORMATION: 40-kDa-PEG

<400> SEQUENCE: 241
cgcauggacu gauccuaguc gguuauguag aucuagugug gugcg            45

<210> SEQ ID NO 242
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(48)
<223> OTHER INFORMATION: L-RNA

<400> SEQUENCE: 242
cgugcggccu aagagguuag ggcuuaaaguc ggucuuuggc caacacg         48

<210> SEQ ID NO 243
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(48)
<223> OTHER INFORMATION: L-RNA

<400> SEQUENCE: 243
cgugauuggu gagggguuag ggcuugaagu cggccuuguc cagucacg         48

<210> SEQ ID NO 244
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(17)
<223> OTHER INFORMATION: L-RNA

<400> SEQUENCE: 244
cgugcgcuug agauagg                                          17

<210> SEQ ID NO 245
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(12)
<223> OTHER INFORMATION: L-RNA

<400> SEQUENCE: 245
```
cugauucuca cg                                                        12

<210> SEQ ID NO 246
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: L-RNA

<400> SEQUENCE: 246
cugauucuca                                                           10

<210> SEQ ID NO 247
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(27)
<223> OTHER INFORMATION: L-RNA

<400> SEQUENCE: 247
aaaguaacac guaaaaugaa agguaac                                        27

<210> SEQ ID NO 248
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: L-RNA

<400> SEQUENCE: 248
gguuagggcu aaagucgg                                                  18

<210> SEQ ID NO 249
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: L-RNA

<400> SEQUENCE: 249
gguuagggcu agaagucgg                                                 19

<210> SEQ ID NO 250
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: misc_feature
<222> LOCATION: (1)..(19)
<223> OTHER INFORMATION: L-RNA

<400> SEQUENCE: 250
gguuagggcu cgaagucgg                                                    19

<210> SEQ ID NO 251
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: L-RNA

<400> SEQUENCE: 251
gguuagggcu ugaagucgg                                                    19
```

SDF-1 BINDING NUCLEIC ACIDS AND THE USE THEREOF

The present invention is related to nucleic acid molecules binding to the CXC chemokine stromal cell-derived factor-1 (SDF-1), methods for the treatment of diseases, and their use in the manufacture of a medicament.

Chemokines. The chemokines are a family of structurally related, heparin-binding basic small proteins of 8-14 kDa. Functionally, they can be classified as proinflammatory, homeostatic, or dual function (Moser, Wolf et al. 2004). Inflammatory chemokines are induced by pathogens, cytokines, or growth factors and recruit effector leukocytes to sites of infection, inflammation, tissue injury, and tumor. Such chemokines regulate the recruitment, activation, and proliferation of white blood cells, also referred to as leukocytes (Schall and Bacon 1994; Springer 1995; Baggiolini 1998). Chemokines selectively induce chemotaxis of neutrophils, eosinophils, basophils, monocytes, macrophages, mast cells, T and B cells. In addition to their chemotactic effect, they can selectively exert other effects in responsive cells like changes in cell shape, transient increase in the concentration of free intracellular calcium ions, degranulation, upregulation of integrins, formation of bioactive lipids such as, but not limited to leukotrienes, prostaglandins, thromboxans, or respiratory burst, i.e. release of reactive oxygen species for destruction of pathogenic organisms or tumor cells. Thus, by provoking the release of further proinflammatory mediators, chemotaxis and extravasation of leukocytes towards sites of infection or inflammation, chemokines trigger escalation of the inflammatory response. Homeostatic chemokines, on the other hand, are expressed predominantly in bone marrow and lymphoid tissues and are involved in hematopoiesis, immune surveillance, and adaptive immune responses (Godessart 2005).

Class of chemokines. Based on the arrangement of the first two of four conserved cystein residues, the chemokines are divided into four classes: CC or β-chemokines in which the cysteins are in tandem, CXC or α-chemokines, where they are separated by one additional amino acid residue, XC or γ chemokines that possess only one disulfide bridge, whereby lymphotactin which is also referred to as XCL1 is the only representant to date, and CX3C-chemokines which feature three amino acid residues between the cysteins with membrane-bound fractalkin being the only class member (Bazan, Bacon et al. 1997). The usually chemokines carry two names, one that is related has been given due to their function and one that is the systematic name, according to sequence characteristics.

CXC chemokines. The CXC chemokines act primarily on neutrophils, in particular those CXC chemokines that carry the amino acid sequence ELR on their amino terminus. Examples of CXC chemokines that are active on neutrophils are IL-8/CXCL8, GROα/CXCL1, GROβ/CXCL2, and GROγ/CXCL3, NAP-2/CXCL7, ENA-78/CXCL5, SDF-1/CXCL12 and GCP-2/CXCL6. The CXC chemokines act on a larger variety of leukocytes, such as monocytes, macrophages, eosinophils, basophils, as well as T and B lymphocytes (Oppenheim, Zachariae et al. 1991; Miller and Krangel 1992; Baggiolini, Dewald et al. 1994; Jose, Griffiths-Johnson et al. 1994; Ponath, Qin et al. 1996). Examples of these are I-309/CCL1; MCP-1/CCL2, MCP-2/CCL8, MCP-3/CCL7, MCP-4/CCL13, MIP-1α/CCL3 and MIP-1β/CCL4, RANTES/CCL5, and eotaxin/CCL11.

CXC chemokine receptors. Chemokines act through receptors that belong to a superfamily of seven transmembrane-spanning G protein-coupled receptors also referred to as GPCRs) (Murphy, Baggiolini et al. 2000)). Generally speaking, chemokine and chemokine receptor interactions tend to be promiscuous in that one chemokine can bind chemokine receptors and conversely a single chemokine receptor can interact with several different chemokines. Some known receptors for the CXC chemokines include CXCR1, which binds GROα, GCP-2, and IL-8; CXCR2, which binds chemokines including GROα, GROβ, GROγ, ENA-78, and IL-8; CXCR3, which binds chemokines including PF4, MIG, IP-10, and I-TAC; CXCR4 which thus far has been found only to signal in response to SDF-1, and CXCR5, which has been shown to signal in response to BCA-1 (Godessart 2005). Besides CXCR4, a new SDF-1 receptor was identified which is referred to as RDC1/CXCR7 (Balabanian, Lagane et al. 2005, Burns, Summers et al. 2006).

SDF-1. Stromal-cell derived factor-1 (abbr.: SDF-1; synonyms, CXCL12; PBSF [pre-B-cell growth-stimulating factor]; TPAR-1 [TPA repressed gene 1]; SCYB12; TLSF [thymic lymphoma cell stimulating factor]; hIRH [human intercrine reduced in hepatomas]) is an angiogenic CXC chemokine that does not contain the ELR motif typical of the IL-8-like chemokines (Salcedo, Wasserman et al. 1999; Salcedo and Oppenheim 2003) but binds and activates the G-protein coupled receptor CXCR4. The chemokine was discovered by three groups independently, either by cloning cDNAs that carry N-terminal signal sequences (Tashiro, Tada et al. 1993), by virtue of its ability to stimulate early B cell progenitors when expressed by the stromal cell line PA6 (Nagasawa, Kikutani et al. 1994), or by isolation from a cDNA library constructed from mouse embryo fibroblasts treated with the protein kinase C-activator tetra dodecanoyl phorbol acetate (abbr.: TPA) (Jiang, Zhou et al. 1994). As a result of alternative splicing, there are two forms of SDF-1, SDF-1α (68 aa) and SDF-1β, which, compared to SDF-1 α carries five additional residues at the C-terminus (Shirozu, Nakano et al. 1995). The biological significance of these two splice variants is not completely understood.

Sequences of SDF-1. The sequence conservation between SDF-1 from different species is remarkable: human SDF-1α (SEQ.ID. 1) and murine SDF-1α (SEQ.ID. 2) are virtually identical. There is only a single conservative change of V to I at position 18 (Shirozu, Nakano et al. 1995).

NMR structure of SDF-1. An NMR structure model exists (PDB access, 1SDF) for SDF-1 [8-68]. SDF-1 was found to be a monomer with a disordered N-terminal region. Differences to other chemokines are found mainly in the packing of the hydrophobic core and surface charge distribution (Crump, Gong et al. 1997).

Physiological activities of SDF-1. Physiological activities of SDF-1: Since the SDF-1 receptor CXCR4 is widely expressed on leukocytes, mature dendritic cells, endothelial cells, brain cells, and megakaryocytes, the activities of SDF-1 are pleiotropic. This chemokine, more than any other identified thus far, exhibits the widest range of biological functions, especially outside of the immune system. The most significant functional effects of SDF-1 are:

Homing and attachment of epithelial cells to neovascular sites in the choroid portion of the retina. SDF-1 has been shown to be involved in homing of epithelial cells to the choroid during neovascularization in eye tissue. The exact role of these cells is still under investigation but the published hypothesis is that epithelial cells are involved in the formation of aberrant blood vessels (Sengupta, Caballero et al. 2005).

Stem cells. SDF-1 is required to maintain stem cells and progenitor cells, e.g. hematopoietic progenitor (usually CD34+) cells in the bone marrow of the adult. AMD3100, a selective CXCR4 antagonist, can be used to mobilize CD34+ cells for hematopoietic stem cell transplantation. CD34+ cells migrate in vitro and in vivo along a gradient of SDF-1 produced by stromal cells (Aiuti, Webb et al. 1997).

B cell development and chemotaxis. SDF-1 supports proliferation of pre-B cells and augments the growth of bone marrow B cell progenitors (Nagasawa, Kikutani et al. 1994); it induces specific migration of pre- and pro-B cells, while not acting as a significant chemoattractant for mature B cells (D'Apuzzo, Rolink et al. 1997; Bleul, Schultze et al. 1998). Presumably, SDF-1 is important for the positioning of B cells within secondary lymphoid tissue.

T cell chemotaxis. SDF-1 is one of the most efficacious T cell chemoattractants; CXCR4 is present on many T cell subsets (Bleul, Farzan et al. 1996).

Embryonic development. SDF-1 and its receptor CXCR4 are essential for embryonic development. SDF-1 and CXCR4 knockout mice die perinatally; they exhibit cardiac ventricular septal defects or abnormal cerebellar development in addition to reduced numbers of B cell and myeloid progenitors (Nagasawa, Hirota et al. 1996; Ma, Jones et al. 1998; Zou, Kottmann et al. 1998). SDF-1 is also required for normal ontogeny of blood development during embryogenesis (Juarez and Bendall 2004).

HIV infection. SDF-1 is able to inhibit T-tropic HIV-1 entry into CXCR4-bearing cell lines, and SDF-1 expression may have an important bearing on AIDS pathogenesis, since a polymorphism in the human SDF-1 gene affects the onset of AIDS (Bleul, Farzan et al. 1996).

Other diseases. Altered expression levels of SDF-1 or its receptor CXCR4 or altered responses towards those molecules are said to be associated with many human diseases, such as retinopathy (Brooks, Caballero et al. 2004; Butler, Guthrie et al. 2005; Meleth, Agron et al. 2005); cancer of breast (Muller, Homey et al. 2001; Cabioglu, Sahin et al. 2005), ovaries (Scotton, Wilson et al. 2002), pancreas (Koshiba, Hosotani et al. 2000), thyroid (Hwang, Chung et al. 2003) and nasopharynx (Wang, Wu et al. 2005); glioma (Zhou, Larsen et al. 2002); neuroblastoma (Geminder, Sagi-Assif et al. 2001); B cell chronic lymphocytic leukemia (Burger, Tsukada et al. 2000); WHIM syndrome (Warts, Hypogammaglobulinemia, Infections, Myelokathexis syndrome) (Gulino, Moratto et al. 2004; Balabanian, Lagane et al. 2005; Kawai, Choi et al. 2005); immunologic deficiency syndromes (Arya, Ginsberg et al. 1999; Marechal, Arenzana-Seisdedos et al. 1999; Soriano, Martinez et al. 2002); pathologic neovascularization (Salvucci, Yao et al. 2002; Yamaguchi, Kusano et al. 2003; Grunewald, Avraham et al. 2006); inflammation (Murdoch 2000; Fedyk, Jones et al. 2001; Wang, Guan et al. 2001); multiple sclerosis (Krumbholz, Theil et al. 2006); rheumatoid arthritis/osteoarthritis (Buckley, Amft et al. 2000; Kanbe, Takagishi et al. 2002; Grassi, Cristino et al. 2004).

Antagonism of SDF-1 and its receptor. In experimental animal settings, antagonists of SDF-1 or of its receptor have proved efficient for blocking growth and/or metastatic spreading of human cancer cells from different origin such as pancreas (Guleng, Tateishi et al. 2005; Saur, Seidler et al. 2005), colon (Zeelenberg, Ruuls-Van Stalle et al. 2003; Guleng, Tateishi et al. 2005), breast (Muller, Homey et al. 2001; Lapteva, Yang et al. 2005), lung (Phillips, Burdick et al. 2003), glioblastoma and medulloblastoma (Rubin, Kung et al. 2003), prostate (Sun, Schneider et al. 2005), osteosarcoma (Perissinotto, Cavalloni et al. 2005), melanoma (Takenaga, Tamamura et al. 2004), stomach (Yasumoto, Koizumi et al. 2006) and multiple myeloma (Menu, Asosingh et al. 2006). In addition, anti-SDF-1 therapy was beneficial in animal models in preventing retinal neovascularization (Butler, Guthrie et al. 2005, Mames, Mattheus et al. 2006), nephritis (Balabanian, Couderc et al. 2003) and arthritis (Matthys, Hatse et al. 2001; Tamamura, Fujisawa et al. 2004; De Klerck, Geboes et al. 2005). Moreover, AMD3100, a selective CXCR4 antagonist, was used to mobilize CD34+ cells for hematopoietic stem cell transplantation. CD34+ cells migrate in vitro and in vivo along a gradient of SDF-1 produced by stromal cells (Aiuti, Webb et al. 1997).

SDF-1 and eye diseases. SDF-1 is a player in the pathology of diseases of the back of the eye such as diabetic retinopathy (abbr. DR) (Fong, Aiello et al. 2004) and age-related macular degeneration (abbr. AMD) (Ambati, Anand et al. 2003). Both of these diseases damage the eye and lead to gradual loss of vision culminating in blindness. The damage occurs due to the inappropriate growth of blood vessels in the back of the eye, a process known as choroidal neovascularization (abbr. CNV). During CNV, new blood vessels that originate from the choroid migrate through a break in the Bruch membrane into the sub-retinal pigment epithelium (abbr. sub-RPE) or subretinal space. The abnormal vessels can bleed, also referred to as intraretinal hemorrhage, or leak fluid under the retina. This can leave scars and can elevate the macula, which distorts vision.

Diabetic retinopathy. DR is a major sequel to diabetes, occurring frequently in patients with both type 1 and type 2 diabetes. There are approximately 16 million diabetics in the U.S., with nearly 8 million having some form of DR. When proliferative diabetic retinopathy (abbr. PDR) is left untreated, about 60% of patients become blind in one or both eyes within 5 years. With the alarming rise in the prevalence of diabetes in North America, Europe and many emerging countries, the patient population is growing quickly. For instance, the incidence of blindness is 25 times higher in patients with diabetes than in the general population. Furthermore, DR is the most common cause of blindness in middle-aged subjects, accounting for at least 12 percent of all new cases in the United States each year. Screening programs are in place so that the vision of diabetes patients can be monitored and treatment, such as is available, can be delivered in time.

The direct causes of DR are poorly understood, but the disease is thought to have its origins in a combination of sources: impaired auto-regulation of retinal blood flow; accumulation of sorbitol inside retinal cells; and accumulation of advanced glycosylation end products in the extracellular fluid. All of these factors are related directly or indirectly to hyperglycemia, the abundance of sugar in the bloodstream.

The symptoms of DR are similar to those of AMD. Patients lose cells in the retina and microaneurysms, i.e. blood leakage, occur in the basement membrane of the retina. In addition, vascular endothelial growth factor (abbr. VEGF), Insulin-like growth factor 1 (IGF-1) and other blood-borne factors, possibly including SDF-1, attract new vascular cells and encourage the formation of damaging blood vessels.

Age-related macular degeneration. AMD destroys a person's central vision. The early stages of the disease may not even be noticeable, because symptoms vary among patients. Sometimes a patient is affected only in one eye. Or vision may be impaired in both eyes but not significantly. The disease causes distortion or faulty color perception. There is often a dark spot in the center of the visual field.

The etiology (this means course) of the disease is poorly understood. AMD is often thought of as the aging of the outermost layer of the retina. The physical alterations occur in the center of the retina, also known as the macula, which is the part of the retina relied upon for the most acute vision.

Wet AMD begins as a sequel to the dry form of the disease. Some 90% of patients suffer from the dry form of AMD, which results in the thinning of macular tissues and disturbances in its pigmentation. The rest have the wet form, which involves choroidal neovascularization and often the formation of a macular edema and retinal or subretinal bleeding. All of these can lead to a rapid deterioration of visual acuity.

Already the most common cause of blindness in people over the age of 55, wet AMD afflicts an estimated 4% to 5% of the United States population aged 65-74 and nearly 10% of those 75 years of age or older. There are already 5 million people in the United States alone over the age of 80 who have this disease and another 5 million people are expected to be affected by 2020.

Tumours. Tumors (including solid and hematological neoplasias and malignancies) are not just masses of cancer cells: infiltration of tumors with immune-cells is a characteristic of cancer. Many human cancers have a complex chemokine network that influences the extent and phenotype of this infiltrate, as well as tumor growth, survival, migration, and angiogenesis. Most solid tumors contain many non-malignant stromal cells. Indeed, stromal cells sometimes outnumber cancer cells. The predominant stromal cells that are found in cancers are macrophages, lymphocytes, endothelial cells and fibroblasts.

SDF-1 in tumours. Cells from different cancer types have different profiles of chemokine-receptor expression, but the SDF-1 receptor CXCR4 is most commonly found in tumor cells of mouse and man: tumor cells from at least 23 different types of human cancers of epithelial, mesenchymal, and haematopoietic origin express CXCR4 (Balkwill 2004) with SDF-1 being the only known ligand for CXCR4. Apart from the bone marrow and secondary lymphoid tissue, where it is constitutively expressed, SDF-1 is found in primary tumor sites in lymphoma (Corcione, Ottonello et al. 2000) and brain tumors of both neuronal and astrocytic lineage. Furthermore, it is present at high levels in ovarian (Scotton, Wilson et al. 2002) and pancreatic cancer (Koshiba, Hosotani et al. 2000) as well as at sites of metastasis in breast (Muller, Homey et al. 2001) and thyroid cancer (Hwang, Chung et al. 2003), neuroblastoma and haematological malignancies (Geminder, Sagi-Assif et al. 2001). In contrast, CXCR4 expression is low or absent on normal breast (Muller, Homey et al. 2001), ovarian (Scotton, Wilson et al. 2002) and prostate epithelia (Sun, Schneider et al. 2005).

Besides CXCR4 and new SDF-1 receptor was identified: RDC1/CXCR7 (Balabanian, Lagane et al. 2005, Burns, Summers et al. 2006). In vitro and in vivo studies with prostate cancer cell lines suggest that alterations in CXCR7/RDC1 expression are associated with enhanced adhesive and invasive activities in addition to a survival advantage. In addition, it was observed that CXCR7/RDC1 levels are regulated by CXCR4 (Wang et al, 2008). In vitro and in vivo studies have shown that both receptors for SDF-1, namely CXCR4 and the CXCR7 promote tumor growth, metastatic potential and resistance to (chemotherapy induced) apoptosis in a number of tumors, e.g breast cancer, glioblastomas, ovarian cancer, neuroblastoma, lung cancer colorectal and prostate cancer (Burns et al, 2006; Li et al, 2008; Scotton et al, 2002; Yang et al, 2008; Zagzag et al, 2008).

CXCR4 and CXCR7 expression thus seems to be a general characteristic of several tumours.

Inhibition of chemokine-receptor signalling as a therapeutic option in cancer treatment. Inhibiting chemokine-receptor signalling on tumor cells has the potential to induce growth arrest or apoptosis, and to prevent invasion and metastasis in vivo as shown by the following evidence: CXCR4 knockdown by siRNA abrogated breast tumor growth (Lapteva, Yang et al. 2005); T-hybridoma cells which were transfected with a construct that prevents surface expression of CXCR4 could no longer metastasize to distant organs when injected intravenously into mice (Zeelenberg, Ruuls-Van Stalle et al. 2001); in similar experiments with colorectal cancer cells, lung and liver metastases were greatly reduced (Zeelenberg, Ruuls-Van Stalle et al. 2003); anti-CXCR4 antibodies inhibited the spread of breast cancer xenografts to the lymph nodes (Muller, Homey et al. 2001); treatment of lymphoblastoid cells with anti-CXCR4 or anti-SDF-1 antibodies delayed tumor growth in (NOD)/SCID mice (Bertolini, Dell'Agnola et al. 2002); anti-SDF-1 antibodies inhibited development of organ metastases of non-small-cell lung cancer (abbr. NSCLC) cells (Phillips, Burdick et al. 2003); systemic administration of the CXCR4 antagonist AMD3100 (by AnorMED Inc.) inhibited the growth of intracranial glioblastoma and medulloblastoma xenografts, and increased tumor cell apoptosis within 24 hours (Rubin, Kung et al. 2003); anti-SDF-1 antibodies inhibited growth of MCF-7 breast cancer cells admixed with carcinoma-associated fibroblasts (Orimo, Gupta et al. 2005); neutralization of CXCR4 with antibodies blocked prostate cancer metastasis and growth in osseous sites (Sun, Schneider et al. 2005); development of lung metastasis after injection of osteosarcoma cells was prevented by administration of the peptidic CXCR4 antagonist T134 (Perissinotto, Cavalloni et al. 2005).

Different authors come to the conclusion that targeting the SDF-1/CXCR4 axis provides new therapeutic options for cancer patients:

Human ovarian tumors strongly express SDF-1 plus, on a lower level, VEGF. Both proteins are triggered by hypoxia in the tumor. Pathologic concentrations of any of the proteins alone were not sufficient to induce in vivo angiogenesis, but together, SDF-1 and VEGF in pathologic concentrations efficiently and synergistically induced neovascularization. Thus, interrupting this synergistic axis, rather than VEGF alone, is a novel efficient antiangiogenesis strategy to treat cancer (Kryczek, Lange et al. 2005);

Breast cancer cell lines, when equipped with the autocrine SDF-1/CXCR4 signalling pathway, display aggressive behavior. This includes an increase in invasiveness and migration together with faster growth. The SDF-1/CXCR4 axis thus provides important information for predicting the aggressive nature and constitute important therapeutic targets in human breast cancer (Kang, Watkins et al. 2005);

Migration and metastasis of small-cell lung cancer (abbr. SCLC) cells—which express high levels of CXCR4—is regulated by SDF-1. Activation of CXCR4 promotes adhesion to accessory cells (such as stromal cells) and extracellular matrix molecules within the tumor microenvironment. These adhesive interactions result in an increased resistance of SCLC cells to chemotherapy. As such, inhibitors of the SDF-1/CXCR4 axis increases the chemosensitivity of SCLC cells and leads to new therapeutic avenues for patients with SCLC (Hartmann, Burger et al. 2004) and other tumors.

Chemokine-receptor signalling and stem cell trafficking. The SDF-1/CXCR4 axis emerges as a pivotal regulator of trafficking of various types of stem cells in the body. Since most if not all malignancies originate in the stem/progenitor cell compartment, cancer stem cells also express CXCR4 on their surface and, as a result, the SDF-1/CXCR4 axis is involved in directing their trafficking/metastasis to organs that express SDF-1 such as, e.g., lymph nodes, lungs, liver, and bones. In consequence, strategies aimed at modulating the SDF-1/CXCR4 axis have important clinical applications both in regenerative medicine to deliver normal stem cells to the tissues and in clinical oncology to inhibit metastasis of cancer stem cells (Kucia, Reca et al. 2005).

Stem Cell Mobilization. Leukocytes, also known as white blood cells, include neutrophils, macrophages, eosinophils, basophils/mast cells, B cells and T cells. White blood cells are continuously replaced via the hematopoietic system, by the action of colony stimulating factors (CSFs) and various cytokines on stem cells and progenitor cells in hematopoietic tissues. The most widely known of these factors is granulocyte colony stimulating factor (abbr. G-CSF) which has been approved for use in counteracting the negative effects of chemotherapy by stimulating the production of white blood cells and progenitor cells (peripheral blood stem cell mobilization). There are a number of cell surface antigens that are used as markers for the characterization of the stem and progenitor cell populations. These markers are also subject to change, whenever new, more specific markers are discovered. Hematopoietic stem cells are currently characterized by being CD34+, c-kit+, Sca-1+, CD45+, lin−, and CD38− (CD 38 is also a lineage marker, this is therefore redundant to lin⁻) The bone marrow is also a host for several other stem cell types that are not hematopoietic, but may give rise to other cell types and tissues: Mesenchymal stem cells are characterized as CD34+, Sca-1+, lin−, BMPR+ and/or STRO-1+, tissue-committed stem cells from bone marrow: are currently defined as being CXCR4+, CD34+, CD45−. Subpopulations of the tussue-committed stem cells from bone marrow are (Majka et al. 2005):

skeletal stem cells: Myf5+, MyoD+
cardiac stem cells: NKx2.5+, GATA4+
liver stem cells: CK19+, α-fetoprotein+
neural stem cells: nestin+, GATA4+

Several other factors have been reported to increase white blood cells and progenitor cells in both human and animal subjects. These agents include granulocyte-macrophage colony stimulating factor (abbr. GM-CSF), Interleukin-1 (abbr. IL-1), Interleukin-3 (abbr. IL-3), Interleukin-8 (abbr. IL-8), PIXY-321 (abbr. GM-CSF/IL-3 fusion protein), macrophage inflammatory protein (abbr. MIP), GROβ (CXCL2) and GROβT(CXCL2Δ4), stem cell factor, thrombopoietin and growth related oncogene, as single agents or in combination (Broxmeyer, Benninger et al. 1995; Glaspy, Davis et al. 1996; Rosenfeld, Bolwell et al. 1996; Glaspy, Shpall et al. 1997; Vadhan-Raj, Murray et al. 1997; Broxmeyer, Orazi et al. 1998; Dale, Liles et al. 1998; Pruijt, Willemze et al. 1999; King, Horowitz et al. 2001).

While endogenous growth factors are pharmacologically effective, the well known disadvantages of employing proteins and peptides as pharmaceuticals underline the need to add to the repertoire of such growth factors further agents which are effective insofar, i. e. which increase progenitor cells of leukocytes and stem cells, respectively, preferably increase the level thereof in peripheral blood of a subject. Accordingly, one problem underlying the instant application is to provide means and methods for increasing progenitor cells of leukocytes and stem cells, respectively, more specifically for increasing the level thereof in peripheral blood of a subject. A further problem underlying the instant application is to provide means and methods for the treatment of diseases which are caused by or associated with low level of progenitor cells of leukocytes and stem cells, respectively.

Stem cells are either mobilized in order to directly enable the repair of damaged tissues in the same patient in which they are mobilized, or they are mobilized and collected from a human leukocyte antigen (HLA) matched donor and administered to the patient either intra venously or directly into an affected tissue. The latter can also be done with stem cells that were mobilized from the patient himself. Before administration of the stem cells, they can be expanded and/or differentiated in vitro.

Allergic airway diseases and contact allergies. SDF-1 was found to act as a chemotactic agent on mature and precursor mast cells—especially when histamine is released from mature mast cells, e.g. by IgE signalling through binding to the Fc-epsilon receptor on the mast cell surface (Godot, Arock et al. 2007). In a mouse model of allergic airway disease, antibody-mediated neutralisation of CXCR4, which is expressed on leukocytes as outlined above, reduced airway hyper-responsiveness. The antibodies also reduced lung eosinophilia, particularly in bronchoalveolar lavage fluid and interstitium, by half, indicating that CXCR4-mediated signals contribute to lung inflammation. SDF-1α neutralization resulted in a similar reduction in both lung allergic inflammation and airway hyper-responsiveness (Gonzalo, Lloyd et al. 2000). There is also evidence that SDF-1 contributes to angiogenesis. This has been explicitly shown by Hoshin et al. in asthma by analysing bronchial biopsies for angiogenesis and SDF-1 expression. Immunohistochemistry on sections of these biopsies showed that asthmatic subjects had a higher degree of vascularity and a greater number of SDF-1 positive cells compared to control subjects (Hoshino, Aoike et al. 2003).

Moreover, clinical and experimental evidence indicates that skin-infiltrating leukocytes play a crucial role in the initiation and maintenance of atopic dermatitis and it has been shown that SDF-1 is an important factor for the recruitment of T-lymphocytes and dendritic cells, especially Langerhans-type dentritic cells (Gombert, Dieu-Nosjean et al. 2005).

Psoriasis. Psoriasis is an inflammatory skin disease with an underlying auto-immune component. Psoriasis is characterised by strong leukocyte infiltration of the affected skin, with T cells playing a prominent role. Zhou et al. found amongst others an increased SDF-1 mRNA expression in psoriatric skin lesions (Zhou, Krueger et al. 2003).

Joint inflammation. There is evidence in the literature for the involvement of the SDF-1-CXCL4-axis in joint inflammation. Matthys et al. showed that AMD3100, a potent and specific antagonist of CXCR4, inhibited autoimmune joint inflammation in IFN-gamma receptor-deficient mice (Matthys, Hatse et al. 2001). Expression of SDF-1 was also observed in synovial biopsies and by RT-PCR from subjects affected by spondyloarthropathy, rheumatoid arthritis, psoriatric arthritis and degenerative joint disease (osteoarthritis). However, over-expression was not seen in all cases (Gu, Marker-Hermann et al. 2002). Similar results were found for CXCR4 using RT-PCR.

Rheumatoid arthritis. More recently, SDF-1 levels were found to be increased in synovial fluid from rheumatoid arthritis patients compared to osteoarthritis patients (Kim, Cho et al. 2007). The authors also described that in cell culture, SDF-1 expression from fibroblast-like synoviocytes was up-regulated by co-culturing these cells with T cells. This effect was also observed by addition of IL-17, a T-cell cytokine, to the culture medium.

Immunohistochemistry on joint biopsy sections revealed that SDF-1 is expressed in the synovium of joints affected by psoriatric arthritis. Rapid and significant clinical improvement was observed after infliximab treatment in all 9 patients. This was accompanied by a reduction of synovial SDF-1 levels amongst other growth factors (biopsies were taken after 8 weeks of therapy) (Gu, Marker-Hermann et al. 2002).

While there are manifestations that leukocyte infiltration is characteristic for allergic diseases, allergic reactions and inflammation in autoimmune diseases, no effective treatment of such diseases could be developed so far. Insofar further agents that affect the course of such diseases, and preferably affect leukocyte infiltration, are needed. Accordingly, a further problem underlying the instant application is to provide means and methods for inhibiting or reducing the infiltration of leukocytes into tissues. A further problem underlying the instant application is to provide means and methods for the treatment of diseases which are caused by or are associated with infiltration of leukocytes into tissues or with an increased level of infiltration of such leukocytes into tissues.

The signalling of SDF-1 and its receptor affects the migration of cells within the body, preferably from one tissue into another tissue, from a tissue into the peripheral blood and/or from the peripheral blood into a tissue, leading to several diseases and disorders. A specific intereference, preferably inhibition of interaction between of SDF-1 and the SDF-1 receptor or receptors, may cause amelioration of several diseases and disorders. In view of the above, a still further, more general problem underlying the instant application is to provide means and methods to affect the migration of cells within the body, preferably from one tissue to another tissue, from a tissue into the peripheral blood and/or from the peripheral blood into a tissue, whereby such migration leads to or is associated with several diseases and disorders. Insofar, a further problem underlying the instant application is to provide means and methods which are caused by or associated with the migration of cells within the body, preferably from one tissue to another tissue, from a tissue into the peripheral blood and/or from the peripheral blood into a tissue, leading to several diseases and disorders.

The problem underlying the present invention is solved by the subject matter of the independent claims. Preferred embodiments may be taken from the dependent claims.

More specifically, the problem underlying the instant application is solved in a first aspect by a nucleic acid molecule binding to SDF-1, whereby the nucleic acid molecule influences migration of cells.

In a first embodiment of the first aspect, the cells express an SDF-receptor, whereby the SDF-1 receptor is one preferably selected from CXCR4 and CXCR7.

In a second embodiment of the first aspect, which is also an embodiment of the first embodiment of the first aspect migration of cells comprises mobilization of progenitor cells, stem cells, cancer cells, long-lived plasma cells, B cells and/or T cells into the peripheral blood of a subject, whereby preferably the B cells and/or T cells are memory B cells and/or memory T cells.

In a third embodiment of the first aspect, which is also an embodiment of the second embodiment of the first aspect the progenitor cells and/or the stem cells comprise CD34+ progenitor cells.

In a fourth embodiment of the first aspect, which is also an embodiment of the second and third embodiment of the first aspect the mobilization of the progenitor cells and/or the stem cells takes place in a hematopoietic tissue.

In a fifth embodiment of the first aspect, which is also an embodiment of the fourth embodiment of the first aspect the hematopoietic tissue is at least one of myeloid tissue and lymphoid tissue, whereby preferably the myeloid tissue is located in the bone marrow, and preferably the lymphoid tissue is located in the mucosa of the digestive tract, the respiratory tract, the lymph nodes, the spleen, the thymus and/or lymphoid follicles in an inflamed tissue.

In a sixth embodiment of the first aspect, the nucleic acid molecule inhibits migration of leukocytes.

In a seventh embodiment of the first aspect, which is also an embodiment of the sixth embodiment of the first aspect the leukocytes are T-lymphocytes, B-lymphocytes, monocytes, macrophages, eosinophils, neutrophils, basophils, dendritic cells and/or mast cells.

In an eighth embodiment of the first aspect, which is also an embodiment of the sixth and seventh embodiment of the first aspect, upon migration of the leukocytes, the leukocytes are accumulated in a tissue, whereby preferably the accumulation of the leukocytes leads to an inflammation in the said tissue.

In a ninth embodiment of the first aspect, which is also an embodiment of the eighth embodiment of the first aspect the tissue comprises skin, mucosa, organs as selected from but not restricted to eye, brain, lung, kidneys, heart, liver, gastrointestinal tract, spleen, bones and/or lymphatic system, preferably skin and/or the mucosa of airways.

In a tenth embodiment of the first aspect, which is also an embodiment of the first aspect and of any of the first to the ninth embodiment of the first aspect the nucleic acid molecule is selected from the group comprising type A nucleic acid molecules, type B nucleic acid molecules, type C nucleic acid molecules and nucleic acid molecules having a nucleic acid sequence according to any of SEQ.ID.No. 142, SEQ.ID.No. 143 and SEQ.ID.No. 144.

In an eleventh embodiment of the first aspect, which is also an embodiment of the tenth embodiment of the first aspect the type A nucleic acid molecules comprise the following core nucleotide sequence:

(SEQ. ID. 19)
5' AAAGYRACAHGUMAAX$_4$UGAAAGGUARC 3' whereby $X_A$ is either absent or is A.

In a twelfth embodiment of the first aspect, which is also an embodiment of the eleventh embodiment of the first aspect the type A nucleic acid molecules comprise a core nucleotide sequence selected from the group comprising
5' AAAGYRACAHGUMAAUGAAAGGUARC 3' (SEQ.ID.No. 20),
5' AAAGYRACAHGUMAAAUGAAAGGUARC 3' (SEQ.ID.No. 21), and
5' AAAGYAACAHGUCAAUGAAAGGUARC 3' (SEQ.ID.No. 22), preferably the core nucleotide sequence comprises 5' AAAGYAACAHGUCAAUGAAAGGUARC 3' (SEQ. ID. No. 22).

In a 13$^{th}$ embodiment of the first aspect, which is also an embodiment of the eleventh and the twelfth embodiment of the first aspect the nucleic acid molecule comprise in 5'→3' direction a first stretch of nucleotides, the core nucleotide sequence, and a second stretch of nucleotides.

In a 14$^{th}$ embodiment of the first aspect, which is also an embodiment of the eleventh and the twelfth embodiment of the first aspect the nucleic acid molecule comprise in 5'→3' direction a second stretch of nucleotides, the core nucleotide sequence, and a first stretch of nucleotides.

In a 15th embodiment of the first aspect, which is also an embodiment of the 13th and the 14th embodiment of the first aspect the nucleic acid molecule comprises the first and the second stretch of nucleotides and said first and said second stretch of nucleotides optionally hybridize with each other, whereby upon hybridization a double-stranded structure is formed.

In a 16th embodiment of the first aspect, which is also an embodiment of any of the 13th to 15th embodiment of the first aspect the double-stranded structure consists of four to six base pairs, preferably five base pairs.

In a 17th embodiment of the first aspect, which is also an embodiment of any of the 13th to 16th embodiment of the first aspect the first stretch of nucleotides comprise a nucleotide sequence of 5' $X_1X_2NNBV$ 3' (SEQ.ID.No. 44) and the second stretch of nucleotides comprises a nucleotide sequence of 5' $BNBNX_3X_4$ 3' (SEQ.ID.No. 45) whereby $X_1$ is either absent or R, $X_2$ is S, $X_3$ is S and $X_4$ is either absent or Y;

or $X_1$ is absent, $X_2$ is either absent or S, $X_3$ is either absent or S and $X_4$ is absent.

In an 18th embodiment of the first aspect, which is also an embodiment of any of the 13th to 17th embodiment of the first aspect the first stretch of nucleotides comprises a nucleotide sequence of 5' RSHRYR 3' (SEQ.ID.No. 23) and the second stretch of nucleotides comprises a nucleotide sequence of 5' YRYDSY 3' (SEQ.ID.No. 24), preferably the first stretch of nucleotides comprises a nucleotide sequence of 5' GCUGUG 3' and the second stretch of nucleotides comprises a nucleotide sequence of 5' CGCAGC 3'.

In a 19th embodiment of the first aspect, which is also an embodiment of any of the 13th to 17th embodiment of the first aspect the first stretch of nucleotides comprises a nucleotide sequence of 5' $X_2BBBS$ 3' (SEQ.ID.No. 42) and the second stretch of nucleotides comprises a nucleotide sequence of 5' $SBBVX_3$ 3' (SEQ.ID.No. 43), whereby $X_2$ is either absent or is S and $X_3$ is either absent or is S;

preferably the first stretch of nucleotides comprises a nucleotide sequence of 5' CUGUG 3' and the second stretch of nucleotides comprises a nucleotide sequence of 5' CGCAG 3';

or the first stretch of nucleotides comprises a nucleotide sequence of 5' GCGUG 3' and the second stretch of nucleotides comprises a nucleotide sequence of 5' CGCGC 3'.

In a 20th embodiment of the first aspect, which is also an embodiment of any of the 11th to 19th embodiment of the first aspect the nucleic acid molecule has a nucleic acid sequence according to any of SEQ.ID.Nos. 5 to 18, 25 to 41, 133, 137, 139 to 141.

In a 21st embodiment of the first aspect, which is also an embodiment of the tenth embodiment of the first aspect the type B nucleic acid molecules comprise the following core nucleotide sequence:

(SEQ. ID. No. 57)
5' GUGUGAUCUAGAUGUADWGGCUGWUCCUAGUYAGG 3'.

In a 22nd embodiment of the first aspect, which is also an embodiment of the 21st embodiment of the first aspect the type B nucleic acid molecules comprise a core nucleotide sequence of (SEQ. ID. No. 58)
GUGUGAUCUAGAUGUADUGGCUGAUCCUAGUCAGG:

In a 23rd embodiment of the first aspect, which is also an embodiment of any of the 21st to 22nd embodiment of the first aspect the nucleic acid molecule comprise in 5'→3' direction a first stretch of nucleotides, the core nucleotide sequence, and a second stretch of nucleotides.

In a 24th embodiment of the first aspect, which is also an embodiment of any of the 21st to 22nd embodiment of the first aspect the nucleic acid molecule comprise in 5'→3' direction a second stretch of nucleotides, the core nucleotide sequence, and a first stretch of nucleotides.

In a 25th embodiment of the first aspect, which is also an embodiment of any of the 23rd to 24th embodiment of the first aspect the nucleic acid molecule comprises the first and the second stretch of nucleotides and said first and said second stretch of nucleotides optionally hybridize with each other, whereby upon hybridization a double-stranded structure is formed.

In a 26th embodiment of the first aspect, which is also an embodiment of any of the 21st to 25th embodiment of the first aspect the double-stranded structure consists of four to six base pairs, preferably five base pairs.

In a 27th embodiment of the first aspect, which is also an embodiment of any of the 23rd to 26th embodiment of the first aspect the first stretch of nucleotides comprises a nucleotide sequence of 5' $X_1X_2SVNS$ 3' (SEQ.ID.No. 77) and the second stretch of nucleotides comprises a nucleotide sequence of 5' $BVBSX_3X_4$ 3' (SEQ.ID.No. 78), whereby $X_1$ is either absent or is A, $X_2$ is G, $X_3$ is C and $X_4$ is either absent or is U;

or $X_1$ is absent, $X_2$ is either absent or is G, $X_3$ is either absent or is C and $X_4$ is absent.

In a 28th embodiment of the first aspect, which is also an embodiment of any of the 23rd to 27th embodiment of the first aspect the first stretch of nucleotides comprises a nucleotide sequence of 5' $X_1GCRWG$ 3' (SEQ.ID.No. 59) and the second stretch of nucleotides comprises a nucleotide sequence of 5' $KRYSCX_4$ 3'(SEQ.ID.No. 60), whereby $X_1$ is either absent or A, and $X_4$ is either absent or U.

In a 29th embodiment of the first aspect, which is also an embodiment of any of the 23rd to 28th embodiment of the first aspect first stretch of nucleotides comprises a nucleotide sequence of 5' $X_1GCGUG$ 3' (SEQ.ID.No. 75) and the second stretch of nucleotides comprises a nucleotide sequence of 5' $UACGCX_4$ 3' (SEQ.ID.No. 76), whereby $X_1$ is either absent or A, and $X_4$ is either absent or U, preferably the first stretch of nucleotides comprises a nucleotide sequence of 5' AGCGUG 3' and the second stretch of nucleotides comprises a nucleotide sequence of 5' UACGCU 3'.

In a 30th embodiment of the first aspect, which is also an embodiment of any of the 23rd to 27th embodiment of the first aspect the first stretch of nucleotides comprises a nucleotide sequence of 5' $X_2SSBS$ 3' (SEQ.ID.No. 73) and the second stretch of nucleotides comprises a nucleotide sequence of 5' $BVSSX_3$ 3' (SEQ.ID.No. 74), whereby $X_2$ is either absent or G, and $X_3$ is either absent or C, preferably the first stretch of nucleotides comprises a nucleotide sequence of 5' GCGUG 3' and the second stretch of nucleotides comprises a nucleotide sequence of 5' UACGC 3'.

In a 31st embodiment of the first aspect, which is also an embodiment of any of the 21st to the 30th embodiment of the first aspect the nucleic acid molecule has a nucleic acid sequence according to any of SEQ.ID.Nos. 46 to 56, 61 to 72, and 132.

In a 32nd embodiment of the first aspect, which is also an embodiment of the tenth embodiment of the first aspect the type C nucleic acid molecules comprise a core nucleotide sequence of GGUYAGGGCUHRX$_A$AGUCGG (SEQ-.ID.No. 90), whereby X$_A$ is either absent or is A.

In a 33rd embodiment of the first aspect, which is also an embodiment of the 32nd embodiment of the first aspect the type C nucleic acid molecules comprise a core nucleotide sequence selected from the group comprising
5' GGUYAGGGCUHRAAGUCGG 3' (SEQ.ID.No. 91),
5' GGUYAGGGCUHRAGUCGG 3' (SEQ.ID.No. 92), and
5' GGUUAGGGCUHGAAGUCGG 3' (SEQ.ID.No. 93),
preferably the core nucleotide sequence comprises 5' GGUUAGGGCUHGAAGUCGG 3' (SEQ. ID. No. 93).

In a 34th embodiment of the first aspect, which is also an embodiment of any of the 32nd to 33rd embodiment of the first aspect the nucleic acid molecule comprises in 5'→3' direction a first stretch of nucleotides, the core nucleotide sequence, and a second stretch of nucleotides.

In a 35th embodiment of the first aspect, which is also an embodiment of any of the 32nd to 33rd embodiment of the first aspect the nucleic acid molecule comprise in 5'→3' direction a second stretch of nucleotides, the core nucleotide sequence, and a first stretch of nucleotides.

In a 36th embodiment of the first aspect, which is also an embodiment of any of the 34th to 35th embodiment of the first aspect the nucleic acid molecule comprises the first and the second stretch of nucleotides and whereby at least a part of said first stretch and at least a part of said second stretch of nucleotides optionally hybridize with each other, whereby upon hybridization a double-stranded structure is formed.

In a 37th embodiment of the first aspect, which is also an embodiment of any of 34th to 36th embodiment of the first aspect the length of the first stretch and the length of the second stretch is individually and independently 0 to 17 nucleotides, preferably 4 to 10 nucleotides and more preferably 4 to 6 nucleotides.

In a 38th embodiment of the first aspect, which is also an embodiment of any of the 36th to 37th embodiment of the first aspect the double-stranded structure comprises 4 to 10 base pairs, preferably 4 to 6 base pairs, more preferably 5 base pairs.

In a 39th embodiment of the first aspect, which is also an embodiment of the 38th embodiment of the first aspect the double-stranded structure comprises 4 to 10 consecutive base pairs, preferably 4 to 6 consecutive base pairs, more preferably 5 consecutive base pairs.

In a 40th embodiment of the first aspect, which is also an embodiment of any of the 34th to 39th embodiment of the first aspect the first stretch of nucleotides comprises a nucleotide sequence of 5' RKSBUSNVGR 3' (SEQ.ID.No. 120) and the second stretch of nucleotides comprises a nucleotide sequence of 5' YYNRCASSMY 3' (SEQ.ID.No. 121), preferably the first stretch of nucleotides comprises a nucleotide sequence of 5' RKSBUGSVGR 3' (SEQ.ID.No. 122) and the second stretch of nucleotides comprises a nucleotide sequence of 5' YCNRCASSMY 3' (SEQ.ID.No. 123).

In a 41st embodiment of the first aspect, which is also an embodiment of any of the 34th to 39th embodiment of the first aspect the first stretch of nucleotides comprises a nucleotide sequence of 5' X$_S$SSSV 3' (SEQ.ID.No. 124) and the second stretch of nucleotides comprises a nucleotide sequence of 5' BSSSX$_S$ 3' (SEQ.ID.No. 125), whereby X$_s$ is either absent or is S.

In a 42nd embodiment of the first aspect, which is also an embodiment of any of the 34th to 39th and the 41st embodiment of the first aspect the first stretch of nucleotides comprises a nucleotide sequence of 5' SSSSR 3' (SEQ.ID.No. 130) and the second stretch of nucleotides comprise a nucleotide sequence of 5' YSBSS 3' (SEQ.ID.No. 131), preferably the first stretch of nucleotides comprises a nucleotide sequence of 5' SGGSR 3' (SEQ.ID.No. 126) and the second stretch of nucleotides comprises a nucleotide sequence of 5' YSCCS 3' (SEQ.ID.No. 127).

In a 43rd embodiment of the first aspect, which is also an embodiment of any of the 34th to 39th, the 41st and the 42nd embodiment of the first aspect the first stretch of nucleotides comprises a nucleotide sequence of 5' GCSGG 3' (SEQ-.ID.No. 128) and the second stretch of nucleotides comprises a nucleotide sequence of 5' CCKGC 3' (SEQ.ID.No. 129), preferably the first stretch of nucleotides comprises a nucleotide sequence of 5' GCCGG 3' and the second stretch of nucleotides comprises a nucleotide sequence of 5' CCGGC 3'.

In a 44th embodiment of the first aspect, which is also an embodiment of any of the 34th to 39th embodiment of the first aspect the first stretch of nucleotides comprises a nucleotide sequence of 5' CGUGCGCUUGAGAUAGG 3' (SEQ ID NO:244) and the second stretch of nucleotides comprises a nucleotide sequence of 5' CUGAUUCUCACG 3' (SEQ ID NO:245).

In a 45th embodiment of the first aspect, which is also an embodiment of any of the 34th to 39th embodiment of the first aspect the first stretch of nucleotides comprises a nucleotide sequence of 5' UGAGAUAGG 3' (SEQ ID NO:244) and the second stretch of nucleotides comprises a nucleotide sequence of 5' CUGAUUCUCA 3' (SEQ ID NO:246).

In a 46th embodiment of the first aspect, which is also an embodiment of any of the 34th to 39th embodiment of the first aspect the first stretch of nucleotides comprises a nucleotide sequence of 5' GAGAUAGG 3' (SEQ ID NO:244) and the second stretch of nucleotides comprises a nucleotide sequence of 5' CUGAUUCUC 3' (SEQ ID NO:246).

In a 47th embodiment of the first aspect, which is also an embodiment of any of the 32nd to 46th embodiment of the first aspect the nucleic acid molecule has a nucleic acid sequence according to any of SEQ.ID.Nos. 79 to 89, 94 to 119, and 134 to 136.

In a 48th embodiment of the first aspect, which is also an embodiment of tenth embodiment of the first aspect the nucleic acid molecule has a nucleic acid sequence according to any of SEQ.ID.Nos. 142 to 144.

In a 49th embodiment of the first aspect, which is also an embodiment of the first aspect and of any of the first to the 48th embodiment of the first aspect the nucleic acid molecule is an antagonist to SDF-1.

In a 50th embodiment of the first aspect, which is also an embodiment of the first aspect and of any of the first to the 48th embodiment of the first aspect the nucleic acid molecule is an antagonist of the SDF-1 receptor system, whereby the SDF-1 receptor of the SDF-1 receptor system is one preferably selected from CXCR4 and CXCR7.

In a 51$^{st}$ embodiment of the first aspect, which is also an embodiment of the first aspect and of any of the first to the 50$^{th}$ embodiment of the first aspect the SDF-1 is a human SDF-1 and/or the SDF-1 receptor of the SDF-1 receptor system is a human SDF-1 receptor.

In a 52$^{nd}$ embodiment of the first aspect, which is also an embodiment of the first aspect and of any of the first to the 51$^{st}$ embodiment of the first aspect SDF-1 comprises an amino acid sequence according to SEQ ID No. 1.

In a 53$^{rd}$ embodiment of the first aspect, which is also an embodiment of the first aspect and of any of the first to the 52$^{nd}$ embodiment of the first aspect the nucleic acid comprises a modification.

In a 54$^{th}$ embodiment of the first aspect, which is also an embodiment of the 53$^{rd}$ embodiment of the first aspect the modification is selected from the group comprising a HES moiety and a PEG moiety.

In a 55$^{th}$ embodiment of the first aspect, which is also an embodiment of the 54$^{th}$ embodiment of the first aspect the modification is a PEG moiety consisting of a straight or branched PEG, whereby the molecular weight of the PEG moiety is preferably from about 2 to 180 kD, more preferably from about 60 to 140 kD and most preferably about 40 kD.

In a 56$^{th}$ embodiment of the first aspect, which is also an embodiment of the 54$^{th}$ embodiment of the first aspect the modification is a HES moiety, whereby preferably the molecular weight of the HES moiety is from about 10 to 130 kD, more preferably from about 30 to 130 kD and most preferably about 100 kD.

57$^{th}$ embodiment of the first aspect which is also an embodiment of the first aspect and of any of the first to the 56$^{th}$ embodiment of the first aspect the nucleotides of the nucleic acid are L-nucleotides, preferably the nucleotides of the sequences according to any of SEQ.ID:No. 19, 20, 21, 22, 57, 58, 90, 91, 92, and 93.

The problem underlying the instant application is solved in a second aspect by a pharmaceutical composition comprising a nucleic acid according to the first aspect and any embodiments thereof, and optionally at least a further constituent, whereby the further constituent is selected from the group comprising pharmaceutically acceptable excipients and pharmaceutically active agents.

The problem underlying the instant application is solved in a third aspect by the use of a nucleic acid according to the first aspect and any embodiments thereof, for the manufacture of a medicament.

In a first embodiment of the third aspect, the medicament is used for mobilization of progenitor cell and/or stem cells into the peripheral blood, and/or for the treatment of diseases and/or disorders preferably selected from the group comprising wound healing; burn; disorders caused by or associated with damaged organ tissue and/or damaged vasculature, whereby such disorders are selected from retinal and choroidal damage, stroke, myocardial damage, myocardial infarct, ischemia after organ transplantation and traumatic injury; and hematopoietic disorders, whereby such disorders are selected from aplastic anemia, leukaemia, drug-induced anemia and leukopenia, and bacterial infection in leukopenia.

In a second embodiment of the third aspect the medicament is for mobilization of cancer cells into the peripheral blood of a subject.

In a third embodiment of the third aspect which is also an embodiment of the second embodiment of the third aspect the cancer cells are selected from leukemic cells, lymphoma cells, cancer stem cells, cancer cells with metastatic potential and cancer metastases.

In a fourth embodiment of the third aspect which is also an embodiment of any of the second to the third embodiment of the third aspect of the medicament is used in combination with a second pharmaceutically active agent, whereby the second pharmaceutically active agent is suitable for mobilizing cancer cells into the peripheral blood of a subject, whereby the second pharmaceutically active agent is preferably selected from cancer cell mobilizing agents.

In a fifth embodiment of the third aspect which is also an embodiment of any of the second to the fourth embodiment of the third aspect the medicament is used in combination with a third pharmaceutically active agent, whereby the third pharmaceutically active agent damages, destroys and/or labels the cancer cells in the peripheral blood, whereby the label leads to an activation of body's defences.

In a sixth embodiment of the third aspect which is also an embodiment of any of the second to the fifth embodiment of the third aspect is subsequently or concomitantly undergoing chemotherapy and/or radiotherapy.

In a seventh embodiment of the third aspect which is also an embodiment of any of the fifth to the sixth embodiment of the third aspect the medicament is used for the treatment and/or prevention of cancer, preferably solid tumours and hematological cancer, more preferably leukemia, lymphoma, and myeloma.

In an eighth embodiment of the third aspect the medicament is for mobilization of long-lived plasma cells, B cells and/or T cells into the peripheral blood of a subject, whereby preferably the B cells and/or T cells are memory B cells and/or memory T cells.

In a ninth embodiment of the third aspect which is also an embodiment of the eighth embodiment of the third aspect the medicament is used in combination with a second pharmaceutically active agent, whereby the second pharmaceutically active agent is used for mobilization of long-lived plasma cells, B cells and/or memory T cells into the peripheral blood of a subject, whereby the second pharmaceutically active agent is preferably selected from cell mobilizing agents.

In a tenth embodiment of the third aspect which is also an embodiment of any of the eighth to the ninth embodiment of the third aspect the medicament is used in combination with a third pharmaceutically active agent and the third pharmaceutically active agent damages, destroys and/or labels the long-lived plasma cells, B cells and/or T cells in the peripheral blood, whereby the label leads to an activation of body's defences.

In an eleventh embodiment of the third aspect which is also an embodiment of any of the eighth to the tenth embodiment of the third aspect the the subject is subsequently or concomitantly undergoing chemotherapy and/or radiotherapy.

In a twelfth embodiment of the third aspect which is also an embodiment of any of the eighth to the eleventh embodiment of the third aspect medicament is used for the treatment and/or prevention of systemic autoimmune diseases whereby such systemic autoimmune disease is preferably selected from allergy, warm and cold autoimmune hemolytic anemia, systemic inflammatory response syndrome, hemorrhagic shock, diabetes type 1, diffuse scleroderma, polychondritis, polyglandular autoimmune syndrome, systemic lupus erythematosus and manifestations thereof, rheumatoid arthritis, rheumatic disease in the eye, brain, lung, kidneys, heart, liver, gastrointestinal tract, spleen, skin, bones, lymphatic system, blood or other organs;

autoimmune diseases of the gastrointestinal tract whereby such autoimmune disease of the gastrointestinal tract is preferably selected from Crohn's disease, colitis ulcerosa, celiac disease, gluten intolerance, inflammatory bowel disease, pancreatitis, eosinophilic esophagitis;

autoimmune diseases of the skin whereby such autoimmune disease of the skin is preferably selected from psoriasis, urticaria, dermatomyositis, pemphigus vulgaris, pemphigus foliaceus, bullous pemphigoid, Morphea/linear scleroderma, vitiligo, dermatitis herpetiformis or Duhring's disease, lichen sclerosis;

autoimmune diseases of the vasculature whereby such autoimmune disease of the vasculature is preferably selected from vasculitides, preferably arteritis temporalis, vasculitis, vascular leakage, polymyalgia rheumatica, atherosclerosis, Churg-Strauss syndrome, Takayasu arteritis, Goodpasture syndrome, preferably mostly affecting the kidneys, more specifically the glomeruli, and/or also mostly affecting the lungs, glomerulonephritis, polyarteritis nodosa, Behçet's disease;

autoimmune diseases of the nervous system whereby such autoimmune disease of the nervous system is preferably selected from multiple sclerosis, chronic inflammatory demyelinating polyneuropathy, neurocognitive dysfunction, stiff-man syndrome, Guillain-Barré syndrome, myasthenia gravis, Lambert-Eaton syndrome;

muscular skeletal autoimmune diseases whereby such muscular skeletal autoimmune disease is preferably selected from ankylosing spodylitis, sarcoidosis, polymyalgia rheumatica, polymyositis, psoriatic arthritis, rheumatic fever, polychondritis, fibromyalgia, juvenile rheumatoid arthritis, Lyme disease, reactive arthritis, spondyloarthropathy, degenerative joint disease;

other autoimmune diseases whereby such other autoimmune diseases are preferably selected from Cogan syndrome, autoimmune adrenalitis, Ménière's disease, local inflammations, alopecia areata, acute inflammatory diseases, primary biliary cirrhosis, Sjörgen's syndrome, scleroderma such as diffuse scleroderma, CREST syndrome and/or Morphea/linear scleroderma, autoimmune uveitis, Hashimoto thyroiditis, Graves disease, autoimmune hepatitis, glomerulonephritis, anti-phospholipid syndrome, idiopatic pulmonar fibrosis, autoimmune infertility, immune complex disorders and peritonitis;

transplant rejection of a transplanted organ, whereby such organ is selected from liver, kidney, intestine, lung, heart, skin, limb, cornea, islets of Langerhans, bone marrow, blood vessels, pancreas;

and/or Graft-versus-Host-Disease after bone marrow transplantation.

In a 13$^{th}$ embodiment of the third aspect the medicament is for inhibition of migration of leukocytes.

In a 14$^{th}$ embodiment of the third aspect which is also an embodiment of the 13$^{th}$ embodiment of the third aspect the medicament is for prevention and/or treatment of transplant rejection of transplanted organs, such as liver, kidney, intestine, lung, heart, skin, limb, cornea, islets of Langerhans, bone marrow, blood vessels and pancreas.

In a 15$^{th}$ embodiment of the third aspect which is also an embodiment of the 13$^{th}$ embodiment of the third aspect the medicament is used for the treatment and/or prevention of inflammation occurring in or being associated with systemic autoimmune diseases whereby such systemic autoimmune disease is preferably selected from allergy, warm and cold autoimmune hemolytic anemia, systemic inflammatory response syndrome, hemorrhagic shock, diabetes type 1, diffuse scleroderma, polychondritis, polyglandular autoimmune syndrome, systemic lupus erythematosus and manifestations thereof, rheumatoid arthritis, rheumatic disease in the eye, brain, lung, kidneys, heart, liver, gastrointestinal tract, spleen, skin, bones, lymphatic system, blood or other organs;

autoimmune diseases of the gastrointestinal tract whereby such autoimmune disease of the gastrointestinal tract is preferably selected from Crohn's disease, colitis ulcerosa, celiac disease, gluten intolerance, inflammatory bowel disease, pancreatitis, eosinophilic esophagitis;

autoimmune diseases of the skin whereby such autoimmune disease of the skin is preferably selected from psoriasis, urticaria, dermatomyositis, pemphigus vulgaris, pemphigus foliaceus, bullous pemphigoid, Morphea/linear scleroderma, vitiligo, dermatitis herpetiformis or Duhring's disease, lichen sclerosis;

autoimmune diseases of the vasculature whereby such autoimmune disease of the vasculature is preferably selected from vasculitides, preferably arteritis temporalis, vasculitis, vascular leakage, polymyalgia rheumatica, atherosclerosis, Churg-Strauss syndrome, Takayasu arteritis, Goodpasture syndrome, preferably mostly affecting the kidneys, more specifically the glomeruli, and/or also mostly affecting the lungs, glomerulonephritis, polyarteritis nodosa, Behçet's disease;

autoimmune diseases of the nervous system whereby such autoimmune disease of the nervous system is preferably selected from multiple sclerosis, chronic inflammatory demyelinating polyneuropathy, neurocognitive dysfunction, stiff-man syndrome, Guillain-Barré syndrome, myasthenia gravis, Lambert-Eaton syndrome;

muscular skeletal autoimmune diseases whereby such muscular skeletal autoimmune disease is preferably selected from ankylosing spodylitis, sarcoidosis, polymyalgia rheumatica, polymyositis, psoriatic arthritis, rheumatic fever, polychondritis, fibromyalgia, juvenile rheumatoid arthritis, Lyme disease, reactive arthritis, spondyloarthropathy, degenerative joint disease;

and/or other autoimmune diseases whereby such other autoimmune diseases are preferably selected from Cogan syndrome, autoimmune adrenalitis, Ménière's disease, local inflammations, alopecia areata, acute inflammatory diseases, primary biliary cirrhosis, Sjörgen's syndrome, scleroderma such as diffuse scleroderma, CREST syndrome and/or Morphea/linear scleroderma, autoimmune uveitis, Hashimoto thyroiditis, Graves disease, autoimmune hepatitis, glomerulonephritis, anti-phospholipid syndrome, idiopatic pulmonar fibrosis, autoimmune infertility, immune complex disorders and peritonitis.

In a 16$^{th}$ embodiment of the third aspect which is also an embodiment of the 13$^{th}$ embodiment of the third aspect the medicament is for the treatment and/or prevention of allergic reactions of the skin and/or the mucosa of airways, preferably hay fever, asthma, airway hyper-responsiveness and/or dermatitis.

In a 17$^{th}$ embodiment of the third aspect which is also an embodiment of the 16$^{th}$ embodiment of the third aspect the the dermatitis is contact dermatitis and/or atopic dermatitis.

The problem underlying the instant application is solved in a fourth aspect by a method for obtaining progenitor cells and/or stem cells from a first subject which method comprises a) administering to the subject a nucleic acid according to the first aspect and any embodiments thereof, in an amount effective to mobilize said progenitor cells and/or stem cells into the peripheral blood of said subject;

b) followed by harvesting said progenitor cells and/or stem cells from said subject.

In a first embodiment of the fourth aspect harvesting of progenitor cells and/or stem cells is done by apheresis, leukapheresis, cell sorting and/or flow cytometry.

In a second embodiment of the fourth aspect, which is also an embodiment of the fourth aspect and the first embodiment of the fourth aspect the first subject or a second subject is subsequently or concomitantly undergoing chemotherapy and/or radiotherapy.

In a third embodiment of the fourth aspect, which is also an embodiment of second embodiment of the fourth aspect, after chemotherapy and/or radiotherapy of the first subject or the second subject the harvested progenitor cells and/or stem cells of the first subject or the second subject are administered into the peripheral blood of the first subject or the second subject.

In a fourth embodiment of the fourth aspect, which is also an embodiment of the fourth aspect and any of the first to the third embodiment of the fourth aspect the harvested progenitor cells and/or stem cells are expanded and the expanded progenitor cells and/or stem cells administered to first subject or to the second subject, whereby preferably the expanded progenitor cells and/or stem cells are administered by intraveneous or local injection.

In a fifth embodiment of the fourth aspect, which is also an embodiment of the fourth aspect and any of the first to the fourth embodiment of the fourth aspect the method is used for the treatment of cancer, preferably solid tumours and hematological malignancies.

The problem underlying the instant application is solved in a fifth aspect by the nucleic acid molecule according to the first aspect and any embodiments thereof, for use in a method according to the fourth aspect any embodiments thereof.

The problem underlying the instant application is solved in a sixth aspect by a method for depletion long-lived plasma cells, B cells and/or T cells from a subject which method comprises a) administering to the subject a nucleic acid according to the first aspect and any embodiments thereof, in an amount effective to mobilize said long-lived plasma cells, B cells and/or T cells into the peripheral blood of said subject;

b) followed by harvesting said long-lived plasma cells, B cells and/or T cells from said subject;

whereby preferably the depleted and harvested T cells are memory T cells.

In a first embodiment of the sixth aspect harvesting of the long-lived plasma cells, B cells and/or T cells is done by apheresis, cell sorting and/or flow cytometry, preferably by flow cytometry with surface markers appropriate for said cells.

In a sixth embodiment of the fourth aspect which is also an embodiment of the fourth aspect and any of the first to the fifth embodiment of the fourth aspect; and which is also a second embodiment of the sixth aspect which is also an embodiment of the sixth aspect and the first embodiment of the sixth aspect, the method is used in the treatment and/or prevention of systemic autoimmune diseases whereby such systemic autoimmune disease is preferably selected from allergy, warm and cold autoimmune hemolytic anemia, systemic inflammatory response syndrome, hemorrhagic shock, diabetes type 1, diffuse scleroderma, polychondritis, polyglandular autoimmune syndrome, systemic lupus erythematosus and manifestations thereof, rheumatoid arthritis, rheumatic disease in the eye, brain, lung, kidneys, heart, liver, gastrointestinal tract, spleen, skin, bones, lymphatic system, blood or other organs;

autoimmune diseases of the gastrointestinal tract whereby such autoimmune disease of the gastrointestinal tract is preferably selected from Crohn's disease, colitis ulcerosa, celiac disease, gluten intolerance, inflammatory bowel disease, pancreatitis, eosinophilic esophagitis;

autoimmune diseases of the skin whereby such autoimmune disease of the skin is preferably selected from psoriasis, urticaria, dermatomyositis, pemphigus vulgaris, pemphigus foliaceus, bullous pemphigoid, Morphea/linear scleroderma, vitiligo, dermatitis herpetiformis or Duhring's disease, lichen sclerosis;

autoimmune diseases of the vasculature whereby such autoimmune disease of the vasculature is preferably selected from vasculitides, preferably arteritis temporalis, vasculitis, vascular leakage, polymyalgia rheumatica, atherosclerosis, Churg-Strauss syndrome, Takayasu arteritis, Goodpasture syndrome, preferably mostly affecting the kidneys, more specifically the glomeruli, and/or also mostly affecting the lungs, glomerulonephritis, polyarteritis nodosa, Behçet's disease;

autoimmune diseases of the nervous system whereby such autoimmune disease of the nervous system is preferably selected from multiple sclerosis, chronic inflammatory demyelinating polyneuropathy, neurocognitive dysfunction, stiff-man syndrome, Guillain-Barré syndrome, myasthenia gravis, Lambert-Eaton syndrome;

muscular skeletal autoimmune diseases whereby such muscular skeletal autoimmune disease is preferably selected from ankylosing spodylitis, sarcoidosis, polymyalgia rheumatica, polymyositis, psoriatic arthritis, rheumatic fever, polychondritis, fibromyalgia, juvenile rheumatoid arthritis, Lyme disease, reactive arthritis, spondyloarthropathy, degenerative joint disease;

other autoimmune diseases whereby such other autoimmune diseases are preferably selected from Cogan syndrome, autoimmune adrenalitis, Ménière's disease, local inflammations, alopecia areata, acute inflammatory diseases, primary biliary cirrhosis, Sjörgen's syndrome, scleroderma such as diffuse scleroderma, CREST syndrome and/or Morphea/linear scleroderma, autoimmune uveitis, Hashimoto thyroiditis, Graves disease, autoimmune hepatitis, glomerulonephritis, anti-phospholipid syndrome, idiopatic pulmonar fibrosis, autoimmune infertility, immune complex disorders and peritonitis;

transplant rejection of a transplanted organ whereby such organ is selected from liver, kidney, intestine, lung, heart, skin, limb, cornea, islets of Langerhans, bone marrow, blood vessels, pancreas;

and/or Graft-versus-Host-Disease after bone marrow transplantation.

The problem underlying the instant application is solved in a seventh aspect by the nucleic acid molecule according to the first aspect and any embodiments thereof, for use in a method according to the sixth aspect and any embodiment thereof.

The problem underlying the instant application is solved in a eighth aspect by the use of a nucleic acid as defined in claim any of the $10^{th}$ to the $57^{th}$ embodiment of the first aspect for the manufacture of a medicament, whereby the medicament is for the treatment and/or prevention of nephropathy, preferably diabetic nephropathy.

The problem underlying the instant application is solved in a ninth aspect by the use of a nucleic acid as defined in claim any of the 10$^{th}$ to the 57$^{th}$ embodiment of the first aspect for the manufacture of a medicament, whereby the medicament is for the treatment and/or prevention of hypertension, preferably pulmonary hypertension.

The problem underlying the instant application is solved in a tenth aspect by the use of a nucleic acid as defined in claim any of the 10$^{th}$ to the 57$^{th}$ embodiment of the first aspect for the manufacture of a medicament, whereby the medicament is for the treatment and/or prevention of fibrosis, preferably idiopathic pulmonary fibrosis.

In a first embodiment of the tenth aspect the medicament is for the treatment and/or prevention of fibrosis within the wound healing process.

The problem underlying the instant application is solved in an eleventh aspect by the use of a nucleic acid as defined in claim any of the 10$^{th}$ to the 57$^{th}$ embodiment for the manufacture of a medicament, whereby the medicament is for the treatment of a disease and/or disorder that involves angiogenesis neovascularization.

In a first embodiment of the eleventh aspect the medicament is used for combination therapy with an agent inhibiting VEGF.

In a second embodiment of the eleventh aspect which is also an embodiment of the first embodiment of the eleventh aspect the medicament is used in subjects that weakly respond to therapy with an agent inhibiting VEGF.

In a third embodiment of the eleventh aspect the medicament is used in subjects that do not respond to therapy with an agent inhibiting VEGF.

In a fourth embodiment of the eleventh aspect the disease and/or disorder involves and/or is associated with choroidal neovascularization.

In a fifth embodiment of the eleventh aspect which is also an embodiment of the eleventh aspect and of any of the first to the fourth embodiment of the eleventh aspect the disease and/or disorder is selected from the group comprising retinal diseases, preferably age-related macular degeneration, diabetic retinopathy, retinal vein occlusion, macular edema and retinal edema.

In a sixth embodiment of the eleventh aspect which is also an embodiment of the eleventh aspect and of any of the first to the third embodiment of the eleventh aspect the disease is selected from the group comprising cancer, preferably solid tumours and metastases.

In an 18$^{th}$ embodiment of the third aspect the medicament is to be administered to a subject which is or is to be undergoing a treatment regimen which depletes progenitor cells and/or stem cells in the subject, preferably depletion in the peripheral blood.

In a 19$^{th}$ embodiment of the third aspect which is also an embodiment of the third aspect and of the 18$^{th}$ embodiment of the third aspect the medicament is to be administered to a subject which is or is to be undergoing chemotherapy and/or radiotherapy.

In a 20$^{th}$ embodiment of the third aspect the medicament is for restoration or improvement of an immune system in a subject.

The problem underlying the instant application is solved in a twelfth aspect by a molecule that inhibits the signalling between SDF-1 and the SDF-1 receptor for the manufacture of a medicament, whereby the medicament is for the treatment and/or prevention of nephropathy, preferably diabetic nephropathy.

In a first embodiment of the twelfth aspect the molecule is an SDF-1 binding molecule or an SDF-1 receptor binding molecule and comprises target-binding nucleic acids like aptamers and Spiegelmers, antibodies and small molecules.

In a second embodiment of the twelfth aspect which is also an embodiment of the twelfth aspect and of the first embodiment of the twelfth aspect the molecule is a nucleic acid molecule as defined in the tenth to the 57$^{th}$ embodiment of the first aspect.

In a third embodiment of the twelfth aspect the molecule is a molecule that inhibits the expression of SDF-1 or the SDF-1 receptor and comprises siRNA molecules, ribozymes, antisense molecules and inhibitors of transcription factors.

The problem underlying the instant application is solved in a 13$^{th}$ aspect by a nucleic acid molecule according to any of the fifth to the 57$^{th}$ embodiment of the first aspect for use in a method for inhibiting the migration of leukocytes.

The problem underlying the instant application is solved in a 14$^{th}$ aspect by an SDF-1 binding molecule that does not cross the blood-brain barrier for use in the mobilization of bone marrow derived stem cells or for use in the manufacture of a medicament, preferably a medicament for the mobilization of bone marrow derived stem cells.

In a first embodiment of the 14$^{th}$ aspect the medicament is used for the amelioration of an injury of the central nervous system and/or for the promotion of tissue repair after stroke, preferably ischemic stroke.

In a second embodiment of the 14$^{th}$ aspect which is also an embodiment of the first embodiment of the 14$^{th}$ aspect the SDF-1 binding molecule comprises target-binding nucleic acids selected from the group comprising aptamers, Spiegelmers, antibodies and small molecules.

In a third embodiment of the 14$^{th}$ aspect which is also an embodiment of the 14$^{th}$ aspect and of any of the first to the second embodiment of the 14$^{th}$ aspect the molecule is a nucleic acid molecule as defined in any of the ninth to 57$^{th}$ embodiments of the first aspect.

The problem underlying the instant application is solved in a 15$^{th}$ aspect by a nucleic acid molecule according to the first aspect and any of the first to the 57$^{th}$ embodiment of the first aspect for use in the treatment of a disease as defined in any of the preceding claims.

The problem underlying the instant application is solved in a 16$^{th}$ aspect by the use of a nucleic acid as defined in the 10$^{th}$ to the 57$^{th}$ embodiment of the first aspect for the manufacture of a medicament, whereby the medicament is for the treatment and/or prevention of the WHIM syndrome.

The problem underlying the instant application is solved in a 17$^{th}$ aspect by the use of a nucleic acid as defined in the 10$^{th}$ to the 57$^{th}$ embodiment of the first aspect for the manufacture of a medicament, whereby the medicament is for the treatment and/or prevention of growth and metastases of cancer, and growth of neoplasia.

The problem underlying the instant application is solved in a 18$^{th}$ aspect by the use of a nucleic acid as defined in the 10$^{th}$ to the 57$^{th}$ embodiment of the first aspect for the manufacture of a medicament, whereby the medicament is administered to a subject prior to chemotherapy, preferably chemotherapy administered for the treatment cancer.

While not wishing to be bound by any theory, the present inventors assume that the nucleic acid molecules according to the present invention inhibit the binding of SDF-1 to its SDF-1 receptor and thus, either directly or indirectly, influence the migration of cells, preferably migration of cells from the peripheral blood into one tissue or more tissue(s) and from tissues into peripheral blood.

However, while not wishing to be bound by any theory, the present inventors assume further that the nucleic acid molecules according to the present invention which inhibit the binding of SDF-1 to the SDF-1 receptor lead to the migration of progenitor cells, stem cells, cancer cells, long-lived plasma cells, B-cells and/or T cells, preferably by mobilization, from tissues into the peripheral blood, by virtue of inhibiting the interaction between SDF-1 and the SDF-1 receptor.

Furthermore and again without wishing to be bound by any theory, the present inventors assume that the nucleic acid molecules according to the present invention which inhibit the binding of SDF-1 to its SDF-1 receptors avoid the migration of leukocytes such as T-lymphocytes, B-lymphocytes, monocytes, macrophages, eosinophils, neutrophils, basophils and/or dendritic and mast cells, preferably in tissues like skin or mucosa, and preferably help to attenuate autoimmune diseases and allergic reactions of skin and mucosa.

In addition and still without wishing to be bound by any theory, the inventors were able to demonstrate that the use of SDF-1 inhibiting agents like the nucleic acid molecules according to the present invention can be used in the treatment of nephropathy, preferably diabetic nephropathy; hypertension, preferably pulmonary hypertension; fibrosis, preferably pulmonary fibrosis, and in the treatment of diseases and/or disorders that involve neovascularization, preferably choroidal nevascularization.

As to the various diseases, conditions and disorders which may be treated or prevented by using the nucleic acid molecules according to the present invention or compositions, preferably pharmaceutical compositions comprising the same, it has to be acknowledged that such diseases, conditions and disorders are those which are described herein, including and in particular those described and set forth in the introductory part of the instant application. Insofar, the respective passages form an integral part of the present disclosure teaching the suitability of the nucleic acid molecules for the prevention and treatment, respectively, for said diseases, conditions, and disorders.

After intravenous administration of a SDF-1 binding nucleic acid molecule such as NOX-A12-JE40, cells are into the blood, whereby the effect of the SDF-1 binding nucleic acid NOX-A12-JE40 was seen after performing a whole blood cell count using a hemocytometer (see Example 10). Whilst hematopoietic stem cells/hematopoietic progenitor cells only represented a small fraction of the mobilized white blood cells, there are other cells types that were released into the blood. Among these are monocytes and neutrophil granulocytes as well as tissue-committed stem/progenitor cells, mesenchymal stem cells, long-lived plasma B-cells, without limiting to these cells.

Based on these results, the inventors concluded that the inhibition of the signalling of SDF-1 to SDF-1 receptor by a SDF-1 binding nucleic acid molecule according to the present invention leads to influence of migration of cells. Preferably the cells express a SDF-1 receptor.

Accordingly, the term migration as preferably used herein refers to migration and/or movement from one tissue into another tissue, from a tissue into the peripheral blood and/or from the peripheral blood into a tissue. Migration of cells can be tested in a TAX-assay (migration in vitro) as shown in Example 5 and/or using a hemocytometer and FACS analysis as shown in Example 10 (in vivo experiment). Additionally, immunehistochemistry of tissue can be done, whereby the migrated cells are detected by antibodies directed to cell-specific surface markers. As used herein the term SDF-1 receptor, regardless whether used in plural or singular, refers to any receptor to which SDF-1 binds. Today there are two receptors known, the CXCR 4 (Godessart 2005) and the CXCR7 (Burns, Summers, et al. 2006) which are preferred SDF-1 binding receptors.

Blood cell development. The development and maturation of blood cells is a complex process. Mature blood cells are derived from hematopoietic precursor cells, also referred as progenitor cells, and stem cells present in specific hematopoietic tissues including bone marrow. Within these environments hematopoietic cells proliferate and differentiate prior to entering the circulation. The chemokine receptor CXCR4 and its natural ligand SDF-1 appear to be important in this process (Maekawa and Ishii 2000; Nagasawa 2000). This has been demonstrated by reports that CXCR4 or SDF-1 knock-out mice exhibit hematopoietic defects (Ma, Jones et al. 1998; Tachibana, Hirota et al. 1998; Zou, Kottmann et al. 1998). It is also known that CD34+ progenitor cells express CXCR4 and require SDF-1 produced by bone marrow stromal cells for chemoattraction and engraftment (Peled, Petit et al. 1999) and that in vitro, SDF-1 is chemotactic for both CD34+ cells (Aiuti, Webb et al. 1997; Viardot, Kronenwett et al. 1998) and for progenitor/stem cells (Jo, Rafii et al. 2000). SDF-1 is also an important chemoattractant, signaling via the CXCR4 receptor, for several other more committed progenitors and mature blood cells including T-lymphocytes and monocytes (Bleul, Fuhlbrigge et al. 1996), pro- and pre-B lymphocytes (Fedyk, Ryyan et al. 1999) and megakaryocytes (Riviere, Subra et al. 1999; Abi-Younes, Sauty et al. 2000; Hodohara, Fujii et al. 2000; Majka, Janowska-Wieczorek et al. 2000; Gear, Suttitanamongkol et al. 2001). Due to this relationship between the various cell types and the involvement of SDF-1 and he SDF-1 receptor, the various cell types may actually be addressed by the nucleic acid molecules according to the present invention.

Thus, in summary, it appears that SDF-1 is able to control the positioning and differentiation of cells bearing SDF-1 receptors, preferably CXCR4 receptors whether these cells are stem cells, i.e., cells which are CD34+, and/or progenitor cells which result in formation of specified types of colonies in response to particular stimuli; that can be CD34+ or CD34−, or cells that are somewhat more differentiated.

Recently, considerable attention has been focused on the number of CD34+ cells mobilized in the pool of peripheral blood progenitor cells used for autologous and allograft stem cell transplantation. The CD34+ population is the component thought to be primarily responsible for the improved recovery time after chemotherapy and the cells most likely responsible for long-term engraftment and restoration of hematopoiesis (Croop, Cooper et al. 2000). The mechanism by which CD34+ cells re-engraft may be due to the chemotactic effects of SDF-1 on CXCR4 expressing cells (Ponomaryov, Peled et al. 2000; Voermans, Kooi et al. 2001). More recently, adult hematopoietic stem cells were shown to be capable of restoring damaged cardiac tissue in mice (Jackson, Majka et al. 2001; Kocher, Schuster et al. 2001).

As preferably used herein, the term progenitor cells refers to cells that, in response to certain stimuli, can form differentiated hematopoietic or myeloid cells. The presence of progenitor cells can be assessed by the ability of the cells in a sample to form colony-forming units of various types, including, for example, CFU-GM (that means colony-forming units granulocyte-macrophage); CFU-GEMM (that means colony-forming units, multipotential); BFU-E (burst-forming units, erythroid); HPP-CFC (that means high proliferative potential colony-forming cells); or other types of differentiated colonies which can be obtained in culture using known protocols.

As preferably used herein, stem cells are less differentiated forms of progenitor cells. Typically, such cells are often positive for CD34. Some stem cells do not contain this marker, however. CD34+ cells can be assayed using fluorescence activated cell sorting (abbr. FACS) and thus their presence can be assessed in a sample using this technique.

In general, CD34+ cells are present only in low levels in the blood, but are present in large numbers in bone marrow. While other types of cells such as endothelial cells and mast cells also may exhibit this marker, CD34 is considered an index of stem cell presence.

Without wishing to be bound by any theory, the inventors have found that in addition to stem cells and/or progenitor cells, cancer cells, long-lived plasma cells, B-cells and/or T cells are affected by the inhibitory effect of the nucleic acid according to the present invention on the signalling between SDF-1 and its SDF-1 receptor. B-cells and T-cells are preferably memory B and memory T-cells. The inhibition of the signalling between SDF-1 and the SDF-1 receptor leads to a migration, comprising mobilization, into the peripheral blood.

Mobilization of the stem cells, progenitor cells, cancer cells, long-lived plasma cells, B-cells and/or T cells preferably takes place in hematopoietic tissues, whereby the hematopoietic tissue is selected from the group consisting of myeloid tissue and lymphoid tissue. Myeloid tissue is located in the bone marrow. The lymphoid tissue is located in the mucosa of the digestive tract and respiratory tract, lymph nodes, the spleen and/or the thymus.

As preferably used herein, cancer cells are neoplastic cells and are preferably selected from leukemic cells, myeloma cells, lymphoma cells, cancer stem cells, cancer cells with metastatic potential and cancer metastases The neoplastic cells typically bear common genetic or epigenetic abnormalities, an evidence of clonality. For some types of neoplasm, e.g. lymphoma and leukemia, the demonstration of clonality is now considered to be necessary (though not sufficient) to define a cellular proliferation as neoplastic.

After an acute immune response with active antibody production by terminally differentiated B cells (plasma cells) the majority of these cells die with the resolution of the disease, and/or the elimination of the foreign antigen (e.g. virus protein). There is however a minority of memory B cells that may be turned into plasmablasts with the help of a T cell. These plasma blasts have the ability to migrate in response to chemotactic stimuli into niches where they survive as long-lived "memory" plasma cells for years. These niches can be both in bone marrow and in the periphery, e.g. in inflamed tissues. These long-lived plasma cells are most likely responsible for the maintenance of the protective antibody plasma titers that are often maintained for years after an infection or a vaccination (Tarlinton et al, 2008).

Mobilization of the progenitor cells and/or the stem cells preferably occurs from hematopoietic tissues, whereby the hematopoietic tissue is selected from the group of myeloid tissue and lymphoid tissue. Myeloid tissue is located in the bone marrow. The lymphoid tissue is located in the mucosa of the digestive tract and respiratory tract, lymph nodes, the spleen, thymus and lyphoid follicles in an inflammed tissue. Preferably, the mobilization of the cells as disclosed before comprises migration of the cells as disclosed before into the peripheral blood.

As shown before, SDF-1 was found to act as a chemotactic agent on mature and precursor mast cells—especially when histamine is released from mature mast cells, e.g. by IgE signalling through binding to the Fc-epsilon receptor on the mast cell surface (Godot, Arock et al. 2007). Diseases like allergic reactions of the skin and mucosa of airways, such as hay fever and asthma, dermatitis, especially contact dermatitis and atopic dermatitis often involve a leukocyte migration to and accumulation in affected tissues. Expression of SDF-1 was also observed in synovial biopsies and by RT-PCR from subjects affected by joint inflammation as spondyloarthropathy, rheumatoid arthritis, psoriatric arthritis and degenerative joint disease (osteoarthritis). Interference with SDF-1 by SDF-1 binding nucleic acids according to the present invention may therefore have positive effects for patients suffering from joint inflammation.

By these means and in view of the outlined involvement of SDF-1 and SDF-1 receptors, the SDF-1 binding and the interaction between SDF-1 and SDF-1 receptor inhibiting nucleic acid molecules according to the present invention can help to attenuate such diseases, whereby inhibition of SDF-1 by the nucleic acid molecules according to the present invention leads to reduction and/or inhibition of migration of leukocytes whereby leukocytes are preferably selected from the group T-lymphocytes, B-lymphocytes, monocytes, macrophages, megakaryocytes, eosinophils, neutrophils, basophils, dendritic cells and/or mast cells.

Migration of leukocytes leads to an accumulation in a tissue, whereby preferably the accumulation of the leukocytes leads to an inflammation of the said tissue, whereby the tissue comprise skin and/or mucosa, preferably mucosa of airways, and several organs as selected from but not restricted to eye, brain, lung, kidneys, heart, liver, gastrointestinal tract, spleen, skin, bones and/or the lymphatic system.

An antagonists to SDF-1 is a molecule that binds to SDF-1 and inhibits the function of SDF-1, preferably in cell-based assay or in an in vivo model as described in the Examples.

Moreover, the present invention is based on the surprising finding that it is possible to generate nucleic acids binding specifically and with high affinity to SDF-1. Such nucleic acids are preferably also referred to herein as the nucleic acid molecules according to the present invention, the nucleic acids according to the present invention, the inventive nucleic acids or the inventive nucleic acid molecules.

SDF-1 is a basic peptide having the amino acid sequence according to SEQ. ID. No. 1. The calculated pI of SDF-1 is 9.70. As used herein the term SDF-1 refers to any SDF-1 including, but not limited to, mammalian SDF-1. Preferably, the mammalian SDF-1 is selected from the group comprising mice, rat, rabbit, hamster, monkey and human SDF-1. More preferably the SDF-1 is human SDF-1 also referred to as SDF-1α (SEQ.ID. No. 1) and/or human SDF-1β (SEQ ID No. 2), most preferably human SDF-1 also referred to as SDF-1α (SEQ.ID. No. 1)

The finding that high affinity binding nucleic acids to SDF-1 could be identified, is insofar surprising as Eaton et al. (Eaton, Gold et al. 1997) observed that the generation of aptamers, i.e. D-nucleic acids binding to a target molecule, directed to a basic protein is in general very difficult because this kind of target produces a high but non-specific signal-to-noise ratio. This high signal-to-noise ratio results from the high non-specific affinity shown by nucleic acids for basic targets such as SDF-1.

The features of the nucleic acid according to the present invention as described herein can be realised in any aspect of the present invention where the nucleic acid is used, either alone or in any combination.

Without wishing to be bound by any theory, the present inventors assume that the observed specificity of the SDF-1 binding nucleic acids according to the present invention share some structural features and in particular one of the nucleotide sequences which are also referred to therein as core sequences which shall be discussed in more detail in the following, whereby reference is made to FIGS. 1 to 8 and to Example 1. However, it is to be understood that said FIGS. and to Example 1 incorporates several of said structural features which do not have to be necessarily realized in each and any of the nucleic acids according to the present invention.

As outlined in more detail in the claims and example 1, the various human SDF-1 binding nucleic acid molecules can be categorised based on said Boxes and some structural features and elements, respectively. The various categories thus defined are also referred to herein as types and more specifically as Type A, Type B and Type C.

In a preferred embodiment the nucleic acid according to the present invention is a single nucleic acid molecule. In a further embodiment, the single nucleic acid molecule is present as a multitude of the single nucleic acid molecule. Preferably, the terms nucleic acid and nucleic acid molecule are used in an interchangeable manner herein if not indicated to the contrary.

It will be acknowledged by the ones skilled in the art that the nucleic acid molecule in accordance with the invention preferably consists of nucleotides which are covalently linked to each other, preferably through phosphodiester links or linkages.

The nucleic acids according to the present invention shall also comprise nucleic acids which are essentially homologous to the particular sequences disclosed herein. The term substantially homologous shall be understood such as the homology is at least 75%, preferably 85%, more preferably 90% and most preferably more that 95%, 96%, 97%, 98% or 99%.

The actual percentage of homologous nucleotides present in the nucleic acid according to the present invention will depend on the total number of nucleotides present in the nucleic acid. The percent modification can be based upon the total number of nucleotides present in the nucleic acid.

The homology can be determined as known to the person skilled in the art. More specifically, a sequence comparison algorithm then calculates the percent sequence identity for the test sequence(s) relative to the reference sequence, based on the designated program parameters. The test sequence is preferably the sequence or nucleic acid molecule which is said to be or to be tested whether it is homologous, and if so, to what extent, to another nucleic acid molecule, whereby such another nucleic acid molecule is also referred to as the reference sequence. In an embodiment, the reference sequence is a nucleic acid molecule as described herein, more preferably a nucleic acid molecule having a sequence according to any of SEQ. ID. NOs. 5 to 144. Optimal alignment of sequences for comparison can be conducted, e.g., by the local homology algorithm of Smith & Waterman (Smith & Waterman, 1981) by the homology alignment algorithm of Needleman & Wunsch (Needleman & Wunsch, 1970) by the search for similarity method of Pearson & Lipman (Pearson & Lipman, 1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity is the algorithm used in the basic local alignment search tool (hereinafter "BLAST"), see, e.g. Altschul et al (Altschul et al. 1990 and Altschul et al, 1997). Software for performing BLAST analyses is publicly available through the National Center for Biotechnology Information (hereinafter "NCBI"). The default parameters used in determining sequence identity using the software available from NCBI, e.g., BLASTN (for nucleotide sequences) and BLASTP (for amino acid sequences) are described in McGinnis et al (McGinnis et al, 2004).

The term inventive nucleic acid or nucleic acid according to the present invention shall also comprise those nucleic acids comprising the nucleic acids sequences disclosed herein or part thereof, preferably to the extent that the nucleic acids or said parts are involved in the binding to SDF-1. Such a nucleic acid may be derived from the ones disclosed herein, e.g., by truncation. Truncation may be related to either or both of the ends of the nucleic acids as disclosed herein. Also, truncation may be related to the inner sequence of nucleotides, i.e. it may be related to the nucleotide(s) between the 5' and the 3' terminal nucleotide, respectively. Moreover, truncation shall comprise the deletion of as little as a single nucleotide from the sequence of the nucleic acids disclosed herein. Truncation may also be related to more than one stretch of the inventive nucleic acid(s), whereby the stretch can be as little as one nucleotide long. The binding of a nucleic acid according to the present invention can be determined by the ones skilled in the art using routine experiments or by using or adopting a method as described herein, preferably as described herein in the example part.

The nucleic acids according to the present invention may be either D-nucleic acids or L-nucleic acids. Preferably, the inventive nucleic acids are L-nucleic acids. In addition it is possible that one or several parts of the nucleic acid are present as D-nucleic acids or at least one or several parts of the nucleic acids are L-nucleic acids. The term "part" of the nucleic acids shall mean as little as one nucleotide. Such nucleic acids are generally referred to herein as D- and L-nucleic acids, respectively. Therefore, in a particularly preferred embodiment, the nucleic acids according to the present invention consist of L-nucleotides and comprise at least one D-nucleotide. Such D-nucleotide is preferably attached to a part different from the stretches defining the nucleic acids according to the present invention, preferably those parts thereof, where an interaction with other parts of the nucleic acid is involved. Preferably, such D-nucleotide is attached at a terminus of any of the stretches and of any nucleic acid according to the present invention, respectively. In a further preferred embodiment, such D-nucleotides may act as a spacer or a linker, preferably attaching modifications such as PEG and HES to the nucleic acids according to the present invention.

It is also within the present invention that each and any of the nucleic acid molecules described herein in their entirety in terms of their nucleic acid sequence(s) are limited to the particular nucleotide sequence(s). In other words, the terms "comprising" or "comprise(s)" shall be interpreted in such embodiment in the meaning of containing or consisting of.

It is also within the present invention that the nucleic acids according to the present invention are part of a longer nucleic acid whereby this longer nucleic acid comprises several parts whereby at least one such part is a nucleic acid, or a part thereof, according to the present invention. The other part(s) of these longer nucleic acids can be either one or several D-nucleic acid(s) or L-nucleic acid(s). Any combination may be used in connection with the present invention. These other part(s) of the longer nucleic acid can exhibit a function which is different from binding, preferably from binding to SDF-1. One possible function is to allow interaction with other molecules, whereby such other molecules preferably are different from SDF-1, such as, e.g., for immobilization, cross-linking, detection or amplification. In a further embodiment of the present invention the nucleic acids according to the invention comprise, as individual or combined moieties, several of the nucleic acids of the present invention. Such nucleic acid comprising several of the nucleic acids of the present invention is also encompassed by the term longer nucleic acid.

L-nucleic acids as used herein are nucleic acids consisting of L-nucleotides, preferably consisting completely of L-nucleotides.

D-nucleic acids as used herein are nucleic acids consisting of D-nucleotides, preferably consisting completely of D-nucleotides.

The terms nucleic acid and nucleic acid molecule are used herein in an interchangeable manner if not explicitly indicated to the contrary.

Also, if not indicated to the contrary, any nucleotide sequence is set forth herein in 5'→3' direction.

Irrespective of whether the inventive nucleic acid consists of D-nucleotides, L-nucleotides or a combination of both with the combination being e.g. a random combination or a defined sequence of stretches consisting of at least one L-nucleotide and at least one D-nucleic acid, the nucleic acid may consist of desoxyribonucleotide(s), ribonucleotide(s) or combinations thereof.

Designing the inventive nucleic acids as L-nucleic acid is advantageous for several reasons. L-nucleic acids are enantiomers of naturally occurring nucleic acids. D-nucleic acids, however, are not very stable in aqueous solutions and particularly in biological systems or biological samples due to the widespread presence of nucleases. Naturally occurring nucleases, particularly nucleases from animal cells are not capable of degrading L-nucleic acids. Because of this the biological half-life of the L-nucleic acid is significantly increased in such a system, including the animal and human body. Due to the lacking degradability of L-nucleic acid no nuclease degradation products are generated and thus no side effects arising therefrom observed. This aspect delimits the L-nucleic acid of factually all other compounds which are used in the therapy of diseases and/or disorders involving the presence of SDF-1. L-nucleic acids which specifically bind to a target molecule through a mechanism different from Watson Crick base pairing, or aptamers which consists partially or completely of L-nucleotides, particularly with those parts of the aptamer being involved in the binding of the aptamer to the target molecule, are also called spiegelmers.

It is within the present invention that the first and the second stretch of nucleotides flanking the core nucleotide sequence can, in principle, hybridise with each other. Upon such hybridisation a double-stranded structure is formed. It will be acknowledged by the one skilled in the art that such hybridisation may or may not occur, particularly under in vitro and/or in vivo conditions. Also, in case of such hybridisation, it is not necessarily the case that the hybridisation occurs over the entire length of the two stretches where, at least based on the rules for base pairing, such hybridisation and thus formation of a double-stranded structure may occur. As preferably used herein, a double-stranded structure is a part of a molecule or a structure formed by two or more separate strands, whereby at least one, preferably two or more base pairs exist which are base pairing preferably in accordance with the Watson-Crick base pairing rules. It will also be acknowledged by the one skilled in the art that other base pairing such as Hoogsten base pairing may exist in or form such double-stranded structure.

It is also within the present invention that the inventive nucleic acids, regardless whether they are present as D-nucleic acids, L-nucleic acids or D, L-nucleic acids or whether they are DNA or RNA, may be present as single stranded or double stranded nucleic acids. Typically, the inventive nucleic acids are single stranded nucleic acids which exhibit defined secondary structures due to the primary sequence and may thus also form tertiary structures. The inventive nucleic acids, however, may also be double stranded in the meaning that two strands which are complementary or partially complementary to each other are hybridised to each other. This confers stability to the nucleic acid which, in particular, will be advantageous if the nucleic acid is present in the naturally occurring D-form rather than the L-form.

The inventive nucleic acids may be modified. Such modifications may be related to the single nucleotide of the nucleic acid and are well known in the art. Examples for such modification are described by, among others, Venkatesan et al. (Venkatesan, Kim et al. 2003) and Kusser (Kusser 2000). Such modification can be a H atom, a F atom or O—$CH_3$ group or $NH_2$-group at the 2' position of the individual nucleotide of which the nucleic acid consists. Also, the nucleic acid according to the present invention can comprises at least one LNA nucleotide. In an embodiment the nucleic acid according to the present invention consists of LNA nucleotides.

In an embodiment, the nucleic acids according to the present invention may be a multipartite nucleic acid. A multipartite nucleic acid as used herein, is a nucleic acid which consists of at least two nucleic acid strands. These at least two nucleic acid strands form a functional unit whereby the functional unit is a ligand to a target molecule. The at least two nucleic acid strands may be derived from any of the inventive nucleic acids by either cleaving the nucleic acid to generate two strands or by synthesising one nucleic acid corresponding to a first part of the inventive, i.e. overall nucleic acid and another nucleic acid corresponding to the second part of the overall nucleic acid. It is to be acknowledged that both the cleavage and the synthesis may be applied to generate a multipartite nucleic acid where there are more than two strands as exemplified above. In other words, the at least two nucleic acid strands are typically different from two strands being complementary and hybridising to each other although a certain extent of complementarity between the various nucleic acid parts may exist.

Finally it is also within the present invention that a fully closed, i.e. circular structure for the nucleic acids according to the present invention is realized, i.e. that the nucleic acids according to the present invention are closed, preferably through a covalent linkage, whereby more preferably such covalent linkage is made between the 5' end and the 3' end of the nucleic acid sequences as disclosed herein.

The present inventors have discovered that the nucleic acids according to the present invention exhibit a very favourable Kd value range.

A possibility to determine the binding constant is surface plasmon resonance measurement by the use of the so called Biacore device (Biacore AB, Uppsala, Sweden), which is also known to the one skilled in the art. Affinity as preferably used herein was also measured by the use of "pull-down binding assay" as described in the examples. An appropriate measure in order to express the intensity of the binding between the nucleic acid and the target which is in the present case SDF-1, is the so-called Kd value which as such as well as the method for its determination are known to the one skilled in the art.

The nucleic acids according to the present invention are characterized by a certain Kd value. Preferably, the Kd value shown by the nucleic acids according to the present invention is below 1 μM. A Kd value of about 1 μM is said to be characteristic for a non-specific binding of a nucleic acid to a target. As will be acknowledged by the ones in the art, the Kd value of a group of compounds such as the nucleic acids according to the present invention are within a certain range. The above-mentioned Kd of about 1 μM is a preferred upper limit for the Kd value. The preferred lower limit for the Kd of target binding nucleic acids can be about 10 picomolar or higher. It is within the present invention that the Kd values of individual nucleic acids binding to ghrelin is preferably within this range. Preferred ranges can be defined by choosing any first number within this range and any second number within this range. Preferred upper values are 250 nM an 100 nM, preferred lower values are 50 nM, 10 nM, 1 nM, 100 pM and 10 pM.

The nucleic acid molecules according to the present invention may have any length provided that they are still able to bind to the target molecule. It will be acknowledged in the art that there are preferred lengths of the nucleic acids according to the present inventions. Typically, the length is between 15 and 120 nucleotides. It will be acknowledged by the ones skilled in the art that any integer between 15 and 120 is a possible length for the nucleic acids according to the present invention. More preferred ranges for the length of the nucleic acids according to the present invention are lengths of about 20 to 100 nucleotides, about 20 to 80 nucleotides, about 20 to 60 nucleotides, about 20 to 50 nucleotides and about 20 to 40 nucleotides.

It is within the present invention that the nucleic acids disclosed herein comprise a moiety which preferably is a high molecular weight moiety and/or which preferably allows to modify the characteristics of the nucleic acid in terms of, among others, residence time in the animal body, preferably the human body. A particularly preferred embodiment of such modification is PEGylation and HESylation of the nucleic acids according to the present invention. As used herein PEG stands for poly(ethylene glycole) and HES for hydroxyethly starch. PEGylation as preferably used herein is the modification of a nucleic acid according to the present invention whereby such modification consists of a PEG moiety which is attached to a nucleic acid according to the present invention. HESylation as preferably used herein is the modification of a nucleic acid according to the present invention whereby such modification consists of a HES moiety which is attached to a nucleic acid according to the present invention. These modifications as well as the process of modifying a nucleic acid using such modifications, is described in European patent application EP 1 306 382, the disclosure of which is herewith incorporated in its entirety by reference.

Preferably, the molecular weight of a modification consisting of or comprising a high molecular weight moiety is about from 2,000 to 200,000 Da, preferably 40,000 to 120,000 Da, particularly in case of PEG being such high molecular weight moiety, and is preferably about from 3,000 to 180,000 Da, more preferably from 60,000 to 140,000 Da, particularly in case of HES being such high molecular weight moiety. The process of HES modification is, e.g., described in German patent application DE 1 2004 006 249.8 the disclosure of which is herewith incorporated in its entirety by reference.

It is within the present invention that either of PEG and HES may be used as either a linear or branched from as further described in the patent applications WO2005074993 and PCT/EP02/11950. Such modification can, in principle, be made to the nucleic acid molecules of the present invention at any position thereof. Preferably such modification is made either to the 5'-terminal nucleotide, the 3'-terminal nucleotide and/or any nucleotide between the 5' nucleotide and the 3' nucleotide of the nucleic acid molecule.

The modification and preferably the PEG and/or HES moiety can be attached to the nucleic acid molecule of the present invention either directly or through a linker. It is also within the present invention that the nucleic acid molecule according to the present invention comprises one or more modifications, preferably one or more PEG and/or HES moiety. In an embodiment the individual linker molecule attaches more than one PEG moiety or HES moiety to a nucleic acid molecule according to the present invention. The linker used in connection with the present invention can itself be either linear or branched. This kind of linkers are known to the ones skilled in the art and are further described in the patent applications WO2005074993 and PCT/EP02/11950.

Without wishing to be bound by any theory, it seems that by modifying the nucleic acids according to the present invention with high molecular weight moiety such as a polymer and more particularly the polymers disclosed herein, which are preferably physiologically acceptable, the excretion kinetic is changed. More particularly, it seems that due to the increased molecular weight of such modified inventive nucleic acids and due to the nucleic acids not being subject to metabolism particularly when in the L form, excretion from an animal body, preferably from a mammalian body and more preferably from a human body is decreased. As excretion typically occurs via the kidneys, the present inventors assume that the glomerular filtration rate of the thus modified nucleic acid is significantly reduced compared to the nucleic acids not having this kind of high molecular weight modification which results in an increase in the residence time in the body. In connection therewith it is particularly noteworthy that, despite such high molecular weight modification the specificity of the nucleic acid according to the present invention is not affected in a detrimental manner. Insofar, the nucleic acids according to the present invention have surprising characteristics—which normally cannot be expected from pharmaceutically active compounds—such that a pharmaceutical formulation providing for a sustained release is not necessarily required to provide for a sustained release. Rather the nucleic acids according to the present invention in their modified form comprising a high molecular weight moiety, can as such already be used as a sustained release-formulation. Insofar, the modification(s) of the nucleic acid molecules as disclosed herein and the thus modified nucleic acid molecules and any composition comprising the same may provide for a distinct, preferably controlled pharmacokinetics and biodistribution thereof. This also includes residence time in circulation and distribution to tissues. Such modifications are further described in the patent application PCT/EP02/11950.

However, it is also within the present invention that the nucleic acids disclosed herein do not comprise any modification and particularly no high molecular weight modification such as PEGylation or HESylation. Such embodiment is particularly preferred when a fast clearance of the nucleic acids from the body after administration is desired. Such fast clearance might be desired in case of in vivo imaging or specific therapeutic dosing requirements using the nucleic acids or medicaments comprising the same, according to the present invention.

The inventive nucleic acids, which are also referred to herein as the nucleic acids according to the present invention, and/or the antagonists according to the present invention may be used for the generation or manufacture of a medicament. Such medicament contains at least one of the inventive nucleic acids, optionally together with further pharmaceutically active compounds, whereby the inventive nucleic acid preferably acts as pharmaceutically active compound itself. Such medicaments comprise in preferred embodiments at least a pharmaceutically acceptable carrier. Such carrier may be, e. g., water, buffer, PBS, glucose solution, sucrose solution, mannose solution, preferably a 5% sucrose balanced solution, starch, sugar, gelatine or any other acceptable carrier substance. Such carriers are generally known to the one skilled in the art. It will be acknowledged by the person skilled in the art that any embodiments, use and aspects of or related to the medicament of the present invention is also applicable to the pharmaceutical composition of the present invention and vice versa.

The indication, diseases and disorders for the treatment and/or prevention of which the nucleic acids, the pharmaceutical compositions and medicaments in accordance with or prepared in accordance with the present invention result from the involvement, either direct or indirect, of SDF-1 in the respective pathogenetic mechanism.

Of course, because the SDF-1 binding nucleic acids according to the present invention interact with or bind to human or murine SDF-1, a skilled person generally understand that the SDF-1 binding nucleic acids according to the present invention can easily be used for the treatment, prevention and/or diagnosis of any disease as described herein of humans and animals. In connection therewith, it is to be acknowledged that the nucleic acid molecules according to the present invention can be used for the treatment and prevention of any of the diseases, disorder or condition described herein, irrespective of the mode of action underlying such disease, disorder and condition.

In the following the rational for the use of the nucleic acid molecules according to the present invention in connection with the various diseases, disorders and conditions is provided, thus rendering the claimed therapeutic, preventive and diagnostic applicability of the nucleic acid molecules according to the present invention plausible. In order to avoid any unnecessary repetition, it should be acknowledged that due to the involvement of the SDF-1-SDF-1 receptor axis as outlined in connection therewith said axis may be addressed by the nucleic acid molecules according to the present invention such that the claimed therapeutic, preventive and diagnostic effect is achieved. It should furthermore be acknowledged that the particularities of the diseases, disorders and conditions, of the patients and any detail of the treatment regimen described in connection therewith, may be subject to preferred embodiments of the instant application.

Enhancing the stem and/or progenitor cells in blood and more specifically peripheral blood, is, among others, helpful in treatments to alleviate the effects of protocols that adversely affect the bone marrow, such as those that result in leukopenia. These are known side-effects of chemotherapy and radiotherapy. The nucleic acids of the present invention also enhance the success of bone marrow transplantation, enhance wound healing and burn treatment, and aid in restoration of damaged organ tissue. They also combat bacterial infections that are prevalent in leukemia. Insofar, the nucleic acid molecules according to the present invention may be used for any such purpose and treatment and prevention, respectively, of any such disease and condition.

Stem cell mobilization for regeneration of tissues. In cases of organ damage, e.g. due to malfunctioning vasculature or trauma, tissue regeneration is desirable but often not achieved. Stem cells from the bone marrow, preferably autologous stern cells have been shown to have beneficial effects in a variety of animal models of diseases and have proven beneficial in some instances in humans.

Repair of the retina and the retinal pigment epithelium. Bone marrow-derived stem cells have been investigated in mouse models of retinal vascular and degenerative diseases. These stem cells were shown to adhere to sites of damage, to stabilize abnormal vasculature and to accelerate neovascularization of hypoxic areas if injected intravitreally or subretinally (Friedlander et al, 2007; Otani et al, 2002). Others have found that a subgroup of bone marrow-derived stem cells that had been mobilized with G-CSF targets the retinal pigment epithelium at sites of damage. Besides the systemic administration no harvesting and intra-ocular injection of stem cells was found to be necessary. On the contrary, the attraction to the site of injury/damage was achieved by the transient localised over-expression of chemokines, e.g. SDF-1 (Li et al, 2007; Li et al, 2006).

Cardiac repair. Cumulative evidence indicates that myocardium responds to growth or injury by recruitment of stem and/or progenitor cells that participate in repair and regenerative processes. In a mouse model of cardiac infarction, Fransioli et al. have shown that c-kit+ cells, that are stem cells, accumulate 1-2 weeks post infarction in the infarcted area, most likely to contribute to repair processes (Fransioli et al, 2008). Dawn et al. reported on the potential therapeutic utility of bone marrow-derived Sca-1+/Lin–/CD45– very small embryonic-like stem cells (abbr. VSELs).

In a mouse model of myocardial infarction (abbr. MI) the transplantation of a relatively small number of CD45– VSELs was sufficient to improve left ventricular function and alleviated myocyte hypertrophy after MI (Dawn et al, 2008).

Repair and amelioration of inflammation after ischemic stroke. Schwarting et al. have investigated the effects of green fluorescent peptide-marked Lin(–)-hematopoietic stem cell injection on infarct size, apoptotic cell death, post-ischemic inflammation and cytokine gene transcription in a mouse model of ischemic brain injury. 24 hours after injection, the cells were found in the spleen and later in ischemic brain parenchyma, expressing microglial but no neural marker proteins. Tissue injury assessment showed significantly smaller infarct volumes and less apoptotic neuronal cell death in peri-infarct areas of Lin(–)-hematopoietic stem cell treated animals. Analysis of immune cell infiltration in ischemic hemispheres revealed a reduction of invading T cells and macrophages in treated mice (Schwarting et al, 2008). Imitola et al. had reported earlier that neuronal stem cells are attracted to sites of central nervous system (abbr. CNS) injury via the SDF-1α/CXCR4 pathway.

In the light of these findings, the mobilization of a sufficient number of stem cells from the bone marrow is likely to be beneficial to induce repair processes (Tang et al, 2007). Blocking SDF-1 or its receptor CXCR4 is a promising approach in this field, since it mobilizes a variety of stem cells from the bone marrow. Correct doses, dosing schemes and potentially localization of the mobilizing agent can be determined by a person skilled in the art performing routine experimentation, whereby it is preferably intended that the stem cells are mobilized but are still capable to respond to chemotactic signals, so that they can be recruited to places of tissue injury.

Because the SDF-1 binding nucleic acid molecules according to the present invention inhibit the signalling between SDF-1 and the SDF-1 receptor, such SDF-1 binding nucleic acid molecules can be used for the generation of a medicament that may be used for, mobilization of progenitor cell and/or stem cells into the peripheral blood, and/or for the treatment of diseases and/or disorders preferably selected from the group comprising wound healing; burn; disorders caused by or associated with damaged organ tissue and/or damaged vasculature, whereby such disorders are selected from retinal and choroidal damage, stroke, myocardial damage, myocardial infarct, ischemia after organ transplantation and traumatic injury; and hematopoietic disorders, whereby such disorders are selected from aplastic anemia, leukaemia, drug-induced anemia and leukopenia, and bacterial infection in leukopenia.

For mobilization of the progenitor cell and/or stem cell the medicament can be used in combination with a second pharmaceutically active agent, whereby the function of said second pharmaceutically active agent is mobilizing of the progenitor cell and/or stem cells. Cell mobilizing agents are selected from but not restricted to granulocyte-macrophage colony stimulating factor (abbr. GM-CSF), Interleukin-8 (abbr. IL-8), macrophage inflammatory protein (abbr. MIP), growth related oncogene, CXCR4 blocking agents like AMD3001 (Aiuti, Webb et al. 1997) and granulocyte colony-stimulating factor (abbr. G-CSF).

In cases of CNS injury, the use of a macromolecular SDF-1 inhibitor for the mobilization of bone marrow derived stem cells may be especially beneficial. Whilst the cells are still sensitive for SDF-1 gradients, these are masked by the macromolecular SDF-1 inhibitor in peripheral tissues as long as a sufficiently high concentration is maintained in the body. However, since the macromolecular SDF-1 inhibitor cannot cross the blood brain barrier, SDF-1 gradients originating from SDF-1 over-expression at sites of CNS hypoxia or injury, persist in the CNS and may attract some of the mobilized cells to the site of injury where they can serve as described above. In a preferred embodiment, such macromolecular SDF-1 inhibitor is a nucleic acid molecule according to the present invention.

Combination of SDF-1 blockade and chemotherapy. Approximately 20% of B-lineage acute lymphoblastic leukemias are not cured by traditional chemotherapy. Preclinical experiments using ex-vivo leukemic cells in co-culture with stromal cells have provided evidence that the interaction of leukemic blasts with bone marrow components protects the leukemic cells against chemotherapy (Mudry, Fortney et al. 2000; Garrido, Appelbaum et al. 2001; Tabe, Jin et al. 2007). There are also reports about mouse models in which the inhibition of cell surface molecules that are important for cell adhesion and thus homing of (malignant) hematopoietic cells improves the efficacy of chemotherapy and leads to eradication of leukemic stem cells (Matsunaga, Takemoto et al. 2003; Jin, Hope et al. 2006). SDF-1 is known to play an important role in homing and retention of stem cells in bone marrow niches. There is accumulating preclinical and one report of clinical evidence that the blockade of CXCR4, a receptor of SDF-1 on hematopoietic cells, leads to the liberation also of acute myeloid leukemia blast from the bone marrow into the peripheral blood, where they can be targeted by chemotherapy (e.g. by the agent cytarabine) (Fierro, Brenner et al. 2008) or other agents that lead to tumor cell death (e.g. biologicals alone or with antibody dependent cell-mediated cytotoxicity or complement dependent cytotoxicity). Additionally Jin et al. have recently observed that treatment of chronic myelogenous leukemia with tyrosine kinase inhibitors (e.g. imatinib) leads to an upregulation of CXCR4 on leukemic cells. This resulted in increased bone marrow homing and induced a G0-G1 cycle block that rendered the cells quiescent and insensitive to further chemotherapy approaches (Jin, Tabe et al. 2008). In the light thereof, the present invention suggests a combination therapy of a chemotherapeutic agent together with a CXCR4 or a SDF-1 inhibitor like the SDF-1 binding nucleic acid molecules according to the present invention, including but not limited to NOX-A12-JE40, in order to decrease bone marrow homing of leukemic cells and to mobilize quiescent leukemic cells that have homed to the bone marrow before. Due to missing niche signals the cells may progress through the cell cycle and are therefore more sensitive to chemotherapy. Chemotherapy and respective agents used in connection therewith are known in the art and, e.g antibodies such as Rituximab, Ibritumomab tiuxetan, Tositumomab; alkylating agents such as cisplatin and carboplatin, as well as oxaliplatin, mechlorethamine; cyclophosphamide, chlorambucil; anti-metabolites such as purineazathioprine, mercaptopurine; plant alkaloids and terpenoids such as vinca alkaloids and taxanes; podophyllotoxi; epothilone; and topoisomerase inhibitors such as camptothecins.

Therefore the medicament as disclosed herein may be used for mobilization of cancer cells into the peripheral blood of a subject, whereby the cancer cells are selected but not restricted to the group of leukemic cells, myeloma cells, lymphoma cells, cancer stem cells, cancer cells with metastatic potential and cancer metastases.

The medicament according to the present invention may be used in combination with a second medicament or a second pharmaceutically active agent that can be used for the mobilization of the cancer cells into the peripheral blood of the subject. The second pharmaceutically active agent comprises cell mobilizing agents as disclosed herein before.

Moreover, the medicaments according to the present invention may be used in combination with a third medicament or third pharmaceutically active agent, whereby the third pharmaceutically active agent damages, destroys and/or labels (the) cancer cells. Such cancer cells destroying medicaments agents are preferably selected from but not restricted to the group of antibodies such as Rituximab, Ibritumomab tiuxetan, Tositumomab; alkylating agents such as cisplatin and carboplatin, as well as oxaliplatin, mechlorethamine; cyclophosphamide, chlorambucil; anti-metabolites such as purineazathioprine, mercaptopurine; plant alkaloids and terpenoids such as vinca alkaloids and taxanes; podophyllotoxi; epothilone; topoisomerase inhibitors such as camptothecins.

The third medicament or pharmaceutically active agent has or may provides the function of a chemotherapy.

Medicaments labeling the cancer cells lead to an activation of a body's defenses directed to the thereby labelled cancer cell, whereby medicaments labeling the cancer cells are selected from but not restricted to the group of monoclonal antibodies. They work by targeting tumour specific antigens, thus enhancing the host's immune response to tumour cells to which the agent attaches itself. Examples are trastuzumab (brand name Herceptin), cetuximab, and rituximab (brand names: Rituxan or Mabthera).

The combination therapy of the medicament according to the present invention can be done with the second and/or the third medicament.

The subject that is treated with the medicament for mobilization of the cancer cells may subsequently or concomitantly undergo radiotherapy. In an embodiment radiotherapy may be used as an alternative treatment for the third medicament or the third pharmaceutically active agent.

The medicament according to the present invention, in combination with or without the second medicament or second pharmaceutically active agent, with or without the third medicament or third pharmaceutically active agent, and with or without radiotherapy, can be used for the treatment and/or prevention of cancer, preferably solid tumours and hematological malignancies, more preferably leukemia, lymphoma, and myeloma whereby preferably the medicament according to the present invention is used in combination with the third medicament or radiotherapy.

Long-Lived Plasma Cells, B Cell and Memory T Cell Mobilization in Autoimmune Disease B cells, and/or memory T cells return from the body to the bone marrow and possibly other places, e.g. lymph nodes, and/or are held there by the SDF-1 gradient that is formed by the SDF-1 expression of stroma cells (Parretta, Cassese et al. 2005; Zhang, Nakajima et al. 2005; Radbruch, Muehlinghaus et al. 2006). In the niches, these cells are in a dormant status whereby they are there not sensitive to disease modifying drugs (e.g. cytostatic drugs or methotrexate) that are normally used for the treatment of autoimmune diseases. Once they leave the niche, they may readily divide and begin to mount a renewed immune response if they encounter teir cognate antigen possibly leading to perpetuated autoimmune disease. Interfering with the SDF-1 gradient in the bone marrow and other niches by SDF-1 binding nucleic acids or CXCR4 blockade may lead to the mobilization of B cells and/or T cells and allows their depletion from the blood via apheresis or targeting them with an appropriate medicament.

After an acute immune response with active antibody production by terminally differentiated B cells (plasma cells) the majority of these cells die with the resolution of the inflammation or the elimination of the foreign antigen (e.g. virus protein). There is however a minority of memory B cells that may be turned into plasmablasts with the help of a T cell. These plasmablasts have the ability to migrate in response to chemotactic stimuli into niches where they survive as long-lived "memory" plasma cells for years. During the transition, the cells lose the expression of CXCR5 and CCR7 and do no longer migrate towards the respective ligands. The expression of CXCR4, however is maintained. Thus the cells will move towards sites of SDF-1 expression, where they may encounter long-term survival signals, that may be distinct from or complementary to SDF-1 (Minges Wols et al, 2007). These niches can be both in bone marrow and in the periphery, e.g. in inflamed tissues. The long-lived plasma cells are most likely responsible for the maintenance of the protective antibody plasma titers that are often maintained for years after an infection or a vaccination (Tarlinton et al, 2008). Plasma cells are not as susceptible to disease modifying drugs as other B- and T cells, most likely because they do not divide. Furthermore they cannot be targeted by anti-CD20 antibody treatment, since plasma cells do not carry CD20. In autoimmune diseases that are maintained by autoantibodies secreted by plasma cells and long-lived plasma cells, it would be beneficial to eliminate these cells, so that the immune system would stop to attack the self tissue. A method to deplete a patient's blood from plasma cells can be done by apheresis, e.g. using anti CD138 (syndecan-1) antibody on an affinity matrix (e.g. a column or beads) (Minges Wols & Witte, 2008; Wijdenes et al, 1996). In order to eliminate not only the circulating plasma cells but also resident long-lived plasma cells, it would be favorable to mobilize the latter from their niches. This can be done by the systemic administration of an SDF-1 binding nucleic acid molecule according to the present invention that destroys SDF-1 gradients and mobilize these cells that move towards SDF-1 into the peripheral blood.

Therefore the medicament according to the present invention may be used for mobilization of long-lived plasma cells long-lived plasma cells, B cells and/or T cells into the peripheral blood of a subject.

The medicament according to the present invention may be used in combination with a second medicament or second pharmaceutically active agent that can be used for the mobilization of the long-lived plasma cells, B cells and/or T cells into the peripheral blood of the subject. The second medicament or pharmaceutically active agent comprises a cell mobilizing agentas described herein before but not restricted thereto.

While the cells are mobilized by a medicament according to the present invention alone or in combination with a second medicament or pharmaceutically active agent as described above, they can be cleared from the blood by apheresis, cell sorting and/or flow cytometry (e.g. by Fluorescence-activated cell sorting [FACS] and/or Magnetic-activated cell sorting [MACS] with appropriate long-lived plasma cell, B-cell or T cell surface markers).

Moreover, the medicament according to the present invention may be used in combination with a third medicament or third pharmaceutically active agent, whereby the third medicament or third pharmaceutically active agent damages, destroys and/or labels the long-lived plasma cells, B cells and/or T cells in the peripheral blood. Such medicaments destroying the long-lived plasma cells, B cells and/or T cells are selected from but but not restricted to to disease modifying drugs, e.g. methotrexate or cytotoxic agents. Examples of medicaments labeling the long-lived plasma cells, B cells and/or T cells leads to an activation of body's defense directed to the thereof labelled long-lived plasma cells, B cells and/or T cells include those, but are not limited thereto, selected from the group consisting of rituximab, IL-6 receptor binding antibodies or syndecan-1 binding antibodies.

The combination therapy of the medicament according to the present invention can be done with the second and/or the third medicament.

The subject that is treated in accordance with the present invention with the medicament according to the present invention for mobilization of the long-lived plasma cells, B cells and/or T cells may subsequently or concomitantly undergo radiotherapy, which damages or destroy the dividing cells of the patient's immune system, that ultimately attacks himself. Radiotherapy may be used as alternative treatment for the third medicament. The use of the medicament according to the present invention, in combination with or without the second medicament or second pharmaceutically active agent, with or without the third medicament or third pharmaceutically active agent, and with or without radiotherapy, can be used for the treatment and/or prevention of autoimmune diseases, mobilization of long-lived plasma cells, B cells and/or T cells alone or within a more complex therapeutic concept can be beneficial for the treatment of various diseases including but not limited to systemic autoimmune diseases whereby such systemic autoimmune disease is preferably selected from allergy, warm and cold autoimmune hemolytic anemia, systemic inflammatory response syndrome, hemorrhagic shock, diabetes type 1, diffuse scleroderma, polychondritis, polyglandular autoimmune syndrome, systemic lupus erythematosus and manifestations thereof, rheumatoid arthritis, rheumatic disease in the eye, brain, lung, kidneys, heart, liver, gastrointestinal tract, spleen, skin, bones, lymphatic system, blood or other organs;

autoimmune diseases of the gastrointestinal tract whereby such autoimmune disease of the gastrointestinal tract is preferably selected from Crohn's disease, colitis ulcerosa, celiac disease, gluten intolerance, inflammatory bowel disease, pancreatitis, eosinophilic esophagitis;

autoimmune diseases of the skin whereby such autoimmune disease of the skin is preferably selected from psoriasis, urticaria, dermatomyositis, pemphigus vulgaris, pemphigus foliaceus, bullous pemphigoid, Morphea/linear scleroderma, vitiligo, dermatitis herpetiformis or Duhring's disease, lichen sclerosis;

autoimmune diseases of the vasculature whereby such autoimmune disease of the vasculature is preferably selected from vasculitides, preferably arteritis temporalis, vasculitis, vascular leakage, polymyalgia rheumatica, atherosclerosis, Churg-Strauss syndrome, Takayasu arteritis, Goodpasture syndrome, preferably mostly affecting the kidneys, more specifically the glomeruli, and also mostly affecting the lungs, glomerulonephritis, polyarteritis nodosa, Behçet's disease;

autoimmune diseases of the nervous system whereby such autoimmune disease of the nervous system is preferably selected from multiple sclerosis, chronic inflammatory demyelinating polyneuropathy, neurocognitive dysfunction, stiff-man syndrome, Guillain-Barré syndrome, myasthenia gravis, Lambert-Eaton syndrome;

muscular skeletal autoimmune diseases whereby such muscular skeletal autoimmune disease is preferably selected from ankylosing spodylitis, sarcoidosis, polymyalgia rheumatica, polymyositis, psoriatic arthritis, rheumatic fever, polychondritis, fibromyalgia, juvenile rheumatoid arthritis, Lyme disease, reactive arthritis, spondyloarthropathy, degenerative joint disease;

and other autoimmune diseases whereby such other autoimmune diseases are preferably selected from Cogan syndrome, autoimmune adrenalitis, Ménière's disease, local inflammations, alopecia areata, acute inflammatory diseases, primary biliary cirrhosis, Sjörgen's syndrome, scleroderma such as diffuse scleroderma, CREST syndrome and/or Morphea/linear scleroderma, autoimmune uveitis, Hashimoto thyroiditis, Graves disease, autoimmune hepatitis, glomerulonephritis, anti-phospholipid syndrome, idiopatic pulmonar fibrosis, autoimmune infertility, immune complex disorders and peritonitis.

Moreover, the use of the medicament according to the present invention, in combination with or without the second medicament or second pharmaceutically active agent, can be used for the treatment and/or prevention of graft versus host disease after bone-marrow transplantation and for transplant rejection of transplanted organs that are preferably selected from liver, kidney, intestine, lung, heart, skin, limb, cornea, islets of Langerhans, bone marrow, blood vessels and pancreas.

In a mouse model of allergic airway disease, an antibody targeting CXCR4 on leukocytes reduced airway hyper-responsiveness and lung eosinophilia, indicating that CXCR4-mediated signals contribute to lung inflammation (Gonzalo, Lloyd et al. 2000). There is also evidence that SDF-1 contributes to angiogenesis. Clinical and experimental evidence indicate that skin-infiltrating leukocytes play a crucial role in the initiation and maintenance of atopic dermatitis and it has been shown that SDF-1 is an important factor for the recruitment of T-lymphocytes and dendritic cells, (Gombert, Dieu-Nosjean et al. 2005). Since leukocytes and specifically T cells express the SDF-1 receptor, CXCR4, and respond chemotactically to SDF-1 gradients, the disruption of these gradients by SDF-1 binding and neutralizing nucleic acid according to the present invention is suitable for helping in inflammatory diseases with overshooting inflammation with and without bacterial or viral origin, inflammation of the lung and/or the skin, preferably psoriasis.

Rheumatoid arthritis is a potentially systemic autoimmune disease that usually begins in the small joints of hands and feet. Its hallmark is the inflammation of the synovial membrane that is characterized by infiltration of the membrane and the surrounding tissue by leukocytes, especially macrophages, T cells and B cells. This process and the secretion of proteases and pro-inflammatory cytokines leads to the thickening of the synovial membrane and the growth of a spongy tissue, called pannus. It proliferates around the joint and invasively into bone and cartilage, leading to their irreversible destruction. The pannus triggers the formation of neovasculature for its own blood supply. Iwamoto et al. have recently found that a number of chemokines are elevated in the synovial tissue and the synovial fluid of RA patients, among them is SDF-1 (Iwamoto et al, 2008). The up-regulation of SDF-1 had also been shown previously in vitro by adding synovial fluid from RA patients to cultured fibroblast-like synoviocytes. This fluid or the addition of IL-17 induced SDF-1 mRNA expression by the synoviocytes. The induction of SDF-1 expression could be abrogated by addition of anti-IL17 antibodies (Kim et al, 2007). In the context of an inflamed joint, SDF-1 may act in a threefold manner. First as a chemoattractant for leukocytes, second as an attractant for endothelial progenitor cells that are needed for angiogenesis or third as a trigger of downstream growth factor expression, such as VEGF, which then leads to the growth of neovasculature.

Based on these experiments, the inventors assume that a medicament that is used for inhibition of migration of leukocytes, preferably from the peripheral blood to a tissue, may permit the treatment and/or prevention of diseases and/or disorders as follows.

The migration of leukocytes can be initiated by non-self antigens of transplanted organs, whereby the transplanted organs are selected from liver, kidney, intestine, lung, heart, skin, limb, cornea, islets of Langerhans, bone marrow, blood vessels and pancreas. Therefore a medicament that leads to an inhibition of migration of leukocytes may be used for the prevention and/or treatment of transplant rejection of transplanted organs as disclosed herein.

Moreover, the migration of leukocytes can be initiated by inflammation that occurs in or is associated with systemic autoimmune diseases whereby such systemic autoimmune disease is preferably selected from allergy, warm and cold autoimmune hemolytic anemia, systemic inflammatory response syndrome, hemorrhagic shock, diabetes type 1, diffuse scleroderma, polychondritis, polyglandular autoimmune syndrome, systemic lupus erythematosus and manifestations thereof, rheumatoid arthritis, rheumatic disease in the eye, brain, lung, kidneys, heart, liver, gastrointestinal tract, spleen, skin, bones, lymphatic system, blood or other organs;

autoimmune diseases of the gastrointestinal tract whereby such autoimmune disease of the gastrointestinal tract is preferably selected from Crohn's disease, colitis ulcerosa, celiac disease, gluten intolerance, inflammatory bowel disease, pancreatitis, eosinophilic esophagitis;

autoimmune diseases of the skin whereby such autoimmune disease of the skin is preferably selected from psoriasis, urticaria, dermatomyositis, pemphigus vulgaris, pemphigus foliaceus, bullous pemphigoid, Morphea/linear scleroderma, vitiligo, dermatitis herpetiformis or Duhring's disease, lichen sclerosis;

autoimmune diseases of the vasculature whereby such autoimmune disease of the vasculature is preferably selected from vasculitides, preferably arteritis temporalis, vasculitis, vascular leakage, polymyalgia rheumatica, atherosclerosis, Churg-Strauss syndrome, Takayasu arteritis, Goodpasture syndrome, preferably mostly affecting the kidneys, more specifically the glomeruli, and also mostly affecting the lungs, glomerulonephritis, polyarteritis nodosa, Behçet's disease;

autoimmune diseases of the nervous system whereby such autoimmune disease of the nervous system is preferably selected from multiple sclerosis, chronic inflammatory demyelinating polyneuropathy, neurocognitive dysfunction, stiff-man syndrome, Guillain-Barrésyndrome, myasthenia gravis, Lambert-Eaton syndrome;

muscular skeletal autoimmune diseases whereby such muscular skeletal autoimmune disease is preferably selected from ankylosing spodylitis, sarcoidosis, polymyalgia rheumatica, polymyositis, psoriatic arthritis, rheumatic fever, polychondritis, fibromyalgia, juvenile rheumatoid arthritis, Lyme disease, reactive arthritis, spondyloarthropathy, degenerative joint disease;

and other autoimmune diseases whereby such other autoimmune diseases are preferably selected from Cogan syndrome, autoimmune adrenalitis, Ménière's disease, local inflammations, alopecia areata, acute inflammatory diseases, primary biliary cirrhosis, Sjörgen's syndrome, scleroderma such as diffuse scleroderma, CREST syndrome and/or Morphea/linear scleroderma, autoimmune uveitis, Hashimoto thyroiditis, Graves disease, autoimmune hepatitis, glomerulonephritis, anti-phospholipid syndrome, idiopatic pulmonar fibrosis, autoimmune infertility, immune complex disorders and peritonitis.

Therefore a medicament that leads to an inhibition or reduction of migration of leukocytes may be used for the prevention and/or treatment of inflammation that occurs in or is associated with the autoimmune diseases as disclosed herein.

As shown in the mouse model of allergic airway disease, the medicament that leads to an inhibition of migration of leukocytes may be effective in treatment and/or prevention of allergic reactions of the skin and/or the mucosa of airways, preferably hay fever, asthma, airway hyper-responsiveness and/or dermatitis, preferably contact dermatitis and/or atopic dermatitis.

The mobilization of progenitor cells and/or stem cells by the nucleic acid according to the present invention provides a method for obtaining these cells from a subject. Thereby an effective amount of the nucleic acid molecules according to the invention is administered a subject, leading to mobilization of progenitor cells and/or stem cells into the peripheral blood of the subject. The cells can be harvested from the subject, from the peripheral blood of the subject respectively, by apheresis, leukapheresis, cell sorting and/or flow cytometry as disclosed herein.

After harvesting the progenitor cells and/or stem cells from the subject, the subject, preferably a first subject, may undergo subsequently or concomitantly chemotherapy or radiotherapy.

Chemotherapy and radiation therapy generally affect cells that divide rapidly. They are used to treat cancer because cancer cells divide more often than most healthy cells. However, because bone marrow cells also divide frequently, high-dose treatments can severely damage or destroy the patient's bone marrow. Without healthy bone marrow, the patient is no longer able to make the blood cells needed to carry oxygen, fight infection, and prevent bleeding. peripheral blood stem cell transplantation replaces stem cells that were destroyed by treatment. The healthy, transplanted stem cells can restore the bone marrow's ability to produce the blood cells the patient needs.

Peripheral blood stem cell transplantation is most commonly used in the treatment of leukemia and lymphoma. It is most effective when the leukemia or lymphoma is in remission (the signs and symptoms of cancer have disappeared). Peripheral blood stem cell transplantation is also used to treat other cancers such as neuroblastoma (cancer that arises in immature nerve cells and affects mostly infants and children) and multiple myeloma. Researchers are evaluating peripheral blood stem cell transplantation in clinical trials (research studies) for the treatment of various types of cancer (NCI, 2001).

As shown in FIGS. 41 and 43 several types of cancer as leukemia and solid tumors, lymphoproliferative disorders and non-malignant disorders such as autoimmune diseases, hematopoietic disorders can be treated by allogenic and/or autologous hematopoietic stem cell transplantation (abbr. HSCT) (Gratwohl, Baldomero et al. 2002).

If the chemotherapy or radiotherapy was subsequently done in the preferably first subject, whereby the chemotherapy or radiotherapy was preferably done or administered in order to damage or destroy tumor cells, the harvested progenitor cells and/or stem cells of the preferably first subject can be administered back into the peripheral blood of the preferably first subject. Alternatively, a second subject can contribute its harvested progenitor cells and/or stem cells to the first subject, that has low level of progenitor cells and/or stem cells or those progenitor cells and/or stem cells destroyed before, e.g. by chemotherapy or radiotherapy.

The method can be used for the treatment of cancer, preferably solid tumours, hematological tumours or malignancies.

In autoimmune disease including but not limited to, e.g., lupus erythematosus, rheumatoid arthritis, especially in severe cases, one of the therapy options is to do a myeloablative or a more selective lymphoablative therapy regimen and return the hematopoietic system to the patient thereafter (Burt, Marmont et al. 2006). The hematopoietic stem cells and hematopoietic progenitor cells that are needed for the grafting of the hematopoietic system are efficiently immobilized by the nucleic acid molecules according to the present invention including but not limited to SDF-1 binding Spiegelmer NOX-A12-JE40, or by other blockade strategy of SDF-1 or of its respective receptor CXCR4.

Alternatively hematopoietic stem cells/hematopoietic progenitor cells are harvested from the blood and are used to reconstitute the patients' immune system after ablation of the hematopoietic system including the autoreactive lymphocytes by chemotherapy and/or radiation therapy. This, in principle, constitutes a curative therapy to autoimmune diseases.

The mobilization of long-lived plasma cells, B cells and/or T cells by the nucleic acid according to the present invention provides a method for depleting these cells from a subject. Thereby an effective amount of the nucleic acid molecule according to the invention is administered to a subject, leading to mobilization of long-lived plasma cells, B cells and/or T cells into the peripheral blood of the subject. Preferably the harvested T cells are memory T cells. The cells can be removed from the subject, from the peripheral blood of the subject respectively, by apheresis, leukapheresis, cell sorting and/or flow cytometry as disclosed herein. Preferably the removal is done by flow cytometry with surface markers appropriate for said cells.

The method for harvesting progenitor cells and/or stem cells and long-lived plasma cells, B cells and/or T cells respectively may be used for treatment and/or prevention of systemic autoimmune diseases, autoimmune diseases of the gastrointestinal tract, autoimmune diseases of the skin, autoimmune diseases of the vasculature, autoimmune diseases of the nervous system, muscular skeletal autoimmune diseases and other autoimmune diseases as disclosed herein.

Diabetic nephropathy (abbr. DN) is a prominent cause of end-stage renal disease. Though angiotensin inhibitors can prevent the disease progression in many cases, there is no viable therapy for those who do not respond. In DN the glomerular tuft undergoes a slow but progressive structural remodelling characterized by glomerular hypertrophy, nodular and diffuse accumulation of extracellular mesangial matrix, and podocyte damage. The latter is thought to account for the progression of microalbuminuria in early stages to overt proteinuria and glomerulosclerosis in late stages of DN. DN onset and progression involves numerous pathomechanisms including the deposition of advanced glycosylation endproducts, endothelial dysfunction, and the increased local expression of growth factors and proinflammatory mediators. Generally, chemokines belong to the latter group of factors because certain chemokines promote inflammation by recruiting and activating immune cells in DN like in other types of kidney diseases. For example, targeted deletion or therapeutic blockade of the monocyte chemoattractant protein MCP-1/CCL2 can prevent glomerulosclerosis by blocking macrophage recruitment to glomeruli of mice with type 1 or type 2 diabetes (T1D/T2D) (Chow et al, 2007; Chow et al, 2006; Kulkarni et al, 2007).

Nothing is known about SDF-1 in DN. DN is devoid of either podocyte proliferation or autoimmunity, hence, the aforementioned studies hardly predict the predominant functional role of SDF-1 in DN. However, the inventors have reasons to assume that progressive remodeling of the glomerular structure to glomerulosclerosis, a morphological variant of wound healing, might involve SDF-1 signaling. Based on the available data from other disease states it appeared unclear whether SDF-1 either predominantly protects from DN, e.g. by maintaining tissue integrity and supporting regeneration, or whether SDF-1 predominately promotes DN, e.g. by enhancing glomerulosclerosis. The inventors' data using the SDF-1-binding nucleic acid NOX-A12-JE40 (SEQ.ID. 132) as a representative molecule of the nucleic acid molecules according to the present invention, in a mouse model of diabetic nephropathy support the latter, which identifies a novel pathomechanism of glomerulosclerosis, and SDF-1 as a potential therapeutic target in DN in Example 12. NOX-A12-JE40 (SEQ.ID. 132) may therefore be useful as a therapy for the treatment or prevention, of diabetic nephropathy. The mechanism of action may potentially also be mediated by the mobilization of bone-marrow derived progenitor and/or stem cells (Ito et al, 2001). Therefore the SDF-1 nucleic acids disclosed herein may be used for manufacture of a medicament, whereby the medicament is for treatment and/or prevention of nephropathy and preferably diabetic nephropathy.

Pulmonary Arterial Hypertension.

PULMONARY HYPERTENSION (abbr. PH) is a serious disease of poorly understood etiology characterized by raised pulmonary artery pressure, leading to progressive right-sided heart failure and ultimately death. PH results from intimal thickening of small pulmonary resistance arteries that results, at least in part, from endothelial and smooth muscle cell dysfunction and proliferation. Increased vascular endothelial cell proliferation and muscularization of the vasculature are the pathological characteristics of pulmonary vascular remodeling, and it has been demonstrated that this process is associated with hypoxia-induced production of angiogenic factors, inflammatory mediators, and vasoconstrictors. Yamaji-Kegan et al. found in an ex vivo mouse lung organ culture study that CXCL12/SDF-1 was upregulated and may be involved in the intrapulmonary recruitment of circulating cells by the overexpressed hypoxia-induced mitogenic factor (abbr. HIMF) (Yamaji-Kegan, Su et al. 2006). The influence of SDF-1 in vascular remodeling in general and in pulmonary arterial hypertension has also been described (Schober and Zernecke 2007). Therefore the blockade of SDF-1 by SDF-binding nucleic acids as disclosed herein may be used for the treatment and/or prevention of hypertension, preferably pulmonary hypertension, more specifically pulmonary arterial hypertension.

Idiopathic Pulmonary Fibrosis

Lung tissue from patients with idiopathic pulmonary fibrosis is described to have higher numbers of cells expressing both SDF-1 and CXCR4 than normal lungs. In a mouse model of bleomycin-induced pulmonary fibrosis, Xu et al. generated data showing that the administration of a CXCR4 antagonist (TN14003) significantly attenuated lung fibrosis. (Xu, Mora et al. 2007). Therefore the blockade of SDF-1 by SDF-binding nucleic acids as disclosed as disclosed may be used for the treatment and/or prevention of idiopathic pulmonary fibrosis.

Fribrosis in Wound Healing

After burn injury, skin of rat, pig and humans has been shown to overexpress SDF-1. While being beneficial during a short period of time after injury, it is believed to promote the attraction of leukocytes (e.g. eosinophils) and fibrosis rather than to promote epithelialization (Avniel, Arik et al. 2006). By inhibition of CXCR4 or SDF-1 by SDF-1 binding nucleic acids as disclosed herein, wound healing with less fibrosis may be obtained.

As described before, SDF-1 has been shown to be involved in homing of endothelial cells to the choroid during neovascularization in eye tissue, whereby the exact role of these cells is still under investigation (Sengupta, Caballero et al. 2005). However, the inventors could show in two independent animal models that the blockade of SDF-1 by SDF-1 binding nucleic according to the present invention as disclosed herein leads to a reduction of neovascularization.

The 'laser-induced choroidal neovascularization' animal model is used to predict the effect of investigational drugs on human retinal and choroidal neovasculature. This occurs in diseases like wet or 'proliferative' age-related macular degeneration (abbr. AMD), diabetic retinopathy and retinal vein occlusion. CXCR4 was shown to be expressed in the laser-induced CNV (Lima e Silva et al., FASEB J. 21: 2007). It was colocalized with CD45 and F4/80 expressing cells suggesting that these cells are BM-derived macrophages. Inhibitors of CXCR4 reduced laser-induced CNV. But it was not investigated if the CXCR4 cells express SDF1, too. As successfully shown in Example 11 herein, the SDF-1 binding nucleic acid NOX-A12-JE40 (SEQ.ID. 132) as a representative nucleic acid molecule according to the present invention blocks neovascularization in a CNV animal model.

The mouse model of oxygen-induced retinopathy is a model for the mimicking of hypoxia-induced neovascularization of the retina, as observed in DR, especially proliferative DR, and in AMD (Smith, Wesolowski et al. 1994). The model is also referred to as retinopathy of prematurity since premature babies that were put into incubators in hospitals became blind due to too high oxygen exposure in the incubators that led to an abnormal retinal vessel growth during the time in the incubator and after their return to normoxic conditions. As described in Example 14, in the mouse model the SDF-1 binding nucleic acid NOX-A12-JE40 (SEQ.ID. 132) as a representative nucleic acid molecule according to the present invention significantly inhibited tuft formation and thus improved the overall retinopathy score as observed on day P17 as disclosed herein.

Moreover, as in shown in Example 9, in a standard angiogenesis organ culture assay, an aortic ring sprouting assay, the SDF-1 binding nucleic acid 193-G2-012-5'-PEG (NOX-A12-JE40 (SEQ.ID. 132) as a representative nucleic acid molecule according to the present invention blocks SDF-1 induced sprouting.

Therefore, the SDF-1 binding nucleic acids as disclosed herein may be used for manufacture of a medicament, whereby the medicament is for the treatment of diseases and/or disorders that involve angiogenesis and/or neovascularization, preferably choroidal neovascularization. The animal model for neovascularization have shown, that SDF-1 binding nucleic acids as disclosed herein can be used as a medicament for the treatment of diseases and/or disorders that are selected from the group comprising retinal diseases, preferably age-related macular degeneration, diabetic retinopathy, retinal vein occlusion, macular edema and retinal edema.

Neovascularization is preferably defined herein as the formation of functional microvascular networks with red blood cell perfusion. Neovascularization differs from angiogenesis in that angiogenesis is mainly characterized by the protrusion and outgrowth of capillary buds and sprouts from pre-existing blood vessels.

Inhibition of Retinal Vascular Edema

In the course of age-related macular degeneration (AMD), diabetic retinopathy and retinal vascular occlusions, the formation of a macular edema is often observed. Generally, an increased permeability of the local vasculature is the cause of the formation of an edema. Often this is a consequence of inflammatory processes that change the vascular architecture or of the formation of immature, leaky neovasculature.

The formation of a macular edema can lead to a rapid deterioration of visual acuity because the retinal supply with nutrients and other signaling molecules is impaired.

SDF-1 contributes to several factors that may lead to the formation of an edema. By inhibiting the expression of the tight junction protein occludin (Butler et al, 2005), the vascular walls may loosen up. It furthermore triggers the invasion of leukocytes that may create a pro-inflammatory environment and it can stimulate the expression of VEGF (Liang et al, 2007; Salcedo et al, 1999), which was first known as "vascular permeability factor", as its presence leads to the formation of leaky vessels.

It was unclear, whether inhibition of SDF-1, e.g. by SDF-1-binding nucleic acids as disclosed in this invention, would lead to any physiological effect, as SDF-1 is only expressed at low levels in healthy eyes (Lima e Silva et al, 2007).

One SDF-1-binding nucleic acid was tested in a rabbit model of VEGF-induced retinal vascular permeability. The permeability that was observed with fluorometry was not due to the direct short-acting effect of the intravitreal VEGF-injection but rather on cascades, that are triggered and respond more slowly (Edelman et al, 2005). The SDF-1-binding nucleic acid significantly reduced the retinal vascular permeability in a dose-dependent manner.

Inhibition of Vasculogenesis Complementary to or after Failure of VEGF-Inhibition Recently, Reddy et al. have shown that SDF-1 can promote tumor vessel growth even with little VEGF present. It seems to be a second, VEGF-independent pathway for the promotion of neovasculature (Reddy, Zhou et al. 2008). Interfering with SDF-1 signaling by SDF-1 bining nucleic acids such as the ones according to the present invention may therefore be beneficial as an antiangiogenesis treatment. This may be especially advantageous in anti-VEGF non-responders, in anti-VEGF therapy refractory patients, or in combination therapy with anti VEGF drugs for all indications that involve angiogenesis, more specifically in proliferative retinal diseases, whereby the proliferative retinal diseases are selected from AMD, DR, and retinal vein occlusion, and in cancer preferably solid tumors and metastases.

Drugs that inhibits the function of VEGF include but are not limited to Bevacizumab (Avastin), Pegaptanib (Macugen) and Ranibizumab (Lucentis).

Insofar, the SDF-1 nucleic acid molecules disclosed herein may be used for manufacture of a medicament, whereby the medicament is for combination therapy with a medicament inhibiting VEGF and/or for use in subjects that weakly or not respond to therapy with a medicament inhibiting VEGF. Weakly as used herein in connection with response to any therapy in connection with any aspect and embodiment of the instant application, means in this context that no remission of the disease is achieved.

WHIM Syndrome

The WHIM syndrome is an immune deficiency that is often characterized by a truncated form of the CXCR4 receptor. This leads to an increased sensitisation to the receptor ligand SDF-1 (CXCL-12) and thus to stronger chemotaxis. Therefore, in order to achieve normal stem cell trafficking it is beneficial to lower the biologically active SDF-1 concentration in the body with an SDF-1 blocking agent like an SDF-1 binding nucleic acid molecule according to the present invention or to use a CXCR4 receptor blocker (Lagane, Chow et al. 2008).

The separation and/or depletion of cells like progenitor cell and/or stem cells, long-lived plasma cells, memory B cells and/or memory T cells from the body, preferably from the blood, can be done by apheresis, cell sorting and flow cytometry.

Apheresis is a technology in which the blood of a subject is passed through an apparatus that separates out one particular constituent or group of constituents and return the remainder to the circulation. Depending on the substances and/cells cells to be removed, different processes were employed in apheresis including stem cell harvesting, absorption procedures and affinity chromatography.

Leukapheresis is a laboratory procedure in which white blood cells are separated from a sample of blood. This may be done to decrease a very high white blood cell count in individuals with cancer (leukemia) or to remove white blood cells for transfusion.

Cell sorting is a process whereby mixed populations of cells separate out into two or more populations as exemplarily shown for flow cytometry, preferably Fluorescence-Activated Cell Sorting (FACS) and Magnetic-Activated Cell Sorting (FACS).

Flow cytometry is a technique for counting, examining, and sorting microscopic particles like different populations of cells suspended in a stream of fluid. It allows simultaneous multiparametric analysis of the physical and/or chemical characteristics of single cells flowing through an optical and/or electronic detection apparatus. Fluorescence-activated cell sorting is a specialised type of flow cytometry. It provides a method for sorting a heterogeneous mixture of biological cells into two or more containers, one cell at a time, based upon the specific light scattering and fluorescent characteristics of each cell. Fluorescent staining of a particle/cell can be done by incubation of the particles/cells with a fluorescent dye that binds to the particle/cell. It is a useful scientific instrument as it provides fast, objective and quantitative recording of fluorescent signals from individual cells as well as physical separation of cells of particular interest. The acronym FACS is trademarked and owned by Becton Dickinson. Magnetic-activated cell sorting (MACS) is a trademark name registered by Miltenyi Biotec for a method for separation of various cell populations depending on their surface antigens (CD molecules). Thereby the mixture of cells to be separated is incubated with magnetic beads coated with antibodies against a particular surface antigen. This causes the cells expressing this antigen to attach to the magnetic beads. Afterwards the cell solution is transferred on a column placed in a strong magnetic field. In this step, the cells attached to the beads (expressing the antigen) stay on the column, while other cells (not expressing the antigen) flow through. With this method, the cells can be separated positively or negatively with respect to the particular antigen(s).

In a further embodiment, the medicament comprises a further pharmaceutically active agent. Such further pharmaceutically active compounds can be those known to the ones skilled in the art and are preferably selected from the group comprising chemokine or cytokine antagonists, corticosteroids, and the like. It will be understood by the one skilled in the art that given the various indications which can be addressed in accordance with the present invention by the nucleic acids according to the present invention, said further pharmaceutically active agent(s) may be any one which in principle is suitable for the treatment and/or prevention of such diseases. The nucleic acid molecules according to the present invention, particularly if present or used as a medicament, are preferably combined with granulocyte-macrophage colony stimulating factor (GM-CSF), Interleukin-1 (IL-1), Interleukin-3 (IL-3), Interleukin-8 (IL-8), PIXY-321 (GM-CSF/IL-3 fusion protein), macrophage inflammatory protein (MIP), stem cell factor, thrombopoietin and growth related oncogene, as single agents or in combination.

Alternatively, or additionally, such further pharmaceutically active agent is a further nucleic acid according to the present invention. Alternatively, the medicament comprises at least one more nucleic acid which binds to a target molecule different from SDF-1 or exhibits a function which is different from the one of the nucleic acids according to the present invention.

As will be acknowledged by the ones of the art the inventive nucleic acids may factually be used in any disease where an antagonist to SDF-1 can be administered to a patient in need of such antagonist and such antagonist is suitable to eliminate the cause of the disease or the disorder or at least to reduce the effects from the disease or the disorder. Such effect includes, but is not limited to pathologic neovascularization, inflammation and metastasis. The applicability of the nucleic acids according to the present invention in connection with these and other diseases or disorders results, among others, from the involvement of SDF-1 as outlined in the introductory part of the present specification which is incorporated herein by reference so as to avoid any unnecessary repetition.

In one embodiment of the medicament of the present invention, such medicament is for use in combination with other treatments for any of the diseases disclosed herein, particularly those for which the medicament of the present invention is to be used.

"Combination therapy" (or "co-therapy") includes the administration of a medicament of the invention and at least a second agent as part of a specific treatment regimen intended to provide the beneficial effect from the co-action of these therapeutic agents, i. e. the medicament of the present invention and said second agent. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to a subject a single capsule having a fixed ratio of each therapeutic agent or in multiple, single capsules for each of the therapeutic agents.

Sequential or substantially simultaneous administration of each therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically.

Alternatively, for example, all therapeutic agents may be administered topically or all therapeutic agents may be administered by injection. The sequence in which the therapeutic agents are administered is not narrowly critical unless noted otherwise. "Combination therapy" also can embrace the administration of the therapeutic agents as described above in further combination with other biologically active ingredients. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

As outlined in general terms above, the medicament according to the present invention can be administered, in principle, in any form known to the ones skilled in the art. A preferred route of administration is systemic administration, more preferably by parenteral administration, preferably by injection. Alternatively, the medicament may be administered locally. Other routes of administration comprise intramuscular, intraperitoneal, and subcutaneous, per orum, intranasal, intratracheal or pulmonary with preference given to the route of administration that is the least invasive, while ensuring efficiency.

Parenteral administration is generally used for subcutaneous, intramuscular or intravenous injections and infusions. Additionally, one approach for parenteral administration employs the implantation of a slow-release or sustained-released systems, which assures that a constant level of dosage is maintained, that are well known to the ordinary skill in the art.

Furthermore, preferred medicaments of the present invention can be administered in intranasal form via topical use of suitable intranasal vehicles, inhalants, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would typically range from 0.01% to 15%, w/w or w/v.

In addition to direct administration to the subject, the preferred medicaments of the present invention can be used in ex vivo treatment protocols to prepare cell cultures which are then used to replenish the blood cells of the subject. Ex vivo treatment can be conducted on autologous cells harvested from the peripheral blood or bone marrow or from allografts from matched donors. The concentration of preferred medicaments of the present invention or in combination with other agents, such as macrophage inflammatory protein is within the skills of a person of the art.

Subjects that will respond favorably to the method of the invention include medical and veterinary subjects generally, including human beings and human patients. Among other subjects for whom the methods and means of the invention are useful are cats, dogs, large animals, avians such as chickens, and the like. In general, any subject who would benefit from an elevation of progenitor cells and/or stem cells, or whose progenitor cells and/or stem cells are desirable for stem cell transplantation are appropriate for administration of the invention method.

Typical conditions which may be ameliorated or otherwise benefited by the method and the means of the invention include hematopoietic disorders, such as aplastic anemia, leukemias, drug-induced anemias, and hematopoietic deficits from chemotherapy or radiation therapy. The method and the means of the invention are also useful in enhancing the success of transplantation during and following immunosuppressive treatments as well as in effecting more efficient wound healing and treatment of bacterial inflammation. The method of the present invention is further useful for treating subjects who are immunocompromised or whose immune system is otherwise impaired. Typical conditions which are ameliorated or otherwise benefited by the method of the present invention, include those subjects who are infected with a retrovirus and more specifically who are infected with human immunodeficiency virus (HIV). The method of the invention thus targets a broad spectrum of conditions for which elevation of progenitor cells and/or stem cells in a subject would be beneficial or, where harvesting of progenitor cells and/or stem cell for subsequent stem cell transplantation would be beneficial.

The nucleic acid of the present invention is, in an embodiment, sign also administered to regenerate myocardium by mobilizing bone marrow stem cells.

The medicament of the present invention will generally comprise an effective amount of the active component(s) of the therapy, including, but not limited to, a nucleic acid molecule of the present invention, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the medicament of the present invention.

In a further aspect the present invention is related to a pharmaceutical composition. Such pharmaceutical composition comprises at least one of the nucleic acids according to the present invention and preferably a pharmaceutically acceptable binder. Such binder can be any binder used and/or known in the art. More particularly such binder is any binder as discussed in connection with the manufacture of the medicament disclosed herein. In a further embodiment, the pharmaceutical composition comprises a further pharmaceutically active agent.

The preparation of a medicament and a pharmaceutical composition will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or sponge.

Upon formulation, a medicament will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the individual or the subject to be treated. Specific amounts of active compound required for administration depend on the judgment of the practitioner and are peculiar to each individual.

A minimal volume of a medicament required to disperse the active compounds is typically utilized. Suitable regimes for administration are also variable, but would be typified by initially administering the compound and monitoring the results and then giving further controlled doses at further intervals.

For instance, for oral administration in the form of a tablet or capsule (e.g., a gelatin capsule), the active drug component, i. e. a nucleic acid molecule of the present invention and/or any further pharmaceutically active agent, also referred to herein as therapeutic agent(s) or active compound (s) can be combined with an oral, non-toxic, pharmaceutically acceptable inert carrier such as ethanol, glycerol, water and the like. Moreover, when desired or necessary, suitable binders, lubricants, disintegrating agents, and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes, and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol, and the like. Disintegrators include, without limitation, starch, methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine.

The medicament of the invention can also be administered in such oral dosage forms as timed release and sustained release tablets or capsules, pills, powders, granules, elixirs, tinctures, suspensions, syrups and emulsions. Suppositories are advantageously prepared from fatty emulsions or suspensions.

The pharmaceutical composition or medicament may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating, or coating methods, and typically contain about 0.1% to 75%, preferably about 1% to 50%, of the active ingredient.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated.

For solid compositions, excipients include pharmaceutical grades of mannitol, lactose, starch, magnesium stearate, sodium saccharin, talcum, cellulose, glucose, sucrose, magnesium carbonate, and the like. The active compound defined above, may be also formulated as suppositories, using for example, polyalkylene glycols, for example, propylene glycol, as the carrier. In some embodiments, suppositories are advantageously prepared from fatty emulsions or suspensions.

The medicaments and nucleic acid molecules, respectively, of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, what is well known to the ordinary skill in the art. For example, the nucleic acid molecules described herein can be provided as a complex with a lipophilic compound or non-immunogenic, high molecular weight compound constructed using methods known in the art. Additionally, liposomes may bear such nucleic acid molecules on their surface for targeting and carrying cytotoxic agents internally to mediate cell killing. An example of nucleic-acid associated complexes is provided in U.S. Pat. No. 6,011,020.

The medicaments and nucleic acid molecules, respectively, of the present invention may also be coupled with soluble polymers as targetable drug carriers. Such polymers can include polyvinylpyrrolidone, pyran copolymer, polyhydroxypropyl-methacrylamide-phenol, polyhydroxyethyl-aspanamidephenol, or polyethyleneoxidepolylysine substituted with palmitoyl residues. Furthermore, the medicaments and nucleic acid molecules, respectively, of the present invention may be coupled to a class of biodegradable polymers useful in achieving controlled release of a drag, for example, polylactic acid, polyepsilon capro lactone, polyhydroxy butyric acid, polyorthoesters, polyacetals, polydihydropyrans, polycyanoacrylates and cross-linked or amphipathic block copolymers of hydrogels.

If desired, the pharmaceutical composition and medicament, respectively, to be administered may also contain minor amounts of non-toxic auxiliary substances such as wetting or emulsifying agents, pH buffering agents, and other substances such as for example, sodium acetate, and triethanolamine oleate.

The dosage regimen utilizing the nucleic acid molecules and medicaments, respectively, of the present invention is selected in accordance with a variety of factors including type, species, age, weight, sex and medical condition of the patient; the severity of the condition to be treated; the route of administration; the renal and hepatic function of the patient; and the particular aptamer or salt thereof employed. An ordinarily skilled physician or veterinarian can readily determine and prescribe the effective amount of the drug required to prevent, counter or arrest the progress of the condition.

Effective plasma levels of the nucleic acid according to the present invention preferably range from 500 fM to 500 µM in the treatment of any of the diseases disclosed herein.

The nucleic acid molecules and medicaments, respectively, of the present invention may preferably be administered in a single daily dose, every second or third day, weekly, every second week, in a single monthly dose or every third month.

It is within the present invention that the medicament as described herein constitutes the pharmaceutical composition disclosed herein.

In a further aspect the present invention is related to a method for the treatment of a subject who is in need of such treatment, whereby the method comprises the administration of a pharmaceutically active amount of at least one of the nucleic acids according to the present invention. In an embodiment, the subject suffers from a disease or is in risk to develop such disease, whereby the disease is any of those disclosed herein, particularly any of those diseases disclosed in connection with the use of any of the nucleic acids according to the present invention for the manufacture of a medicament.

As preferably used herein, the term treatment comprises in a preferred embodiment additionally or alternatively prevention and/or follow-up.

As preferably used herein, the terms disease and disorder shall be used in an interchangeable manner, if not indicated to the contrary.

As used herein, the term comprise is preferably not intended to limit the subject matter followed or described by such term. However, in an alternative embodiment the term comprises shall be understood in the meaning of containing and thus as limiting the subject matter followed or described by such term.

The various SEQ.ID.Nos., the chemical nature of the nucleic acid molecules according to the present invention and the target molecules SDF-1 as used herein, the actual sequence thereof and the internal reference number is summarized in the following table.

It has to be noticed that the nucleic acids were characterized on the aptamer, i. e. D-nucleic acid level (D-RNA) with the biotinylated human D-SDF-1 (SEQ.ID. 4) or on the Spiegelmer level, i. e. L-nucleic acid (L-RNA) with the natural configuration of SDF-1, the L-SDF-1 (human SDF-1 α, SEQ-ID. 1). The different nucleic acids share one internal reference name but one SEQ.ID for the D-RNA (Aptamer) molecule and one SEQ.ID. for the L-RNA (Spiegelmer) molecule, respectively.

TABLE 1

| Seq.-ID | RNA/Peptide | Sequence | Internal Reference |
|---|---|---|---|
| 1 | L-peptide | KPVSLSYRCPCRFFESHVARANVKHLKILNTPNCALQIVARLKNN NRQVCIDPKLKWIQEYLEKALNK | human/monkey/cat SDF-1α human/monkey/cat SDF-1 |
| 2 | L-peptide | KPVSLSYRCPCRFFESHVARANVKHLKILNTPNCALQIVARLKNN NRQVCIDPKLKWIQEYLEKALNKRFKM | human/monkey/cat SDF-1β |
| 3 | L-peptide | KPVSLSYRCPCRFFESHIARANVKHLKILNTPNCALQIVARLKNN NRQVCIDPKLKWIQEYLEKALNK | murine SDF-1α murine SDF-1 |
| 4 | D-peptide | KPVSLSYRCPCRFFESHVARANVKHLKILNTPNCALQIVARLKNN NRQVCIDPKLKWIQEYLEKALNKRFK-Biotin | biotinylated hu D-SDF-1 |
| 5 | L-RNA (SPIEGELMER) | GCUGUGAAAGCAACAUGUCAAUGAAAGGUAGCCGCAGC | 192-A10-001 |
| 6 | L-RNA (SPIEGELMER) | GCUGUGAAAGUAACAUGUCAAUGAAAGGUAACCACAGC | 192-G10 |
| 7 | L-RNA (SPIEGELMER) | GCUGUGAAAGUAACACGUCAAUGAAAGGUAACCGCAGC | 192-F10 |
| 8 | L-RNA (SPIEGELMER) | GCUGUGAAAGUAACACGUCAAUGAAAGGUAACCACAGC | 192-B11 |
| 9 | L-RNA (SPIEGELMER) | GCUGUAAAAGUAACAUGUCAAUGAAAGGUAACUACAGC | 192-C9 |
| 10 | L-RNA (SPIEGELMER) | GCUGUAAAAGUAACAAGUCAAUGAAAGGUAACUACAGC | 192-E10 |
| 11 | L-RNA (SPIEGELMER) | GCUGUGAAAGUAACAAGUCAAUGAAAGGUAACCACAGC | 192-C10 |
| 12 | L-RNA (SPIEGELMER) | GCAGUGAAAGUAACAUGUCAAUGAAAGGUAACCACAGC | 192-D11 |
| 13 | L-RNA (SPIEGELMER) | GCUGUGAAAGUAACAUGUCAAUGAAAGGUAACCACUGC | 192-G11 |
| 14 | L-RNA (SPIEGELMER) | GCUAUGAAAGUAACAUGUCAAUGAAAGGUAACCAUAGC | 192-H11 |
| 15 | L-RNA (SPIEGELMER) | GCUGCGAAAGCGACAUGUCAAUGAAAGGUAGCCGCAGC | 192-D10 |
| 16 | L-RNA (SPIEGELMER) | GCUGUGAAAGCAACAUGUCAAUGAAAGGUAGCCACAGC | 192-E9 |
| 17 | L-RNA (SPIEGELMER) | GCUGUGAAAGUAACAUGUCAAUGAAAGGUAGCCGCAGC | 192-H9 |
| 18 | L-RNA (SPIEGELMER) | AGCGUGAAAGUAACACGUAAAAUGAAAGGUAACCACGCU | 191-A6 |
| 19 | L-RNA (SPIEGELMER) | AAAGYRACAHGUMAAX$_A$UGAAAGGUARC; X$_A$ = A or absent | Type A Formula-1 |
| 20 | L-RNA (SPIEGELMER) | AAAGYRACAHGUMAAUGAAAGGUARC | Type A Formula-2 |
| 21 | L-RNA (SPIEGELMER) | AAAGYRACAHGUMAAAUGAAAGGUARC | Type A Formula-3 |
| 22 | L-RNA (SPIEGELMER) | AAAGYAACAHGUCAAUGAAAGGUARC | Type A Formula-4 |
| 23 | L-RNA (SPIEGELMER | RSHRYR | Type A Formula-5-5' |
| 24 | L-RNA (SPIEGELMER | YRYDSY | Type A Formula-5-3' |
| 25 | L-RNA (SPIEGELMER) | CUGUGAAAGCAACAUGUCAAUGAAAGGUAGCCGCAG | 192-A10-002 |
| 26 | L-RNA (SPIEGELMER) | UGUGAAAGCAACAUGUCAAUGAAAGGUAGCCGCA | 192-A10-003 |
| 27 | L-RNA (SPIEGELMER) | GUGAAAGCAACAUGUCAAUGAAAGGUAGCCGC | 192-A10-004 |
| 28 | L-RNA (SPIEGELMER) | UGAAAGCAACAUGUCAAUGAAAGGUAGCCG | 192-A10-005 |
| 29 | L-RNA (SPIEGELMER) | GAAAGCAACAUGUCAAUGAAAGGUAGCC | 192-A10-006 |
| 30 | L-RNA (SPIEGELMER) | AAAGCAACAUGUCAAUGAAAGGUAGC | 192-A10-007 |
| 31 | L-RNA (SPIEGELMER) | GCGUGAAAGCAACAUGUCAAUGAAAGGUAGCCGCGC | 192-A10-008 |

TABLE 1-continued

| Seq.-ID | RNA/Peptide | Sequence | Internal Reference |
|---|---|---|---|
| 32 | L-RNA (SPIEGELMER) | GCGCGAAAGCAACAUGUCAAUGAAAGGUAGCCGCGC | 192-A10-015 |
| 33 | L-RNA (SPIEGELMER) | GCGGAAAGCAACAUGUCAAUGAAAGGUAGCCCGC | 192-A10-014 |
| 34 | L-RNA (SPIEGELMER) | CGUGAAAGCAACAUGUCAAUGAAAGGUAGCCGCG | 192-A10-016 |
| 35 | L-RNA (SPIEGELMER) | GCGCAAAGCAACAUGUCAAUGAAAGGUAGCGUGC | 192-A10-017 |
| 36 | L-RNA (SPIEGELMER) | GUGCAAAGCAACAUGUCAAUGAAAGGUAGCGCGC | 192-A10-018 |
| 37 | L-RNA (SPIEGELMER) | CGCGAAAGCAACAUGUCAAUGAAAGGUAGCCGUG | 192-A10-019 |
| 38 | L-RNA (SPIEGELMER) | GGGCAAAGCAACAUGUCAAUGAAAGGUAGCGCCC | 192-A10-020 |
| 39 | L-RNA (SPIEGELMER) | GGCCAAAGCAACAUGUCAAUGAAAGGUAGCGGCC | 192-A10-021 |
| 40 | L-RNA (SPIEGELMER) | GCCCAAAGCAACAUGUCAAUGAAAGGUAGCGGGC | 192-A10-022 |
| 41 | L-RNA (SPIEGELMER) | CCCCAAAGCAACAUGUCAAUGAAAGGUAGCGGGG | 192-A10-023 |
| 42 | L-RNA (SPIEGELMER) | $X_2$BBBS; X2 = S or absent | Type A Formula-6-5' |
| 43 | L-RNA (SPIEGELMER) | SBBV$X_3$; $X_3$ = S or absent | Type A Formula-6-3' |
| 44 | L-RNA (SPIEGELMER) | $X_1X_2$NNBV; $X_1$ = R or absent, $X_2$ = S or absent | Type A Formula-7-5' |
| 45 | L-RNA (SPIEGELMER) | BNBN$X_4$; $X_3$ = R or absent, $X_4$ = Y or absent | Type A Formula-7-3' |
| 46 | L-RNA (SPIEGELMER) | AGCGUGGUGUGAUCUAGAUGUAGUGGCUGAUCCUAGUCAGGUACGCU | 193-C2-001 |
| 47 | L-RNA (SPIEGELMER) | AGCGUGGUGUGAUCUAGAUGUAUUGGCUGAUCCUAGUCAGGUACGCU | 193-G2-001 |
| 48 | L-RNA (SPIEGELMER) | AGCGUGGUGUGAUCUAGAUGUAAUGGCUGAUCCUAGUCAGGUGCGCU | 193-F2-001 |
| 49 | L-RNA (SPIEGELMER) | GCGAGGUGUGAUCUAGAUGUAGUGGCUGAUCCUAGUCAGGUGCGC | 193-G1-002 |
| 50 | L-RNA (SPIEGELMER) | GCGUGGUGUGAUCUAGAUGUAGUGGCUGAUCCUAGUCAGGUGCGC | 193-D2-002 |
| 51 | L-RNA (SPIEGELMER) | GCAUGGUGUGAUCUAGAUGUAGUGGCUGAUCCUAGUCAGGUGCCC | 193-A1-002 |
| 52 | L-RNA (SPIEGELMER) | GCGUGGUGUGAUCUAGAUGUAAUGGCUGAUCCUAGUCAGGGACGC | 193-D3-002 |
| 53 | L-RNA (SPIEGELMER) | GCGUGGUGUGAUCUAGAUGUAGAGGCUGAUCCUAGUCAGGUACGC | 193-B3-002 |
| 54 | L-RNA (SPIEGELMER) | GCGUGGUGUGAUCUAGAUGUAAAGGCUGAUCCUAGUCAGGUACGC | 193-H3-002 |
| 55 | L-RNA (SPIEGELMER) | GCGUGGUGUGAUCUAGAUGUAGUGGCUGUUCCUAGUCAGGUAUGC | 193-E3-002 |
| 56 | L-RNA (SPIEGELMER) | GCGUGGUGUGAUCUAGAUGUAGUGGCUGAUCCUAGUUAGGUACGC | 193-D1-002 |
| 57 | L-RNA (SPIEGELMER) | GUGUGAUCUAGAUGUADWGGCUGWUCCUAGUYAGG | Type B Formula-1 |
| 58 | L-RNA (SPIEGELMER) | GUGUGAUCUAGAUGUADUGGCUGAUCCUAGUCAGG | Type B Formula-2 |
| 59 | L-RNA (SPIEGELMER) | $X_1$GCRWG; $X_1$ = A or absent | Type B Formula-3-5' |
| 60 | L-RNA (SPIEGELMER) | KRYSC$X_4$; $X_4$ = U or absent | Type B Formula-3-3' |
| 61 | L-RNA (SPIEGELMER) | GCGUGGUGUGAUCUAGAUGUAGUGGCUGAUCCUAGUCAGGUACGC | 193-C2-002 |
| 62 | L-RNA (SPIEGELMER) | CGUGGUGUGAUCUAGAUGUAGUGGCUGAUCCUAGUCAGGUACG | 193-C2-003 |
| 63 | L-RNA (SPIEGELMER) | GUGGUGUGAUCUAGAUGUAGUGGCUGAUCCUAGUCAGGUAC | 193-C2-004 |
| 64 | L-RNA (SPIEGELMER) | UGGUGUGAUCUAGAUGUAGUGGCUGAUCCUAGUCAGGUA | 193-C2-005 |
| 65 | L-RNA (SPIEGELMER) | GGUGUGAUCUAGAUGUAGUGGCUGAUCCUAGUCAGGU | 193-C2-006 |
| 66 | L-RNA (SPIEGELMER) | GUGUGAUCUAGAUGUAGUGGCUGAUCCUAGUCAGG | 193-C2-007 |
| 67 | L-RNA (SPIEGELMER) | GCGUGGUGUGAUCUAGAUGUAUUGGCUGAUCCUAGUCAGGUACGC | 193-G2-012 |
| 68 | L-RNA (SPIEGELMER) | GCGCGGUGUGAUCUAGAUGUAUUGGCUGAUCCUAGUCAGGCGCGC | 193-G2-013 |
| 69 | L-RNA (SPIEGELMER) | GCGCGUGUGAUCUAGAUGUAUUGGCUGAUCCUAGUCAGGGCGC | 193-G2-014 |

TABLE 1-continued

| Seq.-ID | RNA/Peptide | Sequence | Internal Reference |
|---|---|---|---|
| 70 | L-RNA (SPIEGELMER) | GGGCGUGUGAUCUAGAUGUAUUGGCUGAUCCUAGUCAGGGCCC | 193-G2-015 |
| 71 | L-RNA (SPIEGELMER) | GGCCGUGUGAUCUAGAUGUAUUGGCUGAUCCUAGUCAGGGGCC | 193-G2-016 |
| 72 | L-RNA (SPIEGELMER) | GCCCGUGUGAUCUAGAUGUAUUGGCUGAUCCUAGUCAGGGGGC | 193-G2-017 |
| 73 | L-RNA (SPIEGELMER) | $X_2$SSBS; $X_2$ = G or absent | Type B Formula-4-5' |
| 74 | L-RNA (SPIEGELMER) | BVSS$X_3$; $X_3$ = C or absent | Type B Formula-4-3' |
| 75 | L-RNA (SPIEGELMER) | $X_1$GCGUG; $X_1$ = A or absent | Type B Formula-5-5' |
| 76 | L-RNA (SPIEGELMER) | UACGC$X_4$; $X_4$ = U or absent | Type B Formula-5-3' |
| 77 | L-RNA (SPIEGELMER) | $X_1X_2$SVNS; $X_1$ = A or absent, $X_2$ = G or absent | Type B Formula-6-5' |
| 78 | L-RNA (SPIEGELMER) | BVBS$X_3X_4$; $X_3$ = C or absent, $X_4$ = U or absent | Type B Formula-6-3' |
| 79 | L-RNA (SPIEGELMER) | GUGCUGCGGGGUUAGGGCUAGAAGUCGGCCUGCAGCAC | 197-B2 |
| 80 | L-RNA (SPIEGELMER) | AGCGUGGCGAGGUUAGGGCUAGAAGUCGGUCGACACGCU | 191-D5-001 |
| 81 | L-RNA (SPIEGELMER) | GUGUUGCGGAGGUUAGGGCUAGAAGUCGGUCAGCAGCAC | 197-H1 |
| 82 | L-RNA (SPIEGELMER) | CGUGCGCUUGAGAUAGGGGUUAGGGCUUAAAGUCGGCUGAUUCUCACG | 190-A3-001 |
| 83 | L-RNA (SPIEGELMER) | AGCGUGAAGGGGUUAGGGCUCGAAGUCGGCUGACACGCU | 191-A5 |
| 84 | L-RNA (SPIEGELMER) | GUGCUGCGGGGUUAGGGCUCGAAGUCGGCCCGCAGCAC | 197-H3 |
| 85 | L-RNA (SPIEGELMER) | GUGUUCCCGGGGUUAGGGCUUGAAGUCGGCCGGCAGCAC | 197-B1 |
| 86 | L-RNA (SPIEGELMER) | GUGUUGCAGGGGUUAGGGCUUGAAGUCGGCCUGCAGCAC | 197-E3 |
| 87 | L-RNA (SPIEGELMER) | GUGCUGCGGGGUUAGGGCUCAAAGUCGGCCUGCAGCAC | 197-H2 |
| 88 | L-RNA (SPIEGELMER) | GUGCUGCCGGGGUUAGGGCUAA-AGUCGGCCGACAGCAC | 197-D1 |
| 89 | L-RNA (SPIEGELMER) | GUGCUGUGGGGUCAGGGCUAGAAGUCGGCCUGCAGCAC | 197-D2 |
| 90 | L-RNA (SPIEGELMER) | GGUYAGGGCUHR$X_4$AGUCGG; $X_4$ = A or absent | Type C Formula-1 |
| 91 | L-RNA (SPIEGELMER) | GGUYAGGGCUHRAAGUCGG | Type C Formula-2 |
| 92 | L-RNA (SPIEGELMER) | GGUYAGGGCUHRAGUCGG | Type C Formula-3 |
| 93 | L-RNA (SPIEGELMER) | GGUUAGGGCUHGAAGUCGG | Type C Formula-4 |
| 94 | L-RNA (SPIEGELMER) | UGAGAUAGGGGUUAGGGCUUAAAGUCGGCUGAUUCUCA | 190-A3-003 |
| 95 | L-RNA (SPIEGELMER) | GAGAUAGGGGUUAGGGCUUAAAGUCGGCUGAUUCUC | 190-A3-004 |
| 96 | L-RNA (SPIEGELMER) | GGGGUUAGGGCUUAAAGUCGGCUGAUUCU | 190-A3-007 |
| 97 | L-RNA (SPIEGELMER) | GCGUGGCGAGGUUAGGGCUAGAAGUCGGUCGACACGC | 191-D5-002 |
| 98 | L-RNA (SPIEGELMER) | CGUGGCGAGGUUAGGGCUAGAAGUCGGUCGACACG | 191-D5-003 |
| 99 | L-RNA (SPIEGELMER) | CGGGCGAGGUUAGGGCUAGAAGUCGGUCGACCG | 191-D5-004 |
| 100 | L-RNA (SPIEGELMER) | CGGGCGAGGUUAGGGCUAGAAGUCGGUCGCCCG | 191-D5-005 |
| 101 | L-RNA (SPIEGELMER) | CGGCGAGGUUAGGGCUAGAAGUCGGUCGCCG | 191-D5-006 |
| 102 | L-RNA (SPIEGELMER) | CGGGAGGUUAGGGCUAGAAGUCGGUCCCG | 191-D5-007 |
| 103 | L-RNA (SPIEGELMER) | GGGAGGUUAGGGCUAGAAGUCGGUCCC | 191-D5-010 |
| 104 | L-RNA (SPIEGELMER) | CCGCGGUUAGGGCUAGAAGUCGGGCGG | 191-D5-017 |
| 105 | L-RNA (SPIEGELMER) | CCCGGGUUAGGGCUAGAAGUCGGCGGG | 191-D5-029 |
| 106 | L-RNA (SPIEGELMER) | GGCGGGUUAGGGCUAGAAGUCGGCGCC | 191-D5-024 |
| 107 | L-RNA (SPIEGELMER) | CCCGCGGUUAGGGCUAGAAGUCGGGCGGG | 191-D5-017-29a |
| 108 | L-RNA (SPIEGELMER) | GCCGCGGUUAGGGCUAGAAGUCGGGCGGC | 191-D5-017-29b |

TABLE 1-continued

| Seq.-ID | RNA/Peptide | Sequence | Internal Reference |
|---|---|---|---|
| 109 | L-RNA (SPIEGELMER) | CCCCGGGUUAGGGCUAGAAGUCGGCGGGG | 191-D5-019-29a |
| 110 | L-RNA (SPIEGELMER) | CGGCGGGUUAGGGCUAGAAGUCGGCGCCG | 191-D5-024-29a |
| 111 | L-RNA (SPIEGELMER) | GGGCGGGUUAGGGCUAGAAGUCGGCGCCC | 191-D5-024-29b |
| 112 | L-RNA (SPIEGELMER) | UGCUGCGGGGUUAGGGCUAGAAGUCGGCCUGCAGCA | 197-B2-001 |
| 113 | L-RNA (SPIEGELMER) | GCUGCGGGGUUAGGGCUAGAAGUCGGCCUGCAGC | 197-B2-002 |
| 114 | L-RNA (SPIEGELMER) | CUGGGGGGUUAGGGCUAGAAGUCGGCCUGCAG | 197-B2-003 |
| 115 | L-RNA (SPIEGELMER) | UGCGGGGUUAGGGCUAGAAGUCGGCCUGCA | 197-B2-004 |
| 116 | L-RNA (SPIEGELMER) | GCGGGGUUAGGGCUAGAAGUCGGCCUGC | 197-B2-005 |
| 117 | L-RNA (SPIEGELMER) | GCCGGGGUUAGGGCUAGAAGUCGGCCGGC | 197-B2-006 |
| 118 | L-RNA (SPIEGELMER) | GGCCGGGGUUAGGGCUAGAAGUCGGCCGGCC | 197-B2-006-31a |
| 119 | L-RNA (SPIEGELMER) | CGCCGGGGUUAGGGCUAGAAGUCGGCCGGCG | 197-B2-006-31b |
| 120 | L-RNA (SPIEGELMER) | RKSBUSNVGR | Type C Formula-5-5' |
| 121 | L-RNA (SPIEGELMER) | YYNRCASSMY | Type C Formula-5-3' |
| 122 | L-RNA (SPIEGELMER) | RKSBUGSVGR | Type C Formula-6-5' |
| 123 | L-RNA (SPIEGELMER) | YCNRCASSMY | Type C Formula-6-3' |
| 124 | L-RNA (SPIEGELMER) | $X_S$SSSV; $X_S$ = S or absent | Type C Formula-7-5' |
| 125 | L-RNA (SPIEGELMER) | BSSS$X_S$; $X_S$ = S or absent | Type C Formula-7-3' |
| 126 | L-RNA (SPIEGELMER) | SGGSV | Type C Formula-8-5' |
| 127 | L-RNA (SPIEGELMER) | YSCCS | Type C Formula-8-3' |
| 128 | L-RNA (SPIEGELMER) | GCSGG | Type C Formula-9-5' |
| 129 | L-RNA (SPIEGELMER) | CCKGC | Type C Formula-9-3' |
| 130 | L-RNA (SPIEGELMER) | SSSSR | Type C Formula-10-5' |
| 131 | L-RNA (SPIEGELMER) | YSBSS | Type C Formula-10-3' |
| 132 | L-RNA (SPIEGELMER) | 5'-40 kDa-PEG-GCGUGGUGUGAUCUAGAUGUAUUGGCUGAUCCUAGUCAGGUACGC | 193-G2-012-5'-PEG, NOX-A12-JE40 |
| 133 | L-RNA (SPIEGELMER) | 5'-40 kDa-PEG-GCGUGAAAGCAACAUGUCAAUGAAAGGUAGCCGCGC | 192-A10-008-5'-PEG |
| 134 | L-RNA (SPIEGELMER) | 5'-40 kDa-PEG-CGGGAGGUUAGGGCUAGAAGUCGGUCCCG | 191-D5-007-5'-PEG |
| 135 | L-RNA (SPIEGELMER) | 5'-40 kDa-PEG-GCCGGGGUUAGGGCUAGAAGUCGGCCGGC | 197-B2-006-5'-PEG |
| 136 | L-RNA (SPIEGELMER) | 5'-40 kDa-PEG-CGCCGGGGUUAGGGCUAGAAGUCGGCCGGCG | 197-B2-006-31b-5'PEG |
| 137 | L-RNA (SPIEGELMER) | 5'-40 kDa-PEG-GCUGUGAAAGCAACAUGUCAAUGAAAGGUAGCCGCAGC | 192-A10-001-5'-PEG 192-A10-001-5'-PEG40 |
| 138 | L-RNA (SPIEGELMER) | UAAGGAAACUCGGUCUGAUGCGGUAGCGCUGUGCAGAGCU | Control Spiegelmer |
| 139 | L-RNA (SPIEGELMER) | 5'-30 kDa-PEG-GCUGUGAAAGCAACAUGUCAAUGAAAGGUAGCCGCAGC | 192-A10-001-5'-PEG30 |
| 140 | L-RNA (SPIEGELMER) | 5'-100 kDa-HES-GCUGUGAAAGCAACAUGUCAAUGAAAGGUAGCCGCAGC | 192-A10-001-5'-HES100 |
| 141 | L-RNA (SPIEGELMER) | 5'-130 kDa-HES-GCUGUGAAAGCAACAUGUCAAUGAAAGGUAGCCGCAGC | 192-A10-001-5'-HES130 |
| 142 | L-RNA (SPIEGELMER) | CGUGGUCCGUUGUGUCAGGUCUAUUCGCCCCGGUGCAGGGCAUCCGCG | 194-A2-001 |

TABLE 1-continued

| Seq.-ID | RNA/Peptide | Sequence | Internal Reference |
|---|---|---|---|
| 143 | L-RNA (SPIEGELMER) | GCAGUGUGACGCGGACGUGAUAGGACAGAGCUGAUCCCGCUCAGGUGAG | 196-B12-003 |
| 144 | L-RNA (SPIEGELMER) | CAACAGCAGUGUGACGCGGACGUGAUAGGACAGAGCUGAUCCCGCUCAG | 196-B12-004 |
| 145 | D-RNA (APTAMER) | GCUGUGAAAGCAACAUGUCAAUGAAAGGUAGCCGCAGC | 192-A10-001 |
| 146 | D-RNA (APTAMER) | GCUGUGAAAGUAACAUGUCAAUGAAAGGUAACCACAGC | 192-G10 |
| 147 | D-RNA (APTAMER) | GCUGUGAAAGUAACACGUCAAUGAAAGGUAACCGCAGC | 192-F10 |
| 148 | D-RNA (APTAMER) | GCUGUGAAAGUAACACGUCAAUGAAAGGUAACCACAGC | 192-B11 |
| 149 | D-RNA (APTAMER) | GCUGUAAAAGUAACAUGUCAAUGAAAGGUAACUACAGC | 192-C9 |
| 150 | D-RNA (APTAMER) | GCUGUAAAAGUAACAAGUCAAUGAAAGGUAACUACAGC | 192-E10 |
| 151 | D-RNA (APTAMER) | GCUGUGAAAGUAACAAGUCAAUGAAAGGUAACCACAGC | 192-C10 |
| 152 | D-RNA (APTAMER) | GCAGUGAAAGUAACAUGUCAAUGAAAGGUAACCACAGC | 192-D11 |
| 153 | D-RNA (APTAMER) | GCUGUGAAAGUAACAUGUCAAUGAAAGGUAACCACUGC | 192-G11 |
| 154 | D-RNA (APTAMER) | GCUAUGAAAGUAACAUGUCAAUGAAAGGUAACCAUAGC | 192-H11 |
| 155 | D-RNA (APTAMER) | GCUGCGAAAGCGACAUGUCAAUGAAAGGUAGCCGCAGC | 192-D10 |
| 156 | D-RNA (APTAMER) | GCUGUGAAAGCAACAUGUCAAUGAAAGGUAGCCACAGC | 192-E9 |
| 157 | D-RNA (APTAMER) | GCUGUGAAAGUAACAUGUCAAUGAAAGGUAGCCGCAGC | 192-H9 |
| 158 | D-RNA (APTAMER) | AGCGUGAAAGUAACACGUAAAAUGAAAGGUAACCACGCU | 191-A6 |
| 159 | D-RNA (APTAMER) | CUGUGAAAGCAACAUGUCAAUGAAAGGUAGCCGCAG | 192-A10-002 |
| 160 | D-RNA (APTAMER) | UGUGAAAGCAACAUGUCAAUGAAAGGUAGCCGCA | 192-A10-003 |
| 161 | D-RNA (APTAMER) | GUGAAAGCAACAUGUCAAUGAAAGGUAGCCGC | 192-A10-004 |
| 162 | D-RNA (APTAMER) | UGAAAGCAACAUGUCAAUGAAAGGUAGCCG | 192-A10-005 |
| 163 | D-RNA (APTAMER) | GAAAGCAACAUGUCAAUGAAAGGUAGCC | 192-A10-006 |
| 164 | D-RNA (APTAMER) | AAAGCAACAUGUCAAUGAAAGGUAGC | 192-A10-007 |
| 165 | D-RNA (APTAMER) | GCGUGAAAGCAACAUGUCAAUGAAAGGUAGCCGCGC | 192-A10-008 |
| 166 | D-RNA (APTAMER) | GCGCGAAAGCAACAUGUCAAUGAAAGGUAGCCGCGC | 192-A10-015 |
| 167 | D-RNA (APTAMER) | GCGGAAAGCAACAUGUCAAUGAAAGGUAGCCCGC | 192-A10-014 |
| 168 | D-RNA (APTAMER) | CGUGAAAGCAACAUGUCAAUGAAAGGUAGCCGCG | 192-A10-016 |
| 169 | D-RNA (APTAMER) | GCGCAAAGCAACAUGUCAAUGAAAGGUAGCGUGC | 192-A10-017 |
| 170 | D-RNA (APTAMER) | GUGCAAAGCAACAUGUCAAUGAAAGGUAGCGCGC | 192-A10-018 |
| 171 | D-RNA (APTAMER) | CGCGAAAGCAACAUGUCAAUGAAAGGUAGCCGUG | 192-A10-019 |
| 172 | D-RNA (APTAMER) | GGGCAAAGCAACAUGUCAAUGAAAGGUAGCGCCC | 192-A10-020 |
| 173 | D-RNA (APTAMER) | GGCCAAAGCAACAUGUCAAUGAAAGGUAGCGGCC | 192-A10-021 |
| 174 | D-RNA (APTAMER) | GCCCAAAGCAACAUGUCAAUGAAAGGUAGCGGGC | 192-A10-022 |
| 175 | D-RNA (APTAMER) | CCCCAAAGCAACAUGUCAAUGAAAGGUAGCGGGG | 192-A10-023 |
| 176 | D-RNA (APTAMER) | AGCGUGGUGUGAUCUAGAUGUAGUGGCUGAUCCUAGUCAGGUACGCU | 193-C2-001 |
| 177 | D-RNA (APTAMER) | AGCGUGGUGUGAUCUAGAUGUAUGGCUGAUCCUAGUCAGGUACGCU | 193-G2-001 |
| 178 | D-RNA (APTAMER) | AGCGUGGUGUGAUCUAGAUGUAAUGGCUGAUCCUAGUCAGGUGCGCU | 193-F2-001 |
| 179 | D-RNA (APTAMER) | GCGAGGUGUGAUCUAGAUGUAGUGGCUGAUCCUAGUCAGGUGCGC | 193-G1-002 |
| 180 | D-RNA (APTAMER) | GCGUGGUGUGAUCUAGAUGUAGUGGCUGAUCCUAGUCAGGUGCGC | 193-D2-002 |

TABLE 1-continued

| Seq.-ID | RNA/Peptide | Sequence | Internal Reference |
|---|---|---|---|
| 181 | D-RNA (APTAMER) | GCAUGGUGUGAUCUAGAUGUAGUGGCUGAUCCUAGUCAGGUGCCC | 193-A1-002 |
| 182 | D-RNA (APTAMER) | GCGUGGUGUGAUCUAGAUGUAAUGGCUGAUCCUAGUCAGGGACGC | 193-D3-002 |
| 183 | D-RNA (APTAMER) | GCGUGGUGUGAUCUAGAUGUAGAGGCUGAUCCUAGUCAGGUACGC | 193-B3-002 |
| 184 | D-RNA (APTAMER) | GCGUGGUGUGAUCUAGAUGUAAAGGCUGAUCCUAGUCAGGUACGC | 193-H3-002 |
| 185 | D-RNA (APTAMER) | GCGUGGUGUGAUCUAGAUGUAGUGGCUGUUCCUAGUCAGGUAUGC | 193-E3-002 |
| 186 | D-RNA (APTAMER) | GCGUGGUGUGAUCUAGAUGUAGUGGCUGAUCCUAGUUAGGUACGC | 193-D1-002 |
| 187 | D-RNA (APTAMER) | GCGUGGUGUGAUCUAGAUGUAGUGGCUGAUCCUAGUCAGGUACGC | 193-C2-002 |
| 188 | D-RNA (APTAMER) | CGUGGUGUGAUCUAGAUGUAGUGGCUGAUCCUAGUCAGGUACG | 193-C2-003 |
| 189 | D-RNA (APTAMER) | GUGGUGUGAUCUAGAUGUAGUGGCUGAUCCUAGUCAGGUAC | 193-C2-004 |
| 190 | D-RNA (APTAMER) | UGGUGUGAUCUAGAUGUAGUGGCUGAUCCUAGUCAGGUA | 193-C2-005 |
| 191 | D-RNA (APTAMER) | GGUGUGAUCUAGAUGUAGUGGCUGAUCCUAGUCAGGU | 193-C2-006 |
| 192 | D-RNA (APTAMER) | GUGUGAUCUAGAUGUAGUGGCUGAUCCUAGUCAGG | 193-C2-007 |
| 193 | D-RNA (APTAMER) | GCGUGGUGUGAUCUAGAUGUAUUGGCUGAUCCUAGUCAGGUACGC | 193-G2-012 |
| 194 | D-RNA (APTAMER) | GCGCGGUGUGAUCUAGAUGUAUUGGCUGAUCCUAGUCAGGCGCGC | 193-G2-013 |
| 195 | D-RNA (APTAMER) | GCGCGUGUGAUCUAGAUGUAUUGGCUGAUCCUAGUCAGGGCGC | 193-G2-014 |
| 196 | D-RNA (APTAMER) | GGGCGUGUGAUCUAGAUGUAUUGGCUGAUCCUAGUCAGGGCCC | 193-G2-015 |
| 197 | D-RNA (APTAMER) | GGCCGUGUGAUCUAGAUGUAUUGGCUGAUCCUAGUCAGGGGCC | 193-G2-016 |
| 198 | D-RNA (APTAMER) | GCCCGUGUGAUCUAGAUGUAUUGGCUGAUCCUAGUCAGGGGGC | 193-G2-017 |
| 199 | D-RNA (APTAMER) | GUGCUGCGGGGUUAGGGCUAGAAGUCGGCCUGCAGCAC | 197-B2 |
| 200 | D-RNA (APTAMER) | AGCGUGGCGAGGUUAGGGCUAGAAGUCGGUCGACACGCU | 191-D5-001 |
| 201 | D-RNA (APTAMER) | GUGUUGCGGAGGUUAGGGCUAGAAGUCGGUCAGCAGCAC | 197-H1 |
| 202 | D-RNA (APTAMER) | CGUGCGCUUGAGAUAGGGGUUAGGGCUUAAAGUCGGCUGAUUCUCACG | 190-A3-001 |
| 203 | D-RNA (APTAMER) | AGCGUGAAGGGGUUAGGGCUCGAAGUCGGCUGACACGCU | 191-A5 |
| 204 | D-RNA (APTAMER) | GUGCUGCGGGGUUAGGGCUCGAAGUCGGCCCGCAGCAC | 197-H3 |
| 205 | D-RNA (APTAMER) | GUGUUCCCGGGGUUAGGGCUUGAAGUCGGCCGGCAGCAC | 197-B1 |
| 206 | D-RNA (APTAMER) | GUGUUGCAGGGGUUAGGGCUUGAAGUCGGCCUGCAGCAC | 197-E3 |
| 207 | D-RNA (APTAMER) | GUGCUGCGGGGUUAGGGCUCAAAGUCGGCCUGCAGCAC | 197-H2 |
| 208 | D-RNA (APTAMER) | GUGCUGCCGGGGUUAGGGCUAA-AGUCGGCCGACAGCAC | 197-D1 |
| 209 | D-RNA (APTAMER) | GUGCUGUGGGGUCAGGGCUAGAAGUCGGCCUGCAGCAC | 197-D2 |
| 210 | D-RNA (APTAMER) | UGAGAUAGGGGUUAGGGCUUAAAGUCGGCUGAUUCUCA | 190-A3-003 |
| 211 | D-RNA (APTAMER) | GAGAUAGGGGUUAGGGCUUAAAGUCGGCUGAUUCUC | 190-A3-004 |
| 212 | D-RNA (APTAMER) | GGGGUUAGGGCUUAAAGUCGGCUGAUUCU | 190-A3-007 |
| 213 | D-RNA (APTAMER) | GCGUGGCGAGGUUAGGGCUAGAAGUCGGUCGACACGC | 191-D5-002 |
| 214 | D-RNA (APTAMER) | CGUGGCGAGGUUAGGGCUAGAAGUCGGUCGACACG | 191-D5-003 |
| 215 | D-RNA (APTAMER) | CGGGCGAGGUUAGGGCUAGAAGUCGGUCGACCG | 191-D5-004 |
| 216 | D-RNA (APTAMER) | CGGGCGAGGUUAGGGCUAGAAGUCGGUCGCCCG | 191-D5-005 |
| 217 | D-RNA (APTAMER) | CGGCGAGGUUAGGGCUAGAAGUCGGUCGCCG | 191-D5-006 |
| 218 | D-RNA (APTAMER) | CGGGAGGUUAGGGCUAGAAGUCGGUCCCG | 191-D5-007 |
| 219 | D-RNA (APTAMER) | GGGAGGUUAGGGCUAGAAGUCGGUCCC | 191-D5-010 |

TABLE 1-continued

| Seq.-ID | RNA/Peptide | Sequence | Internal Reference |
|---|---|---|---|
| 220 | D-RNA (APTAMER) | CCGCGGUUAGGGCUAGAAGUCGGGCGG | 191-D5-017 |
| 221 | D-RNA (APTAMER) | CCCGGGUUAGGGCUAGAAGUCGGCGGG | 191-D5-029 |
| 222 | D-RNA (APTAMER) | GGCGGGUUAGGGCUAGAAGUCGGCGCC | 191-D5-024 |
| 223 | D-RNA (APTAMER) | CCCGCGGUUAGGGCUAGAAGUCGGGCGGG | 191-D5-017-29a |
| 224 | D-RNA (APTAMER) | GCCGCGGUUAGGGCUAGAAGUCGGGCGGC | 191-D5-017-29b |
| 225 | D-RNA (APTAMER) | CCCCGGGUUAGGGCUAGAAGUCGGCGGGG | 191-D5-019-29a |
| 226 | D-RNA (APTAMER) | CGGCGGGUUAGGGCUAGAAGUCGGCGCCG | 191-D5-024-29a |
| 227 | D-RNA (APTAMER) | GGGCGGGUUAGGGCUAGAAGUCGGCGCCC | 191-D5-024-29b |
| 228 | D-RNA (APTAMER) | UGCUGCGGGGUUAGGGCUAGAAGUCGGCCUGCAGCA | 197-B2-001 |
| 229 | D-RNA (APTAMER) | GCUGCGGGGUUAGGGCUAGAAGUCGGCCUGCAGC | 197-B2-002 |
| 230 | D-RNA (APTAMER) | CUGCGGGGUUAGGGCUAGAAGUCGGCCUGCAG | 197-B2-003 |
| 231 | D-RNA (APTAMER) | UGCGGGGUUAGGGCUAGAAGUCGGCCUGCA | 197-B2-004 |
| 232 | D-RNA (APTAMER) | GCGGGGUUAGGGCUAGAAGUCGGCCUGC | 197-B2-005 |
| 233 | D-RNA (APTAMER) | GCCGGGGUUAGGGCUAGAAGUCGGCCGGC | 197-B2-006 |
| 234 | D-RNA (APTAMER) | GGCCGGGGUUAGGGCUAGAAGUCGGCCGGCC | 197-B2-006-31a |
| 235 | D-RNA (APTAMER) | CGCCGGGGUUAGGGCUAGAAGUCGGCCGGCG | 197-B2-006-31b |
| 236 | D-RNA (APTAMER) | CGUGGUCCGUUGUGUCAGGUCUAUUCGCCCCGGUGCAGGGCAUCCGCG | 194-A2-001 |
| 236 | D-RNA (APTAMER) | GCAGUGUGACGCGGACGUGAUAGGACAGAGCUGAUCCCGCUCAGGUGAG | 196-B12-003 |
| 238 | D-RNA (APTAMER) | CAACAGCAGUGUGACGCGGACGUGAUAGGACAGAGCUGAUCCCGCUCAG | 196-B12-004 |
| 239 | L-RNA (Spiegelmer) | 5'-PEG-UAAGGAAACUCGGUCUGAUGCGGUAGCGCUGUGCAGAGCU | PEGylated Control Spiegelmer |
| 240 | L-RNA (SPIEGELMER) | 5'-30 kDa-PEG-GCGUGGUGUGAUCUAGAUGUAUUGGCUGAUCCUAGUCAGGUACGC | NOX-A12-NO30 |
| 241 | L-RNA (SPIEGELMER) | 5'-40 kDa-PEG-CGCAUGGACUGAUCCUAGUCGGUUAUGUAGAUCUAGUGUGGUGCG | revNOX-A12-JE40 |

The present invention is further illustrated by the figures, examples and the sequence listing from which further features, embodiments and advantages may be taken, wherein FIG. 1 shows an alignment of sequences of related RNA ligands binding to human SDF-1 indicating the sequence motif ("Type A") that is in a preferred embodiment in its entirety essential for binding to human SDF-1;

FIG. 2A shows derivatives of RNA ligand 192-A10-001 (human SDF-1 RNA ligand of sequence motif "Type A");

FIG. 2B shows derivatives of RNA ligand 192-A10-001 (human SDF-1 RNA ligand of sequence motif "Type A");

FIG. 3 shows an alignment of sequences of related RNA ligands binding to human SDF-1 indicating the sequence motif ("Type B") that is in a preferred embodiment in its entirety essential for binding to human SDF-1;

FIG. 4A shows derivatives of RNA ligands 193-C2-001 and 193-G2-001 (human SDF-1 RNA ligands of sequence motif "Type B");

FIG. 4B shows derivatives of RNA ligands 193-C2-001 and 193-G2-001 (human SDF-1 RNA ligands of sequence motif "Type B");

FIG. 5 shows an alignment of sequences of related RNA ligands binding to human SDF-1 indicating the sequence motif ("Type C") that is in a preferred embodiment in its entirety essential for binding to human SDF-1;

FIG. 6 shows derivatives of RNA ligand 190-A3-001 (human SDF-1 RNA ligand of sequence motif "Type C");

FIG. 7A shows derivatives of RNA ligand 190-D5-001 (human SDF-1 RNA ligand of sequence motif "Type C");

FIG. 7B shows derivatives of RNA ligand 190-D5-001 (human SDF-1 RNA ligand of sequence motif "Type C");

FIG. 8 shows derivatives of RNA ligand 197-B2 (human SDF-1 RNA ligand of sequence motif "Type C");

FIG. 9 shows further RNA ligands binding to human SDF-1:

Figure 13:
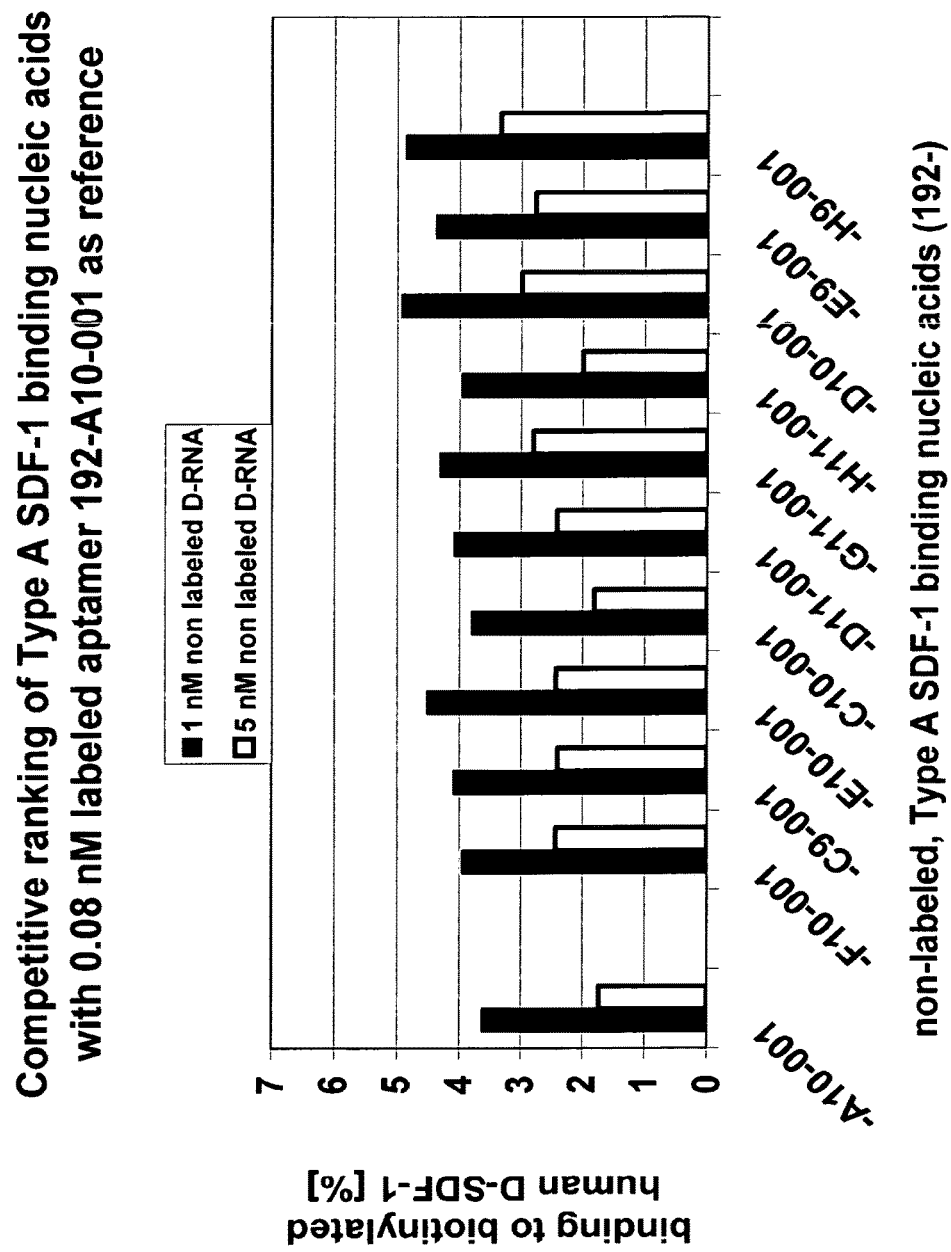
Figure 14:
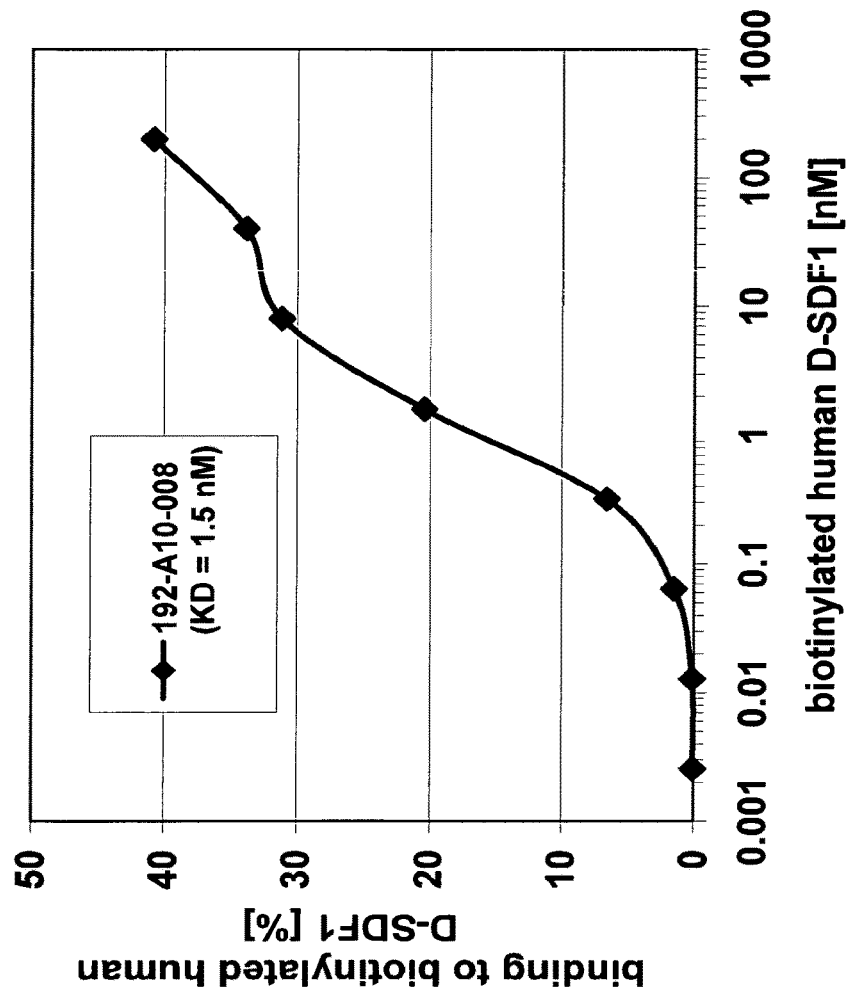
Figure 15:
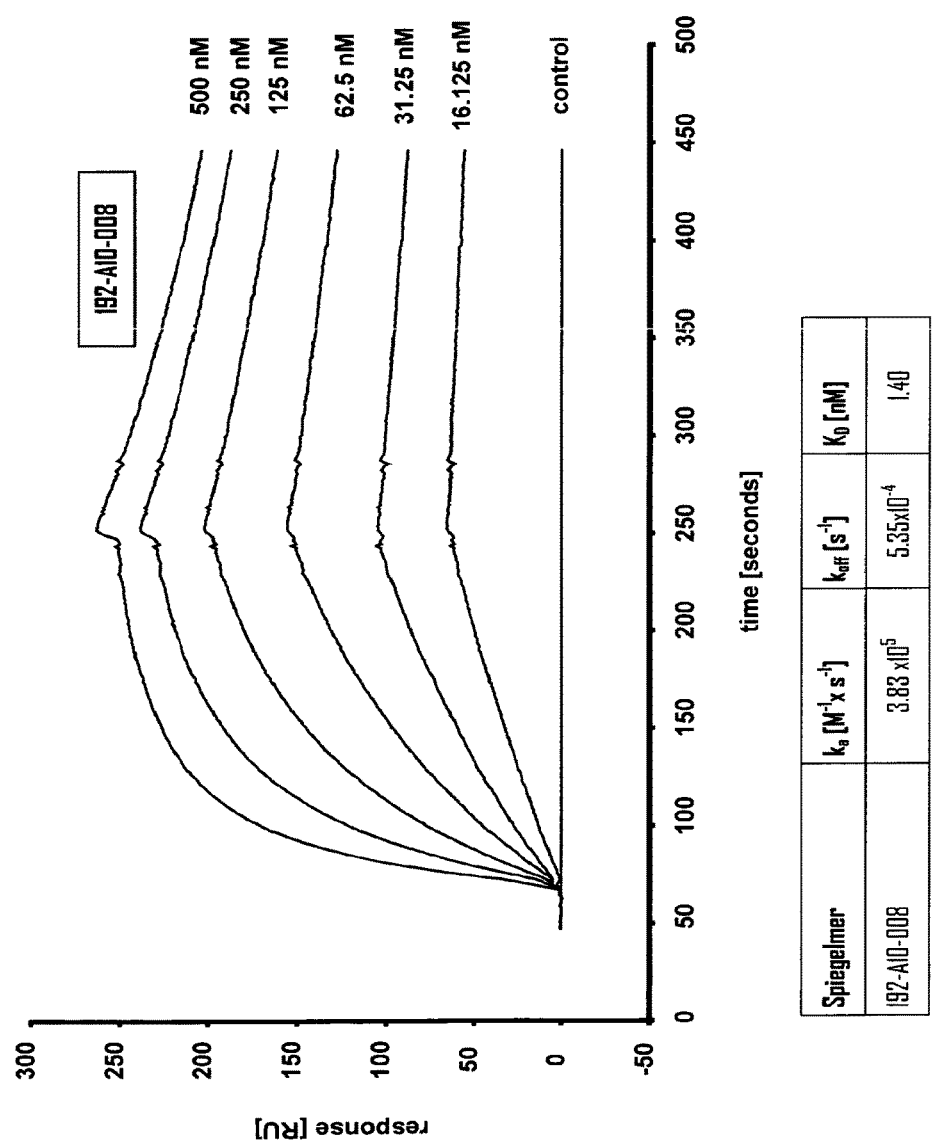
Figure 16:
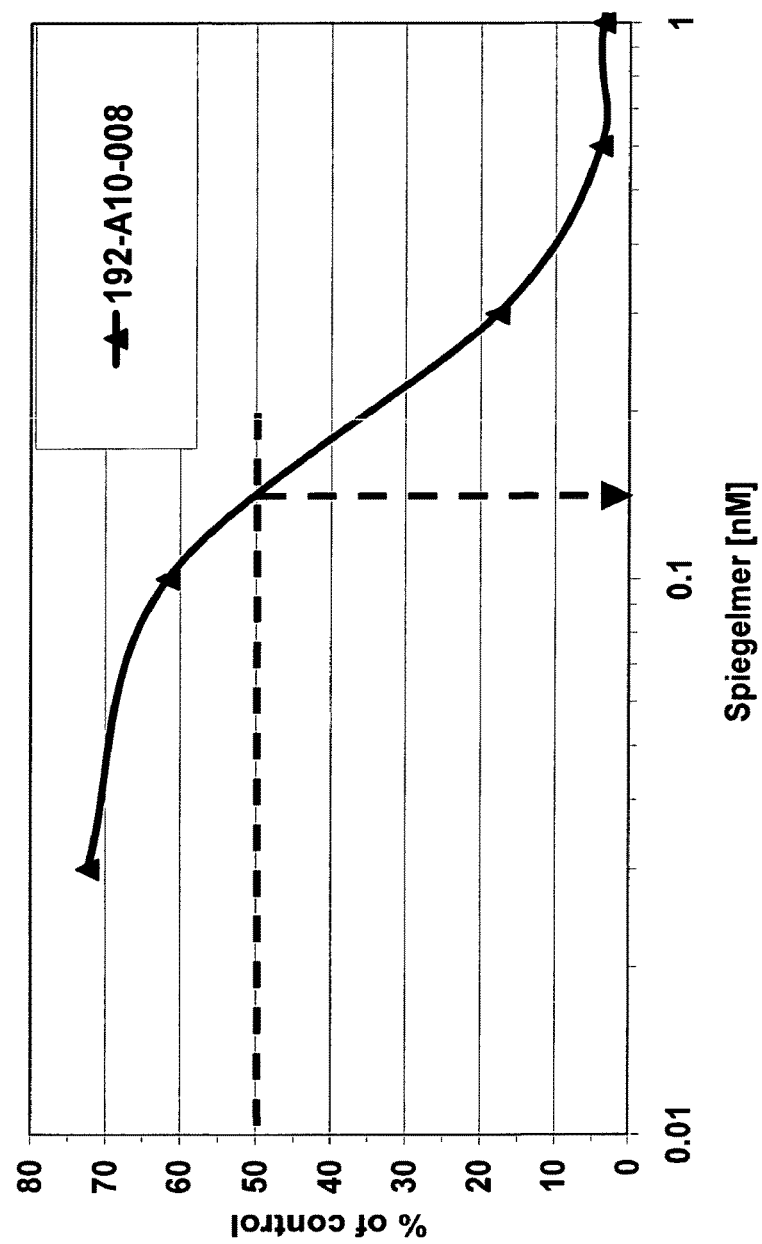
Figure 17:
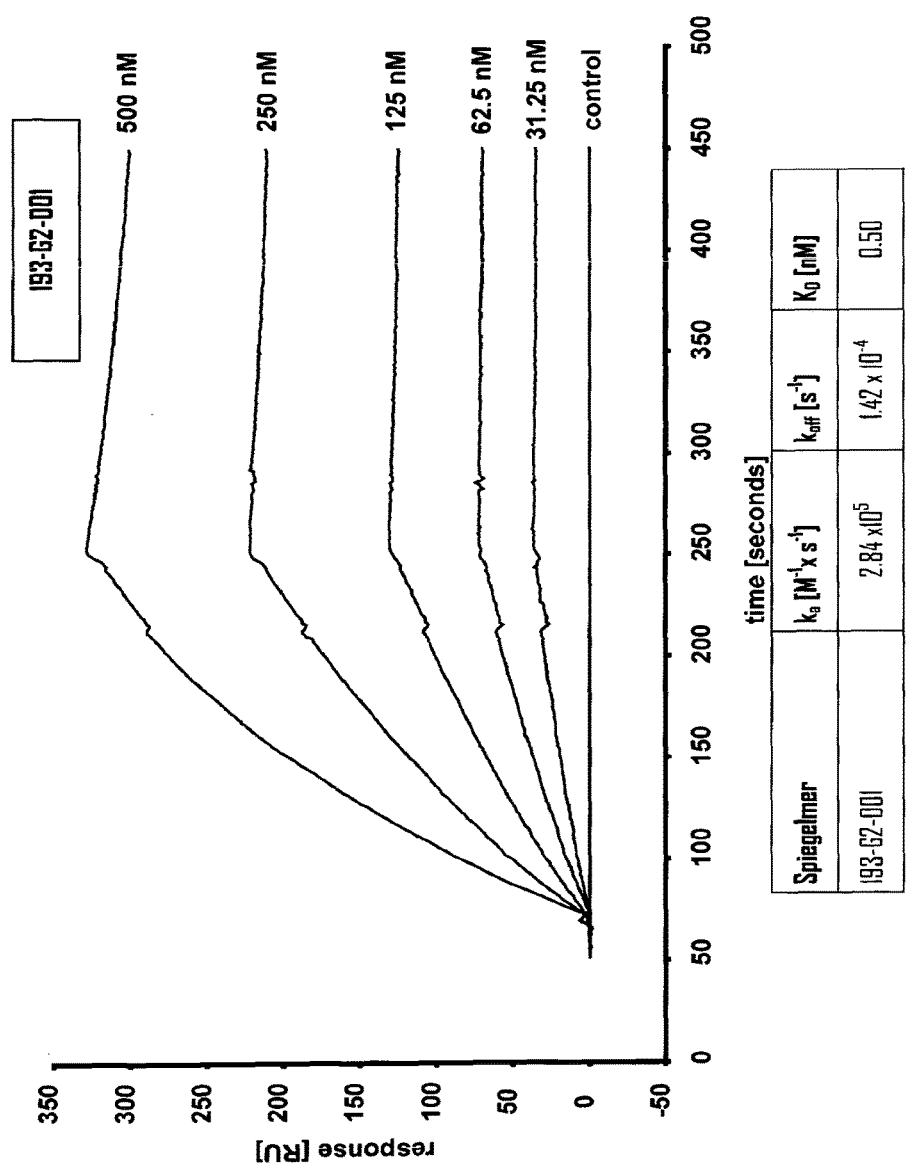
Figure 18:
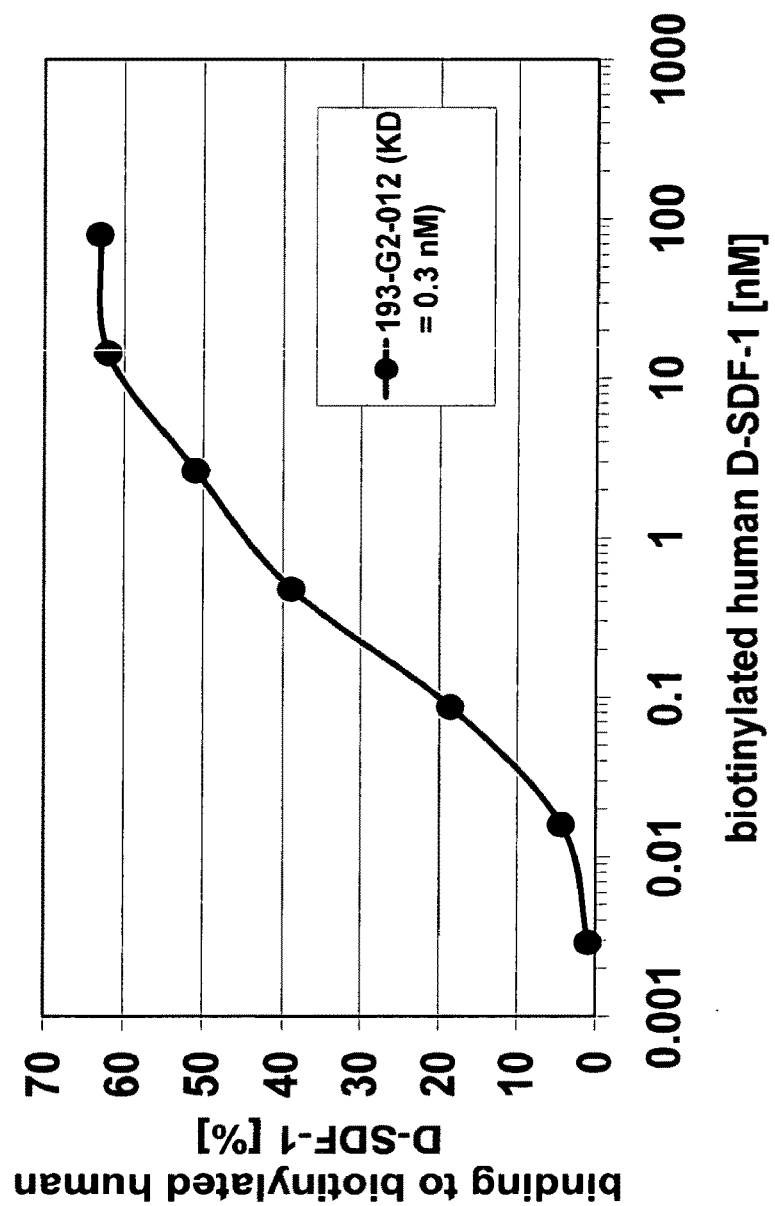
Figure 19:
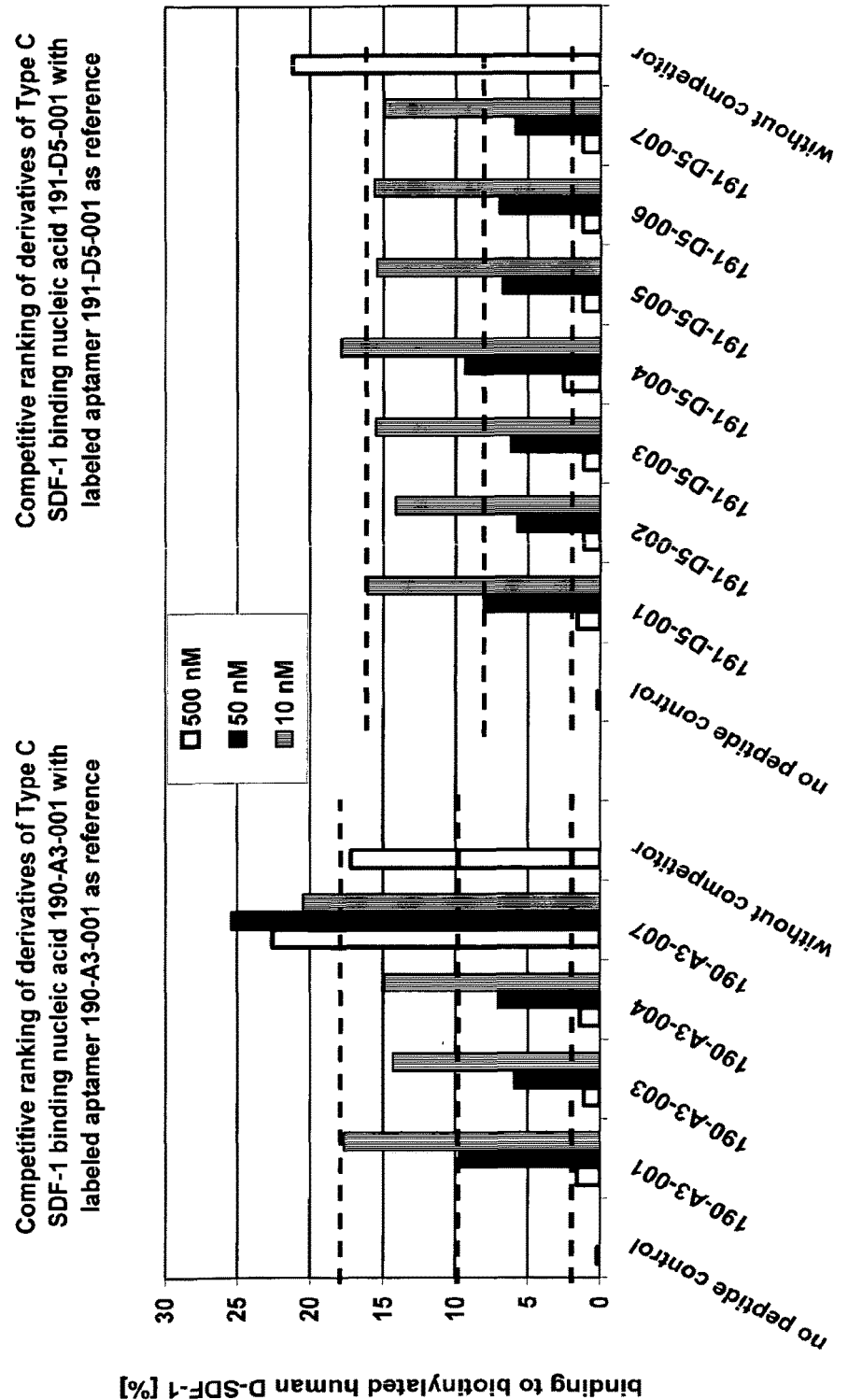
Figure 20:
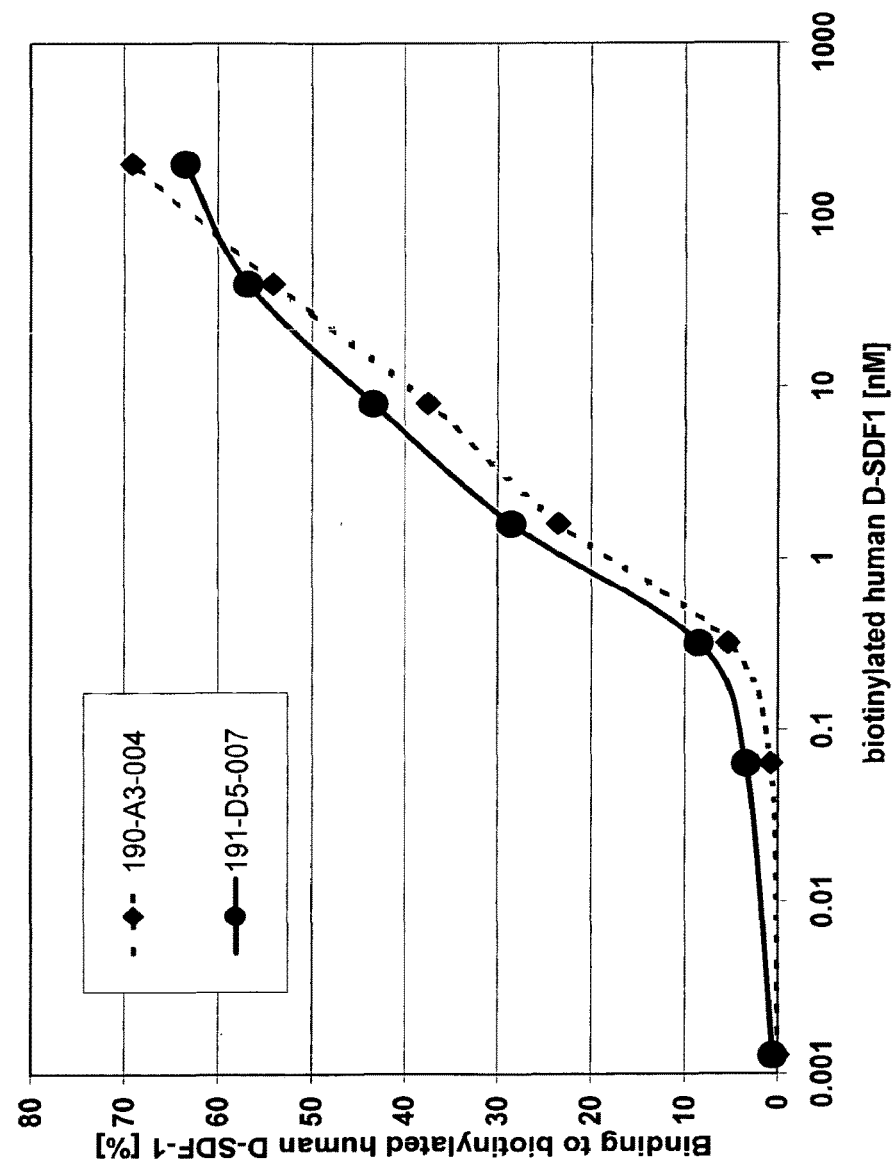
Figure 21:
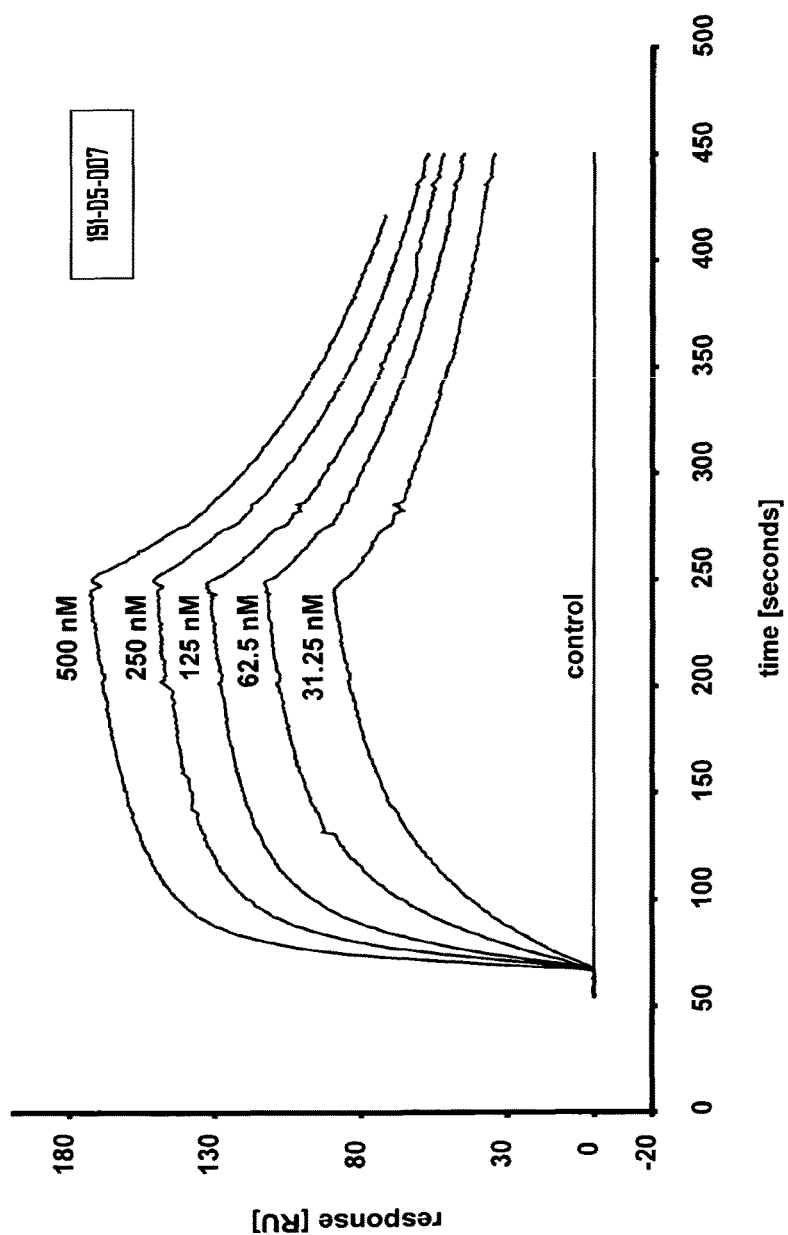
Figure 22:
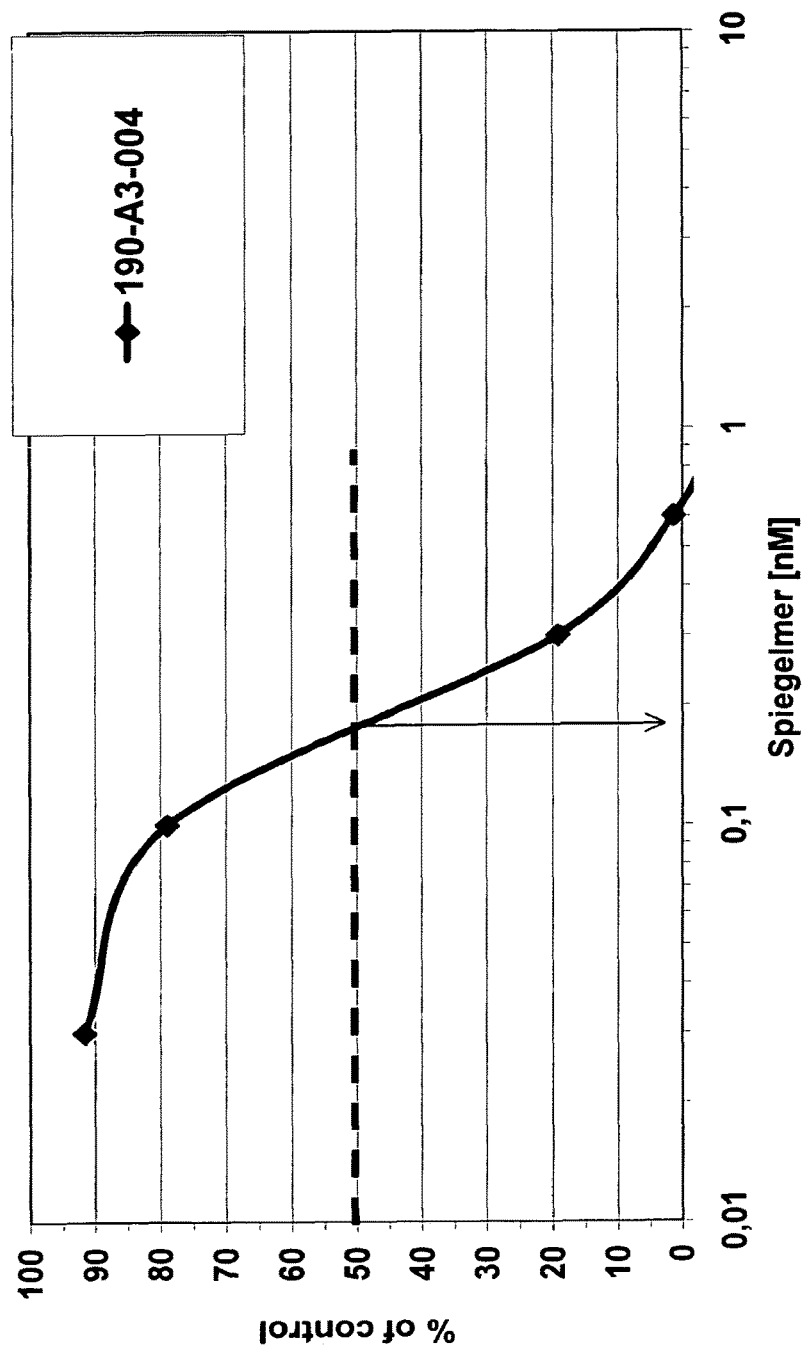
Figure 23A:
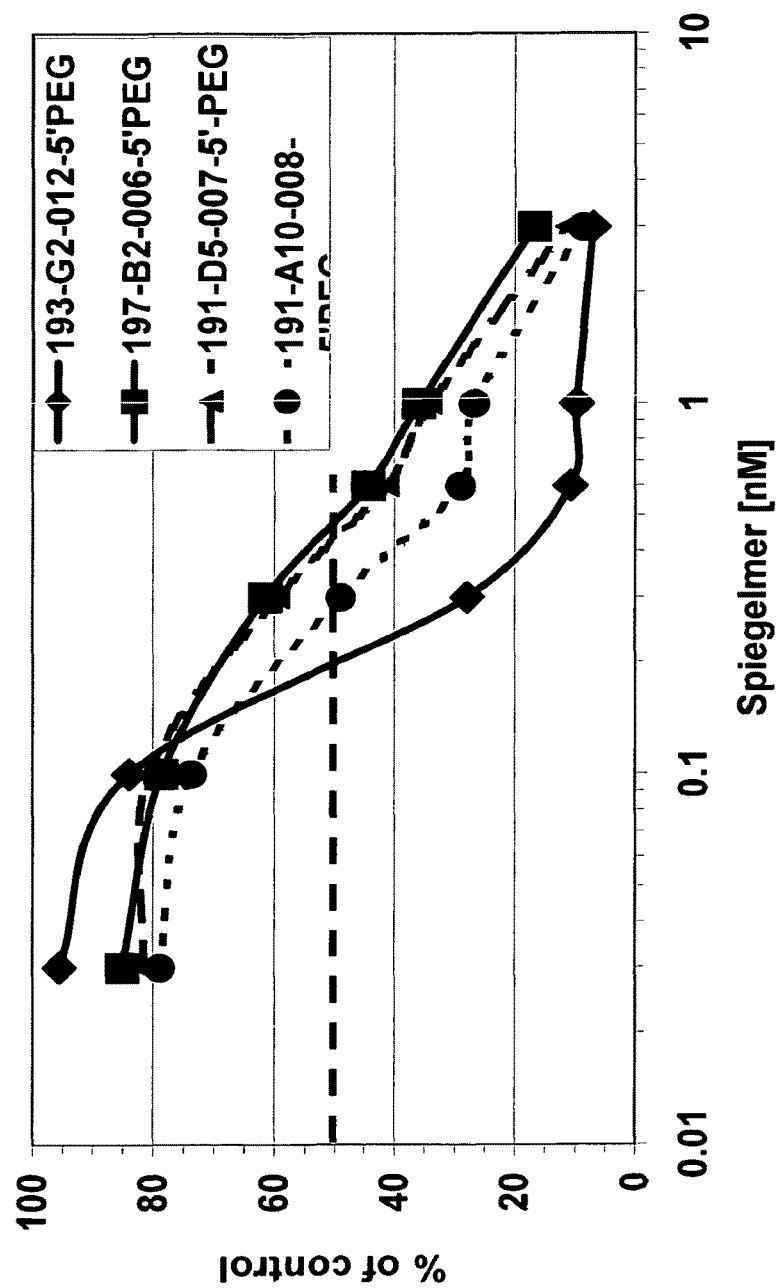
Figure 23B:
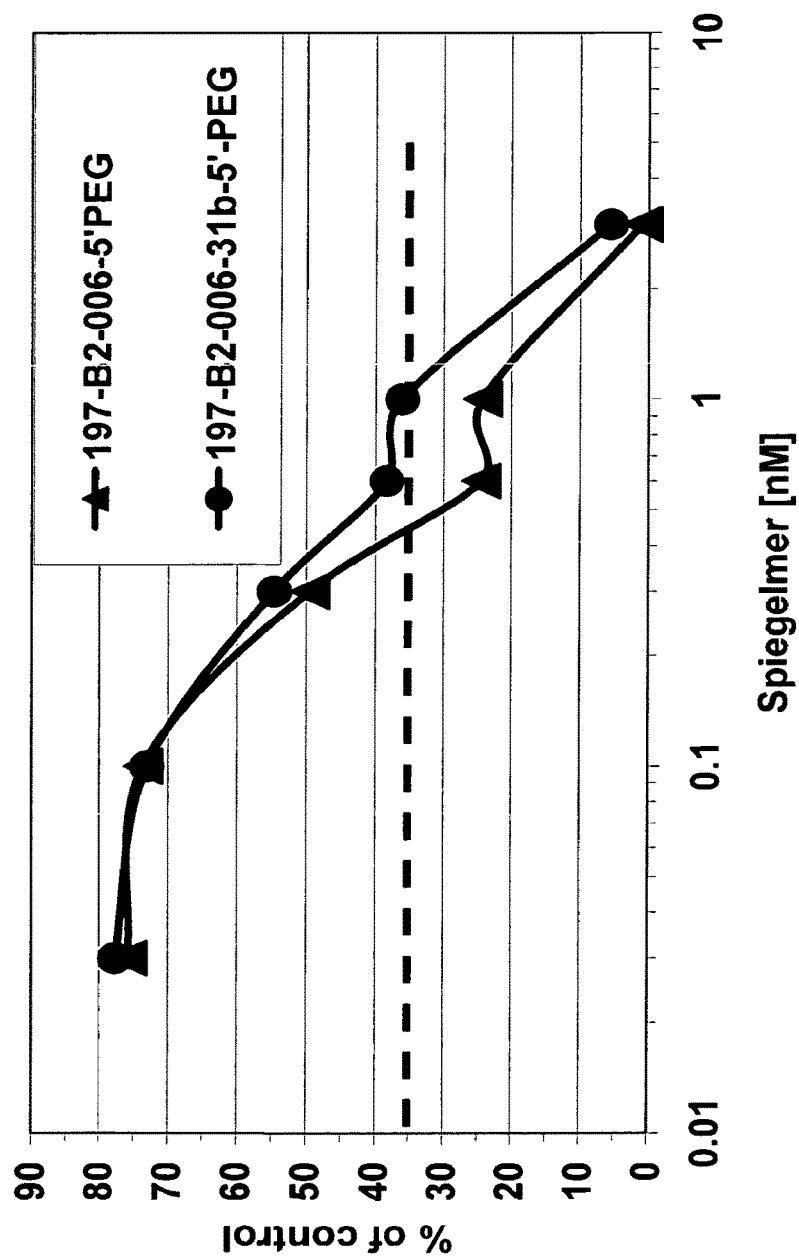
Figure 24:
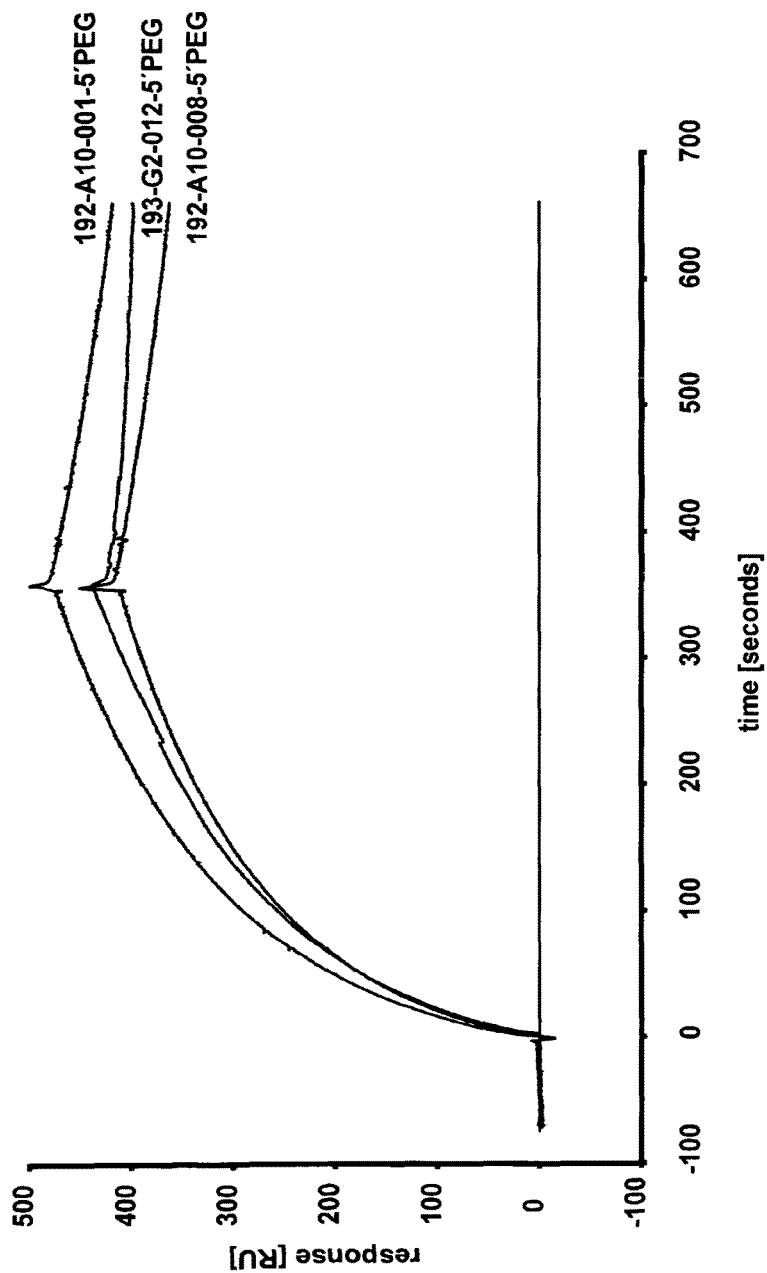
Figure 24B:
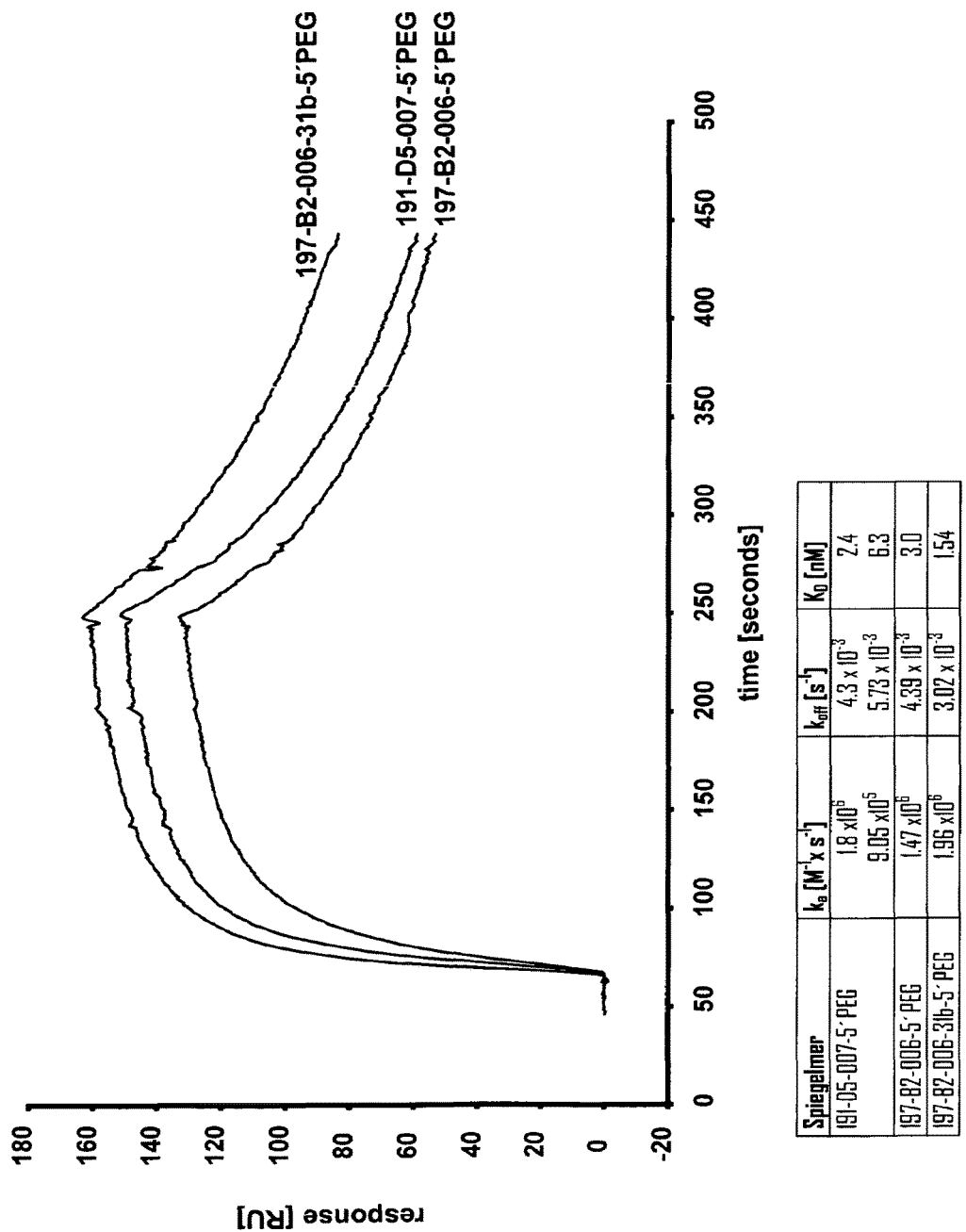
Figure 25A:
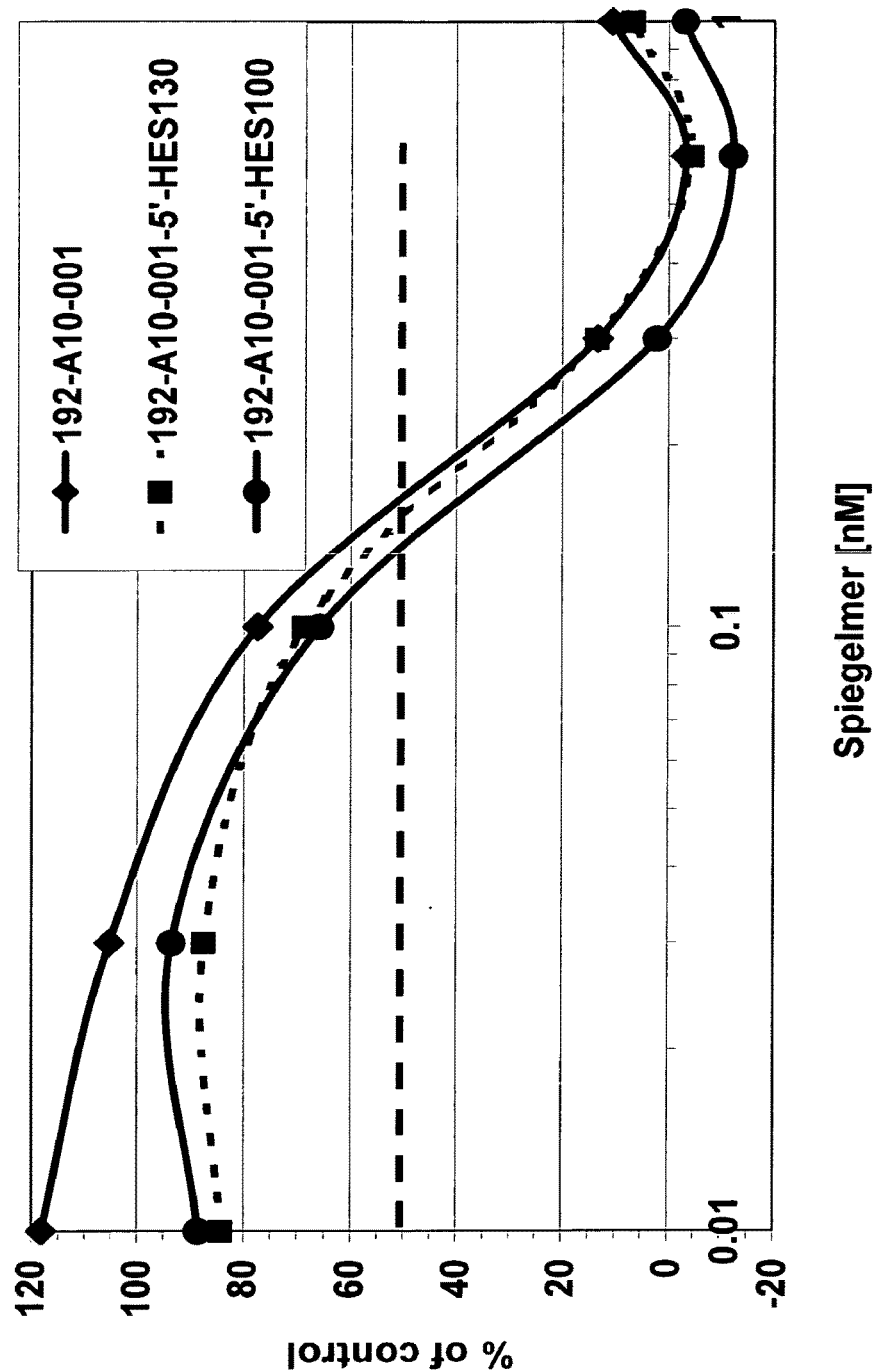
Figure 25B:
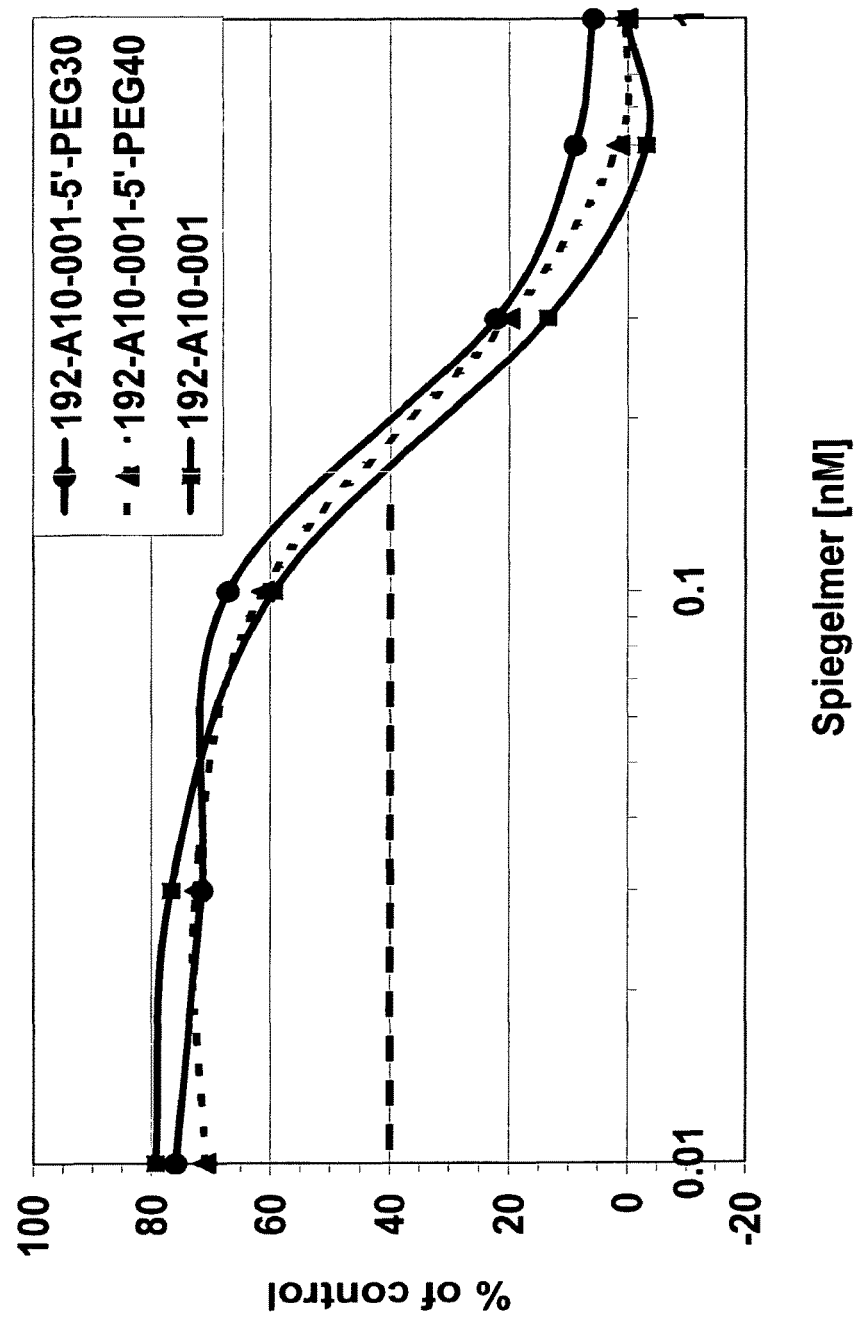
Figure 26:
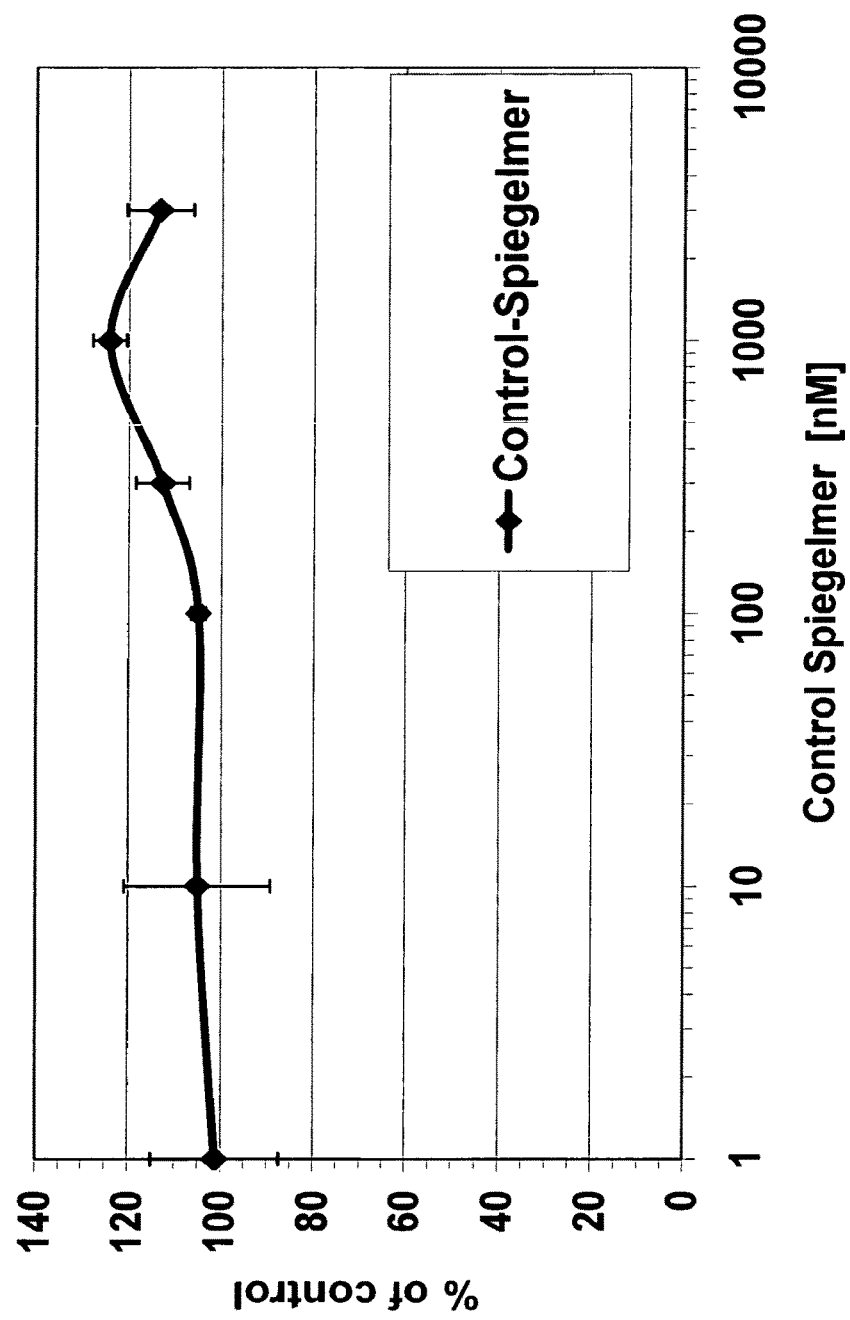
Figure 27:
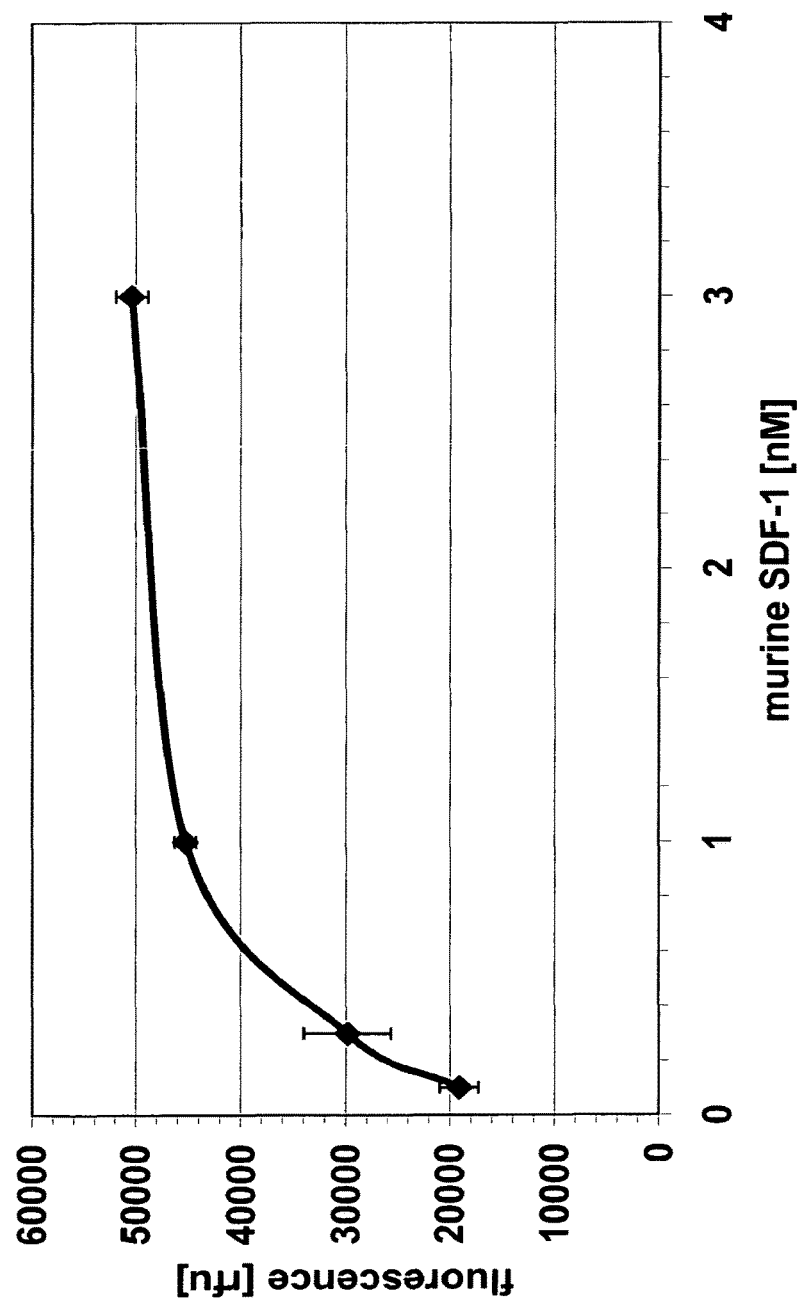
Figure 28:
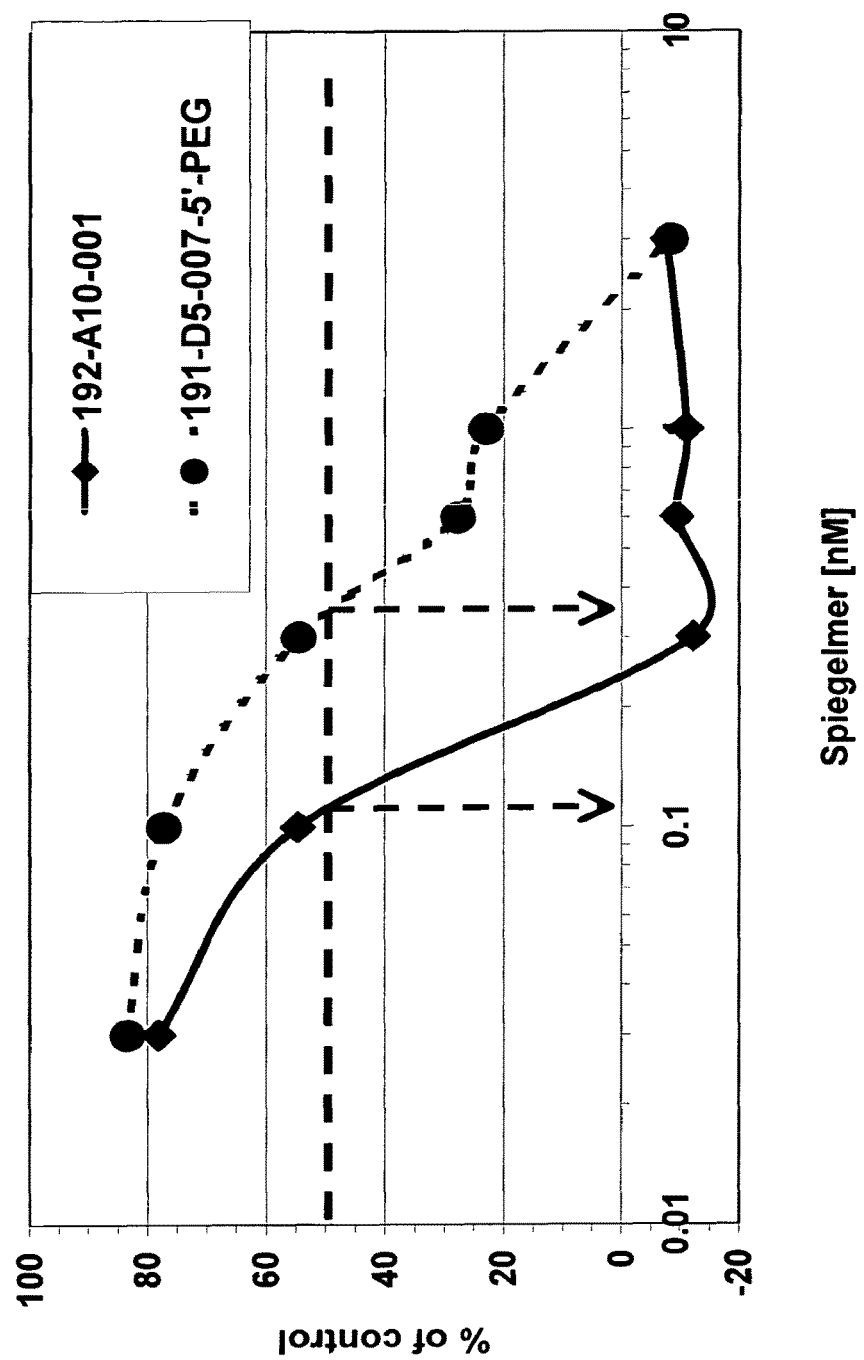
Figure 29:
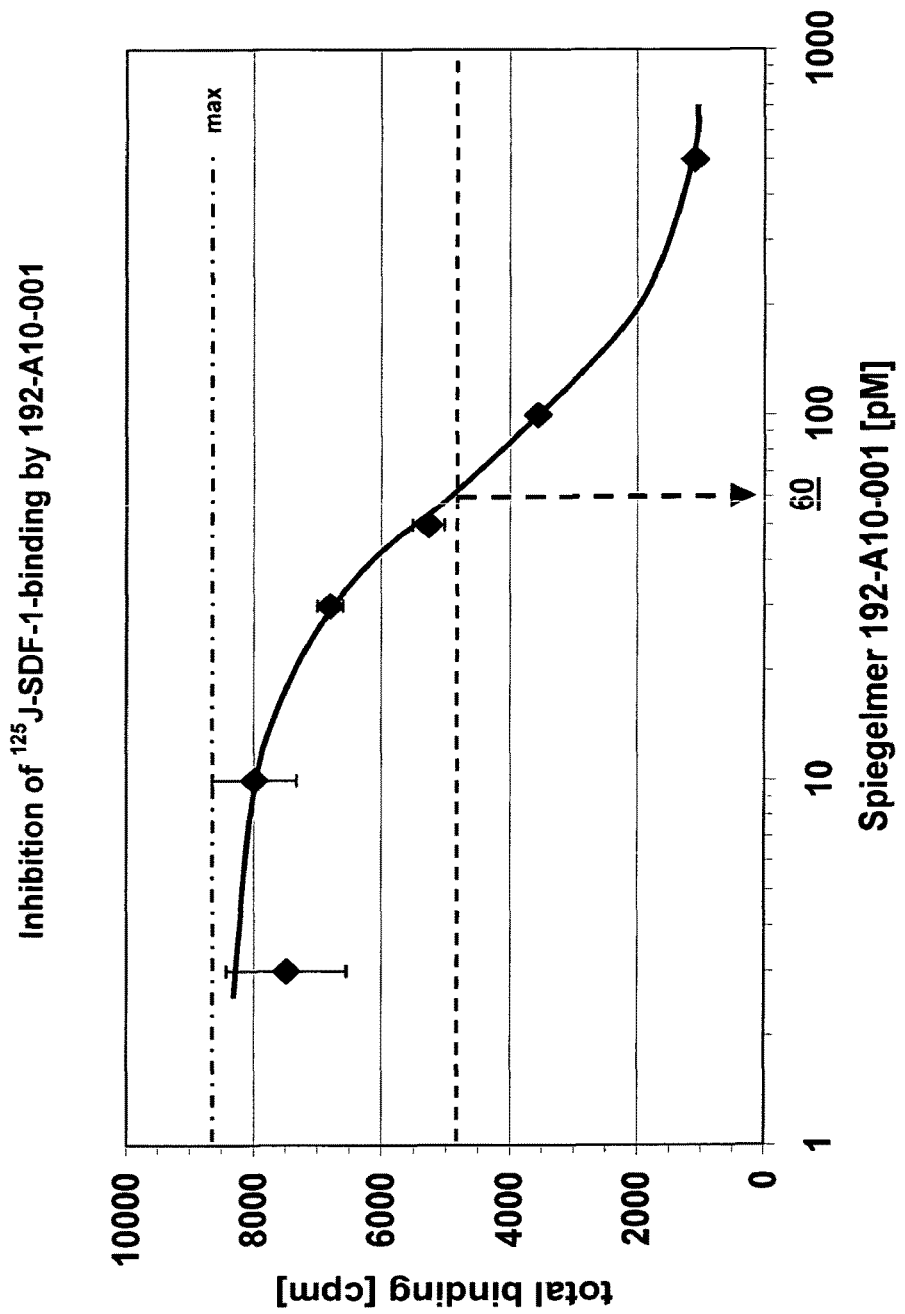
Figure 30:
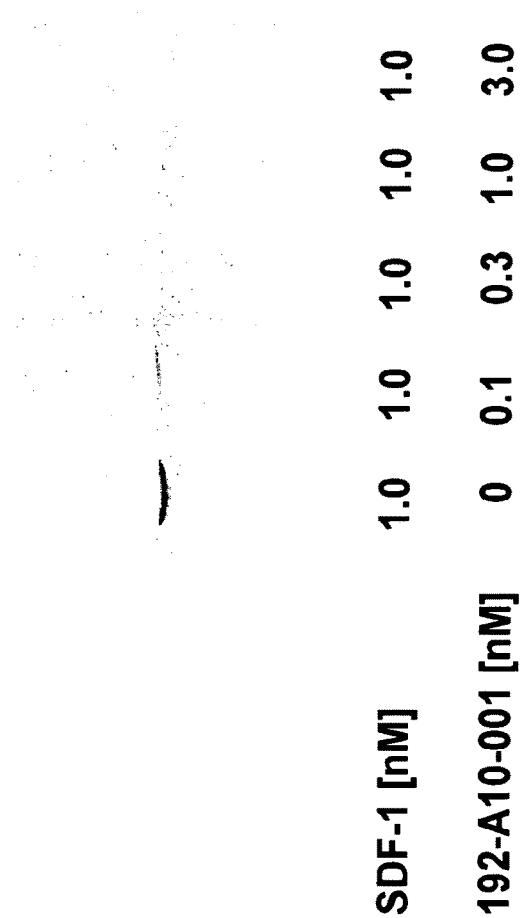
Figure 33:
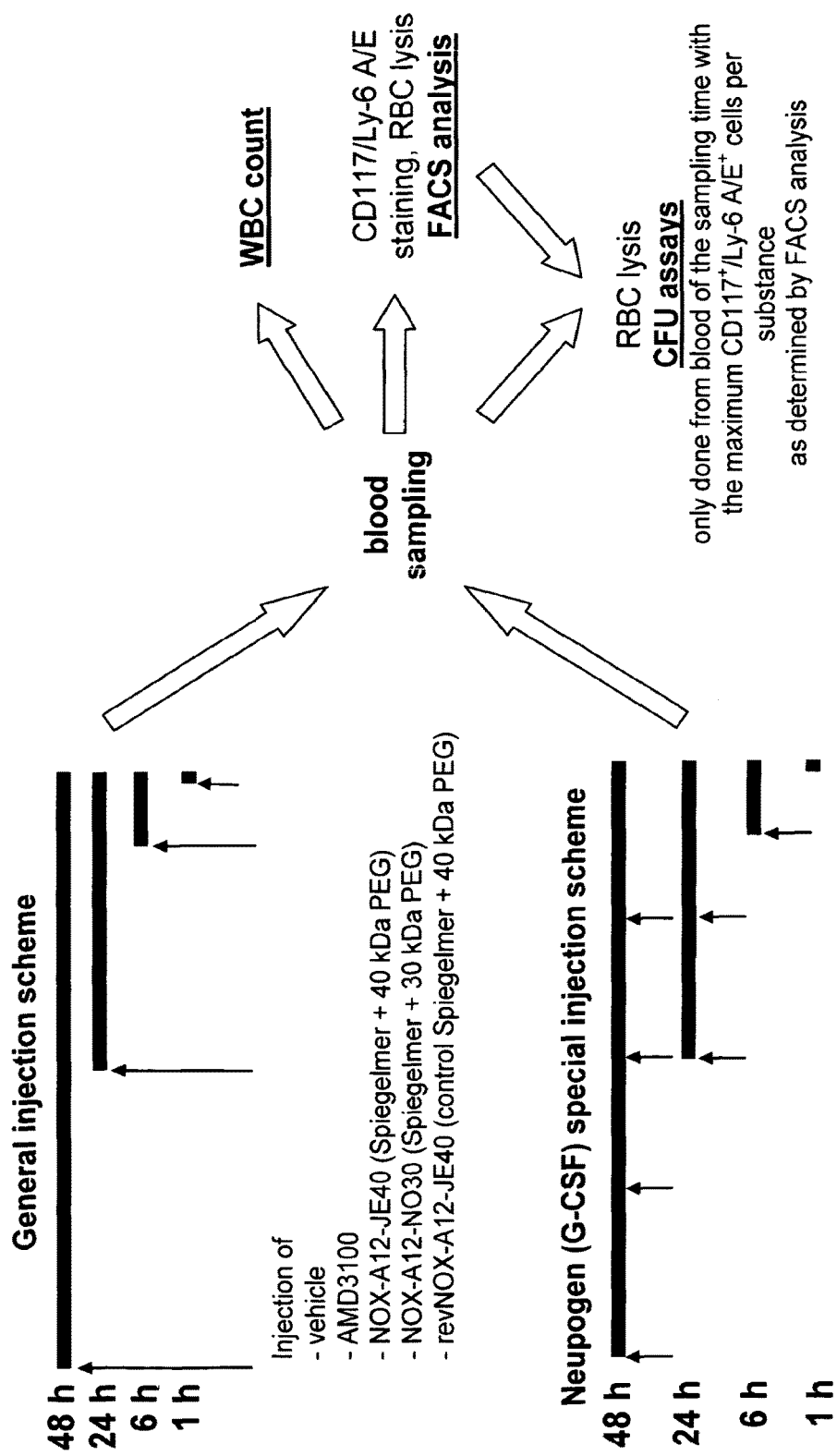
Figure 34:
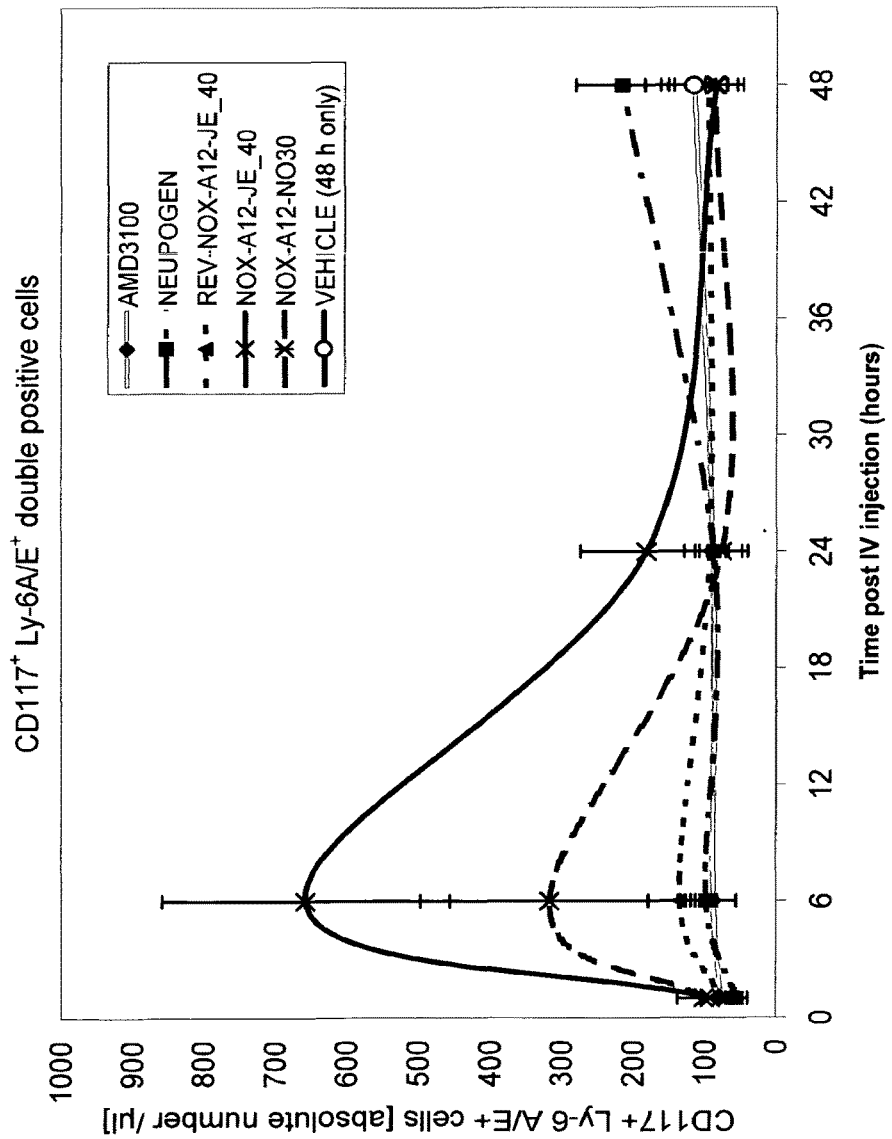
Figure 35:
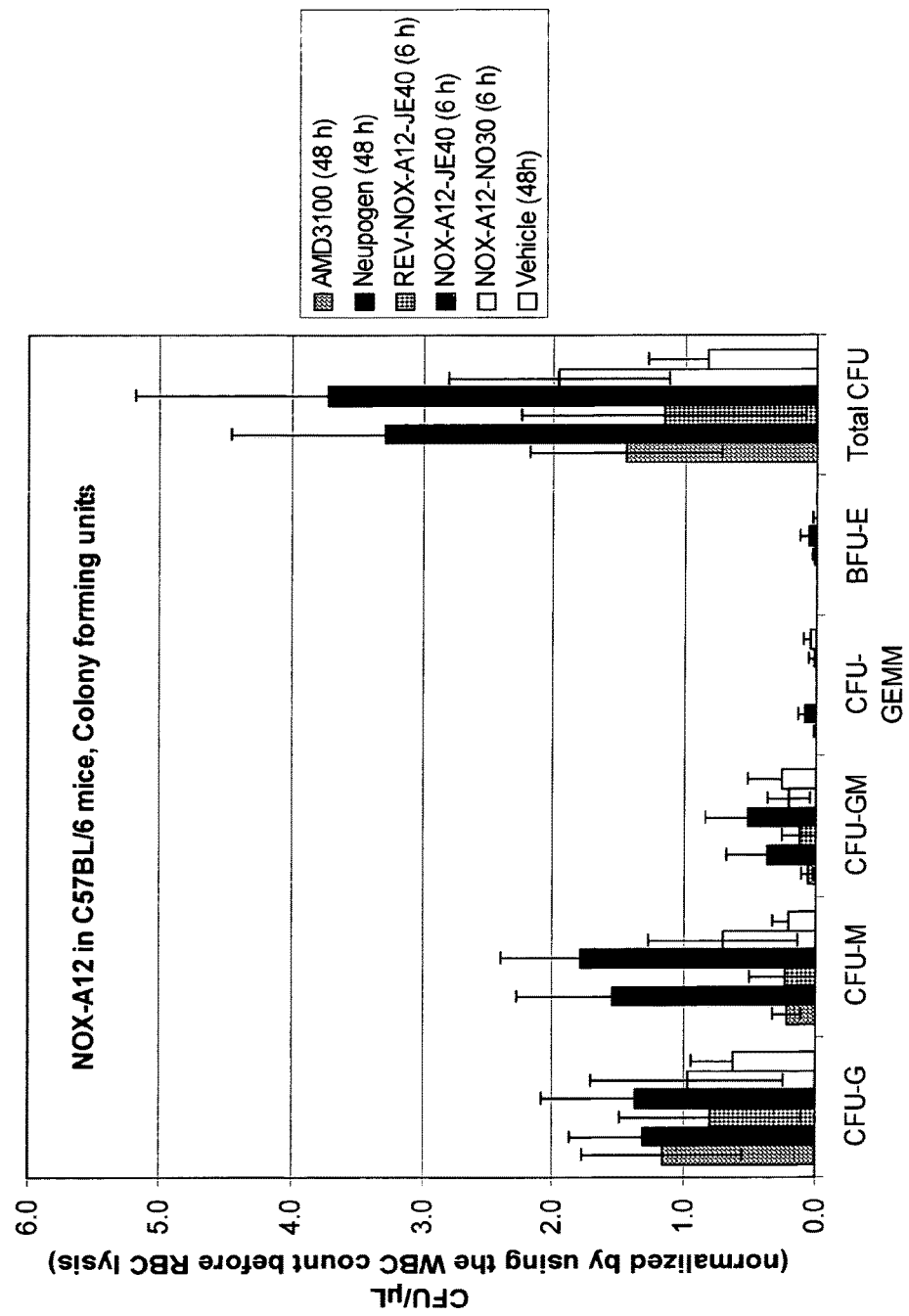
Figure 36:
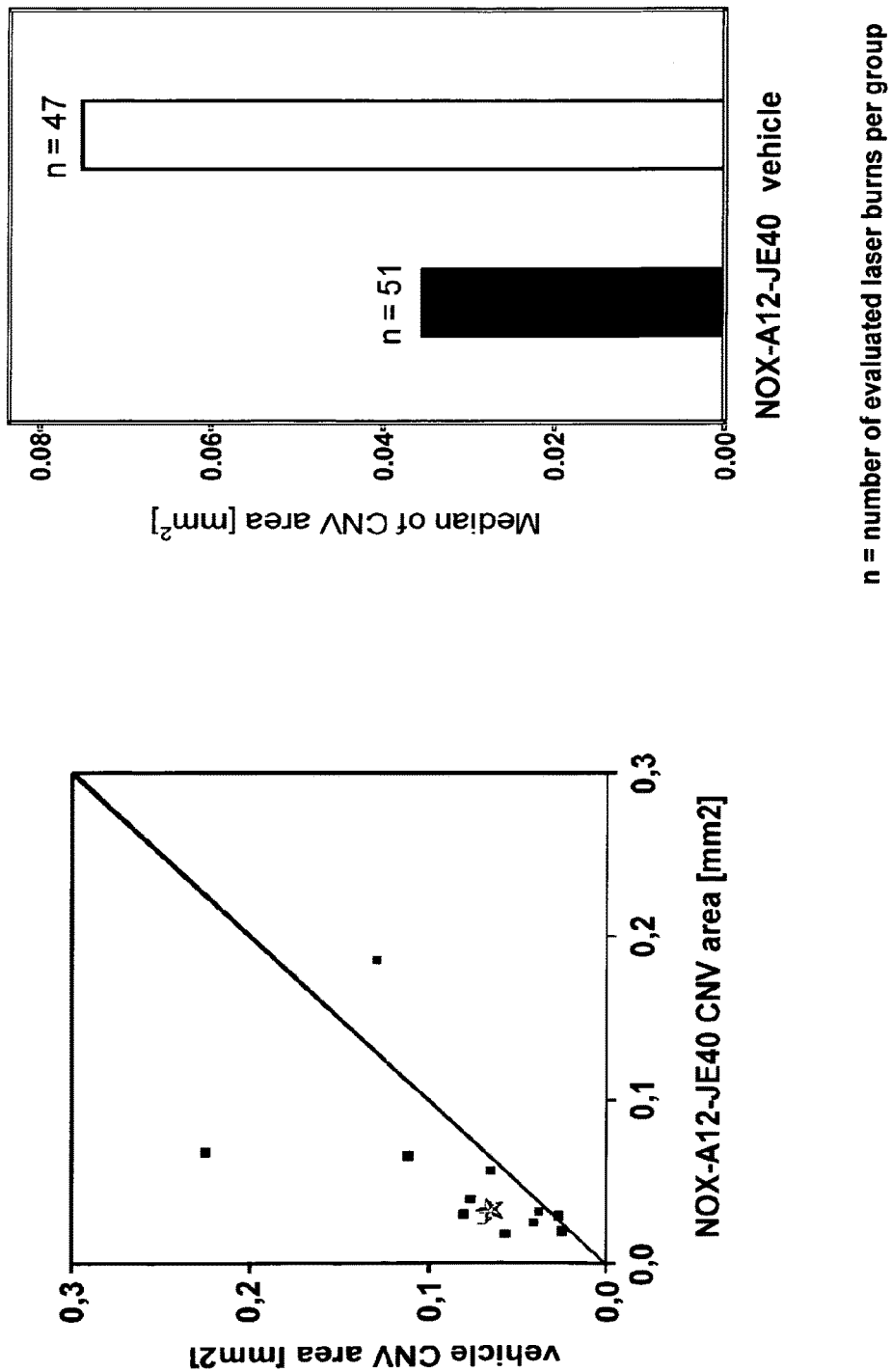
Figure 37:
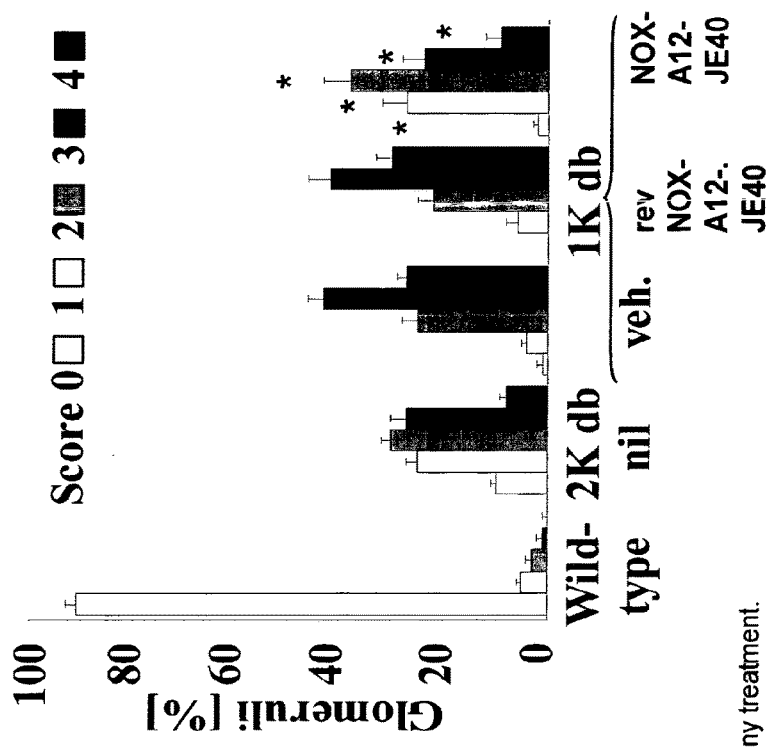
Figure 38:
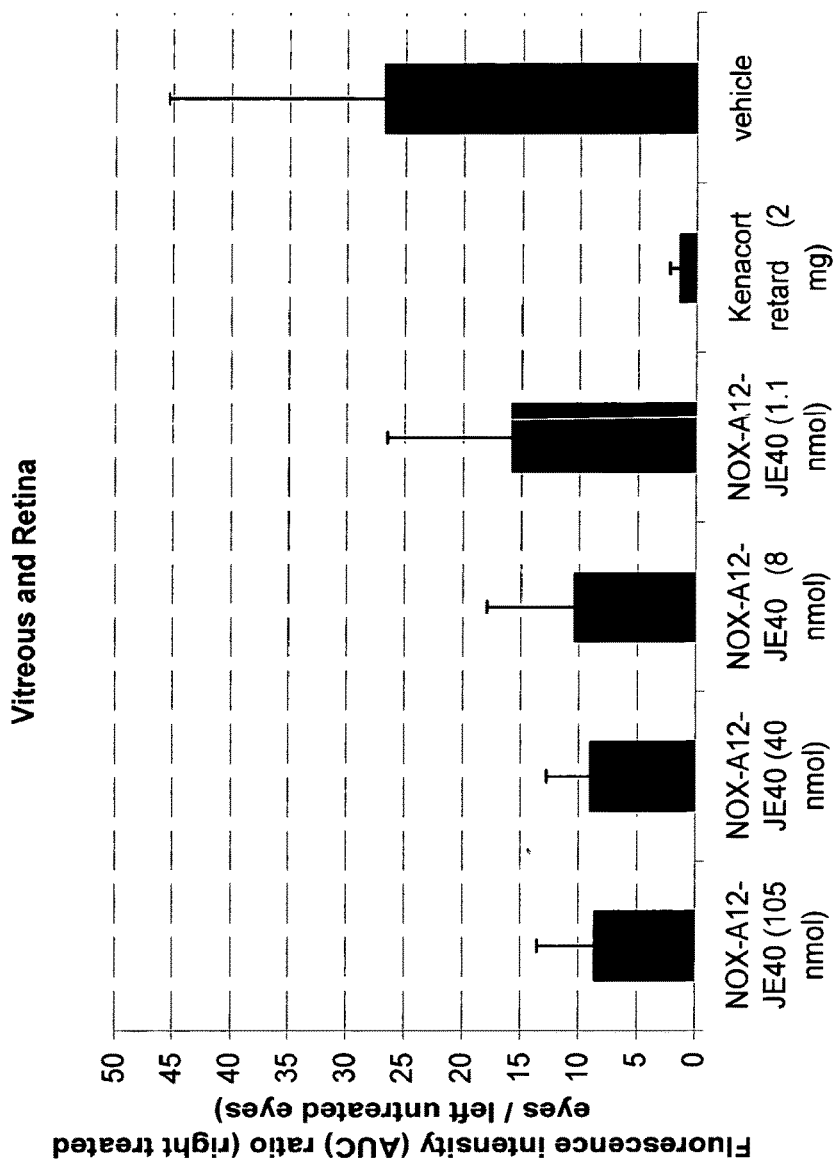
Figure 39:
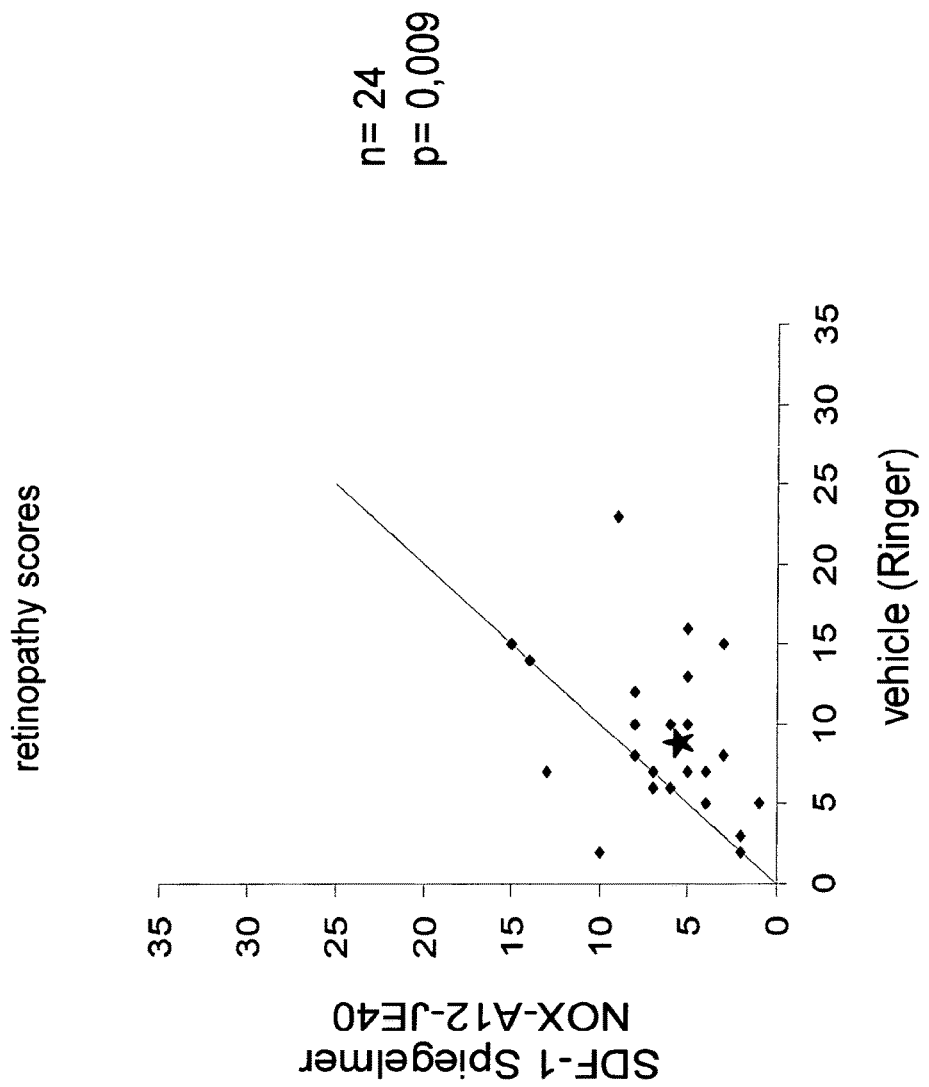

FIG. 13 shows the result of a competitive binding analysis of the human SDF-1 binding aptamers 192-A10-001, 192-F10-001, 192-C9-001, 192-E10-001, 192-C10-001, 192-D11-001, 192-G11-001, 192-H11-001, 192-D10-001, 192-E9-001 and 192-H9-001 to biotinylated human D-SDF-1 at 37° C., represented as binding of the labeled aptamer 192-A10-001 (used as reference that is displaced by the non-labeled aptamers) at 1 nM and 5 nM non-labeled aptamers 192-A10-001, 192-F10-001, 192-C9-001, 192-E10-001, 192-C10-001, 192-D11-001, 192-G11-001, 192-H11-001, 192-D10-001, 192-E9-001 and 192-H9-001;

FIG. 14 shows the result of a binding analysis of the human SDF-1 binding aptamer 192-A10-008 to biotinylated human D-SDF-1 at 37° C., represented as binding of the aptamer over concentration of biotinylated human D-SDF-1;

FIG. 15 shows a Biacore 2000 sensorgram indicating the $K_D$ value of the human SDF-1 binding Spiegelmer 192-A10-008 binding to human SDF-1 which was immobilized on a PioneerF1 sensor chip by amine coupling procedure, represented as response (RU) over time, additionally the on- and off-rates and the $K_D$ values of Spiegelmers 192-A10-008 and 192-A10-001 are listed;

FIG. 16 shows the efficacy of SDF-1 binding Spiegelmer 192-A10-008 in a chemotaxis assay; cells were allowed to migrate towards 0.3 nM human SDF-1 preincubated at 37° C. with various amounts of Spiegelmer 192-A10-008, represented as percentage of control over concentration of Spiegelmer 192-A10-008;

FIG. 17 shows a Biacore 2000 sensorgram indicating the $K_D$ value of Spiegelmer 193-G2-01 binding to human SDF-1 which was immobilized on a PioneerF1 sensor chip by amine coupling procedure, represented as response (RU) over time, additionally the on- and off-rates and the $K_D$ values of Spiegelmers 193-G2-001 and 193-C2-001 are listed;

FIG. 18 shows the result of a binding analysis of the human anti-SDF-1 aptamer 193-G2-012 to biotinylated human D-SDF-1 at 37° C., represented as binding of the aptamer over concentration of biotinylated human D-SDF-1;

FIG. 19 shows the result of a competitive binding analysis of the human SDF-1 binding aptamers 190-A3-001, 190-A3-003, 190-A3-004, 190-A3-007, 191-D5-001, 191-D5-002, 191-D5-003, 191-D5-004, 191-D5-005, 191-D5-006 and 191-D5-007 to biotinylated human D-SDF-1 at 37° C., represented as binding of the labeled aptamer 190-A3-001 or 191-D5-001 (used as reference that is displaced by the non-labeled aptamers) at 500 nM, 50 nM and 10 nM non-labeled aptamers 190-A3-001, 190-A3-003, 190-A3-004, 190-A3-007, 191-D5-001, 191-D5-002, 191-D5-003, 191-D5-004, 191-D5-005, 191-D5-006 and 191-D5-007;

FIG. 20 shows the result of a binding analysis of the human SDF-1 binding aptamers 190-A3-004 and 191-D5-007 to biotinylated human D-SDF-1 37° C., represented as binding of the aptamer over concentration of biotinylated human D-SDF-1;

FIG. 21 shows a Biacore 2000 sensorgram indicating the $K_D$ value of Spiegelmer 191-D5-007 binding to human SDF-1 which was immobilized on a PioneerF1 sensor chip by amine coupling procedure, represented as response (RU) over time, additionally the on- and off-rates and the $K_D$ values of Spiegelmers 191-D5-001, 191-D5-007, 190-A3-003 and 197-B2 are listed;

FIG. 22 shows the efficacy of SDF-1 binding Spiegelmer 190-A3-004 in a chemotaxis assay; cells were allowed to migrate towards 0.3 nM human SDF-1 preincubated at 37° C. with various amounts of Spiegelmer 190-A3-004, represented as percentage of control over concentration of Spiegelmer 190-A3-004;

FIG. 23A shows the efficacy of SDF-1 binding Spiegelmers 193-G2-012-5'-PEG, 197-B2-006-5'-PEG, 191-D5-007-5'-PEG and 191-A10-008-5'-PEG in a chemotaxis assay; cells were allowed to migrate towards 0.3 nM human SDF-1 preincubated at 37° C. with various amounts of Spiegelmers 193-G2-012-5'-PEG, 197-B2-006-5'-PEG, 191-D5-007-5'-PEG and 191-A10-008-5'-PEG, represented as percentage of control over concentration of Spiegelmers 193-G2-012-5'-PEG, 197-B2-006-5'-PEG, 191-D5-007-5'-PEG and 191-A10-008-5'-PEG;

FIG. 23B shows the efficacy of SDF-1 binding Spiegelmers 197-B2-006-5'PEG and 197-B2-006-31b-5'-PEG in a chemotaxis assay; cells were allowed to migrate towards 0.3 nM human SDF-1 preincubated at 37° C. with various amounts of Spiegelmers 197-B2-006-5'PEG and 197-B2-006-31b-5'-PEG, represented as percentage of control over concentration of Spiegelmers 197-B2-006-5'PEG and 197-B2-006-31b-5'-PEG;

FIG. 24A shows a Biacore 2000 sensorgram indicating the $K_D$ values of Spiegelmers 193-G2-012-5'-PEG, 191-A10-008-5'-PEG and 191-A10-001-5'-PEG binding to human SDF-1 which was immobilized on a PioneerF1 sensor chip by amine coupling procedure, represented as response (RU) over time;

FIG. 24B shows a Biacore 2000 sensorgram indicating the $K_D$ values of Spiegelmers 197-B2-006-5'PEG, 197-B2-006-31b-5'-PEG and 191-D5-007-5'-PEG binding to human SDF-1 which was immobilized on a PioneerF1 sensor chip by amine coupling procedure, represented as response (RU) over time;

FIG. 25A shows the efficacy of SDF-1 binding Spiegelmers 192-A10-001, 192-A10-001-5'-HES130 and 192-A10-001-5'-HES100 in a chemotaxis assay; cells were allowed to migrate towards 0.3 nM human SDF-1 preincubated at 37° C. with various amounts of Spiegelmers 192-A10-001, 192-A10-001-5'-HES130 and 192-A10-001-5'-HES100, represented as percentage of control over concentration of Spiegelmers 192-A10-001, 192-A10-001-5'-HES130 and 192-A10-001-5'-HES100;

FIG. 25B shows the efficacy of SDF-1 binding Spiegelmers 192-A10-001, 192-A10-001-5'-PEG30 and 192-A10-001-5'-PEG40 in a chemotaxis assay; cells were allowed to migrate towards 0.3 nM human SDF-1 preincubated at 37° C. with various amounts of Spiegelmers 192-A10-001, 192-A10-001-5'-PEG30 and 192-A10-001-5'-PEG40, represented as percentage of control over concentration of Spiegelmers 192-A10-001, 192-A10-001-5'-PEG30 and 192-A10-001-5'-PEG40;

FIG. 26 shows the inefficacy of a control-Spiegelmer in a chemotaxis assay; cells were allowed to migrate towards 0.3 nM human or murine SDF-1 preincubated at 37° C. with various amounts of control-Spiegelmer, represented as percentage of control over concentration of control Spiegelmer;

FIG. 27 shows the murine SDF-1-induced chemotaxis of Jurkat human T cell leukemia cells whereas after 3 hours migration of Jurkat human T cell leukemia cells towards various SDF-1 concentrations a dose-response curve for SDF-1 was obtained, represented as fluorescence signal;

FIG. 28 shows the efficacy of SDF-1 binding Spiegelmers 192-A10-001 and 191-D5-007-5'PEG in a chemotaxis assay; cells were allowed to migrate towards 0.3 nM murine SDF-1 preincubated at 37° C. with various amounts of Spiegelmers 192-A10-001 and 191-D5-007-5'PEG represented as percentage of control over concentration of Spiegelmers 192-A10-001 and 191-D5-007-5'PEG;

FIG. 29 shows the efficacy of SDF-1 binding Spiegelmer 192-A10-001 in a CXCR4-receptor binding assay using human [$^{125}$J]-SDF-1α that was preincubated at 37° C. with various amounts of Spiegelmers 192-A10-001, specifically bound [$^{125}$J]-SDF-1α was plotted over concentration of Spiegelmer 192-A10-001; and FIG. 30 shows the inhibition of MAP-kinase stimulation of CXCR4-expressing cells with 1 nM human SDF-1α by human SDF-1 binding Spiegelmer 192-A10-001;

FIG. 31 shows the inhibition of SDF-1 induced sprouting by human SDF-1 binding Spiegelmer 193-G2-012-5'-PEG and by PEGylated Control Spiegelmer in aortic ring sprouting assay, whereby rings from rat aorta were embedded in collagen matrix and incubated for 6 days with SDF-1 with or without Spiegelmers (a: control; b: 10 nM SDF-1; c: 10 nM SDF-1+1 µM human SDF-1 binding Spiegelmer 193-G2-012-5'-PEG; d: 10 nM SDF-1+1 µM PEGylated Control Spiegelmer);

FIG. 32 shows the inhibition of SDF-1 induced sprouting by human SDF-1 binding Spiegelmer 193-G2-012-5'-PEG and by PEGylated Control Spiegelmer in aortic ring sprouting assay whereby sprouting indices are shown as mean+/− SD for 5 rings per condition (*: the value for SDF-1 is significantly different from control (Mann-Whitney-test; p=0.009); **: the value for SDF-1+human SDF-1 binding Spiegelmer 193-G2-012-5'-PEG is significantly different from that for SDF-1 (Mann-Whitney-test; p=0.028);

FIG. 33 shows a schematic representation of animal treatment and methods apply to generate the stem cell liberation data according to Example 10;

FIG. 34 shows the absolute number of CD117+ and Ly-6 A/E+ cells (hematopoietic stem cells/hematopoietic progenitor cells) per microliter plasma liberated 1 to 48 hours after intravenous injection of NOX-A12-JE40, NOX-A12-NO30, revNOX-A12-JE40 (control spiegelmer), AMD3100, G-CSF (Neupogen) or vehicle (5% glucose); the graph shows mean values and standard deviation;

FIG. 35 shows colony forming units per µL of blood of C57BL/6 mice after 6 h for NOX-A12-derivatives, and AMD3100, or 48 h for G-CSF (Neupogen) and vehicle injection as indicated in the legend; the diagram shows mean values and standard deviations of 5 mice (triplicates each);

FIG. 36 shows the results of the laser-induced choroidal neovascularization study in mice, whereby NOX-A12-JE40 reduced the neovascularized area in the NOX-A12-JE40 treated eye in direct comparison to the area in the vehicle-treated eye (Ringer solution) of the same animal (left diagram); the median neovascular areas of individual lesions in NOX-A12-JE40 and vehicle-treated mouse eyes after laser injury are shown in diagram on the right;

FIG. 37 shows the results of repeated treatment of healthy mice and diabetic mice with and without uninephrectomy with vehicle, NOX-A12-JE40, revNOX-A12-JE40 (control Spiegelmer) whereby NOX-A12-JE40 improves the glomerulosclerosis scores;

FIG. 38 shows the results of an animal model for retinal vascular leakage after induction by intravitreal administered VEGF and treatment of the animals with different concentrations of the SDF-1 binding Spiegelmer NOX-A12-JE40, vehicle or Kenacort retart; in this model, the permeability of the retinal vasculature was measured by fluorescein photometry 48 h after intravitreal injection of VEGF;

FIG. 39 shows the retinopathy scores (vehicle treated eye [x-axis] vs. Spiegelmer NOX-A12-JE40 treated eye [y-axis]) of individual mice in a mouse model of oxygen-induced retinopathy that is a model for the mimicking of hypoxia-induced neovascularization of the retina, as observed in diabetic retinopathy or AMD;

FIG. 40 shows the p values for the statistical difference between Spiegelmer NOX-A12-JE40-treated and vehicle treated eyes for the individually measured parameters of the retinopathy and of the retinopathy score as measured in the mouse model of oxygen-induced retinopathy that is a model for the mimicking of hypoxia-induced neovascularization of the retina, as observed in diabetic retinopathy and AMD; the p-values were determined using the Wilcoxon signed-ranks test;

FIG. 41 shows white blood cell count after intraveneous administration of 13.4 mg (calculated relating to the oligo part) SDF-1 binding nucleic acid NOX-A12-JE40, whereby only one time point was recorded after vehicle (5% glucose) administration since this was assumed to be constant; however, NOX-A12_JE40 mobilizes a fair amount of white blood cells in a reversible manner;

FIG. 42 shows an overview of indications for allogenic hematopoietic stem cell transplantations (abbr. HSCT) and patient numbers in Europe between 1990-2000 (Gratwohl, Baldomero et al. 2002);

FIG. 43 shows an overview of indications for autologous hematopoietic stem cell transplantations (abbr. HSCT) and patient numbers in Europe between 1990-2000 (Gratwohl, Baldomero et al. 2002).

EXAMPLE 1: NUCLEIC ACIDS THAT BIND HUMAN SDF-1

Using biotinylated human D-SDF-1 as a target, several nucleic acids that bind to human SDF-1 could be generated the nucleotide sequences of which are depicted in FIGS. 1 through 9. The nucleic acids were characterized on the aptamer, i. e. D-nucleic acid level with biotinylated human D-SDF-1 or on the Spiegelmer level, i. e. L-nucleic acid with the natural configuration of SDF-1 (L-SDF-1).

Aptamers were analyzed with biotinylated human D-SDF-1 using competitive or direct pull-down binding assays with biotinylated human D-SDF-1 (Example 4). Spiegelmers were tested with the natural configuration of SDF-1 (L-SDF-1) by surface plasmon resonance measurement using a Biacore 2000 instrument (Example 6) and a cell culture in vitro chemotaxis assay (Example 5).

The nucleic acid molecules thus generated exhibit different sequence motifs, three main types are defined in FIGS. 1, 2A and 2B (Type A), FIGS. 3, 4A and 4B (Type B), FIGS. 5, 6, 7A, 7B and 8 (Type C). For definition of nucleotide sequence motifs, the IUPAC abbreviations for ambiguous nucleotides is used:

| S | strong | G or C; |
|---|---|---|
| W | weak | A or U; |
| R | purine | G or A; |
| Y | pyrimidine | C or U; |
| K | keto | G or U; |
| M | imino | A or C; |
| B | not A | C or U or G; |
| D | not C | A or G or U; |
| H | not G | A or C or U; |
| V | not U | A or C or G; |
| N | all | A or G or C or U |

If not indicated to the contrary, any nucleic acid sequence or sequence of stretches and boxes, respectively, is indicated in the 5'→3' direction.

1.1 Type A SDF-1 Binding Nucleic Acids

As depicted in FIG. 1 all sequences of SDF-1 binding nucleic acids of Type A comprise one core nucleotide sequence which is flanked by 5'- and 3'-terminal stretches that can hybridize to each other. However, such hybridization is not necessarily given in the molecule.

The nucleic acids were characterized on the aptamer level using direct and competitive pull-down binding assays with biotinylated human D-SDF-1 in order to rank them with respect to their binding behaviour (Example 4). Selected sequences were synthesized as Spiegelmers (Example 3) and were tested using the natural configuration of SDF-1 (L-SDF) in a cell culture in vitro chemotaxis assay (Example 5) and by surface plasmon resonance measurement using a Biacore 2000 instrument (Example 6).

The sequences of the defined boxes or stretches may be different between the SDF-1 binding nucleic acids of Type A which influences the binding affinity to SDF-1. Based on binding analysis of the different SDF-1 binding nucleic acids summarized as Type A SDF-1 binding nucleic acids, the core nucleotide sequence and its nucleotide sequences as described in the following are individually and more preferably in their entirety essential for binding to SDF-1:

The core nucleotide sequence of all identified sequences of Type A SDF-1 binding nucleic acids share the sequence

AAAGYRACAHGUMAAX₄UGAAAGGUARC (Type A Formula-1, SEQ ID NO:19), whereby $X_4$ is either absent or is 'A'. If 'A' is absent, the sequence of the core nucleotide sequence can be summarized as Type A Formula-2

(AAAGYRACAHGUMAA

UGAAAGGUARC (SEQ ID NO:20). Type A SDF-1 binding nucleic acid 191-A6 (core nucleotide sequence:

AAAGUAACAGGUAAAUGAAAGGUAAC )

(SEQ ID NO:247) carrying the additional nucleotide 'A' within the core nucleotide sequence and still binding to SDF-1 let conclude an alternative core nucleotide sequence (AAAGYRACAHGUMAAAUGAAAGGUARC, Type A Formula-3, SEQ ID NO:21). Exemplarily for all the other nucleic acids of Type A SDF-1 binding nucleic acids, the Type A SDF-1 binding nucleic acid 192-A10-001 was characterized for its binding affinity to human SDF-1. The equilibrium binding constant $K_D$ was determined using the pull-down binding assay ($K_D$=1.5 nM, FIG. 11) and by surface plasmon resonance measurement ($K_D$=1.0 nM, FIG. 15). The $IC_{50}$ (inhibitory concentration 50%) of 0.12 nM for 192-A10-001 was measured using a cell culture in vitro chemotaxis assay (FIG. 12). Consequently, all Type A SDF-1 binding nucleic acids as depicted in FIG. 1 were analyzed in a competitive pull-down binding assay vs. 192-A10-001 (FIG. 13; not all of Type A SDF-1 binding nucleic acids tested are shown in FIG. 13). The Type A SDF-1 binding nucleic acids 192-B11 and 192-C10 showed equal binding affinities as 192-A10-001 in these competition experiments. Weaker binding affinity was determined for Type A SDF-1 binding nucleic acids 192-G10, 192-F10, 192-C9, 192-E10, 192-D11, 192-G11, 192-H11 and 191-A6. The Type A SDF-1 binding nucleic acids 192-D10, 192-E9 and 192-H9 have much weaker binding affinity than 192-A10-001 (FIG. 13).

As mentioned above, the Type A SDF-1 binding nucleic acid 192-B11 and 192-C10 exhibit equal binding affinity to SDF-1 as 192-A10-001. However, they show slight differences in the nucleotide sequence of the core nucleotide sequence. Therefore the consensus sequence of the three molecules binding to SDF-1 with almost the same high affinity can be summarized by the nucleotide sequence

AAAGYAACAHGUCAAUGAAAGGUARC (Type A Formula-4, SEQ ID NO:22) whereby the nucleotide sequence of the core nucleotide sequence of 192-A10-001 (nucleotide sequence

AAAGCAACAUGUCAAUGAAAGGUAGC )

(SEQ ID NO:30) represents the nucleotide sequence with the best binding affinity of Type A SDF-1 binding nucleic acids.

Five or six out of the six nucleotides of the 5'-terminal stretch of Type A SDF-1 binding nucleic acids may hybridize to the respective five or six nucleotides out of the six nucleotides of the 3'-terminal stretch Type A SDF-1 binding nucleic acids to form a terminal helix. Although these nucleotides are variable at several positions, the different nucleotides allow for hybridization of five or six out of the six nucleotides of the 5'- and 3'-terminal stretches each. The 5'-terminal. and 3'-terminal stretches of Type A SDF-1 binding nucleic acids as shown in FIG. 1 can be summarized in a generic formula for the 5'-terminal stretch ('RSHRYR', Type A Formula-5-5') and for the 3'-terminal stretch ('YRYDSY', Type A Formula-5-3'). Truncated derivatives of Type A SDF-1 binding nucleic acid 192-A10-001 were analyzed in a competitive pull-down binding assay vs. the original molecule 192-A10-001 and 192-A10-008 (FIGS. 2A and 2B). These experiments showed that a reduction of the six terminal nucleotides (5'end: GCUGUG; 3'end: CGCAGC) of 192-A10-001 to five nucleotides (5'end: CUGUG; 3'end: CGCAG) of the derivative 192-A10-002 could be done without reduction of binding affinity. However, the truncation to four terminal nucleotides (5'end: UGUG; 3'end: CGCA; 192-A10-003) or less (192-A10-004/-005/-006/-007) led to reduced binding affinity to SDF-1 (FIG. 2A). The determined 5'-terminal and 3'-terminal stretches with a length of five and four nucleotides of the derivatives of Type A SDF-1 binding nucleic acid 192-A10-

001 as shown in FIGS. 2A and B can be described in a generic formula for the 5'-terminal stretch ('X$_2$BBBS', Type A Formula-6-5') and of the 3'-terminal stretch ('SBBVX$_3$'; Type A Formula-6-3'), whereby X$_2$ is either absent or is 'S' and X$_3$ is either absent or is 'S'.

The nucleotide sequence of the 5'- and 3'-terminal stretches has an influence on the binding affinity of Type A SDF-1 binding nucleic acids. This is not only shown by the nucleic acids 192-F10 and 192-E10, but also by derivatives of 192-A10-001 (FIG. 2B;). The core nucleotide sequences of 192-F10 and 192-E10 are identical to 192-B11 and 192-C10, but comprise slight differences at the 3'-end of 5'-terminal stretch and at the 5'-end of 3'-terminal stretch resulting in reduced binding affinity.

The substitution of 5'- and 3'-terminal nucleotides 'CUGUG' and 'CGCAG' of Type A SDF-1 binding nucleic acid 192-A10-002 by 'GCGCG' and 'CGCGC' (192-A10-015) resulted in a reduced binding affinity whereas substitutions by 'GCGUG' and 'CGCGC' (192-A10-008) resulted in same binding affinity as shown for 192-A10-002 (FIG. 2B, FIG. 15, FIG. 12, FIG. 16). Additionally, nine derivatives of Type A SDF-1 binding nucleic acid 192-A10-001 (192-A10-014/-015/-016/-017/-018/-019/-020/-021/-022/-023) bearing four 5'- and 3'-terminal nucleotides respectively were tested as aptamers for their binding affinity vs. 192-A10-001 or its derivative 192-A10-008 (both have the identical binding affinity to SDF-1). All clones showed weaker, much weaker or very much weaker binding affinity to SDF-1 as 192-A10-001 (six nucleotides forming a terminal helix) or as 192-A10-008 with five terminal nucleotides, respectively (FIG. 2B). Consequently, the sequence and the number of nucleotides of the 5'- and 3'-terminal stretches are essential for an effective binding to SDF-1. As shown for Type A SDF-1 binding nucleic acids 192-A10-002 and 192-A10-08 the preferred combination of 5'- and 3'-terminal stretches are 'CUGUG' and 'CGCAG' (5'- and 3'-terminal stretches of Type A SDF-1 binding nucleic acid 192-A10-002) and 'GCGUG' and 'CGCGC' (5'- and 3'-terminal stretches of Type A SDF-1 binding nucleic acid 192-A10-008).

However, combining the 5'- and 3'-terminal stretches of all tested Type A SDF-1 binding nucleic acids the generic formula for the 5'-terminal stretch of Type A SDF-1 binding nucleic acids is 'X$_1$X$_2$NNBV' (Type A Formula-7-5') and the generic formula for the 3'-terminal stretch of Type A SDF-1 binding nucleic acids is 'BNBNX$_3$X$_4$' (Type A Formula-7-3'), whereas X$_1$ is 'R' or absent, X$_2$ is 'S', X$_3$ is 'S' and X$_4$ is 'Y' or absent;

or

X$_1$ is absent, X$_2$ is 'S' or absent, X$_3$ is 'S' or absent and X$_4$ is absent.

1.2 Type B SDF-1 Binding Nucleic Acids

As depicted in FIG. 3 all sequences of SDF-1 binding nucleic acids of Type B comprise one core nucleotide sequence which is flanked by 5'- and 3'-terminal stretches that can hybridize to each other. However, such hybridization is not necessarily given in the molecule.

The nucleic acids were characterized on the aptamer level using direct and competitive pull-down binding assays with biotinylated human D-1 in order to rank them with respect to their binding behaviour (Example 4). Selected sequences were synthesized as Spiegelmers (Example 3) and were tested using the natural configuration of SDF-1 (L-SDF) in a cell culture in vitro chemotaxis assay (Example 5) and by surface plasmon resonance measurement using a Biacore 2000 instrument (Example 6).

The sequences of the defined boxes or stretches may be different between the SDF-1 binding nucleic acids of Type B which influences the binding affinity to SDF-1. Based on binding analysis of the different SDF-1 binding nucleic acids summarized as Type B SDF-1 binding nucleic acids, the core nucleotide sequence and its nucleotide sequences as described in the following are individually and more preferably in their entirety essential for binding to SDF-1:

The core nucleotide sequence of all identified sequences of Type B SDF-1 binding nucleic acids share the sequence

```
GUGUGAUCUAGAUGUADWGGCUGWUCCUAGUYAGG
```

(Type B Formula-1, SEQ ID NO:57). The Type B SDF-1 binding nucleic acids 193-G2-001, 193-C2-001 and 193-F2-001 that differ in one position of the core nucleotide sequence were analyzed in a competitive pull-down binding assay vs. the Type A SDF-1 binding nucleic acid 192-A10-001 (K$_D$ of 1.5 nM determined in a pull-down binding assay [FIG. 11], K$_D$ of 1.0 nM determined by surface plasmon resonance measurement [FIG. 15], IC$_{50}$ of 0.12 nM; [FIG. 12]). Each of the three tested Type B SDF-1 binding nucleic acids showed superior binding to human SDF-1 in comparison to Type A SDF-1 binding nucleic acid 192-A10-001 whereby the binding affinity of 193-G2-001 is as good as 193-C2-001 and 193-F2-001 (FIG. 3). The data suggests that the difference in the nucleotide sequence of the core nucleotide sequence of Type B SDF-1 binding nucleic acids 193-G2-001, 193-C2-001 and 193-F2-001 has no influence on the binding affinity to SDF-1. Exemplarily the Type B SDF-1 binding nucleic acid 193-G2-001 was characterized for its binding affinity to human SDF-1. The equilibrium binding constant K$_D$ was determined using the pull-down binding assay (K$_D$=0.3 nM) and by surface plasmon resonance measurement (K$_D$=0.5 nM, FIG. 17). The IC$_{50}$ (inhibitory concentration 50%) of 0.08 nM for 193-G2-001 was measured using a cell culture in vitro chemotaxis assay. In contrast, the Type B SDF-1 binding nucleic acids 193-B3-002, 193-H3-002, 193-E3-002 and 193-D1-002 that differ in the sequence of the core nucleotide sequence have worse binding properties (FIG. 3). As result Type B SDF-1 binding nucleic acids with improved binding affinity to SDF-1 share a core nucleotide sequence with the sequence

```
GUGUGAUCUAGAUGUADUGGCUGAUCCUAGUCAGG
```

(Type B Formula-2, SEQ ID NO:58).

Four, five or six nucleotides out of the six nucleotides of the 5'-terminal stretch of Type B SDF-1 binding nucleic acids may hybridize to the respective four, five or six out of the six nucleotides of the 3'-terminal stretch of Type B SDF-1 binding nucleic acids to form a terminal helix. Although the nucleotides are variable at several positions, the different nucleotides allow the hybridization for four, five or six nucleotides out of the six nucleotides of the 5'- and 3'-terminal stretches each. The 5'-terminal and 3'-terminal stretches of Type B SDF-1 binding nucleic acids as shown in FIG. 3 can be summarized in a generic formula for the 5'-terminal stretch (Type B Formula-3-5'; 'X$_1$GCRWG' whereas X$_1$ is 'A' or absent) and of the 3'-terminal stretch (Type B Formula-3-3'; 'KRYSCX$_4$' whereas X$_4$ is 'U' or absent). Type B SDF-1 binding nucleic acids 193-G1-002, 193-D2-002, 193-A1-002 and 193-D3-002 have weaker binding affinities to SDF-1 although they share the identical core nucleotide sequence (Type B Formula-2) with 193-C2-001, 193-G2-001 and 193-F2-001 (FIG. 3). The unfavorable binding properties of Type B SDF-1 binding nucleic acids 193-G1-002, 193-D2-002, 193-A1-002 and 193-D3-002 may be due to the number of nucleotides and sequence of the 5'- and 3'-terminal stretches.

Truncated derivatives of the Type B SDF-1 binding nucleic acids 193-G2-001 and 193-C2-001 were analyzed in a competitive pull-down binding assay vs. 193-G2-001 and 193-G2-012, respectively (FIGS. 4A and 4B). These experiments showed that a reduction of the six terminal nucleotides (5'end: AGCGUG; 3'end: UACGCU) of Type B SDF-1 binding nucleic acids 193-G2-001 and 193-C2-001 to five nucleotides (5'end: GCGUG; 3'end: UACGC) lead to molecules with similar binding affinity (193-C2-002 and 193-G2-012). The equilibrium dissociation constant $K_D$ was determined using the pull-down binding assay ($K_D$=0.3 nM, FIG. 18). A truncation to four (5'end: CGUG; 3'end: UACG; 193-C2-003) or less nucleotides (193-C2-004, 193-C2-005, 193-C2-006, 193-C2-007) resulted in a reduced binding affinity to SDF-1 which was measured by using the competition pull-down binding assay (FIG. 4A). The nucleotide sequence of the five terminal nucleotides at the 5'- and 3'-end, respectively, has an influence on the binding affinity of Type B SDF-1 binding nucleic acids. The substitution of 5'- and 3'-terminal nucleotides 'GCGUG' and 'UACGC' (193-C2-002, 193-G2-12) by 'GCGCG' and 'CGCGC' (193-G2-013) resulted in a reduced binding affinity. Additionally, the four different derivatives of Type B SDF-1 binding nucleic acid 193-G2-001 with a terminal helix with a length of four base-pairing nucleotides (193-G2-014/-015/-016/-017) were tested. All of them showed reduced binding affinity to SDF-1 (FIG. 4B). Therefore the sequence and the length of the 5'- and 3'-terminal nucleotides are essential for an effective binding to SDF-1. The 5'-terminal and 3'-terminal stretches with a length of five and four nucleotides of the derivatives of Type B SDF-1 binding nucleic acids 193-C2-003 and 193-G2-012 as shown in FIGS. 4A and 4B can be described in a generic formula for the 5'-terminal stretch ('$X_2$SSBS', Type B Formula-4-5'), whereby $X_2$ is either absent or is 'G', and of the 3'-terminal stretch ('BVSS$X_3$', Type B Formula-4-3'), and whereby $X_3$ is either absent or is 'C'. As shown for Type B SDF-1 binding nucleic acids 193-G2-001 and 193-C2-01 and their derivatives 193-G2-012 and 193-C2-002 the preferred combination of 5'- and 3'-terminal stretches are '$X_1$GCGUG' (5'-terminal stretch; Type B Formula 5-5') and 'UACGC$X_4$' (3'-terminal stretch; Type B Formula 5-3'), whereas $X_1$ is either 'A' or absent and $X_4$ is 'U' or absent.

However, combining the 5'- and 3'-terminal stretches of all tested Type B SDF-1 binding nucleic acids the generic formula for the 5'-terminal stretch of Type B SDF-1 binding nucleic acids is '$X_1X_2$SVNS' (Type B Formula-6-5') and the generic formula for the 3'-terminal stretch Type B SDF-1 binding nucleic acids is 'BVBS$X_3X_4$' (Type B Formula-6-3'), whereas $X_1$ is 'A' or absent, $X_2$ is 'G', $X_3$ is 'C' and $X_4$ is 'U' or absent;

or $X_1$ is absent, $X_2$ is 'G' or absent, $X_3$ is 'C' or absent and $X_4$ is absent;

1.3 Type C SDF-1 Binding Nucleic Acids

As depicted in FIG. 5 all sequences of SDF-1 binding nucleic acids of Type C comprise one core nucleotide sequence which is flanked by 5'- and 3'-terminal stretches that can hybridize to each other. However, such hybridization is not necessarily given in the molecule.

The nucleic acids were characterized on the aptamer level using direct and competitive pull-down binding assays with biotinylated human D-SDF-1 in order to rank them with respect to their binding behaviour (Example 4). Selected sequences were synthesized as Spiegelmers (Example 3) and were tested using the natural configuration of SDF-1 (L-SDF) in a cell culture in vitro chemotaxis assay (Example 5) and by surface plasmon resonance measurement using a Biacore 2000 instrument (Example 6).

The sequences of the defined boxes or stretches may be different between the SDF-1 binding nucleic acids of Type C which influences the binding affinity to SDF-1. Based on binding analysis of the different SDF-1 binding nucleic acids summarized as Type C SDF-1 binding nucleic acids, the core nucleotide sequence and its nucleotide sequence as described in the following are individually and more preferably in their entirety essential for binding to SDF-1:

The core nucleotide sequence of all identified sequences of Type C SDF-1 binding nucleic acids share the sequence

GGU$X$AGGGCU$RR_A$AGUCGG (Type C Formula-1, SEQ ID NO:90), whereby $X_A$ is either absent or is 'A'. With the exception of Type C SDF-1 binding nucleic acid 197-D1 the core nucleotide sequence of all identified sequences of Type C SDF-1 binding nucleic acids share the nucleotide sequence

GGU$X$AGGGCU$RR$AGUCGG (Type C Formula-2, SEQ ID NO:91). Type C SDF-1 binding nucleic acid 197-D1 (core nucleotide sequence:

GGUUAGGGCUA$X$AGUCGG)

(SEQ ID NO:248) missing one nucleotide 'A' within the core nucleotide sequence and still binding to SDF-1 let conclude an alternative core nucleotide sequence (GGU$X$AGGGCU$RR$-AGUCGG), Type C Formula-3, SEQ ID NO:92). Initially, all Type C SDF-1 binding nucleic acids as depicted in FIG. 5 were analyzed in a competitive pull-down binding assay vs. Type A SDF-1 binding nucleic acid 192-A10-001 ($K_D$=1.5 nM determined by pull-down assay and by surface plasmon resonance measurements; $IC_{50}$=0.12 nM). The Type C SDF-1 binding nucleic acids 191-D5-001, 197-B2, 190-A3-001, 197-H1, 197-H3 and 197-E3 showed weaker binding affinities than 192-A10-001 in competition experiments. Much weaker binding affinity was determined for 191-A5, 197-B1, 197-D1, 197-H2 and 197-D2 (FIG. 5). The molecules or derivatives thereof were further characterized by further competitive pull-down binding assays, plasmon resonance measurements and an in vitro chemotaxis assay. The Type C SDF-1 binding nucleic acid 191-D5-001 was characterized for its binding affinity to human SDF-1 whereas the equilibrium binding constant $K_D$ was determined by surface plasmon resonance measurement ($K_D$=0.8 nM, FIG.

21). The IC$_{50}$ (inhibitory concentration 50%) of 0.2 nM for 191-D5-001 was measured using a cell-culture in vitro chemotaxis assay. The binding affinity of Type C SDF-1 binding nucleic acid 197-B2 for human SDF-1 was determined by surface plasmon resonance measurement (K$_D$=0.9 nM), its IC$_{50}$ (inhibitory concentration 50%) of 0.2 nM was analyzed in a cell-culture in vitro chemotaxis assay. These data indicates that Type C SDF-1 binding nucleic acids 191-D5-001 and 197-B2 have the similar binding affinity to SDF-1 (FIGS. 5 and 8).

Type C SDF-1 binding nucleic acid 190-A3-001 (48 nt) comprises a 5'-terminal stretch of 17 nucleotides and a 3'-terminal stretch of 12 nucleotides whereby on the one hand the four nucleotides at the 5'-end of the 5'-terminal stretch and the four nucleotides at the 3'-end of the 3'-terminal stretch may hybridize to each other to form a terminal helix. Alternatively the nucleotides 'UGAGA' in the 5'-terminal stretch may hybridize to the nucleotides 'UCUCA' in the 3'-terminal stretch to form a terminal helix. A reduction to eight nucleotides of the 5'-terminal stretch ('GAGAUAGG') (SEQ ID NO:244) and to nine nucleotides of the 3'-terminal stretch ('CUGAUUCUC') (SEQ ID NO:246) of molecule 190-A3-001 (whereby six out of the eight/nine nucleotides of the 5'- and 3'-terminal stretch can hybridize to each other) does not have an influence on the binding affinity to SDF-1 (190-A3-004; FIG. 6 and FIG. 19). The equilibrium binding constant K$_D$ of 190-A3-004 was determined using the pull-down binding assay (K$_D$=4.6 nM, FIG. 20) and by surface plasmon resonance measurement (K$_D$=4.7 nM). The IC$_{50}$ (inhibitory concentration 50%) of 0.1 nM for 190-A3-004 was measured using a cell-culture in vitro chemotaxis assay (FIG. 22). However, the truncation to two nucleotides at the 5'-terminal stretch leads to a very strong reduction of binding affinity (190-A3-007; FIG. 6 and FIG. 19).

The Type C SDF-1 binding nucleic acids 191-D5-001, 197-B2 and 197-H1 (core nucleotide sequence:

GGUUAGGGCUAGAAGUCGG ), (SEQ ID NO:249) 197-H3/191-A5 (core nucleotide sequence:

GGUUAGGGCUSGAAGUCGG )

(SEQ ID NO:250) and 197-E3/197-B1 (core nucleotide sequence:

GGUUAGGGCUSGAAGUCGG )

(SEQ ID NO:251) share an almost identical core nucleotide sequence (Type C formula-4; nucleotide sequence:

GGUUAGGGCUSGAAGUCGG ).

(SEQ ID NO:93). 191-D5-001, 197-B2 and 197-H1 do not share a similar 5'- and 3'-terminal stretch (197-H3 and 197-E3 have the identical 5'- and 3'-terminal stretch as 197-B2). However, the respective ten (197-B2, 197-E3, 197-H3) or nine out of the ten (191-D5-001, 197-H1) nucleotides of the 5'-terminal stretch may hybridize to the respective ten (197-B2, 197-E3, 197-H3) or nine out of the ten (191-D5-001, 197-H1) nucleotides of the 3'-terminal stretch (FIG. 5). Thus, the 5'-terminal stretch of Type C SDF-1 binding nucleic acids 197-B2, 191-D5-001, 197-H1, 197-E3 and 197-H3 as mentioned above plus 191-A5, 197-B1, 197-H2, 197-D1 and 197-D2 comprise a common generic nucleotide sequence of 'RKSBUSNVGR' (Type C Formula-5-5'). The 3'-terminal stretch of Type C SDF-1 binding nucleic acids 197-B2, 191-D5-001, 197-H1, 197-E3, and 197-H3 as mentioned above plus 191-A5, 197-B1, 197-H2, 197-D1 and 197-D2 comprise a common generic nucleotide sequence of 'YYNRCASSMY' (Type C Formula-5-3'), whereby the 5' and the 3'-terminal stretches of Type C SDF-1 binding nucleic acids 197-B2, 191-D5-001, 197-H1, 197-E3 and 197-H3 are preferred. These preferred 5'- and 3'-terminal stretches of Type C SDF-1 binding nucleic acids 197-B2, 191-D5-001, 197-H1, 197-E3 and 197-H3 can be summarized in the generic formula 'RKSBUGSVGR' (Type C Formula-6-5'; 5'-terminal stretch, SEQ ID NO:122) and 'YCNRCASSMY' (Type C Formula-6-3'; 3'-terminal stretch, SEQ ID NO:123).

Truncated derivatives of Type C SDF-1 binding nucleic acid 191-D5-001 were constructed and tested in a competitive pull-down binding assay vs. the original molecule 191-D5-001 (FIG. 7A, FIG. 7B and FIG. 19). At first the length of the 5'- and 3'-terminal stretches were shortened from ten nucleotides (191-D5-001) each to seven nucleotides each (191-D5-004) as depicted in FIG. 7A whereby nine out of the ten (191-D5-001) or six out of the seven nucleotides (191-D5-004) of the 5'-terminal stretch and of the 3'-terminal stretch, respectively can hybridize to each other. The reduction to seven nucleotides of the 5'- and 3'-terminal stretch respectively (whereas six out of the seven nucleotides can hybridize to each other) led to reduced binding affinity to SDF-1 (191-D5-004). The terminal stretches of Type C SDF-1 binding nucleic acid 191-D5-004 were modified whereby the non-pairing nucleotide 'A' within the 3'-terminal stretch of 191-D5-004 was substituted by a 'C' (191-D5-005). This modification led to an improvement of binding. This derivative, Type C SDF-1 binding nucleic acid 191-D5-005, showed similar binding to SDF-1 as 191-D5-001. Further truncation of the 5'- and 3'-terminal stretch to five nucleotides respectively led to a molecule with a length of total 29 nucleotides (191-D5-007). Because of the similarities of 191-D5-001 and of the Type C SDF-1 binding nucleic acids 197-B2, 191-D5-001, 197-H1, 191-A5, 197-H3, 197-B1, 197-E3, 197-D1, 197-H2 and 197-D2 and because of the data shown for 191-D5-007 it may assume that the 5'- and 3'-terminal stretch can in principle be truncated down to five nucleotides whereby the nucleotide sequence 'CGGGA' for 5'-terminal stretch and 'UCCCG' for the 3'-terminal stretch was successfully tested (Type C SDF-1 binding nucleic acid 191-D5-007). Type C SDF-1 binding nucleic acid 191-D5-007 surprisingly binds somewhat better to SDF-1 than 191-D5-001 (determined on aptamer level using the competition binding assay). The equilibrium binding constant K$_D$ of 191-D5-007 was determined using the pull-down binding assay (K$_D$=2.2 nM, FIG. 20) and by surface plasmon resonance measurement (K$_D$=0.8 nM, FIG. 21). The IC$_{50}$ (inhibitory concentration 50%) of 0.1 nM for 191-D5-007 was measured using a cell-culture in vitro chemotaxis assay. Further truncation of both terminal stretches to four nucleotides (191-D5-010, FIG. 7A).

Further derivatives of Type C SDF-1 binding nucleic acid 191-D5-001 (191-D5-017/-024/-029) bearing 5'- and 3'-terminal stretches of respectively four nucleotides also showed reduced binding affinity to SDF-1 in the competition pull-down binding assay vs. 191-D5-007 (FIG. 7B). Alternative 5'- and 3'-terminal stretches with a length of respectively five nucleotides were additionally tested, too (191-D5-017-29a, 191-D5-017-29b, 191-D5-019-29a, 191-D5-024-29a, 191-D5-024-29b). The generic formula of these derivatives for the 5'-terminal stretch is '$X_S$SSSV' (Type C Formula-7-5') and for the 3'-stretch is 'BSSS$X_S$' Type C Formula-7-3'), whereby $X_S$ is absent or 'S'. Two out of the five tested variants showed identical binding affinity to SDF-1 as 191-D5-007 (191-D5-024-29a, 191-D5-024-29b; FIG. 7B). The sequences of the 5'-terminal and 3'-terminal stretches of 191-D5-001-derivatives that show the best binding affinity to SDF-1 and comprise a 5'-terminal and 3'-terminal stretch of five nucleotides respectively (191-D5-007, 191-D5-024-29a, 191-D5-024-29b) can be summarized in a generic formula (5'-terminal stretch: 'SGGSR', Type C Formula-8-5'; 3'-terminal stretch, YSCCS', Type C Formula-8-3').

Truncated derivatives of Type C SDF-1 binding nucleic acid 197-B2 were analyzed in a competitive pull-down binding assay vs. the original molecule 197-B2 and 191-D5-007 (FIG. 8). Using the competitive pull-down binding assay vs. 191-D5-007 it was shown that 197-B2 has the same binding affinity to SDF-1 as 191-D5-007. The 5'- and 3'-terminal stretches were shortened without loss of binding affinity from ten nucleotides (197-B2) each to five nucleotides each (197-B2-005) whereby the nucleotides of the 5'-terminal stretch and of the 3'-terminal stretch can completely hybridize to each other. If the 5'-terminal ('GCGGG') and 3'-terminal ('CCUGC') stretch of 197-B2-005 was substituted by 'GCCGG' (5'-terminal stretch) and by 'CCGGC' (3'-terminal stretch) of 197-B2-006, the binding affinity to SDF-1 fully persisted. Because 197-B2 and 191-D5-001 (and their derivatives) share the identical core nucleotide sequence (GGUUAGGGCUAGAAGUCGG)

(SEQ ID NO:249) and several derivatives of 191-D5 with 5'- and 3'-terminal stretches with a length of respectively four nucleotides were tested, a further truncation of the 5'- and 3'-terminal stretch was omitted. Two further derivatives were designed that comprise six nucleotides at the 5'- and 3'-end (5'- and 3'-terminal stretches) respectively. The binding affinity to SDF-1 of both molecules (197-B2-006-31a and 197-B2-006-31b) is the same as shown for 191-D5-007 and 197-B2-006 (FIG. 8). The sequences of the 5'-terminal and 3'-terminal stretches of 197-B2 derivatives that show the best binding affinity to SDF-1 and comprise a 5'-terminal and 3'-terminal stretch of five nucleotides respectively can be summarized in a generic formula (5'-terminal stretch: 'GCSGG', Type C Formula-9-5'; 3'-terminal stretch, CCKGC', Type C Formula-9-3').

Combining the preferred 5'- and 3'-stretches of truncated derivatives of Type C SDF-1 binding nucleic acids 191-D5-001 (5'-terminal stretch: 'SGGSR', Type C Formula-8-5'; 3'-terminal stretch: 'YSCCS', Type C Formula-8-3') and 197-B2 (5'-terminal stretch: 'GCSGG', Type C Formula-9-5'; 3'-terminal stretch: 'CCKGC', Type C Formula-9-3') the common preferred generic formula for the 5'-terminal and the 3'-terminal stretch is 'SSSSR' (5'-terminal stretch, Type C Formula-10-5') and 'YSBSS' (3'-terminal stretch: Type C Formula-10-3').

1.4 Further SDF-1 Binding Nucleic Acids

Additionally, further three SDF-1 binding nucleic acids that do not share the SDF-1 binding motifs of 'Type A', 'Type B' and 'Type C' were identified. There were analyzed as aptamers using the pull-down binding assay (FIG. 9).

It is to be understood that any of the sequences shown in FIGS. 1 through 9 are nucleic acids according to the present invention, including those truncated forms thereof but also including those extended forms thereof under the proviso, however, that the thus truncated and extended, respectively, nucleic acid molecules are still capable of binding to the target.

EXAMPLE 2: 40 KDA-PEG AND OTHER MODIFICATION OF SDF-BINDING SPIEGELMERS

In order to prolong the Spiegelmer's plasma residence time in vivo, the Spiegelmers 193-G2-012, 192-A10-008, 191-D5-007, 197-B2-006 and 197-B2-006-31b were covalently coupled to a 40 kDa polyethylene glycol (PEG) moiety at the 5'-end as described in chapter 3 (PEGylated-clones: 193-G2-012-5'-PEG, 192-A10-008-5'PEG, 191-D5-007-5'PEG, 197-B2-006-5'PEG and 197-B2-006-31b-5'PEG).

The PEGylated Spiegelmer molecules were analyzed in a cell culture in vitro TAX-assay (Chapter 5) and by plasmon resonance measurements using a Biacore (Chapter 6). All 40 kDa-PEG-modified Spiegelmers are still able to inhibit SDF-1 induced chemotaxis and to bind to SDF-1 in low nanomolar range (FIGS. 23A, 23B, 24A and FIG. 24B).

Additionally, SDF-binding Spiegelmer 192-A10-001 was modified with 40 kDa-PEG, 30 kDa-PEG, 100 kDa-HES or 130 kDa-HES (PEGylated-clones: 192-A10-001-5'PEG40, 192-A10-001-5' PEG30, 192-A10-001-5'HES100, 192-A10-001-5'HES130; coupling procedure in chapter 3). As depicted in FIG. 25A and FIG. 25B neither a PEG-moiety or a HES-moiety has an influence on Spiegelmers potency to inhibit SDF-1 induced chemotaxis.

EXAMPLE 3: SYNTHESIS AND DERIVATIZATION OF APTAMERS AND SPIEGELMERS 3.1 Small Scale Synthesis Aptamers and Spiegelmers were produced by solid-phase synthesis with an ABI 394 synthesizer (Applied Biosystems, Foster City, Calif., USA) using 2'TBDMS RNA phosphoramidite chemistry (Damha and Ogilvie, 1993). rA(N-Bz)-, rC(Ac)-, rG(N-ibu)-, and rU-phosphoramidites in the D- and L-configuration were purchased from ChemGenes, Wilmington, Mass. Aptamers and Spiegelmers were purified by gel electrophoresis.

3.2 Large Scale Synthesis Plus Modification

The Spiegelmers were produced by solid-phase synthesis with an ÄktaPilot100 synthesizer (Amersham Biosciences; General Electric Healthcare, Freiburg) using 2'TBDMS RNA phosphoramidite chemistry (Damha and Ogilvie, 1993). L-rA(N-Bz)-, L-rC(Ac)-, L-rG(N-ibu)-, and L-rU-phosphoramidites were purchased from ChemGenes (Wilmington, Mass., USA). The 5'-amino-modifier was purchased from American International Chemicals Inc. (Framingham, Mass., USA). Synthesis of the Spiegelmers was started on L-riboG; L-riboC, L-riboA, L-riboU respectively modified CPG pore size 1000 Å (Link Technology, Glasgow, UK). For coupling (15 min per cycle), 0.3 M benzylthiotetrazole (American International Chemicals Inc., Framingham, Mass., USA) in acetonitrile, and 3.5 equivalents of the respective 0.2 M phosphoramidite solution in acetonitrile was used. An oxidation-capping cycle was used. Further standard solvents and reagents for oligonucleotide synthesis were purchased from Biosolve (Valkenswaard, NL). The Spiegelmers were synthesized DMT-ON; after deprotection, it was purified via preparative RP-HPLC (Wincott F. et al., 1995) using Source15RPC medium (Amersham). The 5'DMT-group was removed with 80% acetic acid (90 min at RT). Subsequently, aqueous 2 M NaOAc solution was added and the Spiegelmer was desalted by tangential-flow filtration using a 5 K regenerated cellulose membrane (Millipore, Bedford, Mass.).

3.3 Pegylation

In order to prolong the Spiegelmer's plasma residence time in vivo, the Spiegelmers were covalently coupled to a 40 kDa polyethylene glycol (PEG) moiety at the 5'-end.

For PEGylation (for technical details of the method for PEGylation see European patent application EP 1 306 382), the purified 5'-amino modified Spiegelmerd were dissolved in a mixture of $H_2O$ (2.5 ml), DMF (5 ml), and buffer A (5 ml; prepared by mixing citric acid • $H_2O$ [7 g], boric acid [3.54 g], phosphoric acid [2.26 ml], and 1 M NaOH [343 ml] and adding water to a final volume of 1 l; pH=8.4 was adjusted with 1 M HCl).

The pH of the Spiegelmer solution was brought to 8.4 with 1 M NaOH. Then, 40 kDa PEG-NHS ester (Nectar Therapeutics, Huntsville, Ala.) was added at 37° C. every 30 min in six portions of 0.25 equivalents until a maximal yield of 75 to 85% was reached. The pH of the reaction mixture was kept at 8-8.5 with 1 M NaOH during addition of the PEG-NHS ester.

The reaction mixture was blended with 4 ml urea solution (8 M), and 4 ml buffer B (0.1 M triethylammonium acetate in $H_2O$) and heated to 95° C. for 15 min. The PEGylated Spiegelmer was then purified by RP-HPLC with Source 15RPC medium (Amersham), using an acetonitrile gradient (buffer B; buffer C: 0.1 M triethylammonium acetate in acetonitrile). Excess PEG eluted at 5% buffer C, PEGylated Spiegelmer at 10-15% buffer C. Product fractions with a purity of >95% (as assessed by HPLC) were combined and mixed with 40 ml 3 M NaOAC. The PEGylated Spiegelmer was desalted by tangential-flow filtration (5 K regenerated cellulose membrane, Millipore, Bedford Mass.).

3.4 HESylation

In order to prolong the Spiegelmer's plasma residence time in vivo, the Spiegelmers were covalently coupled to Hydroxyl Ethyl Starch (HES) of various molecular weights of >130 kDa and substitution degree>0.5. The 5'-end of the Spiegelmer is the preferred site for conjugation.

For HESylation (for technical details of the method for Hesylation of nucleic acids see German Offenlegungsschrift DE 101 12 825 A1, and for D/L-nucleic acids PCT WO 02/080979 A2), the purified 5'-amino modified Spiegelmer was dissolved in sodium bicarbonate (0.3M, 1 ml) and the pH is adjusted to 8.5.

In respect to the Spiegelmer, a 5-fold excess of the free HES acid (3.3 mmol, Supramol, Rosbach, Germany) and di(N-succinimidyl) carbonate (3.3 mmol) were added to N,N-dimethylformamide (1 ml) to yield a solution of the activated N-hydroxysuccimide ester of HES. To dissolve all reactants the mixture was stirred briefly at 60° C., cooled to 25° C. and then stirred for 1.5 h at 25° C. The solution of Spiegelmer was added to the solution of activated HES, and the resulting mixture was stirred at 25° C. and pH 8.5. The reaction was monitored by analytical IEX-HPLC. Typically the conjugation proceeded to >75% within 1 hr.

For IEX-HPLC purification via Source 15Q medium (GE, Freiburg, Germany) the reaction mixture was blended with a 10 fold-quantity of buffer A (1 mM EDTA, 25 mM Tris, 10 mM NaClO4 in water/acetonitrile 9:1, pH 4). Excess HES elutes at 5% buffer A (1 mM EDTA, 25 mM Tris, 500 mM NaClO4 in water/acetonitrile 9:1, pH 4), whereas the HES-Spiegelmer conjugate elutes at 20-30% buffer B. Product fractions with a purity of >95% (as assessed by HPLC) were combined and desalted by tangential-flow filtration (5 K regenerated cellulose membrane, Millipore, Bedford Mass.).

EXAMPLE 4: DETERMINATION OF BINDING CONSTANTS (PULL-DOWN BINDING ASSAY)

4.1 Direct Pull-Down Binding Assay

The affinity of aptamers to biotinlayted human D-SDF-1 was measured in a pull-down binding assay format at 37° C. Aptamers were 5'-phosphate labeled by T4 polynucleotide kinase (Invitrogen, Karlsruhe, Germany) using $[\gamma$-$^{32}$P]-labeled ATP (Hartmann Analytic, Braunschweig, Germany). The specific radioactivity of labeled aptamers was 200,000-800,000 cpm/pmol. Aptamers were incubated after de- and renaturation at 10, 20, 30 or 40 pM concentration at 37° C. in selection buffer (20 mM Tris-HCl pH 7.4; 137 mM NaCl; 5 mM KCl; 1 mM $MgCl_2$; 1 mM $CaCl_2$; 0.1% [w/vol] Tween-20) together with varying amounts of biotinlayted human D-SDF-1 for 4-12 hours in order to reach equilibrium at low concentrations. Selection buffer was supplemented with 10 μg/ml human serum albumin (Sigma-Aldrich, Steinheim, Germany), and 10 μg/ml yeast RNA (Ambion, Austin, USA) in order to prevent adsorption of binding partners with surfaces of used plasticware or the immobilization matrix. The concentration range of biotinlayted human D-SDF-1 was set from 8 pM to 100 nM; total reaction volume was 1 ml. Peptide and peptide-aptamer complexes were immobilized on 1.5 μl Streptavidin Ultralink Plus particles (Pierce Biotechnology, Rockford, USA) which had been preequilibrated with selection buffer and resuspended in a total volume of 6 μl. Particles were kept in suspension for 30 min at the respective temperature in a thermomixer. Immobilized radioactivity was quantitated in a scintillation counter after detaching the supernatant and appropriate washing. The percentage of binding was plotted against the concentration of biotinlayted human D-SDF-1 and dissociation constants were obtained by using software algorithms (GRAFIT; Erithacus Software; Surrey U.K.) assuming a 1:1 stoichiometry.

4.2 Competitive Pull-Down Binding Assay

In order to compare different D-SDF-1 binding aptamers, a competitive ranking assay was performed. For this purpose the most amine aptamer available was radioactively labeled (see above) and served as reference. After de- and renaturation it was incubated at 37° C. with biotinlayted human D-SDF-1 in 1 ml selection buffer at conditions that resulted in around 5-10% binding to the peptide after immobilization and washing on NeutrAvidin agarose or Streptavidin Ultralink Plus (both from Pierce) without competition. An excess of de- and renatured non-labeled D-RNA aptamer variants was added to different concentrations (e.g. 2, 10, and 50 nM) with the labeled reference aptamer to parallel binding reactions. The aptamers to be tested competed with the reference aptamer for target binding, thus decreasing the binding signal in dependence of their binding characteristics. The aptamer that was found most active in this assay could then serve as a new reference for comparative analysis of further aptamer variants.

EXAMPLE 5: ANALYSIS OF THE INHIBITION OF SDF-1-INDUCED CHEMOTAXIS BY SDF-1-BINDING SPIEGELMERS

Jurkat human T cell leukemia cells (obtained from DSMZ, Braunschweig) were cultivated at 37° C. and 5% $CO_2$ in RPMI 1640 medium with Glutamax (Invitrogen, Karlsruhe, Germany) which contains 10% fetal bovine serum, 100 units/ml penicillin and 100 µg/ml streptomycin (Invitrogen, Karlsruhe, Germany). One day before the experiment, cells were seeded in a new flask with a density of $0.3 \times 10^6$/ml ($9 \times 10^6$/30 ml) in standard medium (Invitrogen, Karlsruhe, Germany).

For the experiment, cells were centrifuged (5 min at 300 g), resuspended, counted and washed once with 15 ml HBH (Hanks balanced salt solution containing 1 mg/ml bovine serum albumin and 20 mM HEPES; Invitrogen, Karlsruhe, Germany). Then the cells were resuspended at $3 \times 10^6$/ml or $1.33 \times 10^6$/ml, depending on the type of filter plate used. Cells were then allowed to migrate through the porous membranes of the filter plates for several hours towards a solution containing SDF-1 and various amounts of Spiegelmer. Either Transwell plates and inserts with porous Polycarbonate membrane, 5 µm pore size (Corning; 3421) or Multi-Screen MIC plates (Millipore, MAMIC5S10) were used.

5.1 Protocol for Transwell Plates

The stimulation solutions (SDF-1+ various concentrations of Spiegelmer) were made up in 600 µl HBH in the lower compartments of the Transwell plates and incubated for 20-30 min. All conditions were made up at least twice. The inserts were transferred to the wells containing the stimulation solutions and 100 µl of a cell suspension with $3 \times 10^6$/ml were added to the inserts ($3 \times 10^5$ cells/well). The cells were then allowed to migrate for 3 h at 37° C.

Thereafter, the inserts were removed and 60 µl resazurin (Sigma, Deisenhofen, Germany) working solution (440 µM in PBS; Biochrom, Berlin, Germany) were added to the wells (also to calibration wells). The plates were then incubated at 37° C. for 2.5 to 3 h. After incubation, 200 µl of each well were transferred to a black 96 well plate. Measurement of the fluorescence signals was done at 544 nm (excitation) and 590 nm (emission) in a Fluostar Optima multidetection plate reader (BMG, Offenburg, Germany).

5.2 Protocol for Millipore MultiScreen Plates

The stimulation solutions (SDF-1+various concentrations of Spiegelmer) were made up as 10× solutions in a 0.2 ml low profile 96-tube plate. 135 µl HBH were pipetted into the lower compartments of the MultiScreen plate and 15 µl of the stimulation solutions were added. All conditions were made up as triplicates. After 20 to 30 min the filter plate was inserted into the plate containing the stimulation solutions and 75 µl of a cell suspension with $1.33 \times 10^6$/ml were added to the wells of the filter plate ($1 \times 10^5$ cells/well). The cells were then allowed to migrate for 3 h at 37° C.

Thereafter, the insert plate is removed and 20 µl resazurin working solution (440 µM in PBS) are added to the lower wells. The plates were then incubated at 37° C. for 2.5 to 3 h.

After incubation, 100 µl of each well were transferred to a black 96 well plate. Measurement of the fluorescence signals was performed as described above.

5.3 Evaluation

For evaluation, fluorescence values were corrected for background fluorescence (no cells in well). Then the difference between experimental conditions with and without SDF-1 was calculated. The value for the sample without Spiegelmer (SDF-1 only) was set 100% and the values for the samples with Spiegelmer were calculated as percent of this. For a dose-response curve the percent-values were plotted against Spiegelmer concentration and the $IC_{50}$-value (concentration of Spiegelmer at which 50% of the activity without Spiegelmer is present) was determined graphically from the resulting curve.

5.4 Results 5.4.1 Dose Dependent Stimulation of Jurkat Cells by Human SDF-1

Figure 10:
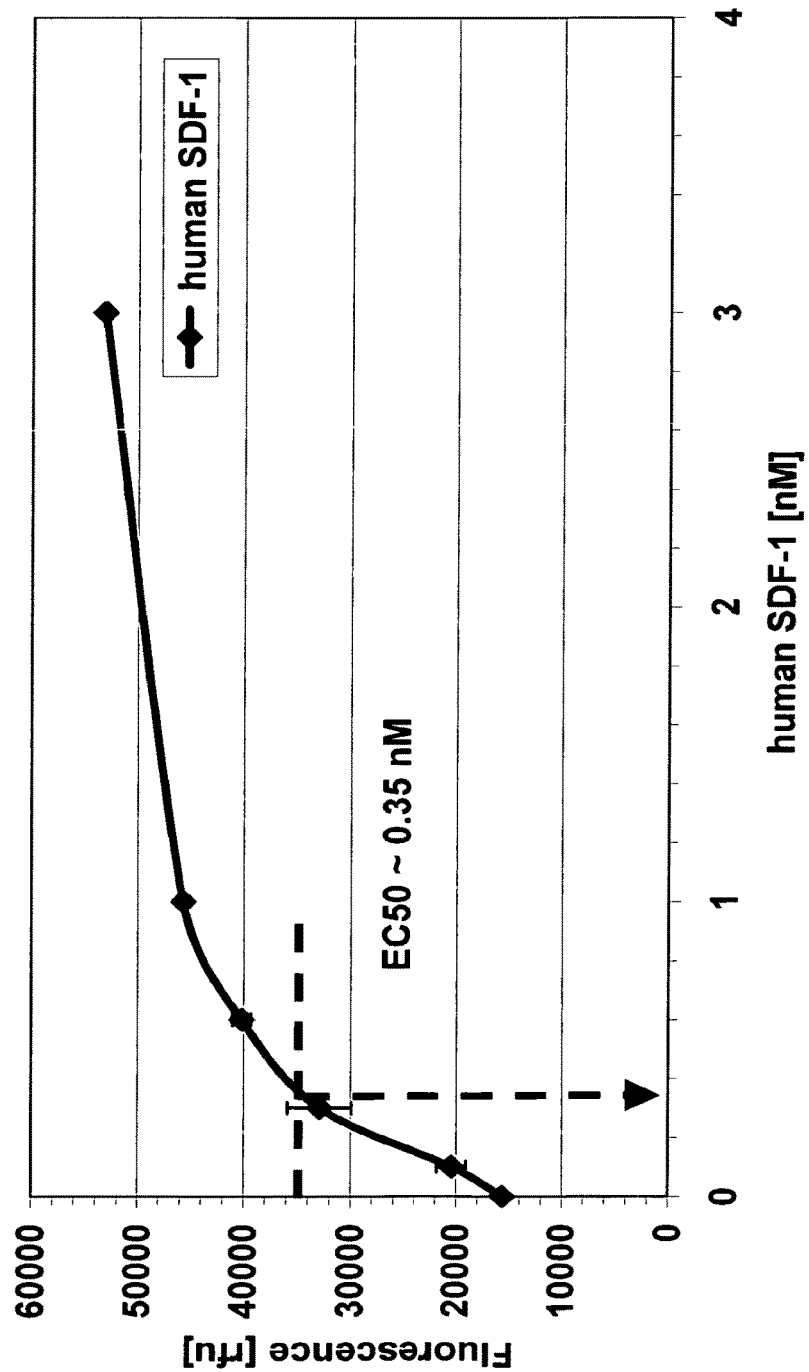
FIG. 10 shows the human SDF-1-induced chemotaxis of Jurkat human T cell leukemia cells whereas after 3 hours migration of Jurkat human T cell leukemia cells towards various human SDF-1 concentrations a dose-response curve for human SDF-1 was obtained, represented as fluorescence signal over concentration of human SDF-1.
Figure 11:
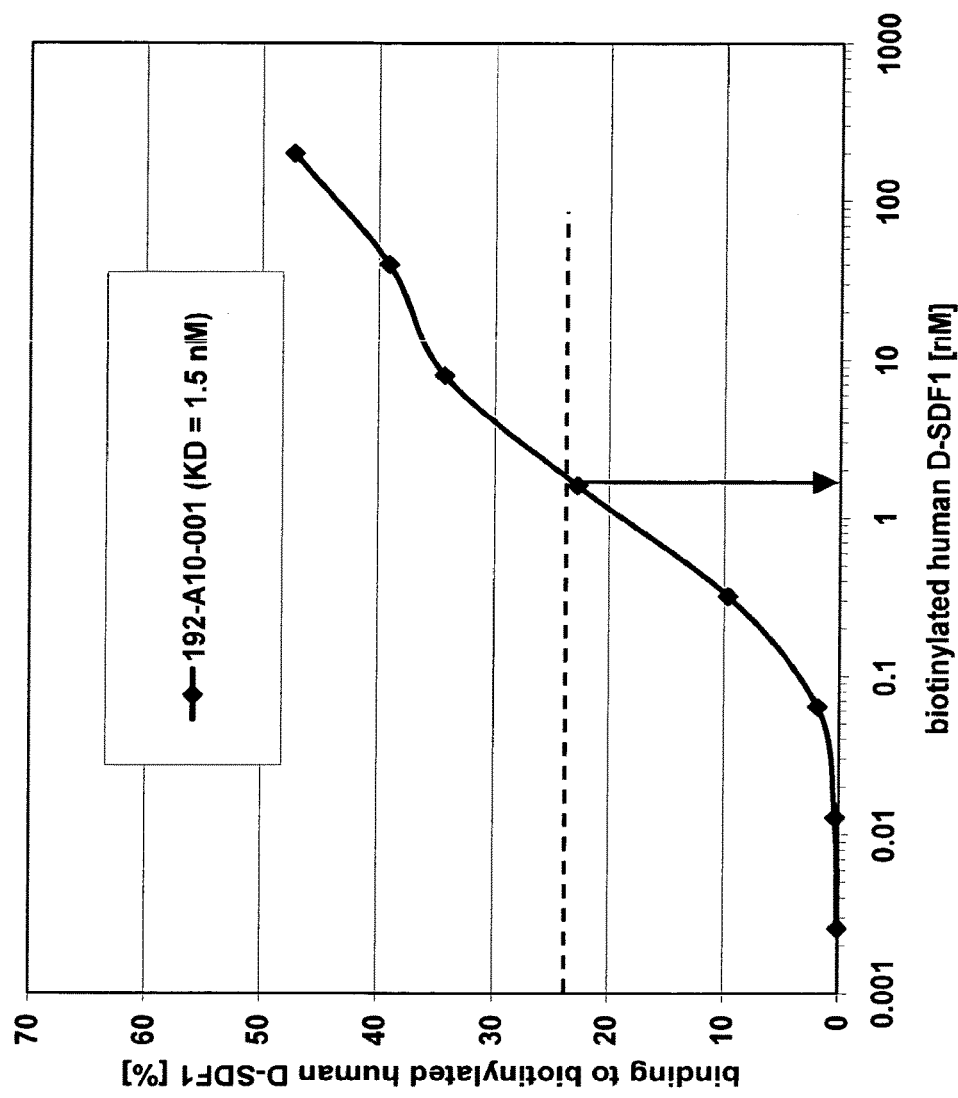
FIG. 11 shows the result of a binding analysis of the human SDF-1 binding aptamer 192-A10-001 to biotinylated human D-SDF-1 37° C., represented as binding of the aptamer over concentration of biotinylated human D-SDF-1.
Figure 12:
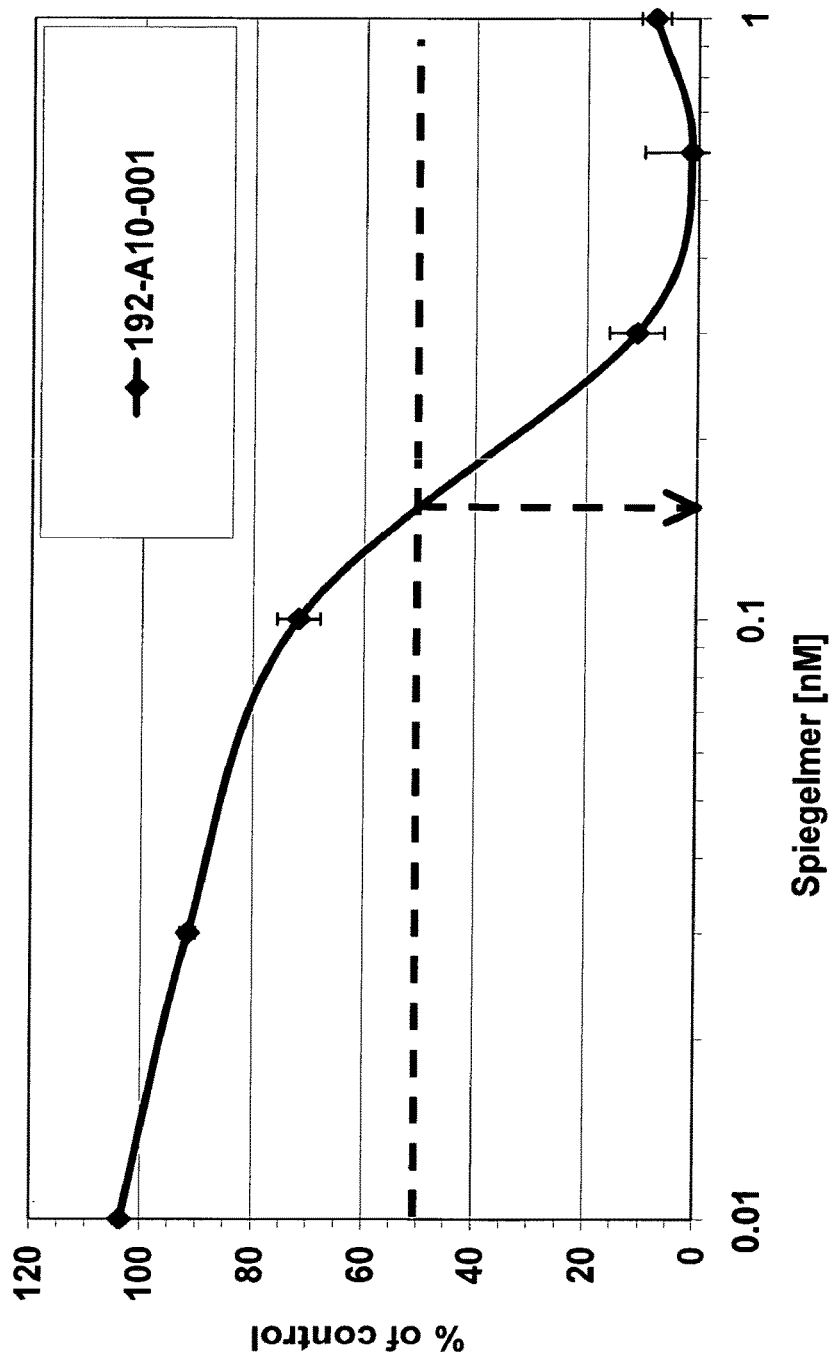
FIG. 12 shows the efficacy of human SDF-1 binding Spiegelmer 192-A10-001 in a chemotaxis assay; cells were allowed to migrate towards human 0.3 nM SDF-1 preincubated at 37° C. with various amounts of Spiegelmer 192-A10-001, represented as percentage of control over concentration of Spiegelmer 192-A10-001.

Human SDF-1 was found to stimulate migration of Jurkat cells in an dose dependent manner, with half-maximal stimulation at about 0.3 nM (FIG. 11).

5.4.2 Dose Dependent Inhibition of Human SDF-1 Induced Chemotaxis by SDF-1 Binding Spiegelmers When cells were allowed to migrate towards a solution containing human SDF-1 plus increasing concentrations of SDF-1 binding Spiegelmers, dose-dependent inhibition was observed. The respective IC50s of the tested Spiegelmers are specified in Example 1. When an unspecific Control Spiegelmer was used instead of SDF-1 binding Spiegelmers, no inhibitory effect was observed up to 1 µM (FIG. 26).

5.4.3 Dose Dependant Inhibition of Mouse SDF-1 Induced Chemotaxis by SDF-1 Binding Spiegelmers SDF-1 is well conserved across species: SDF-1 from mouse differs from human SDF-1a in one amino acid (isoleucin at position 18 instead of valine). Murine SDF-1 can stimulate chemotaxis of Jurkat cells (FIG. 27) and this action was found to be inhibited by Spiegelmers 192-A10-001 and 191-D5-007-5'-PEG with the same potency as in the case of human SDF-1 (FIG. 28).

EXAMPLE 6: BINDING ANALYSIS BY SURFACE PLASMON RESONANCE MEASUREMENT

The Biacore 2000 instrument (Biacore AB, Uppsala, Sweden) was used to analyze binding of Spiegelmers to human SDF-1α. When coupling of SDF-1α was to be achieved via amine groups, SDF-1α was dialyzed against water for 1-2 h (Millipore VSWP mixed cellulose esters; pore size, 0.025 µM) to remove interfering amines. CM4 sensor chips (Biacore AB, Uppsala, Sweden) were activated before protein coupling by a 35-µl injection of a 1:1 dilution of 0.4 M NHS and 0.1 M EDC at a flow of 5 µl/min Chemokine was then injected in concentrations of 0.1-1.5 µg/ml at a flow of 2 µl/min until the instrument's response was in the range of 1000-2000 RU (relative units). Unreacted NHS esters were deactivated by injection of 35 µl ethanolamine hydrochloride solution (pH 8.5) at a flow of 5 µl/min. The sensor chip was primed twice with binding buffer and equilibrated at 10 µl/min for 1-2 hours until the baseline appeared stable. For all proteins, kinetic parameters and dissociation constants were evaluated by a series of Spiegelmer injections at concentrations of 1000, 500, 250, 125, 62.5, 31.25, and 0 nM in selection buffer (Tris-HCl, 20 mM; NaCl, 137 mM; KCl, 5 mM; $CaCl_2$, 1 mM; $MgCl_2$, 1 mM; Tween20, 0.1% [w/v]; pH 7.4). In all experiments, the analysis was performed at 37° C. using the Kinject command defining an association time of 180 and a dissociation time of 360 seconds at a flow of 10 µl/min. Data analysis and calculation of dissociation constants ($K_D$) was done with the BIAevaluation 3.0 software (BIACORE AB, Uppsala, Sweden) using the Langmuir 1:1 stochiometric fitting algorithm.

EXAMPLE 7: INHIBITION OF [$^{125}$J]-SDF-1-BINDING TO CXCR4 EXPRESSING CELLS BY SDF-1-BINDING SPIEGELMERS 7.1 Method A cDNA clone coding for human CXCR4-receptor (NM_003467.2) was purchased from OriGene Technologies (Rockville, Md.) and cloned into the pCR3.1-vector (Invitrogen, Karlsruhe, Germany). The resulting vector was transfected into CHO-K1 cells (DSMZ, Braunschweig, Germany) using Lipofectamin 2000 (Invitrogen) and stable expressing cell lines were selected by treatment with geneticin. Expression of receptors was verified by RT-PCR.

For binding assays CXCR4-expressing cells were seeded into polylysine-coated 24-well plates at a cell density of $1 \times 10^5$ cells/well and cultivated overnight at 37° C. and 5% $CO_2$ in CHO-Ultra medium (Cambrex, Verviers, Belgium) containing 50 units/ml penicillin, 50 µg/ml streptomycin and 0.5 mg/ml geneticin.

For the binding experiment, the medium was removed and the cells were washed once with Hanks balanced salt solution, additionally containing 20 mM HEPES, 1 mg/ml bovine serum albumin, 0.1 mg/ml bacitracin (HBB). Then the cells were incubated in 0.2 ml HBB for 1 h at room temperature together with 50 pM [$^{125}$J]-SDF-1 (PerkinElmer, Rodgau, Germany) and varying concentrations of Spiegelmer.

Non-specific binding was determined by adding unlabeled human SDF-1 (R & D Systems, Wiesbaden, Germany) to a final concentration of 0.5 µM to several wells.

After the incubation period the supernatant was removed and the wells were washed 3 times with ice-cold HBB. Thereafter the cells were lysed with 0.1 ml 0.1 M NaOH. Lysates were transferred into szintillation vials and after addition of 4 ml Unisafe 1 Liquid Szintillation cocktail (Zinsser, Frankfurt, Germany) were counted in a Beckman LS6500 szintillation counter.

Since the values for non-specific binding (binding in the presence of high amount of unlabeled SDF-1) were somewhat higher than the values for total binding in the presence of high concentrations (500 pM) of Spiegelmer, the difference between maximal binding ("max") and binding in the presence of 500 pM Spiegelmer was used for calculation of $IC_{50}$-values.

7.2 Results

Plotting bound [$^{125}$J]-SDF-1 against Spiegelmer concentration revealed that binding of SDF-1 could be blocked by Spiegelmer 192-A10-001 with an $IC_{50}$ of about 60 pM (FIG. 29).

EXAMPLE 8: INHIBITION OF SDF-1-INDUCED MAP-KINASE ACTIVATION BY SDF-1-BINDING SPIEGELMERS 8.1 Method CXCR4-expressing CHO cells were seeded in 6-well plates at a density of $0.5 \times 10^6$ cells/well and cultivated for about three hours at 37° C. and 5% $CO_2$ in CHO-Ultra medium (Cambrex, Verviers, Belgium) containing 50 units/ml penicillin, 50 µg/ml streptomycin and 0.5 mg/ml geneticin. After cell attachment the medium was removed and replaced by Ham's F12 medium containing 50 units/ml penicillin, 50 µg/ml streptomycin. Cells were then incubated overnight at 37° C. and 5% $CO_2$. Three hours before stimulation the medium was replaced once more by fresh Ham's F12 medium. Cells were stimulated with human 1 nM SDF-1 and various amounts of Spiegelmer for 5 or 10 minutes. Thereafter the medium was removed and the cells were quickly washed once with 1 ml ice-cold phosphate buffered saline (PBS), followed by lysis with SDS-sample buffer (Tris/HCl, pH 6.8, 62.5 mM; glycerol, 10%; SDS, 2%; bromophenolblue, 0.01%; beta-mercaptoethanol, 5%). 1 µl 0.5 u/µl Benzonase (Merck, Darmstadt, Germany) was added to each well and after incubation for 5 to 10 min at room temperature, lysates were transferred to Eppendorf tubes, incubated at 95° C. for 5 min and stored at −20° C. until further analysis. 25 µl of the lysates were separated on 10% denaturing SDS-polyacrylamide gels. Proteins were then transferred by electroblotting onto HybondECL nitrocellulose membranes (Amersham/GE Healthcare, Munich, Germany). After blotting, the membranes were stained with Ponceau-red (0.2% in 3% trichloroacetic acid) for control of protein loading and transfer and then blocked by incubation in TBS-T (Tris-buffered saline (20 mM Tris/HCl, pH 7.6, 137 mM NaCl) with 0.1% Tween 20) containing 10% nonfat dried milk at 2-8° C. overnight.

The membrane was then incubated with a rabbit anti-Phospho-MAP-kinase antibody (1:1000 in 10% milk in TBS-T) for 2 h at room temperature. After washing three times for 5 min with TBS-T, the membrane was incubated with anti-rabbit-IgG-HRP-conjugate (1:2000 in 10% milk in TBS-T) for 1 h at room temperature. Then the membrane was again washed three times for 5 min with TBS-T, followed by incubation for 1 min in LumiGlo® chemiluminescent reagent. Luminescence was detected by exposure to Hyperfilm™ECL chemiluminescence films (Amersham/GE Healthcare) for 30 seconds to 2 minutes. The antibodies and the luminescence detection reagent were components of the PhosphoPlus p44/42 MAP Kinase (Thr202/Tyr204) Antibody kit from Cell Signaling Technology (New England Biolabs, Frankfurt a.M., Germany)

8.2 Results

Stimulation of CXCR4-expressing cells with 1 nM human SDF-1 for 5 min led to a profound stimulation of MAP-kinase, indicated by an increase in intensity of the band reflecting activated MAP-kinase. This activation of MAP-kinase could be dose-dependently inhibited by Spiegelmer 191-A10-001 (FIG. 30).

EXAMPLE 9: FUNCTIONAL ANALYSIS OF HUMAN SDF-1 BINDING SPIEGELMER 193-G2-012-5'-PEG IN AN AORTIC RING SPROUTING ASSAY

To test whether human SDF-1 binding Spiegelmer 193-G2-012-5'-PEG is functional also in a standard angiogenesis organ culture assay, aortic ring sprouting assays were performed. This assay, in which the length and abundance of vessel-like extensions from the explants are evaluated, has become the most widely used organ culture model for angiogenesis (Auerbach et al. 2003). It has already been shown that SDF-1 induces sprouting in this type of assay (Salcedo et al. 1999).

Rat aortae were cut into rings, embedded in a collagen matrix and incubated with SDF-1 and SDF-1 plus human SDF-1 binding Spiegelmer 193-G2-012-5'-PEG or SDF plus an non-functional PEGylated Control Spiegelmer that does not bind SDF-1. After 6 to 7 days, sprouting (i.e. outgrowth of endothelial cells) was analysed by taking pictures and determining a sprouting index.

9.1 Method

Aortae from male rats were obtained from Bagheri Life sciences (Berlin, Germany). The aortae were prepared freshly and transported on ice in MCDB 131-Medium (Invitrogen, Karlsruhe, Germany) containing 50 units/ml penicillin, 50 µg/ml streptomycin (both Invitrogen, Karlsruhe, Germany) and 2.5 µg/ml fungizone (Cambrex, USA).

For an experiment a single aorta was transferred to a cell culture dish together with the medium and residual connective tissue was removed. Then the aorta was cut with a scalpel into rings of about 1 to 2 mm length. The rings were washed intensively (at least five times) in Medium 199 (Invitrogen, Karlsruhe, Germany) and then placed in wells of a 24 well plate, containing 450 µl of collagen solution per well. This collagen solution was prepared by mixing 9 ml rat tail collagen (3 mg/ml in 0.1% acetic acid; Sigma, Deisenhofen, Germany) with 1.12 ml 10× Medium 199 (Invitrogen, Karlsruhe, Germany), 1.12 ml 10× Collagen-buffer (0.05 N NaOH, 200 mM HEPES, 260 mM $NaHCO_3$) and 0.6 ml 200 mM Glutamin. The rings were oriented such that the trimmed edges were perpendicular to the bottom of the well. The collagen was allowed to solidify by incubating the plates for at least one hour at 37° C. Thereafter 1 ml MCDB 131-medium with additions (SDF-1 and Spiegelmers) was added per well. Rings were then incubated at 37° C. for six to seven days. As control for sprouting the experiments were additionally done with VEGF (Vascular endothelial growth factor).

Sprouting was documented by taking pictures with a digital camera. In some cases rings were fixed by addition of 1 ml 10% paraformaldehyde and stored at 2-8° C. for further documentation. Pictures were analysed with the Scion Image image processing software. After calibration with the help of a picture taken from a stage micrometer, a line was drawn in a distance of 0.33 mm from one edge of a ring. A plot histogram along this line was generated by the software, histograms were printed and peaks (representing sprouts crossing the line) were counted. This number was taken as sprouting index. 4 to 5 rings per condition were evaluated. Statistical analysis was performed with WinSTAT for Excel.

9.2 Results

It could be demonstrated that SDF-1 induces sprouting and that this effect could be blocked with human SDF-1 binding Spiegelmer 193-G2-012-5'-PEG No blockage of SDF-1 induced sprouting was observed by the non-functional PEGylated Control Spiegelmer (FIGS. 31 and 32).

EXAMPLE 10: MOBILIZATION OF HEMATOPOIETIC STEM CELLS/HEMATOPOIETIC PROGENITOR CELLS (HSC/HPC) IN MICE BY A SINGLE INTRAVENOUS INJECTION OF NOX-A12 THAT WAS DERIVATIZED WITH 30 OR 40 KDA PEG 10.1 Test Substances and Administration Scheme Mice were injected i.v. with 13.4 mg/kg of SDF-1 binding Spiegelmer NOX-A12-JE40 (SEQ.ID. 132), SDF-1 binding Spiegelmer NOX-A12-NO30 (SEQ.ID. 242) or control Spiegelmer revNOX-A12 (SEQ.ID. 243) that has no binding activity to SDF-1. One, six, 24 or 48 h after the injection [5 mice per substance and time point] the animals were terminated and blood was won. Control groups were injected with vehicle (5% glucose), AMD-3100 (Sigma, France, 5 mg/kg s.c.) or Granulocyte-colony stimulating factor (G-CSF, Neupogen) (2.5 µg/mouse/injection, every 12 h). Termination of animals was done at the same time points as above (see FIG. 33). For the G-CSF (Neupogen) group: Due to the injection scheme of one injection every 12 h the animals that are terminated after one, and six hours have therefore received only one injection, the group terminated at 24 h received 2 injections (at 0 and 12 h), the group terminated at 48 h received four injections (at 0, 12, 24 and 36 h) (see FIG. 33). Blood cell counts were determined in a hemocytometer.

10.2 Detection of HSC/HPC

Fifty (50) µl of whole blood were first incubated with FcR blocking reagent (Ref 130-092-575, Miltenyi Biotec, Paris, France) in staining buffer (PBS [Ref 17-516F, Lonza], 0.2% BSA [Ref A7030, Sigma], 0.02% NaN3 [Ref S2002, Sigma] and then incubated at room temperature in the dark for 30 min with FITC conjugated anti-CD117 and PE conjugated anti-Ly-6A/E antibodies or with corresponding isotypes (as described in table below).

| Antigens | Clone | Isotype | Fluorochrome | Ref | Source | Quantity |
| --- | --- | --- | --- | --- | --- | --- |
| CD117 | 2B8 | $IgG_{2b}$ | FITC | 553354 | BD Biosciences | 1 □g |
| CD117 control isotype | | $IgG_{2b}$ | FITC | 553998 | BD Biosciences | 1 □g |
| Ly-6A/E | D7 | $IgG_{2a}$ | PE | 553108 | BD Biosciences | 1 □g |
| Ly-6A/E control isotype | | $IgG_{2a}$ | PE | 553930 | BD Biosciences | 1 □g |

Red blood cells were lysed using the "Fix and Lyse" procedure. Briefly, "Fix and Lyse" buffer will prepared by adding 25 µl of IOTest solution 3 (10× Fixative Solution [Ref A07800, Beckman Coulter, Villepinte, France]) to 1 ml of VersaLyse [Ref A09777, Beckman Coulter] and 1 ml of the mixture was added to the stained cells. After being vortexed and incubated for 10 min in the dark at room temperature, cells were centrifuged and washed once with 3 ml of staining buffer and resuspended in 1 ml of reference microbeads solution (PKH26, Ref P7458, 220,000 beads/ml, Sigma, ½ diluted in staining buffer). The samples were stored on ice protected from light exposure until FACS analysis.

The surface fluorescence of cells was analyzed with a flow cytometer apparatus (FACS, CyFlow® space) using a 488 nm wavelength laser excitation. A total of 10,000 events were collected for each sample.

10.3 Calculation of Absolute Cell Numbers Per µL

The volume of the blood samples was 50 µl. At the end of the preparation procedure, the white blood cells (which were contained in the 50 µl blood sample) were resuspended in 0.75 ml of a microbead solution (obtained by a ½ dilution of a stock solution containing 220,000 beads in 1 mL). The number of cells per mL of this latter solution is: (CN/BN)× (220000/2) and the total number of cells is: (CN/BN)× (220000/2)×(0.75/1), where CN is the number of counts for cells and BN is the number of counts for microbeads.

Therefore, this total number of cells was contained in the 50 µl of blood and the absolute number of cells (ACN) per µl of blood is: (CN/BN)×(220000/2)×(0.75/1)×(1/50).

10.4 Determination of Colony Forming Units (CFU)

Only blood from those time points with the maximum amount of hematopoietic progenitor cells (HPC)/hematopoietic stem cells (HSC) was chosen to be subjected to CFU assays (an identical time point for all mice per substance). The red blood cells (RBCs) depletion of normal peripheral blood samples was performed by adding 10 volumes 10× lysis buffer (0.8% NH4Cl with 0.1 mM EDTA) (ref 07800, StemCell Technologies) to peripheral blood, mixing by inverting the tube 3-4 times and incubation on ice for 5-15 minutes. After centrifugation for 7 min at 1,200 rpm, white blood cells (WBCs) were washed twice with Iscove's Modified Dulbecco's Medium (IMDM) containing 2% heat-inactivated foetal bovine serum (FBS, Ref DE14-802F, Lonza). Nucleated WBCs were counted using a hemacytometer (MS9-5 counter (Melet Schloesing, Osny, France)) after being 1/20 diluted in 3% acetic acid with methylene blue (Ref 07060, StemCell Technologies).

Cells were plated in triplicate in 0.9% methylcellulose containing IMDM (Ref MethoCult® M03434, StemCell Technologies) already containing 2% heat-inactivated FBS, recombinant mouse (rm) stem cell factor (SCF, growth of mast cells and myeloid and lymphoid progenitors), rm IL-3 and rh IL-6 (growth of early myeloid progenitors of all lineages), and recombinant human erythropoietin (rh EPO, growth of erythroid progenitors). Briefly, 10-fold concentrated WBCs (0.4 ml) were diluted in methylcellulose complete IMDM (final concentration to be defined during the validation experiment), thoroughly vortexed and let stand for 2-5 minutes to allow bubbles to dissipate before dispensing. 1.1 ml of methylcellulose medium containing cells mixture were dispensed using a luer-lock syringe and a 16 G blunt-end needle (Ref 28110, StemCell Technologies) to each of three 35 mm culture dishes (Ref 27150, StemCell Technologies). Dishes were gently tilted and rotated to distribute methylcellulose evenly. Large dishes with an additional uncovered sterile water containing 35 mm dish were used to hold 35 mm dishes during incubation at 37° C., 5% $CO_2$, with 95% humidity for 7 to 12 days.

At the end of the incubation, colonies were manually counted as BFU-E (Burst-forming unit-erythroid), CFU-GM (Colony-forming unit-granulocyte and/or macrophage) and CFU-GEMM (Colony-forming unit-granulocyte, erythroid, macrophage and megakaryocyte) using an inverted microscope and a 60 mm gridded scoring dish (Ref 27500, StemCell Technologies). The number of colonies was normalized to CFU/mL blood.

10.5 Results of Flow Cytometry

SDF-1 binding Spiegelmers NOX-A12-JE40 and NOX-A12-NO30 led to a marked increase of HPC/HSC as measured by CD117 and Ly-6 A/E double staining in the FACS analysis (see FIG. 34). The peak was observed 6 h after Spiegelmer administration. NOX-A12-JE40 led to the liberation of 700 $CD117^+Ly$-6 $A/E^+$ cells per μL. SDF-1 binding Spiegelmer NOX-A12-NO30 liberated 300 $CD117^+$ Ly-6 $A/E^+$ cells per μL of blood. In the vehicle group 100 $CD117^+Ly$-6 $A/E^+$ cells per μL of blood were counted. A HSC/HPC-mobilizing effect of G-CSF was seen in the mice that had received 4 G-CSF injections and were sacrificed 48 h after the first injection (250 $CD117^+Ly$-6 $A/E^+$ cells per μL). AMD-3100 and SDF-1 binding Spiegelmer revNOX-A12-JE40 did not show any effect. (see FIG. 34 for a graphical representation of all time points and all groups).

In consequence of SDF-1 binding Spiegelmer NOX-A12-JE40 treatment, the transient increase of HSC/HPCs was accompanied by a transient increase in the total white blood cell count, which is mainly driven by increased numbers of macrophages, granulocytes and neutrophils and by eonisophils. Neupogen was found to induce an increase in white blood cell count (WBC count) coupled with a decrease in eosinophils [%] (see FIG. 41).

10.6 Results of the CFU Assays

Compared to vehicle (0.8 CFU/mL), all substances led to increased mean values of total CFUs. However revNOX-A12-JE40 (6 h) and AMD3100 (6 h) only showed marginal effects (1.1 and 1.5 CFU/mL respectively). One injection of SDF-1 binding Spiegelmer NOX-A12-JE40 led to about as much CFUs/mL of blood after 6 h, as four injections of G-CSF (measured 48 h after the first injection and 12 h after the $4^{th}$ injection) (3.7 and 3.2 CFU/mL respectively). This is four time the value found for vehicle. SDF-1 binding Spiegelmer NOX-A12-NO30 doubled the CFU count compared to vehicle (1.9 CFU/mL). See FIG. 35 for an overview.

EXAMPLE 11: INHIBITION OF CHOROIDAL NEOVASCULARIZATION (CNV)

The "laser-induced choroidal neovascularization" animal model is used to predict the effect of investigational drugs on human retinal and choroidal neovasculature. This occurs in diseases like wet or 'proliferative' age-related macular degeneration (AMD), diabetic retinopathy and retinal vein occlusion. CXCR4 was shown to be expressed in the laser-induced CNV (Lima e Silva et al., FASEB J. 21: 2007). It was colocalized with CD45 and F4/80 expressing cells suggesting that these cells are BM-derived macrophages. Inhibitors for CXCR4 reduced laser-induced CNV. But it was not investigated if these cells express SDF1, too. In this study we evaluated whether the SDF-1 binding Spiegelmer NOX-A12-JE40 (SEQ.ID. 132) blocks neovascularization.

11.1 Methods

Twenty-two C57/BL6J mice not younger than 12 weeks were anesthetized and treated with 3 laser burns per eye. The animals develop choroidal neovascularization at the laser sites. One day later, 2 μl of a 440 μM solution of SDF-1 binding Spiegelmer NOX-A12-JE40 dissolved in Ringer solution were injected intravitreally in one eye (dose: 0.88 nmol=12.9 μg [oligo part of the molecule only]=48 μg [total molecule including PEG]) while the other eye received Ringer solution as a control. 14 days after laser treatment, the animals were perfused with dextran-fluorescein, and choroidal whole mounts were prepared. The whole mounts were evaluated for vascular changes of the choroid and the area of the CNV membrane.

As one eye was injected with Spiegelmer and the other eye of each animal received buffer only, the Wilcoxon signed ranks test which is concerning the difference between treated and control eye of each animal was used. The Wilcoxon signed rank test analyses the differences between two related measurements, in our case the treated and control eyes of each animal. It recognizes significant differences even if the set of the treated eyes and the set of the control eyes are not statistically different. The following R command was used: wilcoxsign_test (V1~V2, data=d0, distribution="exact") p<0.05 is significant at the 95% level.

11.2 Results

Thirteen of the 22 mice could be evaluated. The mean of the neovascularization area of the NOX-A12-JE40-treated eyes was smaller than the mean of the eyes treated with Ringer solution, indicating that the Spiegelmer reduced CNV formation. The p value calculated by the Wilcoxon matched-pairs signed-ranks test was 0.021. Therefore, it is concluded that the SDF-1 binding Spiegelmer NOX-A12-JE40 significantly reduces laser-induced choroidal neovascularization in the CNV mouse model, suggesting potential therapeutic benefit (see FIG. 36).

EXAMPLE 12: EFFICACY IN DIABETIC NEPHROPATHY

Glomerulosclerosis, e.g. in diabetes, remains a leading cause of end-stage renal disease because targeting the angiotensin-dependent pathomechanisms does not always prevent disease progression. Hence, other treatment strategies are required to add on to the therapeutic armament for glomerulosclerosis. Data from recent experimental studies relate the progression of glomerulosclerosis in diabetic mice and humans to intrarenal inflammation. For example, mycophenolate mofetil, methotrexate, or irradiation reduce urinary albumin excretion, and glomerulosclerosis in rats with streptozotocin-induced diabetes. Yet, the molecular and cellular mechanisms of intrarenal inflammation in diabetic nephropathy remain poorly characterized. Patients with diabetic nephropathy have increased serum levels of acute phase markers of inflammation but this may not represent intrarenal inflammation.

In this study the late-onset blockade of SDF-1 with SDF-1 binding Spiegelmer NOX-A12-JE40 (SEQ.ID. 132) was tested in db/db mice that had received an uninephrectomy at the age of 6 weeks. The administration of NOX-A12-JE40 began at the age of 4 months and was done 3 times a week at a dose of 50 mg/kg s.c (corresponds to 13.4 mg/kg oligonucleotide part). Two months later, the animals were sacrificed and the glomerulosclerosis score was determined.

By this score, individual glomeruli are scored for infiltration of leukocytes, and scarring of tissue. A score of 0 describes a healthy glomerulus, while a score of 4 describes the completely fibrotic form (Ninichuk, Clauss et al. 2008).
12.2 Results While wild-type mice have almost no kidney damage at the age of six months, db/db mice of the same age display a marked kidney damage. The kidney damage in db/db mice that were uninephrectomized at the age of six weeks is even stronger.

SDF-1 binding Spiegelmer NOX-A12-JE40 (SEQ.ID. 132), but not the non-specific control Spiegelmer revNOX-A12-JE40 (SEQ.ID. 243) of the reverse sequence significantly ameliorated the kidney damage that was observed in uninephrectomized db/db mice after six months: There were significantly lower numbers of glomeruli with the highest damage score (3 and 4). Instead, more subtle alterations (leukocyte infiltration) were observed in a higher number of glomeruli (see FIG. 37).

EXAMPLE 13: SDF-1 BINDING SPIEGELMER NOX-A12-JE40 INHIBITS VEGF-INDUCED RETINAL VASCULAR LEAKAGE IN PIGMENTED RABBITS

Vascular leakage of retinal vessels occurs in several eye diseases, like age-related macular degeneration and retinal vein occlusion. It leads to macular edema that impairs vision.
13.1 Methods In an animal model, retinal vascular leakage can be induced by an intravitreal VEGF injection in rabbits. In this model, the permeability of the retinal vasculature is measured by fluorescein photometry 48 h after intravitreal injection of VEGF. Test item injection had been done 5 days before the VEGF stimulus. The permeability that is observed two days after the VEGF administration is considered not to be directly related to the permeability increase that is transiently observed after a VEGF stimulus, but rather an effect of longer-lasting downstream processes that are triggered by the VEGF injection (Edelman, Lutz et al. 2005).

In this study eight pigmented rabbits (Fauve de Burgogne, 2-3 months old) were used per group. The groups were:
4 dose groups of NOX-A12-JE40 (105 nmol, 40 nmol, 8 nmol, 1.6 nmol)

a reference substance group (Kenacort retard(R) (4% triamcinolone acetonide), 2 mg i.vt.) and
vehicle (5% glucose for infusion).

The injection volume was 50 µL for all groups. Five days after substance administration in right eyes, VEGF was also only administered into the right eyes: 500 ng recombinant human $VEGF_{165}$ in 50 µL PBS. 48 h later, the retinal permeability was measured in anesthetized animals by ocular fluorometry (1 h after an i.v. injection of sodium fluorescein (10% in 0.9% sodium chloride, 50 mg/kg)). Briefly, the fluorescence intensity is scanned in vivo along the optical axis from the cornea to the retina of both eyes using a fluorotron device (FM-2 Fluorotron Master). The resulting intensity distribution curves are integrated and the ratio of the area under the curve (AUC) of the treated eye to the untreated eye were calculated. Group mean values and standard deviations were then calculated and depicted in a graph.
13.2 Results Intravitreal injection of 105 and 40 nmol SDF-1 binding Spiegelmer NOX-A12-JE40 in 50 µL glucose 5 days before injection of recombinant human $VEGF_{165}$ (500 ng in 50 µL) significantly inhibited the VEGF-induced permeabilization of the retinal vasculature 48 h after the VEGF stimulus. The reference item triamcinolone also showed a strong reduction in vascular permeability. BiaCore experiments that had been done previously had confirmed that no VEGF-binding of SDF-1 binding Spiegelmer NOX-A12-JE40 occurred at the concentrations used. Therefore it can be assumed that NOX-A12-JE40 blocks a downstream pathway of VEGF (e.g. recruitment of leukocytes, loosening of tight endothelial junctions as an effect of SDF-1 overexpression) that leads to the prolonged vascular permeability (see FIG. 38). NOX-A12-JE40 may therefore be useful for the treatment of macular or retinal edema itself or secondary to age-related macular degeneration or retinal vein occlusion.

EXAMPLE 14: SDF-1 BINDING SPIEGELMER NOX-A12-JE40 INHIBITS ANGIOGENESIS IN OXYGEN-INDUCED RETINOPATHY

The mouse model of oxygen-induced retinopathy is a model for the mimicking of hypoxia-induced neovascularization of the retina, as observed in diabetic retinopathy, especially proliferative diabetic retinopathy, and in age-related macular degeneration (Smith, Wesolowski et al. 1994). The model is also referred to as retinopathy of prematurity since premature babies that were put into incubators in the hospitals became blind due to too high oxygen exposure in the incubators that led to an abnormal retinal vessel growth during the time in the incubator and after their return to normoxic conditions.
14.1 Methods In the mouse model, newborn C57BL/6Jmice were incubated at 75% oxygen from the postnatal days P5-P12. After return to normal oxygen the animals develop retinal neovascularization due to relative hypoxia. SDF-1 binding Spiegelmer NOX-A12-JE40 (880 pmol in 2 µL Ringer solution) was injected on day P12. On day P17 mice were perfused with dextran-fluorescein to visualize the retinal vasculature. Retinal whole mounts were used to evaluate the vascular changes of the retinal vasculature in a coded fashion by a scoring system. FITC-Dextran perfusion allows the evaluation of perfused vessels only. In order to visualize immature, not-yet perfused vessels, the whole mounts were stained for isolectin-B4 and analyzed under a fluorscence microscope accordingly. Eyes treated with SDF-1 binding Spiegelmer were compared with vehicle treated eyes in an intra-individual manner. The significance was calculated by the Wilcoxon signed rank-test. p=0.05 corresponds to 95% confidence.

The following parameters were scored:
1. Number of vessel clusters
2. absolute cluster area size
3. relative cluster area size
4. number of sprouting vessels (tufts)
5. absolute size of the avascular zone
6. relative size of the avascular zone The retinopathy score was calculated from these parameters on the FITC-dextran images (Higgins, Yu et al. 1999). The significance levels for the parameters and the retinopathy score are shown in FIG. 40.

14.2 Results

Out of 34 mice tested, 24 whole mounts were could be evaluated after FITC-dextran perfusion, and 15 could be evaluated after isolectin staining. A single injection of 880 pmol SDF-1 binding Spiegelmer NOX-A12-JE40 on day P12 significantly inhibited tuft formation and thus improved the overall retinopathy score as observed on day P17 (see FIGS. 39 and 40). Therefore NOX-A12-JE40 may have a beneficial effect in diseases with hypoxia-induced neovascularization, especially of the eye (e.g. diabetic retinopathy, AMD).

REFERENCES

The complete bibliographic data of the documents recited herein are, if not indicated to the contrary, as follows, whereby the disclosure of said references is incorporated herein by reference.

Abi-Younes, S., A. Sauty, et al. (2000). "The stromal cell-derived factor-1 chemokine is a potent platelet agonist highly expressed in atherosclerotic plaques." Circ Res 86(2): 131-8.

Aiuti, A., I. J. Webb, et al. (1997). "The chemokine SDF-1 is a chemoattractant for human CD34+ hematopoietic progenitor cells and provides a new mechanism to explain the mobilization of CD34+ progenitors to peripheral blood." J Exp Med 185(1): 111-20.

Altschul S F, Gish W, Miller W, Myers E W, Lipman D J (1990), Basic local alignment search tool. J Mol Biol. 215(3):403-10.

Altschul S F, Madden T L, Schaffer A A, Zhang J, Zhang Z, Miller W, Lipman D J (1997). Gapped BLAST and PSI-BLAST: a new generation of protein database search programs. Nucleic Acids Res. 25(17):3389-402.

Ambati, J., A. Anand, et al. (2003). An animal model of age-related macular degeneration in senescent Ccl-2- or Ccr-2-deficient mice. Nat Med. 9: 1390-7.

Arya, S. K., C. C. Ginsberg, et al. (1999). "In vitro phenotype of SDF1 gene mutant that delays the onset of human immunodeficiency virus disease in vivo." J Hum Virol 2(3): 133-8.

Auerbach et al. (2003) Angiogenesis assays: a critical overview. Clin.Chem. 49: 32-40.

Avniel, S., Z. Arik, et al. (2006). "Involvement of the CXCL12/CXCR4 pathway in the recovery of skin following burns." J Invest Dermatol 126(2): 468-76.

Baggiolini, M. (1998). "Chemokines and leukocyte traffic." Nature 392(6676): 565-8.

Baggiolini, M., B. Dewald, et al. (1994). "Interleukin-8 and related chemotactic cytokines-CXC and CC chemokines." Adv Immunol 55: 97-179.

Balabanian K, Lagane B, Infantino S, Chow K Y, Harriague J, Moepps B, Arenzana-Seisdedos F, Thelen M, Bachelerie F (2005) The chemokine SDF-1/CXCL12 binds to and signals through the orphan receptor RDC1 in T lymphocytes. J Biol Chem 280(42): 35760-35766

Balabanian, K., B. Lagane, et al. (2005). "WHIM syndromes with different genetic anomalies are accounted for by impaired CXCR4 desensitization to CXCL12." Blood 105(6): 2449-57.

Balabanian, K., J. Couderc, et al. (2003). "Role of the chemokine stromal cell-derived factor 1 in autoantibody production and nephritis in murine lupus." J Immunol 170(6): 3392-400.

Balkwill, F. (2004). "Cancer and the chemokine network." Nat Rev Cancer 4(7): 540-50.

Bazan, J. F., K. B. Bacon, et al. (1997). "A new class of membrane-bound chemokine with a CX3C motif." Nature 385(6617): 640-4.

Bertolini, F., C. Dell'Agnola, et al. (2002). "CXCR4 neutralization, a novel therapeutic approach for non-Hodgkin's lymphoma." Cancer Res 62(11): 3106-12.

Bleul, C. C., J. L. Schultze, et al. (1998). "B lymphocyte chemotaxis regulated in association with microanatomic localization, differentiation state, and B cell receptor engagement." J Exp Med 187(5): 753-62.

Bleul, C. C., M. Farzan, et al. (1996). "The lymphocyte chemoattractant SDF-1 is a ligand for LESTR/fusin and blocks HIV-1 entry." Nature 382(6594): 829-33.

Bleul, C. C., R. C. Fuhlbrigge, et al. (1996). "A highly efficacious lymphocyte chemoattractant, stromal cell-derived factor 1 (SDF-1)." J Exp Med 184(3): 1101-9.

Brooks, H. L., Jr., S. Caballero, Jr., et al. (2004). "Vitreous levels of vascular endothelial growth factor and stromal-derived factor 1 in patients with diabetic retinopathy and cystoid macular edema before and after intraocular injection of triamcinolone." Arch Ophthalmol 122(12): 1801-7.

Broxmeyer, H. E., A. Orazi, et al. (1998). "Myeloid progenitor cell proliferation and mobilization effects of BB 10010, a genetically engineered variant of human macrophage inflammatory protein-1 alpha, in a phase I clinical trial in patients with relapsed/refractory breast cancer." Blood Cells Mol Dis 24(1): 14-30.

Broxmeyer, H. E., L. Benninger, et al. (1995). "Effects of in vivo treatment with PIXY321 (GM-CSF/IL-3 fusion protein) on proliferation kinetics of bone marrow and blood myeloid progenitor cells in patients with sarcoma." Exp Hematol 23(4): 335-40.

Buckley, C. D., N. Amft, et al. (2000). "Persistent induction of the chemokine receptor CXCR4 by TGF-beta 1 on synovial T cells contributes to their accumulation within the rheumatoid synovium." J Immunol 165(6): 3423-9.

Burger, J. A., N. Tsukada, et al. (2000). "Blood-derived nurse-like cells protect chronic lymphocytic leukemia B cells from spontaneous apoptosis through stromal cell-derived factor-1." Blood 96(8): 2655-63.

Burns J M, Summers B C, Wang Y, Melikian A, Berahovich R, Miao Z, Penfold M E, Sunshine M J, Littman D R, Kuo C J, Wei K, McMaster B E, Wright K, Howard M C, Schall T J (2006) A novel chemokine receptor for SDF-1 and I-TAC involved in cell survival, cell adhesion, and tumor development. J Exp Med 203(9): 2201-2213

Burt, R. K., A. Marmont, et al. (2006). "Randomized controlled trials of autologous hematopoietic stem cell transplantation for autoimmune diseases: the evolution from myeloablative to lymphoablative transplant regimens." Arthritis Rheum 54(12): 3750-60.

Butler J M, Guthrie S M, Koc M, Afzal A, Caballero S, Brooks H L, Mames R N, Segal M S, Grant M B, Scott E W (2005) SDF-1 is both necessary and sufficient to promote proliferative retinopathy. J Clin Invest 115(1): 86-93

Butler, J. M., S. M. Guthrie, et al. (2005). "SDF-1 is both necessary and sufficient to promote proliferative retinopathy." J Clin Invest 115(1): 86-93.

Cabioglu, N., A. Sahin, et al. (2005). "Chemokine receptor CXCR4 expression in breast cancer as a potential predictive marker of isolated tumor cells in bone marrow." Clin Exp Metastasis 22(1): 39-46.

Chow F Y, Nikolic-Paterson D J, Ma F Y, Ozols E, Rollins B J, Tesch G H (2007) Monocyte chemoattractant protein-1-induced tissue inflammation is critical for the development of renal injury but not type 2 diabetes in obese db/db mice. Diabetologia 50(2): 471-480

Chow F Y, Nikolic-Paterson D J, Ozols E, Atkins R C, Rollin B J, Tesch G H (2006) Monocyte chemoattractant protein-1 promotes the development of diabetic renal injury in streptozotocin-treated mice. Kidney Int 69(1): 73-80

Corcione, A., L. Ottonello, et al. (2000). "Stromal cell-derived factor-1 as a chemoattractant for follicular center lymphoma B cells." J Natl Cancer Inst 92(8): 628-35.

Croop, J. M., R. Cooper, et al. (2000). "Large-scale mobilization and isolation of CD34+ cells from normal donors." Bone Marrow Transplant 26(12): 1271-9.

Crump, M. P., J. H. Gong, et al. (1997). "Solution structure and basis for functional activity of stromal cell-derived factor-1; dissociation of CXCR4 activation from binding and inhibition of HIV-1." Embo J 16(23): 6996-7007.

Dale, D. C., W. C. Liles, et al. (1998). "Effects of granulocyte-macrophage colony-stimulating factor (GM-CSF) on neutrophil kinetics and function in normal human volunteers." Am J Hematol 57(1): 7-15.

Damha, M. J., Ogilvie, K. K. (1993) Methods in Molecular Biology, Vol. 20 Protocols for oligonucleotides and analogs, ed. S. Agrawal, p. 81-114, Humana Press Inc. 1993

D'Apuzzo, M., A. Rolink, et al. (1997). "The chemokine SDF-1, stromal cell-derived factor 1, attracts early stage B cell precursors via the chemokine receptor CXCR4." Eur J Immunol 27(7): 1788-93.

Dawn B, Tiwari S, Kucia M J Zuba-Surma E K, Guo Y, Sanganalmath S K, Abdel-Latif A, Hunt G, Vincent R J, Taher H, Reed N J, Ratajczak M Z, Bolli R (2008) Transplantation of bone marrow-derived very small embryonic-like stem cells attenuates left ventricular dysfunction and remodeling after myocardial infarction. Stem Cells 26(6): 1646-1655

De Klerck, B., L. Geboes, et al. (2005). "Pro-inflammatory properties of stromal cell-derived factor-1 (CXCL12) in collagen-induced arthritis." Arthritis Res Ther 7(6): R1208-20.

Eaton, B. E., L. Gold, et al. (1997). "Post-SELEX combinatorial optimization of aptamers." Bioorg Med Chem 5(6): 1087-96.

Edelman J L, Lutz D, Castro M R (2005) Corticosteroids inhibit VEGF-induced vascular leakage in a rabbit model of blood-retinal and blood-aqueous barrier breakdown. Exp Eye Res 80(2): 249-258

Edelman, J. L., D. Lutz, et al. (2005). "Corticosteroids inhibit VEGF-induced vascular leakage in a rabbit model of blood-retinal and blood-aqueous barrier breakdown." Exp Eye Res 80(2): 249-58.

Fedyk, E. R., D. H. Ryyan, et al. (1999). "Maturation decreases responsiveness of human bone marrow B lineage cells to stromal-derived factor 1 (SDF-1)." J Leukoc Biol 66(4): 667-73.

Fedyk, E. R., D. Jones, et al. (2001). "Expression of stromal-derived factor-1 is decreased by IL-1 and TNF and in dermal wound healing." J Immunol 166(9): 5749-54.

Fierro, F. A., S. Brenner, et al. (2008). "Combining SDF-1/CXCR4 antagonism and chemotherapy in relapsed acute myeloid leukemia." Leukemia.

Fong, D. S., L. P. Aiello, et al. (2004). "Diabetic retinopathy." Diabetes Care 27(10): 2540-53.

Fransioli J, Bailey B, Gude N A, Cottage C T, Muraski J A, Emmanuel G, Wu W, Alvarez R, Rubio M, Ottolenghi S, Schaefer E, Sussman M A (2008) Evolution of the c-kit-positive cell response to pathological challenge in the myocardium. Stem Cells 26(5): 1315-1324

Friedlander M, Dorrell M I, Ritter M R, Marchetti V, Moreno S K, El-Kalay M, Bird A C, Banin E, Aguilar E (2007) Progenitor cells and retinal angiogenesis. Angiogenesis 10(2): 89-101

Garrido, S. M., F. R. Appelbaum, et al. (2001). "Acute myeloid leukemia cells are protected from spontaneous and drug-induced apoptosis by direct contact with a human bone marrow stromal cell line (HS-5)." Exp Hematol 29(4): 448-57.

Gear, A. R., S. Suttitanamongkol, et al. (2001). "Adenosine diphosphate strongly potentiates the ability of the chemokines MDC, TARC, and SDF-1 to stimulate platelet function." Blood 97(4): 937-45.

Geminder, H., O. Sagi-Assif, et al. (2001). "A possible role for CXCR4 and its ligand, the CXC chemokine stromal cell-derived factor-1, in the development of bone marrow metastases in neuroblastoma." J Immunol 167(8): 4747-57.

Glaspy, J. A., E. J. Shpall, et al. (1997). "Peripheral blood progenitor cell mobilization using stem cell factor in combination with filgrastim in breast cancer patients." Blood 90(8): 2939-51.

Glaspy, J., M. W. Davis, et al. (1996). "Biology and clinical potential of stem-cell factor." Cancer Chemother Pharmacol 38 Suppl: S53-7.

Godessart, N. (2005). "Chemokine receptors: attractive targets for drug discovery." Ann N Y Acad Sci 1051: 647-57.

Godot, V., M. Arock, et al. (2007). "H4 histamine receptor mediates optimal migration of mast cell precursors to CXCL12." J Allergy Clin Immunol 120(4): 827-34.

Gombert, M., M. C. Dieu-Nosjean, et al. (2005). "CCL1-CCR8 interactions: an axis mediating the recruitment of T cells and Langerhans-type dendritic cells to sites of atopic skin inflammation." J Immunol 174(8): 5082-91.

Gonzalo, J. A., C. M. Lloyd, et al. (2000). "Critical involvement of the chemotactic axis CXCR4/stromal cell-derived factor-1 alpha in the inflammatory component of allergic airway disease." J Immunol 165(1): 499-508.

Grassi, F., S. Cristino, et al. (2004). "CXCL12 chemokine up-regulates bone resorption and MMP-9 release by human osteoclasts: CXCL12 levels are increased in synovial and bone tissue of rheumatoid arthritis patients." J Cell Physiol 199(2): 244-51.

Gratwohl A, Baldomero H, Horisberger B, Schmid C, Passweg J, Urbano-Ispizua A (2002) Current trends in hematopoietic stem cell transplantation in Europe. Blood 100(7): 2374-2386

Grunewald, M., I. Avraham, et al. (2006). "VEGF-induced adult neovascularization: recruitment, retention, and role of accessory cells." Cell 124(1): 175-89.

Gu, J., E. Marker-Hermann, et al. (2002). "A 588-gene microarray analysis of the peripheral blood mononuclear cells of spondyloarthropathy patients." Rheumatology (Oxford) 41(7): 759-66.

Guleng, B., K. Tateishi, et al. (2005). "Blockade of the stromal cell-derived factor-1/CXCR4 axis attenuates in vivo tumor growth by inhibiting angiogenesis in a vascular endothelial growth factor-independent manner." Cancer Res 65(13): 5864-71.

Gulino, A. V., D. Moratto, et al. (2004). "Altered leukocyte response to CXCL12 in patients with warts hypogammaglobulinemia, infections, myelokathexis (WHIM) syndrome." Blood 104(2): 444-52.

Hartmann, T. N., M. Burger, et al. (2004). "The role of adhesion molecules and chemokine receptor CXCR4 (CD184) in small cell lung cancer." J Biol Regul Homeost Agents 18(2): 126-30.

Higgins, R. D., K. Yu, et al. (1999). "Diltiazem reduces retinal neovascularization in a mouse model of oxygen induced retinopathy." Curr Eye Res 18(1): 20-7.

Hodohara, K., N. Fujii, et al. (2000). "Stromal cell-derived factor-1 (SDF-1) acts together with thrombopoietin to enhance the development of megakaryocytic progenitor cells (CFU-MK)." Blood 95(3): 769-75.

Hoshino, M., N. Aoike, et al. (2003). "Increased immunoreactivity of stromal cell-derived factor-1 and angiogenesis in asthma." Eur Respir J 21(5): 804-9.

Hwang, J. H., H. K. Chung, et al. (2003). "CXC chemokine receptor 4 expression and function in human anaplastic thyroid cancer cells." J Clin Endocrinol Metab 88(1): 408-16.

Ito T, Suzuki A, Imai E, Okabe M, Hori M (2001) Bone marrow is a reservoir of repopulating mesangial cells during glomerular remodeling. J Am Soc Nephrol 12(12): 2625-2635

Iwamoto T, Okamoto H, Toyama Y, Momohara S (2008) Molecular aspects of rheumatoid arthritis: chemokines in the joints of patients. FEBS J Jackson, K. A., S. M. Majka, et al. (2001). "Regeneration of ischemic cardiac muscle and vascular endothelium by adult stem cells." J Clin Invest 107(11): 1395-402.

Jiang, W., P. Zhou, et al. (1994). "Molecular cloning of TPAR1, a gene whose expression is repressed by the tumor promoter 12-O-tetradecanoylphorbol 13-acetate (TPA)." Exp Cell Res 215(2): 284-93.

Jin, L., K. J. Hope, et al. (2006). "Targeting of CD44 eradicates human acute myeloid leukemic stem cells." Nat Med 12(10): 1167-74.

Jin, L., Y. Tabe, et al. (2008). "CXCR4 up-regulation by imatinib induces chronic myelogenous leukemia (CML) cell migration to bone marrow stroma and promotes survival of quiescent CML cells." Mol Cancer Ther 7(1): 48-58.

Jo, D. Y., S. Rafii, et al. (2000). "Chemotaxis of primitive hematopoietic cells in response to stromal cell-derived factor-1." J Clin Invest 105(1): 101-11.

Jose, P. J., D. A. Griffiths-Johnson, et al. (1994). "Eotaxin: a potent eosinophil chemoattractant cytokine detected in a guinea pig model of allergic airways inflammation." J Exp Med 179(3): 881-7.

Juarez, J. and L. Bendall (2004). "SDF-1 and CXCR4 in normal and malignant hematopoiesis." Histol Histopathol 19(1): 299-309.

Kanbe, K., K. Takagishi, et al. (2002). "Stimulation of matrix metalloprotease 3 release from human chondrocytes by the interaction of stromal cell-derived factor 1 and CXC chemokine receptor 4." Arthritis Rheum 46(1): 130-7.

Kang, H., G. Watkins, et al. (2005). "Stromal cell derived factor-1: its influence on invasiveness and migration of breast cancer cells in vitro, and its association with prognosis and survival in human breast cancer." Breast Cancer Res 7(4): R402-10.

Kawai, T., U. Choi, et al. (2005). "Enhanced function with decreased internalization of carboxy-terminus truncated CXCR4 responsible for WHIM syndrome." Exp Hematol 33(4): 460-8.

Kim K W, Cho M L, Kim H R, Ju J H, Park M K, Oh H J, Kim J S, Park S H, Lee S H, Kim H Y (2007) Up-regulation of stromal cell-derived factor 1 (CXCL12) production in rheumatoid synovial fibroblasts through interactions with T lymphocytes: role of interleukin-17 and CD40L-CD40 interaction. Arthritis Rheum 56(4): 1076-1086

King, A. G., D. Horowitz, et al. (2001). "Rapid mobilization of murine hematopoietic stem cells with enhanced engraftment properties and evaluation of hematopoietic progenitor cell mobilization in rhesus monkeys by a single injection of SB-251353, a specific truncated form of the human CXC chemokine GRObeta." Blood 97(6): 1534-42.

Kocher, A. A., M. D. Schuster, et al. (2001). "Neovascularization of ischemic myocardium by human bone-marrow-derived angioblasts prevents cardiomyocyte apoptosis, reduces remodeling and improves cardiac function." Nat Med 7(4): 430-6.

Koshiba, T., R. Hosotani, et al. (2000). "Expression of stromal cell-derived factor 1 and CXCR4 ligand receptor system in pancreatic cancer: a possible role for tumor progression." Clin Cancer Res 6(9): 3530-5.

Krumbholz, M., D. Theil, et al. (2006). "Chemokines in multiple sclerosis: CXCL12 and CXCL13 up-regulation is differentially linked to CNS immune cell recruitment." Brain 129: 200-211.

Kryczek, I., A. Lange, et al. (2005). "CXCL12 and vascular endothelial growth factor synergistically induce neoangiogenesis in human ovarian cancers." Cancer Res 65(2): 465-72.

Kucia, M., R. Reca, et al. (2005). "Trafficking of normal stem cells and metastasis of cancer stem cells involve similar mechanisms: pivotal role of the SDF-1-CXCR4 axis." Stem Cells 23(7): 879-94.

Kulkarni O, Pawar R D, Purschke W, Eulberg D, Sel e N, Buchner K, Ninichuk V, Segerer S, Vielhauer V, Klussmann S, Anders H J (2007) Spiegelmer inhibition of CCL2/MCP-1 ameliorates lupus nephritis in MRL-(Fas) lpr mice. J Am Soc Nephrol 18(8): 2350-2358

Kusser, W. (2000). "Chemically modified nucleic acid aptamers for in vitro selections: evolving evolution." J Biotechnol 74(1): 27-38.

Lagane, B., K. Y. Chow, et al. (2008). "CXCR4 dimerization and {beta}-arrestin-mediated signaling account for the enhanced chemotaxis to CXCL12 in WHIM syndrome." Blood.

Lapteva, N., A. G. Yang, et al. (2005). "CXCR4 knockdown by small interfering RNA abrogates breast tumor growth in vivo." Cancer Gene Ther 12(1): 84-9.

Li J K, Yu L, Shen Y, Zhou L S, Wang Y C, Zhang J H (2008) Inhibition of CXCR4 activity with AMD3100 decreases invasion of human colorectal cancer cells in vitro. World J Gastroenterol 14(15): 2308-2313

Li Y, Atmaca-Sonmez P, Schanie C L, Ildstad S T, Kaplan H J, Enzmann V (2007) Endogenous bone marrow derived cells express retinal pigment epithelium cell markers and migrate to focal areas of RPE damage. Invest Ophthalmol Vis Sci 48(9): 4321-4327

Li Y, Reca R G, Atmaca-Sonmez P, Ratajczak M Z, Ildstad S T, Kaplan H J, Enzmann V (2006) Retinal pigment epithelium damage enhances expression of chemoattractants and migration of bone marrow-derived stem cells. Invest Ophthalmol Vis Sci 47(4): 1646-1652

Liang Z, Brooks J, Willard M, Liang K, Yoon Y, Kang S, Shim H (2007) CXCR4/CXCL12 axis promotes VEGF-mediated tumor angiogenesis through Akt signaling pathway. Biochem Biophys Res Commun 359(3): 716-722

Lima e Silva R, Shen J, Hackett S F, Kachi S, Akiyama H, Kiuchi K, Yokoi K, Hatara M C, Lauer T, Aslam S, Gong Y Y, Xiao W H, Khu N H, Thut C, Campochiaro P A (2007) The SDF-1/CXCR4 ligand/receptor pair is an important contributor to several types of ocular neovascularization. FASEB J 21(12): 3219-3230

Ma, Q., D. Jones, et al. (1998). "Impaired B-lymphopoiesis, myelopoiesis, and derailed cerebellar neuron migration in CXCR4- and SDF-1-deficient mice." Proc Natl Acad Sci USA 95(16): 9448-53.

Maekawa, T. and T. Ishii (2000). "Chemokine/receptor dynamics in the regulation of hematopoiesis." Intern Med 39(2): 90-100.

Majka M, Kucia M, Ratajczak M Z (2005) Stem cell biology—a never ending quest for understanding. Acta Biochim Pol 52(2): 353-358

Majka, M., A. Janowska-Wieczorek, et al. (2000). "Stromal-derived factor 1 and thrombopoietin regulate distinct aspects of human megakaryopoiesis." Blood 96(13): 4142-51.

Mames R N, Mattheus A, Butler J, Brown G, Jorgensen M, Scott E (2006). New anti SDF-1 antinody prevents retinal neovascularization in primates. ARVO; May 1, 2006; Fort Lauderdale.

Marechal, V., F. Arenzana-Seisdedos, et al. (1999). "Opposite effects of SDF-1 on human immunodeficiency virus type 1 replication." J Virol 73(5): 3608-15.

Matsunaga, T., N. Takemoto, et al. (2003). "Interaction between leukemic-cell VLA-4 and stromal fibronectin is a decisive factor for minimal residual disease of acute myelogenous leukemia." Nat Med 9(9): 1158-65.

Matthys, P., S. Hatse, et al. (2001). "AMD3100, a potent and specific antagonist of the stromal cell-derived factor-1 chemokine receptor CXCR4, inhibits autoimmune joint inflammation in IFN-gamma receptor-deficient mice." J Immunol 167(8): 4686-92.

McGinnis S, Madden T L (2004). BLAST: at the core of a powerful and diverse set of sequence analysis tools. Nucleic Acids Res. 32(Web Server issue):W20-5.

Meleth, A. D., E. Agron, et al. (2005). "Serum inflammatory markers in diabetic retinopathy." Invest Ophthalmol Vis Sci 46(11): 4295-301.

Menu, E., K. Asosingh, et al. (2006). "The involvement of stromal derived factor 1 alpha in homing and progression of multiple myeloma in the 5TMM model." Haematologica.

Miller, M. D. and M. S. Krangel (1992). "Biology and biochemistry of the chemokines: a family of chemotactic and inflammatory cytokines." Crit Rev Immunol 12(1-2): 17-46.

Minges Wols H A, Ippolito J A, Yu Z, Palmer J L, White F A, Le P T, Witte P L (2007) The effects of microenvironment and internal programming on plasma cell survival. Int Immunol 19(7): 837-846

Minges Wols H A, Witte P L (2008) Plasma cell purification from murine bone marrow using a two-step isolation approach. J Immunol Methods 329(1-2): 219-224

Moser, B., M. Wolf, et al. (2004). "Chemokines: multiple levels of leukocyte migration control." Trends Immunol 25(2): 75-84.

Mudry, R. E., J. E. Fortney, et al. (2000). "Stromal cells regulate survival of B-lineage leukemic cells during chemotherapy." Blood 96(5): 1926-32.

Muller, A., B. Homey, et al. (2001). "Involvement of chemokine receptors in breast cancer metastasis." Nature 410(6824): 50-6.

Murdoch, C. (2000). "CXCR4: chemokine receptor extraordinaire." Immunol Rev 177: 175-84.

Murphy, P. M., M. Baggiolini, et al. (2000). "International union of pharmacology. XXII. Nomenclature for chemokine receptors." Pharmacol Rev 52(1): 145-76.

Nagasawa, T. (2000). "A chemokine, SDF-1/PBSF, and its receptor, CXC chemokine receptor 4, as mediators of hematopoiesis." Int J Hematol 72(4): 408-11.

Nagasawa, T., H. Kikutani, et al. (1994). "Molecular cloning and structure of a pre-B-cell growth-stimulating factor." Proc Natl Acad Sci USA 91(6): 2305-9.

Nagasawa, T., S. Hirota, et al. (1996). "Defects of B-cell lymphopoiesis and bone-marrow myelopoiesis in mice lacking the CXC chemokine PBSF/SDF-1." Nature 382 (6592): 635-8.

NCI NCI. (2001) Bone Marrow Transplantation and Peripheral Blood Stem Cell Transplantation: Questions and Answers. Fact Sheet, Vol. 2008.

Needleman & Wunsch (1970), A general method applicable to the search for similarities in the amino acid sequence of two proteins. J Mol Biol. 48(3):443-53.

Ninichuk, V., S. Clauss, et al. (2008). "Late onset of Ccl2 blockade with the Spiegelmer mNOX-E36-3'PEG prevents glomerulosclerosis and improves glomerular filtration rate in db/db mice." Am J Pathol 172(3): 628-37.

Oppenheim, J. J., C. O. Zachariae, et al. (1991). "Properties of the novel proinflammatory supergene "intercrine" cytokine family." Annu Rev Immunol 9: 617-48.

Orimo, A., P. B. Gupta, et al. (2005). "Stromal fibroblasts present in invasive human breast carcinomas promote tumor growth and angiogenesis through elevated SDF-1/CXCL12 secretion." Cell 121(3): 335-48.

Otani A, Kinder K, Ewalt K, Otero F J, Schimmel P, Friedlander M (2002) Bone marrow-derived stem cells target retinal astrocytes and can promote or inhibit retinal angiogenesis. Nat Med 8(9): 1004-1010

Parretta, E. G. Cassese, et al. (2005). "CD8 cell division maintaining cytotoxic memory occurs predominantly in the bone marrow." J Immunol 174(12): 7654-64.

Pearson & Lipman (1988), Improved tools for biological sequence comparison. Proc. Nat'l. Acad. Sci. USA 85: 2444

Peled, A., I. Petit, et al. (1999). "Dependence of human stem cell engraftment and repopulation of NOD/SCID mice on CXCR4." Science 283(5403): 845-8.

Perissinotto, E., G. Cavalloni, et al. (2005). "Involvement of chemokine receptor 4/stromal cell-derived factor 1 system during osteosarcoma tumor progression." Clin Cancer Res 11(2 Pt 1): 490-7.

Phillips, R. J., M. D. Burdick, et al. (2003). "The stromal derived factor-1/CXCL12-CXC chemokine receptor 4 biological axis in non-small cell lung cancer metastases." Am J Respir Crit Care Med 167(12): 1676-86.

Ponath, P. D., S. Qin, et al. (1996). "Cloning of the human eosinophil chemoattractant, eotaxin. Expression, receptor binding, and functional properties suggest a mechanism for the selective recruitment of eosinophils." J Clin Invest 97(3): 604-12.

Ponomaryov, T., A. Peled, et al. (2000). "Induction of the chemokine stromal-derived factor-1 following DNA damage improves human stem cell function." J Clin Invest 106(11): 1331-9.

Pruijt, J. F., R. Willemze, et al. (1999). "Mechanisms underlying hematopoietic stem cell mobilization induced by the CXC chemokine interleukin-8." Curr Opin Hematol 6(3): 152-8.

Radbruch, A., G. Muehlinghaus, et al. (2006). "Competence and competition: the challenge of becoming a long-lived plasma cell." Nat Rev Immunol 6(10): 741-50.

Reddy, K., Z. Zhou, et al. (2008). "Stromal cell-derived factor-1 stimulates vasculogenesis and enhances Ewing's sarcoma tumor growth in the absence of vascular endothelial growth factor." Int J Cancer.

Riviere, C., F. Subra, et al. (1999). "Phenotypic and functional evidence for the expression of CXCR4 receptor during megakaryocytopoiesis." Blood 93(5): 1511-23.

Rosenfeld, C. S., B. Bolwell, et al. (1996). "Comparison of four cytokine regimens for mobilization of peripheral blood stem cells: IL-3 alone and combined with GM-CSF or G-CSF." Bone Marrow Transplant 17(2): 179-83.

Rubin, J. B., A. L. Kung, et al. (2003). "A small-molecule antagonist of CXCR4 inhibits intracranial growth of primary brain tumors." Proc Natl Acad Sci USA 100(23): 13513-8.

Salcedo R, Wasserman K, Young H A, Grimm M C, Howard O M, Anver M R, Kleinman H K, Murphy W J, Oppenheim J J (1999) Vascular endothelial growth factor and basic fibroblast growth factor induce expression of CXCR4 on human endothelial cells: In vivo neovascularization induced by stromal-derived factor-1 alpha. Am J Pathol 154(4): 1125-1135

Salcedo, R. and J. J. Oppenheim (2003). "Role of chemokines in angiogenesis: CXCL12/SDF-1 and CXCR4 interaction, a key regulator of endothelial cell responses." Microcirculation 10(3-4): 359-70.

Salcedo, R., K. Wasserman, et al. (1999). "Vascular endothelial growth factor and basic fibroblast growth factor induce expression of CXCR4 on human endothelial cells: In vivo neovascularization induced by stromal-derived factor-1 alpha." Am J Pathol 154(4): 1125-35.

Salvucci, O., L. Yao, et al. (2002). "Regulation of endothelial cell branching morphogenesis by endogenous chemokine stromal-derived factor-1." Blood 99(8): 2703-11.

Saur, D., B. Seidler, et al. (2005). "CXCR4 expression increases liver and lung metastasis in a mouse model of pancreatic cancer." Gastroenterology 129(4): 1237-50.

Schall, T. J. and K. B. Bacon (1994). "Chemokines, leukocyte trafficking, and inflammation." Curr Opin Immunol 6(6): 865-73.

Schober, A. and A. Zemecke (2007). "Chemokines in vascular remodeling." Thromb Haemost 97(5): 730-7.

Schwarting S, Litwak S, Hao W, Bahr M, Weise J, Neumann H (2008) Hematopoietic Stem Cells Reduce Postischemic Inflammation and Ameliorate Ischemic Brain Injury. Stroke Scotton C J, Wilson J L, Scott K, Stamp G, Wilbanks G D, Fricker S, Bridger G, Balkwill F R (2002) Multiple actions of the chemokine CXCL12 on epithelial tumor cells in human ovarian cancer. Cancer Res 62(20): 5930-5938

Scotton, C. J., J. L. Wilson, et al. (2002). "Multiple actions of the chemokine CXCL12 on epithelial tumor cells in human ovarian cancer." Cancer Res 62(20): 5930-8.

Sengupta, N., S. Caballero, et al. (2005). "Preventing stem cell incorporation into choroidal neovascularization by targeting homing and attachment factors." Invest Ophthalmol Vis Sci 46(1): 343-8.

Shirozu, M., T. Nakano, et al. (1995). "Structure and chromosomal localization of the human stromal cell-derived factor 1 (SDF1) gene." Genomics 28(3): 495-500.

Smith & Waterman (1981), Adv. Appl. Math. 2: 482

Smith, L. E., E. Wesolowski, et al. (1994). "Oxygen-induced retinopathy in the mouse." Invest Ophthalmol Vis Sci 35(1): 101-11.

Soriano, A., C. Martinez, et al. (2002). "Plasma stromal cell-derived factor (SDF)-1 levels, SDF1-3'A genotype, and expression of CXCR4 on T lymphocytes: their impact on resistance to human immunodeficiency virus type 1 infection and its progression." J Infect Dis 186(7): 922-31.

Springer, T. A. (1995). "Traffic signals on endothelium for lymphocyte recirculation and leukocyte emigration." Annu Rev Physiol 57: 827-72.

Stem Cells: Scientific Progress and Future Research Directions. Department of Health and Human Services. June 2001. <http://stemcells.nih.gov/info/scireport/2001report>.

Sun, Y. X., A. Schneider, et al. (2005). "Skeletal localization and neutralization of the SDF-1(CXCL12)/CXCR4 axis blocks prostate cancer metastasis and growth in osseous sites in vivo." J Bone Miner Res 20(2): 318-29.

Tabe, Y., L. Jin, et al. (2007). "Activation of integrin-linked kinase is a critical prosurvival pathway induced in leukemic cells by bone marrow-derived stromal cells." Cancer Res 67(2): 684-94.

Tachibana, K., S. Hirota, et al. (1998). "The chemokine receptor CXCR4 is essential for vascularization of the gastrointestinal tract." Nature 393(6685): 591-4.

Takenaga, M., H. Tamamura, et al. (2004). "A single treatment with microcapsules containing a CXCR4 antagonist suppresses pulmonary metastasis of murine melanoma." Biochem Biophys Res Commun 320(1): 226-32.

Tamamura, H., M. Fujisawa, et al. (2004). "Identification of a CXCR4 antagonist, a T140 analog, as an anti-rheumatoid arthritis agent." FEBS Lett 569(1-3): 99-104.

Tang Y, Yasuhara T, Hara K, Matsukawa N, Maki M, Yu G, Xu L, Hess D C, Borlongan C V (2007) Transplantation of bone marrow-derived stem cells: a promising therapy for stroke. Cell Transplant 16(2): 159-169

Tarlinton D, Radbruch A, Hiepe F, Dorner T (2008) Plasma cell differentiation and survival. Curr Opin Immunol 20(2): 162-169

Tashiro, K., H. Tada, et al. (1993). "Signal sequence trap: a cloning strategy for secreted proteins and type I membrane proteins." Science 261(5121): 600-3.

Vadhan-Raj, S., L. J. Murray, et al. (1997). "Stimulation of megakaryocyte and platelet production by a single dose of recombinant human thrombopoietin in patients with cancer." Ann Intern Med 126(9): 673-81.

Venkatesan, N., S. J. Kim, et al. (2003). "Novel phosphoramidite building blocks in synthesis and applications toward modified oligonucleotides." Curr Med Chem 10(19): 1973-91.

Viardot, A., R. Kronenwett, et al. (1998). "The human immunodeficiency virus (HIV)-type 1 coreceptor CXCR-4 (fusin) is preferentially expressed on the more immature CD34+ hematopoietic stem cells." Ann Hematol 77(5): 193-7.

Voermans, C., M. L. Kooi, et al. (2001). "In vitro migratory capacity of CD34+ ells is related to hematopoietic recovery after autologous stem cell transplantation." Blood 97(3): 799-804.

Wang J, Shiozawa Y, Wang Y, Jung Y, Pienta K J, Mehra R, Loberg R, Taichman R S (2008) The role of CXCR7/RDC1 as a chemokine receptor for CXCL12/SDF-1 in prostate cancer. J Biol Chem 283(7): 4283-4294

Wang, J., E. Guan, et al. (2001). "Role of tyrosine phosphorylation in ligand-independent sequestration of CXCR4 in human primary monocytes-macrophages." J Biol Chem 276(52): 49236-43.

Wang, N., Q. L. Wu, et al. (2005). "Expression of chemokine receptor CXCR4 in nasopharyngeal carcinoma: pattern of expression and correlation with clinical outcome." J Transl Med 3: 26.

Wijdenes J, Vooijs W C, Clement C, Post J, Morard F, Vita N, Laurent P, Sun R X, Klein B, Dore J M (1996) A plasmocyte selective monoclonal antibody (B-B4) recognizes syndecan-1. Br J Haematol 94(2): 318-323

Wincott F, DiRenzo A, Shaffer C, Grimm S, Tracz D, Workman C, Sweedler D, Gonzalez C, Scaringe S, Usman N (1995). Synthesis, deprotection, analysis and purification of RNA and ribozymes. Nucleic Acids Res. 23(14): 2677-84.

Xu, J., A. Mora, et al. (2007). "Role of the SDF-1/CXCR4 axis in the pathogenesis of lung injury and fibrosis." Am J Respir Cell Mol Biol 37(3): 291-9.

Yamaguchi, J., K. F. Kusano, et al. (2003). "Stromal cell-derived factor-1 effects on ex vivo expanded endothelial progenitor cell recruitment for ischemic neovascularization." Circulation 107(9): 1322-8.

Yamaji-Kegan, K., Q. Su, et al. (2006). "Hypoxia-induced mitogenic factor has proangiogenic and proinflammatory effects in the lung via VEGF and VEGF receptor-2." Am J Physiol Lung Cell Mol Physiol 291(6): L1159-68.

Yang J, Zhang B, Lin Y, Yang Y, Liu X, Lu F (2008) Breast cancer metastasis suppressor 1 inhibits SDF-1 alpha-induced migration of non-small cell lung cancer by decreasing CXCR4 expression. Cancer Lett Yasumoto, K., K. Koizumi, et al. (2006). "Role of the CXCL12/CXCR4 axis in peritoneal carcinomatosis of gastric cancer." Cancer Res 66(4): 2181-7.

Zagzag D, Esencay M, Mendez O, Yee H, Smirnova I, Huang Y, Chiriboga L, Lukyanov E, Liu M, Newcomb E W (2008) Hypoxia- and vascular endothelial growth factor-induced stromal cell-derived factor-1 alpha/CXCR4 expression in glioblastomas: one plausible explanation of Scherer's structures. Am J Pathol 173(2): 545-560

Zeelenberg, I. S., L. Ruuls-Van Stalle, et al. (2001). "Retention of CXCR4 in the endoplasmic reticulum blocks dissemination of a T cell hybridoma." J Clin Invest 108(2): 269-77.

Zeelenberg, I. S., L. Ruuls-Van Stalle, et al. (2003). "The chemokine receptor CXCR4 is required for outgrowth of colon carcinoma micrometastases." Cancer Res 63(13): 3833-9.

Zhang, X., T. Nakajima, et al. (2005). "Tissue trafficking patterns of effector memory CD4+ T cells in rheumatoid arthritis." Arthritis Rheum 52(12): 3839-49.

Zhou, Y., P. H. Larsen, et al. (2002). "CXCR4 is a major chemokine receptor on glioma cells and mediates their survival." J Biol Chem 277(51): 49481-7.

Zou, Y. R., A. H. Kottmann, et al. (1998). "Function of the chemokine receptor CXCR4 in haematopoiesis and in cerebellar development." Nature 393(6685): 595-9.

The features of the present invention disclosed in the specification, the claims and/or the drawings may both separately and in any combination thereof be material for realizing the invention in various forms thereof.

The invention claimed is:

1. A method for the treatment of nephropathy or hypertension, wherein the method comprises administering to a subject in need of treatment, an L-nucleic acid that inhibits signalling between SDF-1 and an SDF-1 receptor,
  wherein the L-nucleic acid comprises an SDF-1 binding molecule selected from the group consisting of a type A L-nucleic acid, a type B L-nucleic acid, a type C L-nucleic acid, SEQ ID NO:142, SEQ ID NO:143 and SEQ ID NO:144,
  wherein the type A L-nucleic acid comprises a core nucleotide sequence:

```
                                           (SEQ ID NO: 19)
5' AAAGYRACAHGUMAAX₄UGAAAGGUARC 3'
``` wherein $X_A$ is either absent or is A,
  wherein the type B L-nucleic acid comprises a core nucleotide sequence:

```
                                           (SEQ ID NO: 57)
5' GUGUGAUCUAGAUGUADWGGCUGWUCCUAGUYAGG 3'
``` and
  wherein the type C L-nucleic acid comprises a core nucleotide sequence:

```
                                           (SEQ ID NO: 90)
5' GGUYAGGGCUHRX₄AGUCGG 3',
``` wherein $X_A$ is either absent or is A;
  and said SDF-1 receptor comprises CXCR4 or CXCR7.

2. The method according to claim 1, wherein said nephropathy comprises diabetic nephropathy.

3. The method according to claim 1, wherein
  the type A L-nucleic acid comprises a nucleotide sequence selected from the group consisting of SEQ ID NOs:5 to 18, 25 to 41, 133, 137, 139, 140 and 141;
  the type B L-nucleic acid comprises a nucleotide sequence selected from the group consisting of SEQ ID NOs:46 to 56, 61 to 72 and 132; and
  the type C L-nucleic acid comprises a nucleotide sequence selected from the group consisting of SEQ ID NOs:79 to 89, 94 to 119, 134, 135 and 136.

4. The method according to claim 1, wherein the SDF-1 is a human SDF-1 or the SDF-1 receptor is a human SDF-1 receptor.

5. The method according to claim 1, wherein the L-nucleic acid comprises a modification.

6. The method according to claim 5, wherein the modification is selected from the group consisting of a HES moiety and a PEG moiety.

7. The method according to claim 5, wherein the modification comprises a PEG moiety consisting of a straight or branched PEG, wherein the molecular weight of the PEG moiety is from about 2 to 180 kD, 60 to 140 kD or about 40 kD.

8. The method according to claim 1, wherein said hypertension comprises pulmonary hypertension.

9. A method for inhibiting the migration of leukocytes, wherein the method comprises administering to a subject in need of treatment an L-nucleic acid that inhibits signalling between SDF-1 and an SDF-1 receptor,
  wherein said L-nucleic acid comprises an SDF-1 binding molecule selected from the group consisting of a type A L-nucleic acid, a type B L-nucleic acid, a type C L-nucleic acid, SEQ ID NO:142, SEQ ID NO:143 and SEQ ID N:144,
  wherein the type A L-nucleic acid comprises a core nucleotide sequence:

```
                                           (SEQ ID NO: 19)
5' AAAGYRACAHGUMAAX₄UGAAAGGUARC 3'
``` wherein $X_A$ is either absent or is A,
  wherein the type B L-nucleic acid molecule comprises a core nucleotide sequence:

```
                                           (SEQ ID NO: 57)
5' GUGUGAUCUAGAUGUADWGGCUGWUCCUAGUYAGG 3';
``` and
  wherein the type C L-nucleic acid molecule comprises a core nucleotide sequence of

```
                                           (SEQ ID NO: 90)
                   GGUYAGGGCUHRX₄AGUCGG,
``` wherein $X_A$ is either absent or is A,
and said SDF-1 receptor comprises CXCR4 or CXCR7.

10. The method according to claim 9, wherein
the type A L-nucleic acid comprises a nucleotide sequence selected from the group consisting of SEQ ID NOs:5 to 18, 25 to 41, 133, 137, 139, 140 and 141;
the type B L-nucleic acid comprises a nucleotide sequence selected from the group consisting of SEQ ID NOs:46 to 56, 61 to 72 and 132; and
the type C L-nucleic acid comprises a nucleotide sequence selected from the group consisting of SEQ ID NOs:79 to 89, 94 to 119, 134, 135 and 136.

11. The method according to claim 9, wherein the SDF-1 is a human SDF-1 or the SDF-1 receptor is a human SDF-1 receptor.

12. The method according to claim 9, wherein the L-nucleic acid comprises a modification.

13. The method according to claim 12, wherein the modification is selected from the group consisting of a HES moiety and a PEG moiety.

14. The method according to claim 12, wherein the modification comprises a PEG moiety consisting of a straight or branched PEG, wherein the molecular weight of the PEG moiety is from about 2 to 180 kD, from about 60 to 140 kD or about 40 kD.

* * * * *